(12) United States Patent
Looney et al.

(10) Patent No.: US 11,970,787 B2
(45) Date of Patent: Apr. 30, 2024

(54) COMPOSITIONS AND METHODS FOR IMMUNE REPERTOIRE SEQUENCING

(71) Applicant: Life Technologies Corporation, Carlsbad, CA (US)

(72) Inventors: Timothy Looney, Austin, TX (US); Geoffrey Lowman, Carlsbad, CA (US); Lifeng Lin, Dublin, CA (US)

(73) Assignee: Life Technologies Corporation, Carlsbad, CA (US)

( * ) Notice: Subject to any disclaimer, the term of this patent is extended or adjusted under 35 U.S.C. 154(b) by 216 days.

(21) Appl. No.: 17/248,722

(22) Filed: Feb. 4, 2021

(65) Prior Publication Data

US 2021/0164047 A1    Jun. 3, 2021

Related U.S. Application Data

(62) Division of application No. 15/873,862, filed on Jan. 17, 2018, now Pat. No. 10,920,273.
(Continued)

(51) Int. Cl.
| | |
|---|---|
| *C40B 50/06* | (2006.01) |
| *C12Q 1/6811* | (2018.01) |
| *C12Q 1/6844* | (2018.01) |
| *C12Q 1/6869* | (2018.01) |
| *C12Q 1/6876* | (2018.01) |

(Continued)

(52) U.S. Cl.
CPC ............ *C40B 50/06* (2013.01); *C12Q 1/6811* (2013.01); *C12Q 1/6844* (2013.01); *C12Q 1/6869* (2013.01); *C12Q 1/6876* (2013.01); *C12Q 1/6881* (2013.01); *C12Q 1/6883* (2013.01); *C07K 14/7051* (2013.01); *C12Q 2600/136* (2013.01); *C12Q 2600/156* (2013.01);
(Continued)

(58) Field of Classification Search
None
See application file for complete search history.

(56) References Cited

U.S. PATENT DOCUMENTS

| | | |
|---|---|---|
| 7,785,783 B2 | 8/2010 | Morley et al. |
| 8,236,503 B2 | 8/2012 | Faham et al. |

(Continued)

FOREIGN PATENT DOCUMENTS

| | | |
|---|---|---|
| WO | WO-2012027503 A2 | 3/2012 |
| WO | WO-2014055561 A1 | 4/2014 |

(Continued)

OTHER PUBLICATIONS

Arden., "Human T-cell receptor variable gene segment families", Immunogenetics, 1995, 42(6), pp. 455-500.
(Continued)

*Primary Examiner* — Christian C Boesen

(57) ABSTRACT

The present disclosure provides methods, compositions, kits, and systems useful in the determination and evaluation of the immune repertoire. In one aspect, target-specific primer panels provide for the effective amplification of sequences of T cell receptor and/or B cell receptor chains with improved sequencing accuracy and resolution over the repertoire. Variable regions associated with the immune cell receptor are resolved to effectively portray clonal diversity of a biological sample and/or differences associated with the immune cell repertoire of a biological sample.

12 Claims, 10 Drawing Sheets

Specification includes a Sequence Listing.

Step A          Step B          Step C

Related U.S. Application Data

(60) Provisional application No. 62/586,099, filed on Nov. 14, 2017, provisional application No. 62/553,736, filed on Sep. 1, 2017, provisional application No. 62/539,409, filed on Jul. 31, 2017, provisional application No. 62/480,227, filed on Mar. 31, 2017, provisional application No. 62/447,348, filed on Jan. 17, 2017.

(51) Int. Cl.
  *C12Q 1/6881* (2018.01)
  *C12Q 1/6883* (2018.01)
  *C07K 14/725* (2006.01)

(52) U.S. Cl.
  CPC ... *C12Q 2600/158* (2013.01); *C12Q 2600/16* (2013.01); *C12Q 2600/166* (2013.01)

(56) References Cited

U.S. PATENT DOCUMENTS

| | | | |
|---|---|---|---|
| 8,883,418 B2 | 11/2014 | Pasqual et al. | |
| 9,068,224 B2 | 6/2015 | Fire et al. | |
| 9,234,240 B2 | 1/2016 | Quake et al. | |
| 9,957,558 B2 | 5/2018 | Leamon et al. | |
| 2013/0059738 A1 | 3/2013 | Leamon et al. | |
| 2016/0024493 A1* | 1/2016 | Robins | C12Q 1/6846 506/9 |
| 2017/0292149 A1* | 10/2017 | Sherwood | C12Q 1/6811 |

FOREIGN PATENT DOCUMENTS

| | | |
|---|---|---|
| WO | WO-2014145992 A1 | 9/2014 |
| WO | WO-2015134787 A2 | 9/2015 |
| WO | WO-2017210469 A2 | 12/2017 |

OTHER PUBLICATIONS

Arstila et al., "A direct estimate of the human alphabeta T cell receptor diversity", Science, Oct. 29, 1999, 286(5441), pp. 958-961.
Bolotin et al., "Next generation sequencing for TCR repertoire profiling: platform-specific features and correction algorithms", Eur J Immunol., Nov. 2012, 42(11), pp. 3073-3083.
Brochet et al., "IMGT/V-Quest: the highly customized and integrated system for IG and TR standardized V-J and V-D-J sequence analysis", Nucleic Acids Res., Jul. 1, 2008, 36:W503-508.
Calis et al., "Characterizing immune repertoires by high throughput sequencing: strategies and applications", Trends Immunol., Dec. 2014, 35(12), pp. 581-590.
Carlson et al., "Using synthetic templates to design an unbiased multiplex PCR assay", Nature Communications, 2013, 4(2680), pp. 1-9.
Chothia et al., "Canonical structures for the hypervariable regions of immunoglobulins", J. Mol. Biol., Aug. 20, 1987, 196(4), pp. 901-917.
Davis et al., "T-cell antigen receptor genes and T-cell recognition", Nature, 1998, vol. 334, pp. 395-402.
Hou X., et al., "Analysis of the Repertoire Features of TCR Beta Chain CDR3 in Human by High-Throughput Sequencing," Cellular Physiology and Biochemistry, vol. 39, No. 2, Jul. 29, 2016 (Jul. 29, 2016), pp. 651-667, XP055528308, CH, ISSN: 1015-8987, DOI: 10.1159/000445656.
International Search Report and Written Opinion for Application No. PCT/US2018/014111, dated Aug. 9, 2018, 23 pages.
Layton et al., "Estimating T-cell repertoire diversity: limitations of classical estimators and a new approach", (2015) Philosophical Transactions B, 370:20140291, pp. 1-11.
Liu et al., "Systematic Comparative Evaluation of Methods for Investigating the TCRβ Repertoire", PLOS One, Mar. 28, 2016, pp. 1-18.
Mackelprang, et al.,"Sequence diversity, natural selection and linkage disequilibrium in the human T cell receptor alpha/delta locus", Hum Genet., Apr. 2006, 119(3), pp. 255-266.
Robins H.S., et al., "Comprehensive assessment of T-cell receptor β-chain diversity in αβ T cells", Blood, vol. 114, No. 19, Nov. 5, 2009 (Nov. 5, 2009), pp. 4099-4107.
Rosati E., et al., "Overview of Methodologies for T-Cell Receptor Repertoire Analysis," BMC Biotechnology, vol. 17, No. 1, Jul. 10, 2017 (Jul. 10, 2017), pp. 1-16, XP055518303, DOI: 10.1186/s12896-017-0379-9.
Rowen et al., "The complete 685-kilobase DNA sequence of the human beta T cell receptor locus", Science, Jun. 21, 1996, 272(5269), pp. 1755-1762.
Sandberg, et al., "Human T-cell lines with well-defined T-cell receptor gene rearrangements as controls for the BIOMED-2 multiplex polymerase chain reaction tubes", Leukemia, Feb. 2007, 21(2), pp. 230-237.
Van Dongen et al., "Design and standardization of PCR primers and protocols for detection of clonal immunoglobulin and T-cell receptor gene recombinations in suspect lymphoproliferations: Report of the BIOMED-2 Concerted Action BMH4-CT98-3936," Leukemia, Dec. 2003, 17(12):2257-317.
Extended European Search Report, issued in EP App. No. 22166477.4 dated Jul. 22, 2022, 11 pages.

* cited by examiner

FIG. 10

TABLE 1 SEQUENCE CORRECTION WORKFLOW

| | |
|---|---|
| A. Raw bam file | |
| B. IgBLAST annotation and indel correction | → Report high-quality fastq |
| C. Select for productive reads | → Unproductive or off-target reads |
| D. Filter chimeras | |
| E. Filter simple indel errors | → Frequency-based filtering |
| F. Filter singleton reads | |
| G. Filter truncated reads | |
| H. Filter for rearrangements with bidirectional support | |
| I. Stepwise clustering and lineage reporting | → Described in FIG. 1 |

SEQUENCE LISTING

```
<160> NUMBER OF SEQ ID NOS: 522

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaatacctg gtcacacaga cggga                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagataccgg gttacccagt ttgga                                          25

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 3
actcaaactc caagacatct gatcaaaacg                                    30

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agaatcccag acacaagatc acaaa                                         25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agagtccaag acacaagatc acaga                                         25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtccccaag acatctgatc agaga                                         25

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atcaatggcc agcgaccctg g                                             21

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccaaagtccc acacacctga tcaaa                                         25

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
cccagacacc aaaatacctg g                                              21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctcaacatcc gagtagggtt atctgta                                        27

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcagtcccc aaagtacctg t                                              21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctggaatcac ccagagccc                                                 19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctggagtctc ccacaaccc                                                 19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctggagtctc ccagaaccc                                                 19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 15
ctggagtctc ccaggaccc                                                    19

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctggagtcac tcaaactcca agatatct                                          28

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaaagccagt gaccctgagt tg                                                22

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cccagagctc gagatatcta gtcaa                                             25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaaagccaag cagggatatc tgtc                                              24

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaaatacctg gtcacacaga tggga                                             25

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
```
aaaattccac gtcctgaaga cagg                                           24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaaattccag gtcctgaaga cagg                                           24

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaaattccac atcctgaaga caggac                                         26

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaagcacctg atcacagcaa ctg                                            23

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aacatccgag cagggttatc tgta                                           24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aacatccgag ctgggttatc tgta                                           24

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aacccaagat acctcatcac agtgac                                          26

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aagacacaga atcattggga cagg                                            24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagcatgagg tgacagaaat ggga                                            24

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaggcacaag gtgacagaga tg                                              22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aatacctggt cacacagatg ggaa                                            24

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aattctcaag acacagaatc attgggaca                                       29

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acaaagtccc acacacctga tcaaa                                           25

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acacaaggtc accaacatgg g                                            21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acaccaagac acctggtcat g                                            21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
accaacatct cagatcctgg ca                                           22

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
accagacccc aagatacctt gttata                                       26

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
accccaagga ataggatcac aaaga                                        25

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39 accccccagta acaaggtcac a                                           21

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acctagactt ctggtcaaag caagtg                                          26

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acctagattt ctggtcaaag caaatga                                         27

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
actccaggat atttggtcaa aggaaaagga a                                    31

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agacaccaaa acacctggtc atg                                             23

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agactattca tcaatggcca gcga                                            24

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agagcccaag atacaagatc acaga                                           25

-continued

```
<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agccacagcg taatagagaa ggg                                         23

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aggacatttg gtcaaaggaa aaggac                                      26

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agtccccaag acatctgatc aaaga                                       25

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agtccctgag acacaaggta gca                                         23

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agtctcccag atataagatt atagagaaaa ggc                              33

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agtctcccag gtacaaagtc aca                                         23

<210> SEQ ID NO 52
```

-continued

```
<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agtggttcag tctcccagat ataagattat ag                                  32

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agtaacaagg tcacagagaa ggga                                           24

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
caaaattccg ggtcctgaag aca                                            23

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caagacacct ggtcaggagg ag                                             22

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cagactccaa aacatcttgt cagagg                                         26

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cagccatcag gtcacacaga tg                                             22

<210> SEQ ID NO 58
<211> LENGTH: 24
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccaaggtaca aagtcgcaaa gagg                                        24

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cccaaaattc cgcatcctga agata                                       25

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cccagtcccc cagatataag attaca                                      26

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccctaggtac aaagtcgcaa agaga                                       25

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgccatgagg tgacagagat gg                                          22

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cggcacgagg tgacagagat g                                           21

<210> SEQ ID NO 64
<211> LENGTH: 22
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 64
gtcacccagg cacaaagtga ca                                           22

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
caagatatct gatcaaaacg agaggacag                                    29

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccaagatatc tgatcaaaac gagaggac                                     28

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ctccaagata tctgatcaaa acgagagg                                     28

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gagaggacag caagtgacac tg                                           22

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gagtcactca aactccaaga tatctgatca                                   30

<210> SEQ ID NO 70
<211> LENGTH: 23
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 70
gctggagtca ctcaaactcc aag                                              23

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggagtcactc aaactccaag atatctgat                                        29

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ggctggagtc actcaaactc c                                                21

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
catggtcatc cagaacccaa gatac                                            25

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccatggtcat ccagaaccca ag                                               22

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gatgccatgg tcatccagaa cc                                               22

<210> SEQ ID NO 76
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 76
ggaaagccag tgaccctgag                                                 20

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggttacccag tttggaaagc ca                                              22

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gtttggaaag ccagtgaccc t                                               21

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gttacccagt ttggaaagcc agt                                             23

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tgccatggtc atccagaacc                                                 20

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ttacccagtt tggaaagcca gtg                                             23

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
tttggaaagc cagtgaccct g                                            21

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
agagctcgag atatctagtc aaaaggac                                     28

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
agctcgagat atctagtcaa aaggacg                                      27

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cgagatatct agtcaaaagg acggga                                       26

<210> SEQ ID NO 86
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gaaagtaacc cagagctcga gatatctag                                    29

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gatgtgaaag taacccagag ctcg                                         24

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 88
gtaacccaga gctcgagata tctagtc                                          27

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gtgaaagtaa cccagagctc gag                                              23

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 90
aaaauacctg gucacacaga cggga                                            25

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 91
aagataccgg gutacccagt tugga                                            25

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 92
actcaaacuc caagacatct gaucaaaacg                                       30

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 93
agaaucccag acacaagatc acaaa                                              25

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 94
agaguccaag acacaagatc acaga                                              25

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 95
agtccccaag acauctgauc agaga                                              25

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 96
atcaauggcc agcgacccug g                                                  21

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 97
ccaaaguccc acacacctga ucaaa                                              25

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 98
cccagacacc aaaauaccug g                                                  21

```
<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 99
ctcaacatcc gaguagggtt atctgua                                          27

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 100
ctcagucccc aaagtaccug t                                                21

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 101
cuggaaucac ccagagccc                                                   19

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 102
cuggagtcuc ccacaaccc                                                   19

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 103
cuggagtcuc ccagaaccc                                                   19
```

```
<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 104
cuggagucuc ccaggaccc                                                    19

<210> SEQ ID NO 105
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 105
ctggagtcac ucaaactcca agatauct                                          28

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 106
gaaagccagu gaccctgagt ug                                                22

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 107
cccagagcuc gagatatcta gucaa                                             25

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 108
aaaagccaag cagggauauc tguc                                              24
```

```
<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 109
aaaatacctg gucacacaga uggga                                           25

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 110
aaaatuccac gtccugaaga cagg                                            24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 111
aaaatuccag gtccugaaga cagg                                            24

<210> SEQ ID NO 112
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 112
aaaautccac atccugaaga caggac                                          26

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 113
aaagcacctg aucacagcaa cug                                             23
```

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 114
aacatccgag cagggutatc tgua                                          24

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 115
aacatccgag cugggttatc tgua                                          24

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 116
aacccaagau acctcatcac agugac                                        26

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 117
aagacacaga aucatuggga cagg                                          24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 118
aagcatgagg ugacagaaau ggga                                            24

<210> SEQ ID NO 119
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 119
aaggcacaag gugacagaga ug                                              22

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 120
aatacctggu cacacagaug ggaa                                            24

<210> SEQ ID NO 121
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 121
aattcucaag acacagaatc atugggaca                                       29

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 122
acaaaguccc acacacctga ucaaa                                           25

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 123
acacaagguc accaacaugg g                                               21

<210> SEQ ID NO 124
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 124
acaccaagac accuggtcau g                                            21

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 125
accaacatcu cagatccugg ca                                           22

<210> SEQ ID NO 126
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 126
accagacccc aagauacctt gttaua                                       26

<210> SEQ ID NO 127
<211> LENGTH: 25
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 127
accccaagga auaggaucac aaaga                                        25

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 128
acccccagua acaaggucac a                                            21

<210> SEQ ID NO 129
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<223> OTHER INFORMATION: Description of Combined DNA/RNA Molecule:
      Synthetic primer

<400> SEQUENCE: 129
acctagactt cuggtcaaag caagug                                         26

<210> SEQ ID NO 130
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 130
acctagattt cuggtcaaag caaauga                                        27

<210> SEQ ID NO 131
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 131
acuccaggat atttggucaa aggaaaagga a                                   31

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 132
agacaccaaa acaccuggtc aug                                            23

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 133
agacuattca tcaauggcca gcga                                           24

<210> SEQ ID NO 134
<211> LENGTH: 25
<212> TYPE: RNA
<213> ORGANISM: Artificial Sequence
<220> FEATURE:
<223> OTHER INFORMATION: Description of Artificial Sequence: Synthetic
``` primer

<400> SEQUENCE: 134
agagcccaag auacaagauc acaga                                        25

<210> SEQ ID NO 135
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 135
agccacagcg uaauagagaa ggg                                          23

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 136
aggacauttg gucaaaggaa aaggac                                       26

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 137
agtccccaag acauctgauc aaaga                                        25

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 138
agtcccugag acacaaggua gca                                          23

<210> SEQ ID NO 139
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

```
<400> SEQUENCE: 139
agtctcccag auataagatt auagagaaaa ggc                              33

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 140
agtctcccag guacaaaguc aca                                         23

<210> SEQ ID NO 141
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 141
agtggttcag tcucccagat ataagattau ag                               32

<210> SEQ ID NO 142
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 142
aguaacaagg ucacagagaa ggga                                        24

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 143
caaaatuccg ggtccugaag aca                                         23

<210> SEQ ID NO 144
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 144
caagacaccu ggucaggagg ag                                          22
```

```
<210> SEQ ID NO 145
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 145
cagacuccaa aacatcttgu cagagg                                          26

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 146
cagccatcag gucacacaga ug                                              22

<210> SEQ ID NO 147
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 147
ccaagguaca aagucgcaaa gagg                                            24

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 148
cccaaaattc cgcaucctga agaua                                           25

<210> SEQ ID NO 149
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 149
cccagucccc cagatataag atuaca                                          26

<210> SEQ ID NO 150
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 150
cccuaggtac aaagucgcaa agaga                                    25

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 151
cgccatgagg ugacagagau gg                                       22

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 152
cggcacgagg ugacagagau g                                        21

<210> SEQ ID NO 153
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 153
gucacccagg cacaaaguga ca                                       22

<210> SEQ ID NO 154
<211> LENGTH: 25
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 154
agaguccaag acacaagauc acaga                                    25

<210> SEQ ID NO 155
<211> LENGTH: 25
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 155
```
agaaucccag acacaagauc acaaa                                          25

<210> SEQ ID NO 156
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 156
cuccaagata tctgaucaaa acgagagg                                       28

<210> SEQ ID NO 157
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 157
gagaggacag caagugacac ug                                             22

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 158
gagtcactca aacuccaaga tatctgauca                                     30

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 159
gctggaguca ctcaaacucc aag                                            23

<210> SEQ ID NO 160
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 160
ggagtcactc aaacuccaag atatcugat                                      29

```
<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 161
ggctggaguc actcaaacuc c                                            21

<210> SEQ ID NO 162
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 162
catggtcauc cagaacccaa gauac                                        25

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 163
ccauggtcau ccagaaccca ag                                           22

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 164
gatgccaugg tcauccagaa cc                                           22

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 165
ggaaagccag ugacccugag                                              20

<210> SEQ ID NO 166
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 166
ggutacccag ttuggaaagc ca                                              22

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 167
gttuggaaag ccagugaccc t                                               21

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 168
gutacccagt tuggaaagcc agt                                             23

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 169
tgccauggtc auccagaacc                                                 20

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 170
ttacccagtt uggaaagcca gug                                             23
```

```
<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 171
tttggaaagc cagugacccu g                                               21

<210> SEQ ID NO 172
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 172
agagcucgag atatctaguc aaaaggac                                        28

<210> SEQ ID NO 173
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 173
agctcgagau atctagucaa aaggacg                                         27

<210> SEQ ID NO 174
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 174
cgagauatct agucaaaagg acggga                                          26

<210> SEQ ID NO 175
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 175
gaaagtaacc cagagcucga gatatcuag                                       29
```

```
<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 176
gatgtgaaag uaacccagag cucg                                           24

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 177
gtaacccaga gcucgagata tctaguc                                        27

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 178
gtgaaaguaa cccagagcuc gag                                            23

<210> SEQ ID NO 179
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 179
caagauatct gaucaaaacg agaggacag                                      29

<210> SEQ ID NO 180
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 180
ccaagauatc tgaucaaaac gagaggac                                       28
```

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
    primer

<400> SEQUENCE: 181
cgaccucggg ugggaacac                                              19

<210> SEQ ID NO 182
<211> LENGTH: 19
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Description of Combined DNA/RNA Molecule:
    Synthetic primer

<400> SEQUENCE: 182
cgaccutggg ugggaacac                                              19

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 183
cgacctcggg tgggaacac                                              19

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 184
cgaccttggg tgggaacac                                              19

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 185
aatcttcaca tcaattccct ggag                                        24

<210> SEQ ID NO 186
<211> LENGTH: 17
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 186
acatccgctc accaggc                                              17

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
acctacacac cctgcagc                                             18

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
aggctggagt cagctgc                                              17

<210> SEQ ID NO 189
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
aggtgcagcc tgcagaa                                              17

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
atgaatgtga gcaccttgga g                                         21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
atgaatgtga gtgccttgga g                                         21

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
caagctggag tcagctgc                                                                18

<210> SEQ ID NO 193
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
catgagctcc ttggagctg                                                               19

<210> SEQ ID NO 194
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
cattctgagt tctaagaagc tcctc                                                        25

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cctgaccctg aagtctgct                                                               19

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
cctgagctct ctggagctg                                                               19

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
ctagacatcc gctcaccagg c                                                            21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ctcaagatcc agcctgcaaa g                                                            21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
ctcaagatcc agcctgcaga g                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ctcacgttgg cgtctgctgt a                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ctcactctgg agtcagctac c                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ctcactctgg agtccgctac c                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ctcactctgg agtctgctgc c                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ctcactgtga catcggccca a                                              21

```
<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ctgaagatcc agccctcaga a                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ctgaagatcc agcctgcaga g                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ctgaagatcc ggtccacaaa g                                              21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ctgaatgtga acgccttgtt g                                              21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ctgaatgtga acgccttgga g                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
ctgacagtga ccagtgccca t                                              21
```

```
<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ctgacagtga cctgtgccca t                                              21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
ctgaccctga agtctgccag c                                              21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
ctgactgtga gcaacatgag c                                              21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
ctgaggatcc agcaggtagt g                                              21

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
ctgaggatcc agcccatgga a                                              21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
ctgaggatcc agccctcaga a                                              21

<210> SEQ ID NO 217
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
ctggcaatcc tgtcctcaga a                                              21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
ctggcaatcc tgtcctcgga a                                              21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
ctgtccctag agtctgccat c                                              21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ctcaagatcc agccagcaga g                                              21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
ctgaagatcc atcccgcaga g                                              21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
ctgaagatcc agcgcacaca g                                              21

<210> SEQ ID NO 223
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
ctgaagatcc agcgcacaga g                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
ctgaagttcc agcgcacaca g                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ctgacgattc agcgcacaga g                                              21

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ctgacgatcc agcgcaca                                                  18

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
ctgactgtga gcaacaggag a                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
ctgattctgg agtccgccag c                                              21

<210> SEQ ID NO 229
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 229
gccttgagat ccaggctacg                                             20

<210> SEQ ID NO 230
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
ggctggagtt ggctgct                                                17

<210> SEQ ID NO 231
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
ggttggagtc ggctgct                                                17

<210> SEQ ID NO 232
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
tcacctacac gccctgc                                                17

<210> SEQ ID NO 233
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
tcaggctgct gtcggct                                                17

<210> SEQ ID NO 234
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
tcaggctgga gtcggct                                                17

<210> SEQ ID NO 235
<211> LENGTH: 17
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 235
tcaggctggt gtcggct                                                       17

<210> SEQ ID NO 236
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
tcatcctgag ttctaagaag ctcc                                               24

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tcctgagttc taagaagctc ctc                                                23

<210> SEQ ID NO 238
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
tctcaagatc caacctgcaa ag                                                 22

<210> SEQ ID NO 239
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
tgaccctgga gtctgcc                                                       17

<210> SEQ ID NO 240
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
tgatcctgga gtcgccc                                                       17

<210> SEQ ID NO 241
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 241
tgtggtcgca ctgcagc                                                    17

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
ttggagatcc agtccacgga g                                               21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
ttggagatcc agcgcacaga g                                               21

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
catgagctcc ttggagctgg                                                 20

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
aacatgagct ccttggagct g                                               21

<210> SEQ ID NO 246
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gaacatgagc tccttggagc tg                                              22

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 247
tgaactgaac atgagctcct tgg                                           23

<210> SEQ ID NO 248
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
ctgaactgaa catgagctcc ttgg                                          24

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 249
aatcttcaca ucaattcccu ggag                                          24

<210> SEQ ID NO 250
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 250
acauccgcuc accaggc                                                  17

<210> SEQ ID NO 251
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 251
accuacacac ccugcagc                                                 18

<210> SEQ ID NO 252
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 252
aggcuggagt cagcugc                                                  17

<210> SEQ ID NO 253

```
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 253
aggugcagcc ugcagaa                                                    17

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 254
atgaatguga gcacctugga g                                               21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 255
atgaatguga gtgcctugga g                                               21

<210> SEQ ID NO 256
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 256
caagcuggag tcagcugc                                                   18

<210> SEQ ID NO 257
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 257
catgagcucc ttggagcug                                                  19

<210> SEQ ID NO 258
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 258
cattctgagt tcuaagaagc tccuc                                           25

<210> SEQ ID NO 259
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 259
cctgacccug aagtcugct                                                  19

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 260
cctgagcuct ctggagcug                                                  19

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 261
ctagacaucc gcucaccagg c                                               21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 262
ctcaagaucc agccugcaaa g                                               21

<210> SEQ ID NO 263
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 263
ctcaagaucc agccugcaga g                                              21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 264
ctcacgtugg cgtctgctgu a                                              21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 265
ctcactcugg agtcagcuac c                                              21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 266
ctcactcugg agtccgcuac c                                              21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 267
ctcactcugg agtctgcugc c                                              21

<210> SEQ ID NO 268
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 268
ctcacugtga caucggccca a                                              21

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 269
ctgaagaucc agcccucaga a                                              21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 270
ctgaagaucc agccugcaga g                                              21

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 271
ctgaagaucc gguccacaaa g                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 272
ctgaatguga acgccttgtu g                                              21
```

```
<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 273
ctgaatguga acgcctugga g                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 274
ctgacaguga ccagugccca t                                              21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 275
ctgacaguga cctgugccca t                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 276
ctgacccuga agtcugccag c                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 277
ctgactguga gcaacaugag c                                              21
```

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
     primer
<220> FEATURE:
<223> OTHER INFORMATION: Description of Combined DNA/RNA Molecule:
     Synthetic primer

<400> SEQUENCE: 278
ctgaggaucc agcaggtagu g                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
     primer
<220> FEATURE:
<223> OTHER INFORMATION: Description of Combined DNA/RNA Molecule:
     Synthetic primer

<400> SEQUENCE: 279
ctgaggaucc agcccaugga a                                              21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
     primer
<220> FEATURE:
<223> OTHER INFORMATION: Description of Combined DNA/RNA Molecule:
     Synthetic primer

<400> SEQUENCE: 280
ctgaggaucc agcccucaga a                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
     primer
<220> FEATURE:
<223> OTHER INFORMATION: Description of Combined DNA/RNA Molecule:
     Synthetic primer

<400> SEQUENCE: 281
ctggcaaucc tgtccucaga a                                              21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
     primer
<220> FEATURE:
<223> OTHER INFORMATION: Description of Combined DNA/RNA Molecule:
     Synthetic primer

<400> SEQUENCE: 282
ctggcaaucc tgtccucgga a                                              21

```
<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 283
ctgtcccuag agtctgccau c                                            21

<210> SEQ ID NO 284
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 284
cucaagaucc agccagcaga g                                            21

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 285
cugaagatcc aucccgcaga g                                            21

<210> SEQ ID NO 286
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 286
cugaagaucc agcgcacaca g                                            21

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 287
cugaagaucc agcgcacaga g                                            21

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer
<220> FEATURE:
<223> OTHER INFORMATION: Description of Combined DNA/RNA Molecule:
    Synthetic primer

<400> SEQUENCE: 288
cugaagtucc agcgcacaca g                                              21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Description of Combined DNA/RNA Molecule:
    Synthetic primer

<400> SEQUENCE: 289
cugacgatuc agcgcacaga g                                              21

<210> SEQ ID NO 290
<211> LENGTH: 18
<212> TYPE: RNA
<213> ORGANISM: Artificial Sequence
<220> FEATURE:
<223> OTHER INFORMATION: Description of Artificial Sequence: Synthetic
    primer

<400> SEQUENCE: 290
cugacgaucc agcgcaca                                                  18

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Description of Combined DNA/RNA Molecule:
    Synthetic primer

<400> SEQUENCE: 291
cugactguga gcaacaggag a                                              21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Description of Combined DNA/RNA Molecule:
    Synthetic primer

<400> SEQUENCE: 292
cugattctgg aguccgccag c                                              21

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
    primer
<220> FEATURE:

```
<223> OTHER INFORMATION: Description of Combined DNA/RNA Molecule:
      Synthetic primer

<400> SEQUENCE: 293
gccttgagau ccaggcuacg                                                 20

<210> SEQ ID NO 294
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 294
ggctggagut ggcugct                                                    17

<210> SEQ ID NO 295
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 295
ggttggaguc ggcugct                                                    17

<210> SEQ ID NO 296
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 296
tcaccuacac gcccugc                                                    17

<210> SEQ ID NO 297
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 297
tcaggcugct gucggct                                                    17

<210> SEQ ID NO 298
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<223> OTHER INFORMATION: Description of Combined DNA/RNA Molecule:
      Synthetic primer

<400> SEQUENCE: 298
tcaggcugga gucggct                                                    17

<210> SEQ ID NO 299
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 299
tcaggcuggt gucggct                                                    17

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 300
tcatcctgag utctaagaag cucc                                            24

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 301
tcctgagttc uaagaagctc cuc                                             23

<210> SEQ ID NO 302
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 302
tctcaagauc caaccugcaa ag                                              22

<210> SEQ ID NO 303
<211> LENGTH: 17
<212> TYPE: DNA
<213> ORGANISM: Artificial Sequence
<220> FEATURE:
<223> OTHER INFORMATION: Description of Artificial Sequence: Synthetic
```

```
                    primer
<220> FEATURE:
<223> OTHER INFORMATION: Description of Combined DNA/RNA Molecule:
      Synthetic primer

<400> SEQUENCE: 303
tgacccugga gtcugcc                                                    17

<210> SEQ ID NO 304
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 304
tgatccugga gucgccc                                                    17

<210> SEQ ID NO 305
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 305
tgtggucgca cugcagc                                                    17

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 306
ttggagaucc aguccacgga g                                               21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 307
tuggagaucc agcgcacaga g                                               21

<210> SEQ ID NO 308
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 308
catgagcucc ttggagcugg                                                    20

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 309
aacatgagcu ccttggagcu g                                                  21

<210> SEQ ID NO 310
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 310
gaacatgagc uccttggagc ug                                                 22

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 311
tgaactgaac augagctcct ugg                                                23

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 312
ctgaactgaa caugagctcc tugg                                               24

<210> SEQ ID NO 313
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 313
aaccaggagt cctccgc                                                   17

<210> SEQ ID NO 314
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
acggtcagcc tagagcctt                                                 19

<210> SEQ ID NO 315
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
agtctggtgc cttgtccaa                                                 19

<210> SEQ ID NO 316
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
cacggtcagc ctgctgc                                                   17

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
cccatcacca aaatgctggg                                                20

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
cctgggccaa aatactgcg                                                 19

<210> SEQ ID NO 319
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 319
cggcccgaag tactgct                                                  17

<210> SEQ ID NO 320
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
cggcgccgaa gtactga                                                  17

<210> SEQ ID NO 321
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
ctggcccgaa gaactgc                                                  17

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
gagccaactt ccctctccaa                                               20

<210> SEQ ID NO 323
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
gcctggtccc attcccaaa                                                19

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
gctgggttcc actgccaaa                                                19

<210> SEQ ID NO 325
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 325
tcccgttccc aaagtggag                                            19

<210> SEQ ID NO 326
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
tgaccgtgag cctggtg                                              17

<210> SEQ ID NO 327
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
tggcccgaag tactggg                                              17

<210> SEQ ID NO 328
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
ttaacctggt ccccgaacc                                            19

<210> SEQ ID NO 329
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
gaccgtgagc ctggtgc                                              17

<210> SEQ ID NO 330
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
caggagccgc gtgcctg                                              17

<210> SEQ ID NO 331
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 331
agcactgtca gccgggt                                                17

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
ccagcacggt cagcctg                                                17

<210> SEQ ID NO 333
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
ctagcacggt gagccgt                                                17

<210> SEQ ID NO 334
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
agcactgaga gccgggtc                                               18

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
cagtacggtc agcctagagc                                             20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
ccagaaccag gagtcctccg                                             20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 337
ctgtcacagt gagcctggtc                                              20

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
ccaagacaga gagctgggtt c                                            21

<210> SEQ ID NO 339
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
ctacaactgt gagtctggtg cc                                           22

<210> SEQ ID NO 340
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
ctaggatgga gagtcgagtc cc                                           22

<210> SEQ ID NO 341
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
ctacaacggt taacctggtc cc                                           22

<210> SEQ ID NO 342
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
ctacaacagt gagccaactt ccc                                          23

<210> SEQ ID NO 343
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
```
gtgaccgtga gcctggt                                                17

<210> SEQ ID NO 344
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
tgtgaccgtg agcctgg                                                17

<210> SEQ ID NO 345
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
gtgaccgtga gcctggtg                                               18

<210> SEQ ID NO 346
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
tgtgaccgtg agcctggt                                               18

<210> SEQ ID NO 347
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
ctgtgaccgt gagcctgg                                               18

<210> SEQ ID NO 348
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
caggagtcct ccgccca                                                17

<210> SEQ ID NO 349
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349

```
accaggagtc ctccgcc                                                    17
```

<210> SEQ ID NO 350
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350

```
actgagagcc gggtccc                                                    17
```

<210> SEQ ID NO 351
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351

```
cactgagagc cgggtcc                                                    17
```

<210> SEQ ID NO 352
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352

```
gcactgagag ccgggtc                                                    17
```

<210> SEQ ID NO 353
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353

```
gcacggtcag cctgctg                                                    17
```

<210> SEQ ID NO 354
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354

```
cagcacggtc agcctgc                                                    17
```

<210> SEQ ID NO 355
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355

```
tagcacggtg agccgtg                                                    17
```

<210> SEQ ID NO 356
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
ccaggagccg cgtgcctg                                                 18

<210> SEQ ID NO 357
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
aaccaggagt cctccgcc                                                 18

<210> SEQ ID NO 358
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gaaccaggag tcctccgc                                                 18

<210> SEQ ID NO 359
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
tagcacggtg agccgtgt                                                 18

<210> SEQ ID NO 360
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
accaggagcc gcgtgcctg                                                19

<210> SEQ ID NO 361
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
aacggttaac ctggtcccc                                                19

<210> SEQ ID NO 362
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
agaaccagga gtcctccgc                                                    19

<210> SEQ ID NO 363
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
cagaaccagg agtcctccg                                                    19

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
tacggtcagc ctagagcctt                                                   20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
gtacggtcag cctagagcct                                                   20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
ggatggagag tcgagtccca                                                   20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
caacggttaa cctggtcccc                                                   20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 368
agtacggtca gcctagagcc                                         20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 369
aggatggaga gtcgagtccc                                         20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 370
acaacggtta acctggtccc                                         20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 371
tgtcacagtg agcctggtcc                                         20

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 372
caactgtgag tctggtgcct t                                       21

<210> SEQ ID NO 373
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 373
gtacggtcag cctagagcct t                                       21

<210> SEQ ID NO 374

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
ggatggagag tcgagtccca t                                              21

<210> SEQ ID NO 375
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
acaactgtga gtctggtgcc t                                              21

<210> SEQ ID NO 376
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
agtacggtca gcctagagcc t                                              21

<210> SEQ ID NO 377
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
aggatggaga gtcgagtccc a                                              21

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
tacaactgtg agtctggtgc c                                              21

<210> SEQ ID NO 379
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
caagacagag agctgggttc c                                              21

<210> SEQ ID NO 380
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
taggatggag agtcgagtcc c                                              21

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
tacaacggtt aacctggtcc c                                              21

<210> SEQ ID NO 382
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
acaactgtga gtctggtgcc tt                                             22

<210> SEQ ID NO 383
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
aagacagaga gctgggttcc ac                                             22

<210> SEQ ID NO 384
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
aggatggaga gtcgagtccc at                                             22

<210> SEQ ID NO 385
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
acaacagtga gccaacttcc ct                                             22

<210> SEQ ID NO 386
<211> LENGTH: 22
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 386
tacaactgtg agtctggtgc ct    22

<210> SEQ ID NO 387
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 387
caagacagag agctgggttc ca    22

<210> SEQ ID NO 388
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 388
taggatggag agtcgagtcc ca    22

<210> SEQ ID NO 389
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 389
tacaacggtt aacctggtcc cc    22

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 390
tacaactgtg agtctggtgc ctt    23

<210> SEQ ID NO 391
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 391
taggatggag agtcgagtcc cat    23

<210> SEQ ID NO 392
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 392
tacaacagtg agccaacttc cct                                            23

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
ctacaactgt gagtctggtg cct                                            23

<210> SEQ ID NO 394
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
ctaggatgga gagtcgagtc cca                                            23

<210> SEQ ID NO 395
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
ctacaactgt gagtctggtg cctt                                           24

<210> SEQ ID NO 396
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
ctaggatgga gagtcgagtc ccat                                           24

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
ctacaacagt gagccaactt ccct                                           24

<210> SEQ ID NO 398
<211> LENGTH: 17
<212> TYPE: RNA
<213> ORGANISM: Artificial Sequence
<220> FEATURE:
```

<223> OTHER INFORMATION: Description of Artificial Sequence: Synthetic
      primer

<400> SEQUENCE: 398
aaccaggagu ccuccgc                                                    17

<210> SEQ ID NO 399
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 399
acggtcagcc uagagccut                                                  19

<210> SEQ ID NO 400
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 400
agtctggugc cttguccaa                                                  19

<210> SEQ ID NO 401
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 401
cacggucagc ctgcugc                                                    17

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 402
cccaucacca aaatgcuggg                                                 20

<210> SEQ ID NO 403
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<223> OTHER INFORMATION: Description of Combined DNA/RNA Molecule:
      Synthetic primer

<400> SEQUENCE: 403
ccugggccaa aatacugcg                                                    19

<210> SEQ ID NO 404
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 404
cggcccgaag uacugct                                                      17

<210> SEQ ID NO 405
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 405
cggcgccgaa guacuga                                                      17

<210> SEQ ID NO 406
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 406
cuggcccgaa gaacugc                                                      17

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 407
gagccaacut ccctcuccaa                                                   20

<210> SEQ ID NO 408
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 408
```

-continued gcctggucccatucccaaa                                                19

<210> SEQ ID NO 409
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 409 gctgggutccacugccaaa                                                19

<210> SEQ ID NO 410
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 410 tcccgtucccaaaguggag                                                19

<210> SEQ ID NO 411
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 411 tgaccgugagcctggug                                                  17

<210> SEQ ID NO 412
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 412 tggcccgaaguacuggg                                                  17

<210> SEQ ID NO 413
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

```
<400> SEQUENCE: 413
tuaacctggu ccccgaacc                                                19

<210> SEQ ID NO 414
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 414
gaccgugagc ctggugc                                                  17

<210> SEQ ID NO 415
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 415
caggagccgc gugccug                                                  17

<210> SEQ ID NO 416
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 416
agcacuguca gccgggt                                                  17

<210> SEQ ID NO 417
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 417
ccagcacggu cagccug                                                  17

<210> SEQ ID NO 418
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 418
cuagcacggu gagccgt                                                  17
```

```
<210> SEQ ID NO 419
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 419
agcacugaga gccggguc                                                 18

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 420
cagtacgguc agccuagagc                                               20

<210> SEQ ID NO 421
<211> LENGTH: 20
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 421
ccagaaccag gaguccuccg                                               20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 422
ctgtcacagu gagcctgguc                                               20

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 423
ccaagacaga gagcugggtu c                                             21

<210> SEQ ID NO 424
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 424
ctacaactgu gagtctggug cc                                              22

<210> SEQ ID NO 425
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 425
ctaggaugga gagtcgaguc cc                                              22

<210> SEQ ID NO 426
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 426
ctacaacggu taacctgguc cc                                              22

<210> SEQ ID NO 427
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 427
ctacaacagu gagccaactu ccc                                             23

<210> SEQ ID NO 428
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 428
gtgaccguga gccuggt                                                    17

<210> SEQ ID NO 429
<211> LENGTH: 17
<212> TYPE: DNA
<213> ORGANISM: Artificial Sequence -continued

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 429
tgtgaccgug agccugg                                                  17

<210> SEQ ID NO 430
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 430
gtgaccguga gcctggug                                                 18

<210> SEQ ID NO 431
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 431
tgtgaccgug agccuggt                                                 18

<210> SEQ ID NO 432
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 432
ctgtgaccgu gagccugg                                                 18

<210> SEQ ID NO 433
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 433
caggaguccu ccgccca                                                  17

<210> SEQ ID NO 434
<211> LENGTH: 17
<212> TYPE: RNA
<213> ORGANISM: Artificial Sequence
<220> FEATURE:
<223> OTHER INFORMATION: Description of Artificial Sequence: Synthetic
```

```
                         primer

<400> SEQUENCE: 434
accaggaguc cuccgcc                                                17

<210> SEQ ID NO 435
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 435
acugagagcc ggguccc                                                17

<210> SEQ ID NO 436
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 436
cacugagagc cgggucc                                                17

<210> SEQ ID NO 437
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 437
gcacugagag ccggguc                                                17

<210> SEQ ID NO 438
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 438
gcacggucag cctgcug                                                17

<210> SEQ ID NO 439
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 439
cagcacgguc agccugc                                                17

<210> SEQ ID NO 440
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 440
tagcacggug agccgug                                                   17

<210> SEQ ID NO 441
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 441
ccaggagccg cgugccug                                                  18

<210> SEQ ID NO 442
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 442
aaccaggagu ccuccgcc                                                  18

<210> SEQ ID NO 443
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 443
gaaccaggag uccuccgc                                                  18

<210> SEQ ID NO 444
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 444
tagcacggug agccgugt                                                  18

<210> SEQ ID NO 445
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 445
accaggagcc gcgugccug                                                 19
```

<210> SEQ ID NO 446
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 446
aacggtuaac ctgguccccc                                              19

<210> SEQ ID NO 447
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 447
agaaccagga guccuccgc                                               19

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 448
cagaaccagg aguccuccg                                               19

<210> SEQ ID NO 449
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 449
tacggtcagc cuagagccut                                              20

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 450
gtacggucag ccuagagcct                                              20

<210> SEQ ID NO 451
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 451
ggatggagag ucgaguccca                                              20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 452
caacggtuaa cctgguccccc                                             20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 453
agtacgguca gccuagagcc                                              20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 454
aggatggaga gucgaguccc                                              20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 455
acaacgguta acctgguccc                                              20

<210> SEQ ID NO 456
<211> LENGTH: 20
<212> TYPE: DNA
```

<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 456
tgtcacagug agccuggucc    20

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 457
caactgtgag uctggtgccu t    21

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 458
gtacggucag cctagagccu t    21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 459
ggatggagag ucgaguccca t    21

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 460
acaactguga gtctggugcc t    21

<210> SEQ ID NO 461
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 461
agtacgguca gccuagagcc t                                              21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 462
aggatggaga gucgaguccc a                                              21

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 463
tacaactgug agtctggugc c                                              21

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 464
caagacagag agcugggtuc c                                              21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 465
taggauggag agtcgagucc c                                              21

<210> SEQ ID NO 466
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 466
tacaacggut aacctggucc c                                              21

<210> SEQ ID NO 467
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 467
acaactgtga guctggtgcc ut                                             22

<210> SEQ ID NO 468
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 468
aagacagaga gcugggtucc ac                                             22

<210> SEQ ID NO 469
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 469
aggatggaga gucgaguccc at                                             22

<210> SEQ ID NO 470
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 470
acaacaguga gccaactucc ct                                             22
```

```
<210> SEQ ID NO 471
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 471
tacaactgug agtctggugc ct                                              22

<210> SEQ ID NO 472
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 472
caagacagag agcugggtuc ca                                              22

<210> SEQ ID NO 473
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 473
taggauggag agtcgagucc ca                                              22

<210> SEQ ID NO 474
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 474
tacaacggut aacctggucc cc                                              22

<210> SEQ ID NO 475
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 475
tacaactgtg aguctggtgc cut                                             23
```

```
<210> SEQ ID NO 476
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 476
taggauggag agtcgagucc cat                                              23

<210> SEQ ID NO 477
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 477
tacaacagug agccaactuc cct                                              23

<210> SEQ ID NO 478
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 478
ctacaactgu gagtctggug cct                                              23

<210> SEQ ID NO 479
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 479
ctaggaugga gagtcgaguc cca                                              23

<210> SEQ ID NO 480
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 480
ctacaactgt gaguctggtg ccut                                             24
```

<210> SEQ ID NO 481
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 481
ctaggaugga gagtcgaguc ccat                                          24

<210> SEQ ID NO 482
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 482
ctacaacagu gagccaactu ccct                                          24

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 483
aactatgttt tggtatcgtc a                                             21

<210> SEQ ID NO 484
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
cacgatgttc tggtaccgtc agca                                          24

<210> SEQ ID NO 485
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
cagtgtgtcc tggtaccaac ag                                            22

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 486 aacccttat tggtaccgac a                                          21

<210> SEQ ID NO 487
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487 atccctttt tggtaccaac ag                                         22

<210> SEQ ID NO 488
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
aaccctttat tggtatcaac ag                                        22

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
cgctatgtat tggtacaagc a                                         21

<210> SEQ ID NO 490
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
ctcccgtttt ctggtacaga cagac                                     25

<210> SEQ ID NO 491
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491
cgctatgtat tggtataaac ag                                        22

<210> SEQ ID NO 492
<211> LENGTH: 26
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 492
ttatgtttac tggtatcgta agaagc                                              26

<210> SEQ ID NO 493
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 493
caaaatgtac tggtatcaac aa                                                  22

<210> SEQ ID NO 494
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 494
atacatgtac tggtatcgac aagac                                               25

<210> SEQ ID NO 495
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
ggccatgtac tggtatagac aag                                                 23

<210> SEQ ID NO 496
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 496
gtatatgtcc tggtatcgac aaga                                                24

<210> SEQ ID NO 497
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
taacctttat tggtatcgac gtgt                                                24

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 498
ggccatgtac tggtaccgac a                                              21

<210> SEQ ID NO 499
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 499
tcatgtttac tggtatcggc ag                                             22

<210> SEQ ID NO 500
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 500
ttatgtttat tggtatcaac agaatca                                        27

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
caacctatac tggtaccgac a                                              21

<210> SEQ ID NO 502
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
taccctttac tggtaccggc ag                                             22

<210> SEQ ID NO 503
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
atacttctat tggtacagac aaatct                                         26

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 504
```

```
cacggtctac tggtaccagc a                                              21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 505
cgtcatgtac tggtaccagc a                                              21

<210> SEQ ID NO 506
<211> LENGTH: 238
<212> TYPE: DNA
<213> ORGANISM: Homo sapiens

<400> SEQUENCE: 506
agagaaaagg cagagtgtgg cttttggtg caatcctata tctggccatg ctacccttta     60
ctggtaccag cagatcctgg gacagggccc aaagcttctg attcagtttc agaataacgg   120
tgtagtggat gattcacagt tgcctaaggt tcgatttttct gcagagaggc tcaaaggagt  180
agactccact ctcaagatcc agcctgcaaa gcttgaggac tcggccgtgt atctctgt    238

<210> SEQ ID NO 507
<211> LENGTH: 255
<212> TYPE: DNA
<213> ORGANISM: Homo sapiens

<400> SEQUENCE: 507
cccagatata agattataga gaaaaaacag cctgtggctt tttggtgcaa tcctatttct    60
ggccacaata ccctttactg gtaccggcag aacttgggac agggcccgga gcttctgatt  120
cgatatgaga atgaggaagc agtagacgat tcacagttgc ctaaggatcg attttctgca  180
gagaggctca aggagtaga ctccactctc aagatccagc ctgcagagct tggggactcg   240
gccgtgtatc tctgt                                                    255

<210> SEQ ID NO 508
<211> LENGTH: 241
<212> TYPE: DNA
<213> ORGANISM: Homo sapiens

<400> SEQUENCE: 508
gacagagatg ggacaagaag tgactctgag atgtaaacca atttcaggac acgactacct    60
tttctggtac agacagacca tgatgcaggg actggagttg ctcatttact ttaacaacaa   120
cgttccgata gatgattcag ggatgcccga ggatcgattc tcagctaaga tgcctaatgc   180
atcattctcc actctgaaga tccagccctc agaacccagg gactcagctg tgtacttctg   240
t                                                                   241

<210> SEQ ID NO 509
<211> LENGTH: 241
<212> TYPE: DNA
<213> ORGANISM: Homo sapiens

<400> SEQUENCE: 509
gacagagatg ggacaagaag taacaatgag atgtcagcca attttaggcc acaatactgt    60
tttctggtac agacagacca tgaagcaagg actggagttg ctggcttact tccgcaaccg   120
```

```
ggctcctcta gatgattcgg ggatgccgaa ggatcgattc tcagcagaga tgcctgatgc    180
aactttagcc actctgaaga tccagccctc agaacccagg gactcagctg tgtattttg    240 t                                                                    241

<210> SEQ ID NO 510
<211> LENGTH: 241
<212> TYPE: DNA
<213> ORGANISM: Homo sapiens

<400> SEQUENCE: 510
gttcagaaag gaaggacaga atgtgaccct gagttgtgaa cagaatttga accacgatgc    60
catgtactgg taccaacagg acccagggca agggctgaga ttgatctact actcacagat    120
agtaaatgac tttcagaaag gagatatagc tgaagggtac agcgtctctc gggagaagaa    180
ggaatccttt cctctcactg tgacatcggc ccaaaagaac ccgacagctt tctatctctg    240
t                                                                    241

<210> SEQ ID NO 511
<211> LENGTH: 241
<212> TYPE: DNA
<213> ORGANISM: Homo sapiens

<400> SEQUENCE: 511
caaaggaaaa ggacagaaaa caaagatgga ttgtaccccc gaaaaaggac atacttttgt    60
ttattggtat caacagaatc agaataaaga gtttatgctt ttgatttcct ttcagaatga    120
acaagttctt caagaaacgg agatgcacaa gaagcgattc tcatctcaat gccccaagaa    180
cgcaccctgc agcctggcaa tcctgtcctc agaaccggga gacacggcac tgcatctctg    240
c                                                                    241

<210> SEQ ID NO 512
<211> LENGTH: 238
<212> TYPE: DNA
<213> ORGANISM: Homo sapiens

<400> SEQUENCE: 512
cacaaagaca ggaaagagga ttatgctgga atgttctcag actaagggtc atgatagaat    60
gtactggtat cgacaagacc caggactggg cctacagttg atctattact cctttgatgt    120
caaagatata aacaaggag agatctctga tggatacagt gtctctcgac aggcacaggc    180
taaattctcc ctgtccctag agtctgccat ccccaaccag acagctcttt acttctgt     238

<210> SEQ ID NO 513
<211> LENGTH: 238
<212> TYPE: DNA
<213> ORGANISM: Homo sapiens

<400> SEQUENCE: 513
caaaacgaga ggacagcaag tgactctgag atgctctcct atctctgggc acagcagtgt    60
gtcctggtac aacaggcccc cgggtcaggt gccccagttt atctttgaat atgctaatga    120
gttaaggaga tcagaaggaa acttccctaa tcgattctca gggcgccagt tccatgactg    180
ttgctctgag atgaatgtga gtgccttgga gctgggggac tcggccctgt atctctgt     238

<210> SEQ ID NO 514
<211> LENGTH: 252
<212> TYPE: DNA
```

<213> ORGANISM: Homo sapiens

<400> SEQUENCE: 514

| cccacacacc tgatcaaaac gagaggacag caagtgactc tgagatgctc tcctatctct | 60 |
| gggcacacca gtgtgtactg gtaccaacag gccctgggtc tgggcctcca gttcctcctt | 120 |
| tggtatgacg agggtgaaga gagaaacaga ggaaacttcc ctcctagatt ttcaggtcgc | 180 |
| cagttcccta attatagctc tgagctgaat gtgaatgcct tggagctgga ggactcggcc | 240 |
| ctgtatctct gt | 252 |

<210> SEQ ID NO 515
<211> LENGTH: 235
<212> TYPE: DNA
<213> ORGANISM: Homo sapiens

<400> SEQUENCE: 515

| gaagacagga cagagcatga cactgcagtg tgcccaggat atgaaccata actccatgta | 60 |
| ctggtatcga caagacccag gcatgggact gaggctgatt tattactcag cttctgaggg | 120 |
| taccactgac aaaggagagg tccctgatgg ctacaatgtc tccagattaa aaaaacagaa | 180 |
| tttcctgctg gggttggagt cggctgctcc ctcccaaaca tctgtgtact tctgt | 235 |

<210> SEQ ID NO 516
<211> LENGTH: 235
<212> TYPE: DNA
<213> ORGANISM: Homo sapiens

<400> SEQUENCE: 516

| gaagacagga cagagcatga cactgcagtg tgcccaggat atgaaccatg aatacatgtc | 60 |
| ctggtatcga caagacccag gcatggggct gaggctgatt cattactcag ttagtgctgg | 120 |
| tatcactgac caaggagaag tccccaatgg ctacaatgtc tccagatcaa ccacagagga | 180 |
| tttcccgctc aggctgctgt cggctgctcc ctcccagaca tctgtgtact tctgt | 235 |

<210> SEQ ID NO 517
<211> LENGTH: 240
<212> TYPE: DNA
<213> ORGANISM: Homo sapiens

<400> SEQUENCE: 517

| acagagaaaa gccaggctgt ggcttttttgg tgtgatccta tttctggccg tgctacccct | 60 |
| tattggtacc ggcagatcct gggacagggc ccggagcttc tggttcgatt tcaggatgag | 120 |
| agtgtagtag atgattcaca gttgcctaag gatcgatttt ctgcagagag gctcaaagga | 180 |
| gtagactcca ctctcaagat ccagcctgca gagcttgggg actcggccat gtatctctgt | 240 |

<210> SEQ ID NO 518
<211> LENGTH: 254
<212> TYPE: DNA
<213> ORGANISM: Homo sapiens

<400> SEQUENCE: 518

| ggccagcgac cctggtgcag cctgtgggca gcccgctctc tctggagtgc actgtggagg | 60 |
| gaacatcaaa ccccaaccta tactggtacc gacaggctgc aggcaggggc ctccagctgc | 120 |
| tcttctactc cgttggtatt ggccagatca gctctgaggt gccccagaat ctctcagcct | 180 |
| ccagacccca ggaccggcag ttcatcctga gttctaagaa gctccttctc agtgactcta | 240 |
| gcttctatct ctgt | 254 |

```
<210> SEQ ID NO 519
<211> LENGTH: 238
<212> TYPE: DNA
<213> ORGANISM: Homo sapiens

<400> SEQUENCE: 519
caaaacgaga ggacagcaag tgactctgag atgctctcct atctctgggc acaagagtgt      60
gtcctggtac caacaggtcc tgggtcaggg gccccagttt atctttcagt attatgagaa     120
agaagagaga ggaagaggaa acttccctga tcgattctca gctcgccagt tgcctaacta     180
tagctctgag ctgaatgtga acgccttgtt gctgggggac tcggccctgt atctctgt      238

<210> SEQ ID NO 520
<211> LENGTH: 238
<212> TYPE: DNA
<213> ORGANISM: Homo sapiens

<400> SEQUENCE: 520
caaaacgaga ggacagcaag tgactctgag atgctctcct aagtctgggc atgacactgt      60
gtcctggtac caacaggccc tgggtcaggg gccccagttt atctttcagt attatgagga     120
ggaagagaga cagagaggca acttccctga tcgattctca ggtcaccagt tccctaacta     180
tagctctgag ctgaatgtga acgccttgtg gctgggggac tcggccctct atctctgt      238

<210> SEQ ID NO 521
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
aaaatttggt                                                             10

<210> SEQ ID NO 522
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
aaaattttta tccccccccg gg                                               22
```

COMPOSITIONS AND METHODS FOR IMMUNE REPERTOIRE SEQUENCING

CROSS-REFERENCE TO RELATED APPLICATIONS

This application is a divisional application of U.S. Nonprovisional application Ser. No. 15/873,862, filed Jan. 17, 2018, which claims priority to and the benefit of U.S. Provisional Application No. 62/586,099 filed Nov. 14, 2017, U.S. Provisional Application No. 62/553,736 filed Sep. 1, 2017, U.S. Provisional Application No. 62/539,409 filed Jul. 31, 2017, U.S. Provisional Application No. 62/480,227 filed Mar. 31, 2017, and U.S. Provisional Application No. 62/447,348 filed Jan. 17, 2017. The entire contents of each of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Mar. 12, 2018, is named LT01212_SL.txt and is 138,329 bytes in size.

BACKGROUND

Adaptive immune response comprises selective response of B and T cells recognizing antigens. The immunoglobulin genes encoding antibody (Ab, in B cell) and T-cell receptor (TCR, in T cell) antigen receptors comprise complex loci wherein extensive diversity of receptors is produced as a result of recombination of the respective variable (V), diversity (D), and joining (J) gene segments, as well as subsequent somatic hypermutation events during early lymphoid differentiation. The recombination process occurs separately for both subunit chains of each receptor and subsequent heterodimeric pairing creates still greater combinatorial diversity. Calculations of the potential combinatorial and junctional possibilities that contribute to the human immune receptor repertoire have estimated that the number of possibilities greatly exceeds the total number of peripheral B or T cells in an individual. See, for example, Davis and Bjorkman (1988) Nature 334:395-402; Arstila et al. (1999) Science 286:958-961; van Dongen et al., In: Leukemia, Henderson et al. (eds) Philadelphia: WB Saunders Company, 2002, pp 85-129.

Extensive efforts have been made over years to improve analysis of the immune repertoire at high resolution. Means for specific detection and monitoring of expanded clones of lymphocytes would provide significant opportunities for characterization and analysis of normal and pathogenic immune reactions and responses. Despite efforts, effective high resolution analysis has provided challenges. Low throughput techniques such as Sanger sequencing may provide resolution, but are limited to provide efficient means to broadly capture the entire immune repertoire. Recent advances in next generation sequencing (NGS) have provided access to capturing the repertoire, however, due to the nature of the numerous related sequences and introduction of sequence errors as a result of the technology, efficient and effective reflection of the true repertoire has proven difficult. Thus, new methods for effective profiling of vast repertoires of immune cell receptors are increasingly sought to better understand immune cell response, enhance diagnostic capabilities, and devise new therapeutics. Accordingly, there remains a need for improved sequencing methodologies and workflows capable of resolving complex populations of highly variable immune cell receptor sequences.

SUMMARY OF THE INVENTION

In one aspect of the invention compositions are provided for a single stream determination of an immune repertoire in a sample. In some embodiments the composition comprises at least one set of primers i) and ii), wherein i) consists of a plurality of variable (V) gene primers directed to a majority of different variable regions of an immune receptor coding sequence; and ii) consists one or more constant (C) gene primers directed to at least a portion of the respective target constant region of the respective immune receptor coding sequence. In some embodiments the composition comprises at least one set of primers i) and ii), wherein i) consists of a plurality of variable (V) gene primers directed to a majority of different V genes of an immune receptor coding sequence; and ii) consists of a plurality of joining (J) gene primers directed to a majority of different J genes of the respective target immune receptor coding sequence. In some embodiments the composition for analysis of an immune repertoire in a sample comprises at least one set of primers i) and ii), wherein i) consists of (a) a plurality of V gene primers directed to a majority of different V genes of at least one immune receptor coding sequence comprising at least a portion of framework region 1 (FR1) within the V gene, or (b) a plurality of V gene primers directed to a majority of different V genes of at least one immune receptor coding sequence comprising at least a portion of framework region 3 (FR3) within the V gene; and ii) consists of (a) one or more C gene primers directed to at least a portion of a C gene of the at least one immune receptor coding sequence, or (b) a plurality of J gene primers directed to at least a portion of a majority of different J genes of the at least one immune receptor coding sequence; wherein each set of i) and ii) primers directed to coding sequences of the same target immune receptor gene selected from a T cell receptor or an antibody receptor; and wherein each set of i) and ii) primers directed to the same target immune receptor is configured to amplify the target immune receptor repertoire.

In some embodiments the V gene primers recognize at least a portion of framework region 1 (FR1) within the V gene. In some embodiments the V gene primers recognize at least a portion of framework region 2 (FR2) within the V gene. In some embodiments the V gene primers recognize at least a portion of framework region 3 (FR3) within the V gene. Each set of i) and ii) primers are directed to the same target immune receptor sequence selected from the group consisting of a T cell receptor and an antibody receptor, and configured such that resulting amplicons generated using such compositions represent the repertoire of sequences of the respective receptor in a sample. In particular embodiments, provided compositions include a plurality of primer pair reagents selected from Table 2 and Table 4. In particular embodiments, provided compositions include a plurality of primer pair reagents selected from Table 3 and Table 4. In particular embodiments, provided compositions include a plurality of primer pair reagents selected from Table 2 and Table 5. In particular embodiments, provided compositions include a plurality of primer pair reagents selected from Table 3 and Table 5. In some embodiments, provided compositions include a plurality of primer pair reagents selected from Table 4 and Table 6 or selected from Table 5 and Table 6. In some embodiments a multiplex assay comprising compositions of the invention is provided. In some embodiments a test kit comprising compositions of the invention is provided.

In other aspects of the invention, methods are provided for determining immune repertoire activity in a biological sample. Such methods comprise performing multiplex amplification of a plurality of target expression sequences from a biological sample containing target immune receptor sequences. In some embodiments, amplification comprises contacting at least a portion of the sample comprising multiple target sequences of interest using at least one set of primers comprising i) and ii), wherein i) comprises a plurality of V gene target-specific primers directed to a majority of different variable regions of at least one immune receptor coding sequence and ii) comprises one or more C gene target specific primers directed to at least a portion of the respective target constant region of the immune receptor coding sequence. In some embodiments, amplification comprises contacting at least a portion of the sample comprising multiple target sequences of interest using at least one set of primers comprising i) and ii), wherein i) comprises a plurality of V gene target-specific primers directed to a majority of different V genes of at least one immune receptor coding sequence and ii) comprises a plurality of -J gene primers directed to a majority of different J genes of the respective target immune receptor coding sequence. Each set of primers i) and ii) is directed to the same target immune receptor coding sequence wherein each target immune receptor is selected from a T cell receptor or an antibody receptor sequence, and performing amplification using each one or more sets results in amplicon sequences representing the entire repertoire sequences of the respective immune receptor(s) in the sample of interest. In certain embodiments, methods comprise amplification of expression nucleic acid sequences of an immune receptor repertoire in a sample comprising performing a multiplex amplification reaction in the presence of a polymerase under amplification conditions to produce a plurality of amplified target expression sequences comprising one or more immune receptors of interest having a variable, diversity, joining, and constant (VDJC) gene portion or one or more immune receptors of interest having a variable, joining, and constant (VJC) gene portion.

In some embodiments, the method for amplification of expression nucleic acid sequences of an immune receptor repertoire in a sample comprises performing a single multiplex amplification reaction to amplify expressed target immune receptor nucleic acid template molecules using at least one set of:
 i) (a) a plurality of V gene primers directed to a majority of different V genes of at least one immune receptor coding sequence comprising at least a portion of framework region 1 (FR1) within the V gene,
  (b) a plurality of V gene primers directed to a majority of different V genes of at least one immune receptor coding sequence comprising at least a portion of framework region 2 (FR2) within the V gene, or
  (c) a plurality of V gene primers directed to a majority of different V genes of at least one immune receptor coding sequence comprising at least a portion of framework region 3 (FR3) within the V gene; and
 ii) (a) one or more C gene primers directed to at least a portion of a C gene of the at least one immune receptor coding sequence, or
  (b) a plurality of J gene primers directed to at least a portion of a majority of different J genes of the at least one immune receptor coding sequence;

wherein each set of i) and ii) primers is directed to coding sequences of the same target immune receptor gene selected from a T cell receptor gene or an antibody receptor gene and wherein performing the amplification using the at least one set of i) and ii) primers results in amplicon molecules representing the target immune receptor repertoire in the sample; thereby generating immune receptor amplicon molecules comprising the target immune receptor repertoire.

In certain embodiments at least a portion of the first framework region (FR1) of the V gene to at least a portion of the C gene of the immune receptor sequence is encompassed within amplified target immune receptor sequences. In certain embodiments at least a portion of the second framework region (FR2) of the V gene to at least a portion of the C gene of the immune receptor sequence is encompassed within amplified target immune receptor sequences. In certain embodiments at least a portion of the third framework region (FR3) of the V gene to at least a portion of the C gene of the immune receptor sequence is encompassed within amplified target immune receptor sequences. In other embodiments, methods comprise amplification of expression nucleic acid sequences of an immune receptor repertoire in a sample comprising performing a multiplex amplification reaction in the presence of a polymerase under amplification conditions to produce a plurality of amplified target expression sequences comprising one or more immune receptors of interest having a variable, diversity, and joining (VDJ) gene portion or one or more immune receptors of interest having a variable and joining (VJ) gene portion. In certain embodiments at least a portion of the first framework region (FR1) of the V gene to at least a portion of the joining (J) gene of the immune receptor sequence is encompassed within amplified target immune receptor sequences. In certain embodiments at least a portion of the second framework region (FR2) of the V gene to at least a portion of the joining (J) gene of the immune receptor sequence is encompassed within amplified target immune receptor sequences. In certain embodiments at least a portion of the third framework region (FR3) of the V gene to at least a portion of the joining (J) gene of the immune receptor sequence is encompassed within amplified target immune receptor sequences.

Methods of the invention further comprise preparing an immune receptor repertoire library using the amplified target immune receptor sequences through introducing adapter sequences to the termini of the amplified target sequences. In some embodiments, the adapter-modified immune receptor repertoire library is clonally amplified.

The methods further comprise detecting sequences of the immune repertoire of each of the immune receptors in the sample and/or expression of each of the plurality of target immune receptor sequences, wherein a change in the level of repertoire sequences and/or expression of one or more target immune receptor markers as compared with a second sample or a control sample determines a change in immune repertoire activity in the sample. In certain embodiments sequencing of the immune receptor amplicon molecules is carried out using next generation sequence analysis to determine sequence of the immune receptor amplicons. In particular embodiments determining the sequence of the immune receptor amplicon molecules includes obtaining initial sequence reads, aligning and identifying productive reads and correcting errors to generate rescued productive reads and determining the sequences of the resulting total productive reads, thereby providing sequence of the immune repertoire in the sample. Provided methods described herein utilize compositions of the invention provided herein. In still other aspects of the invention, particular analysis methodology for error correction is provided in order to generate comprehensive, effective sequence information from methods provided herein.

BRIEF DESCRIPTION OF THE DRAWINGS

FIG. 3A depicts characteristics of sample through library sequence process; FIG. 3B depicts resulting read lengths; and FIG. 3C depicts results of numbers of reads and characterization of read quality (productive/rescued productive/unproductive/off target-short).

FIG. 4A depicts correlation plots of TCR V gene usage comparing 5'-RACE and BIOMED-2 primer set for sample preparation. FIG. 4B depicts correlation plots of TCR V gene usage comparing 5'-RACE and the presently provided primers and workflows for sample preparation.

FIG. 10 depicts Table 1, which is a diagram of an exemplary workflow for use in identifying and removing PCR or sequencing-derived errors from immune receptor sequencing data.

DESCRIPTION OF THE INVENTION

Figure 1:
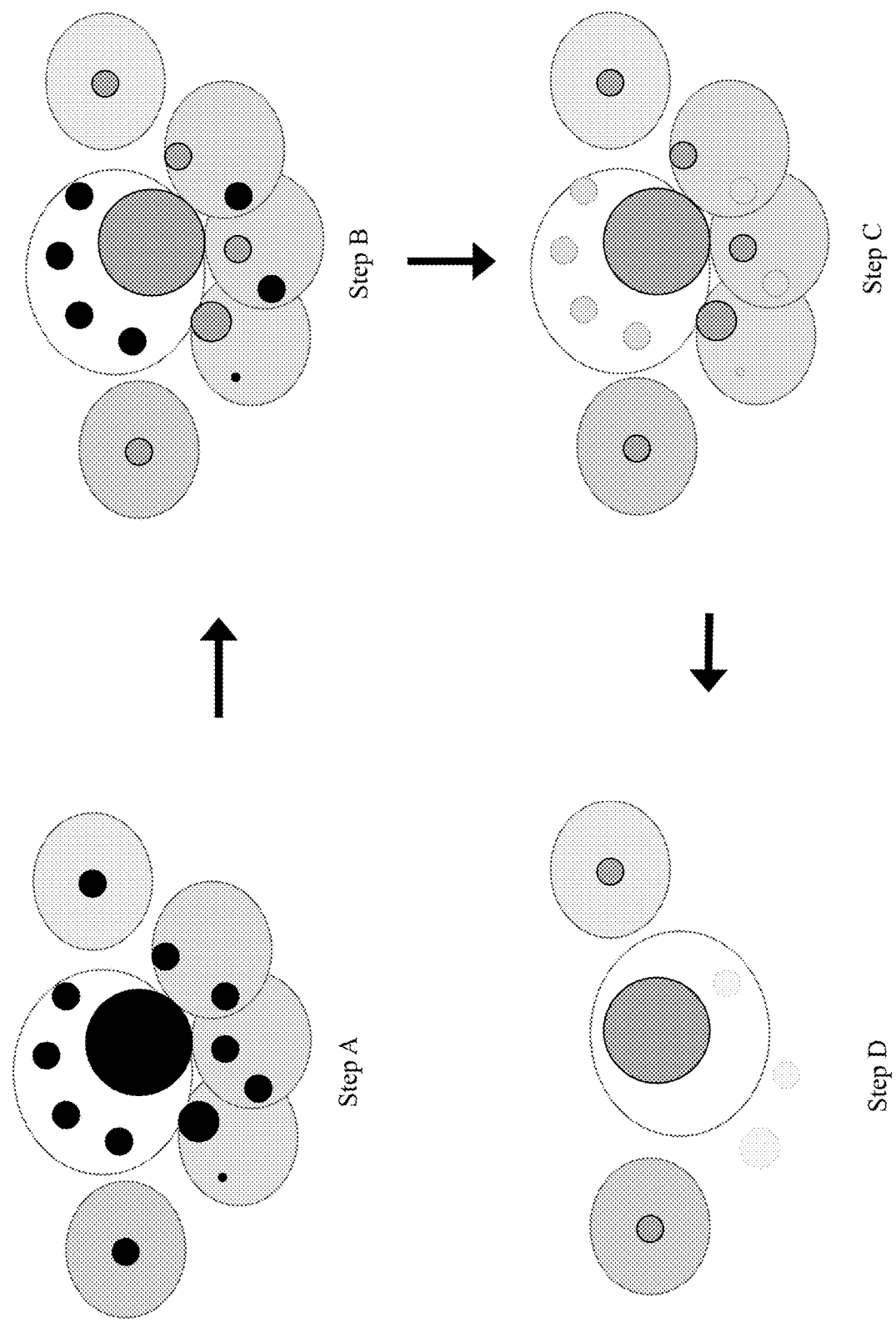
FIG. 1 is a diagram of an exemplary workflow for removal of PCR or sequencing-derived errors using stepwise clustering of similar CDR3 nucleotides sequences with steps: (A) very fast heuristic clustering into groups based on similarity (cd-hit-est); (B) cluster representative chosen as most common sequence, randomly picked for ties; (C) merge reads into representatives; (D) compare representatives and if within allotted hamming distance, merge clusters.

We have developed a multiplex next generation sequencing workflow for effective detection and analysis of the immune repertoire in a sample. Provided methods, compositions, systems, and kits are for use in high accuracy amplification and sequencing of immune cell receptor sequences (e.g., T cell receptor (TCR), B cell receptor (BCR or Ab) targets) in monitoring and resolving complex immune cell repertoire(s) in a subject. In certain embodiments, the present disclosure provides methods, compositions, and systems that use nucleic acid amplification, such as polymerase chain reaction (PCR), to enrich expressed variable regions of immune receptor target nucleic acid for subsequent sequencing. In certain embodiments, the present disclosure also provides methods and systems for effective identification and removal of amplification or sequencing-derived error(s) to improve read assignment accuracy and lower the false positive rate. In particular, provided methods described herein may improve accuracy and performance in sequencing applications with nucleotide sequences associated with genomic recombination and high variability. In some embodiments, methods, compositions, systems, and kits provided herein are for use in amplification and sequencing of the complementarity determining regions of an expressed immune receptor in a sample. Thus, provided herein are multiplex immune cell receptor expression compositions for multiplex library preparation, use in conjunction with next generation sequencing technologies and workflow solutions (e.g., manual or automated), for effective detection and characterization of the immune repertoire in a sample.

The complementarity determining regions (CDRs) of a TCR or BCR results from genomic DNA undergoing recombination of the V(D)J gene segments as well as addition and/or deletion of nucleotides at the gene segment junctions. With the stochastic nature of VDJ recombination, it is often the case that rearrangement of the T or B cell receptor genomic DNA will fail to produce a functional receptor, instead producing what is termed an "unproductive" rearrangement. Typically, unproductive rearrangements have out-of-frame Variable and Joining coding segments, and lead to the presence of premature stop codons and synthesis of irrelevant peptides. However, unproductive TCR or BCR gene rearrangements are generally rare in cDNA-based repertoire sequencing for a number of biological or physiological reasons such as: 1) nonsense-mediated decay, which destroys mRNA containing premature stop codons, 2) B and T cell selection, where only B and T cells with a functional receptor survive, and 3) allelic exclusion, where only a single rearranged receptor allele is expressed in any given B or T cell.

Accordingly, in some embodiments, methods and compositions are provided for amplifying the recombined, expressed variable regions of immune cell receptor mRNA, eg TCR and BCR mRNA. In some embodiments, RNA extracted from biological samples is converted to cDNA.

Multiplex amplification is used to enrich for a portion of TCR or BCR cDNA which includes at least a portion of the variable region of the receptor. In some embodiments, the amplified cDNA includes one or more complementarity determining regions CDR1, CDR2, and/or CDR3 for the target receptor. In some embodiments, the amplified cDNA includes one or more complementarity determining regions CDR1, CDR2, and/or CDR3 for TCR beta.

TCR and BCR sequences can also appear as unproductive rearrangements from errors introduced during amplification reactions or during sequencing processes. For example, an insertion or deletion (indel) error during a target amplification or sequencing reaction can cause a frameshift in the reading frame of the resulting coding sequence. Such a change may result in a target sequence read of a productive rearrangement being interpreted as an unproductive rearrangement and discarded from the group of identified clonotypes. Accordingly, in some embodiments, the provided methods and systems include processes for identification and/or removing PCR or sequencing-derived error from the determined immune receptor sequence.

As used herein, "immune cell receptor" and "immune receptor" are used interchangeably.

As used herein, the terms "complementarity determining region" and "CDR" refer to regions of a T cell receptor or an antibody where the molecule complements an antigen's conformation, thereby determining the molecule's specificity and contact with a specific antigen. In the variable regions of T cell receptors and antibodies, the CDRs are interspersed with regions that are more conserved, termed framework regions (FR). Each variable region of a T cell receptor and an antibody contains 3 CDRs, designated CDR1, CDR2 and CDR3, and also contains 4 framework sub-regions, designated FR1, FR2, FR3 and FR4.

As used herein, the term "framework" or "framework region" or "FR" refers to the residues of the variable region other than the CDR residues as defined herein. There are four separate framework sub-regions that make up the framework: FR1, FR2, FR3, and FR4.

The particular designation in the art for the exact location of the CDRs and FRs within the receptor molecule (TCR or immunoglobulin) varies depending on what definition is employed. Unless specifically stated otherwise, the IMGT designations are used herein in describing the CDR and FR regions (see Brochet et al. (2008) Nucleic Acids Res. 36:W503-508, herein specifically incorporated by reference). As one example of CDR/FR amino acid designations, the residues that make up the FRs and CDRs of T cell receptor beta have been characterized by IMGT as follows: residues 1-26 (FR1), 27-38 (CDR1), 39-55 (FR2), 56-65 (CDR2), 66-104 (FR3), 105-117 (CDR3), and 118-128 (FR4).

Other well-known standard designations for describing the regions include those found in Kabat et al., (1991) Sequences of Proteins of Immunological Interest, 5th Ed. Public Health Service, National Institutes of Health, Bethesda, Md., and in Chothia and Lesk (1987) J. Mol. Biol. 196:901-917; herein specifically incorporated by reference. As one example of CDR designations, the residues that make up the six immunoglobulin CDRs have been characterized by Kabat as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region; and by Chothia as follows: residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region.

The term "T cell receptor" or "T cell antigen receptor" or "TCR," as used herein, refers to the antigen/MHC binding heterodimeric protein product of a vertebrate, e.g. mammalian, TCR gene complex, including the human TCR alpha, beta, gamma and delta chains. For example, the complete sequence of the human TCR beta locus has been sequenced, see, for example, Rowen et al. (1996) Science 272:1755-1762; the human TCR alpha locus has been sequenced and resequenced, see, for example, Mackelprang et al. (2006) Hum Genet. 119:255-266; and see, for example, Arden (1995) Immunogenetics 42:455-500 for a general analysis of the T-cell receptor V gene segment families; each of which is herein specifically incorporated by reference for the sequence information provided and referenced in the publication.

The term "antibody" or immunoglobulin" or "B cell receptor" or "BCR," as used herein, is intended to refer to immunoglobulin molecules comprised of four polypeptide chains, two heavy (H) chains and two light (L) chains (lambda or kappa) inter-connected by disulfide bonds. An antibody has a known specific antigen with which it binds. Each heavy chain of an antibody is comprised of a heavy chain variable region (abbreviated herein as HCVR, HV or VH) and a heavy chain constant region. The heavy chain constant region is comprised of three domains, CH1, CH2 and CH3. Each light chain is comprised of a light chain variable region (abbreviated herein as LCVR or VL or KV or LV to designate kappa or lambda light chains) and a light chain constant region. The light chain constant region is comprised of one domain, CL.

The diversity of the TCR chain CDRs is created by recombination of germline variable (V), diversity (D), and joining (J) gene segments, as well as by independent addition and deletion of nucleotides at each of the gene segment junctions during the process of TCR gene rearrangement. In the nucleic acid encoding a TCR beta and a TCR delta, for example, CDR1 and CDR2 are found in the V gene segments and CDR3 includes some of the V gene segment, and the D and J gene segments. In the nucleic acid encoding a TCR alpha and a TCR gamma, CDR1 and CDR2 are found in the V gene segments and CDR3 includes some of the V gene segment and the J gene segment. In the rearranged DNA encoding a BCR heavy chain, CDR1 and CDR2 are found in the V gene segment and CDR3 includes some of the V gene segment and the D and J gene segments. In the rearranged DNA encoding a BCR light chain, CDR1 and CDR2 are found in the V gene segment and CDR3 includes some of the V gene segment and the J gene segment.

In some embodiments, a multiplex amplification reaction is used to amplify cDNA derived from mRNA expressed from rearranged TCR or BCR genomic DNA. In some embodiments, a multiplex amplification reaction is used to amplify at least a portion of a TCR or BCR CDR from cDNA derived from a biological sample. In some embodiments, a multiplex amplification reaction is used to amplify at least two CDRs of a TCR or BCR from cDNA derived from a biological sample. In some embodiments, a multiplex amplification reaction is used to amplify at least three CDRs of a TCR or BCR from cDNA derived from a biological sample. In some embodiments, the resulting amplicons are used to determine the nucleotide sequences of the TCR or BCR CDRs expressed in the sample. In some embodiments, determining the nucleotide sequences of such amplicons comprising at least 3 CDRs is used to identify and characterize novel TCR or BCR alleles. In some embodiments, determining the nucleotide sequences of such amplicons comprising at least 3 CDRs is used to identify and characterize novel TCR or BCR alleles.

In the multiplex amplification reactions, each primer set used target a same TCR or BCR region however the different primers in the set permit targeting the gene's different V(D)J gene rearrangements. For example, the primer set for amplification of the expressed TCR beta are all designed to target the same region(s) from TCR beta mRNA but the individual primers in the set lead to amplification of the various TCR beta VDJ gene combinations. In some embodiments, at least one primer or primer set is directed to a relatively conserved region (eg, a portion of the C gene) of an immune receptor gene and the other primer set includes a variety of primers directed to a more variable region of the same gene (eg, a portion of the V gene). In other embodiments, at least one primer set includes a variety of primers directed to at least a portion of J gene segments of an immune receptor gene and the other primer set includes a variety of primers directed to at least a portion of V gene segments of the same gene.

In some embodiments, multiplex amplification reactions are performed with primer sets designed to generate amplicons which include the expressed CDR1, CDR2, and/or CDR3 regions of the target immune receptor. In some embodiments, multiplex amplification reactions are performed using (i) one set of primers in which each primer is directed to at least a portion of the framework region FR1 of a V gene and (ii) at least one primer directed to a portion of the C gene of the target immune receptor. In other embodiments, multiplex amplification reactions are performed using (i) one set of primers in which each primer is directed to at least a portion of the framework region FR2 of a V gene and (ii) at least one primer directed to a portion of the C gene of the target immune receptor. In other embodiments, multiplex amplification reactions are performed using (i) one set of primers in which each primer is directed to at least a portion of the framework region FR3 of a V gene and (ii) at least one primer directed to a portion of the C gene of the target immune receptor. In some embodiments, the C gene-directed primer is directed C gene coding sequences within about 200 nucleotides of the 5' end of the C gene. In some embodiments, the C gene-directed primer is directed C gene coding sequences within about 150 nucleotides of the 5' end of the C gene. In some embodiments, the C gene-directed primer is directed C gene coding sequences within about 100 nucleotides of the 5' end of the C gene. In some embodiments, the C gene-directed primer is directed C gene coding sequences within about 50 nucleotides, within about 50 to about 150, within about 75 to about 175, or within about 100 to about 200 nucleotides of the 5' end of the C gene.

In some embodiments, multiplex amplification reactions are performed using (i) one set of primers in which each primer is directed to at least a portion of the framework region FR1 of a V gene and (ii) one set of primers in which each primer is directed to at least a portion of the J gene of the target immune receptor. In other embodiments, multiplex amplification reactions are performed using (i) one set of primers in which each primer is directed to at least a portion of the framework region FR2 of a V gene and (ii) one set of primers in which each primer is directed to at least a portion of the J gene of the target immune receptor. In other embodiments, multiplex amplification reactions are performed using (i) one set of primers in which each primer is directed to at least a portion of the framework region FR3 of a V gene and (ii) one set of primers in which each primer is directed to at least a portion of the J gene of the target immune receptor.

In some embodiments, a multiplex amplification reaction is used to amplify cDNA derived from mRNA expressed from rearranged TCR genomic DNA, including rearranged TCR beta, TCR alpha, TCR gamma, and TCR delta genomic DNA. In some embodiments, at least a portion of a TCR CDR, for example CDR3, is amplified from cDNA in a multiplex amplification reaction. In some embodiments, at least two CDR portions of TCR are amplified from cDNA in a multiplex amplification reaction. In certain embodiments, a multiplex amplification reaction is used to amplify at least the CDR1, CDR2, and CDR3 regions of a TCR cDNA. In some embodiments, the resulting amplicons are used to determine the expressed TCR CDR nucleotide sequence.

In some embodiments, the multiplex amplification reaction uses (i) a set of primers each of which anneals to at least a portion of the V gene FR1 region and (ii) at least one primer which anneals to a portion of the constant (C) gene to amplify TCR cDNA such that the resultant amplicons include the CDR1, CDR2, and CDR3 coding portions of the TCR mRNA. In certain embodiments, an FR1-directed primer set is combined with a set of at least two C gene-directed primers to generate amplicons which include at least the CDR1, CDR2, and CDR 3 coding portions of a TCR mRNA. For example, exemplary primers specific for TCR beta (TRB) V gene FR1 regions are shown in Table 2 and exemplary primers specific for TRB C genes are shown in Table 4.

In some embodiments, the multiplex amplification reaction uses (i) a set of primers each of which anneals to at least a portion of the V gene FR2 region and (ii) at least one primer which anneals to a portion of the C gene to amplify TCR cDNA such that the resultant amplicons include the CDR2 and CDR3 coding portions of the TCR mRNA. In certain embodiments, such a FR2-directed primer set is combined with at least two C gene-directed primers to generate amplicons which include the CDR2 and CDR3 coding portions of a TCR mRNA. Exemplary FR2-directed primers include the BIOMED-2 primers developed and standardized by a consortium of European academic laboratories and research hospitals (van Dongen et al. (2003) Leukemia 17:2257-2327) and shown in Table 6. Exemplary primers specific for TRB C genes are shown in Table 4.

In some embodiments, the multiplex amplification reaction uses (i) a set of primers each of which anneals to at least a portion of the V gene FR3 region and (ii) at least one primer which anneals to a portion of the C gene to amplify TCR cDNA such that the resultant amplicons include primarily the CDR3 coding portion of the TCR mRNA. In certain embodiments, such a FR3-directed primer set is combined with at least two C gene-directed primers to generate amplicons with the CDR 3 coding portion of a TCR mRNA. For example, exemplary primers specific for TCR beta (TRB) V gene FR3 regions are shown in Table 3 and exemplary primers specific for TRB C genes are shown in Table 4.

In some embodiments, the multiplex amplification reaction uses (i) a set of primers each of which anneals to at least a portion of the V gene FR1 region and (ii) a set of primers which anneal to a portion of the J gene to amplify TCR cDNA such that the resultant amplicons include the CDR1, CDR2, and CDR3 coding portions of the TCR mRNA. For example, exemplary primers specific for TCR beta (TRB) V gene FR1 regions are shown in Table 2 and exemplary primers specific for TRB J genes are shown in Table 5.

In some embodiments, the multiplex amplification reaction uses (i) a set of primers each of which anneals to at least a portion of the V gene FR2 region and (ii) a set of primers which anneal to a portion of the J gene to amplify TCR cDNA such that the resultant amplicons include the CDR2 and CDR3 coding portions of the TCR mRNA. For example, exemplary primers specific for TRB V gene FR2 regions are shown in Table 6 and exemplary primers specific for TRB J genes are shown in Table 5.

In some embodiments, the multiplex amplification reaction uses (i) a set of primers each of which anneals to at least a portion of the V gene FR3 region and (ii) a set of primers which anneal to a portion of the J gene to amplify TCR cDNA such that the resultant amplicons include primarily the CDR3 coding portion of the TCR mRNA. For example, exemplary primers specific for the TRB V gene FR3 regions are shown in Table 3 and exemplary primers specific for TRB J genes are shown in Table 5.

In some embodiments, provided are compositions for multiplex amplification of at least a portion of an expressed TCR or BCR variable region. In some embodiments, the composition comprises a plurality of sets of primer pair reagents directed to a portion of a V gene framework region and a portion of a constant (C) gene of rearranged target immune receptor genes selected from the group consisting of TCR beta, TCR alpha, TCR gamma, TCR delta, immunoglobulin heavy chain, immunoglobulin light chain lambda, and immunoglobulin light chain kappa. In some embodiments, the composition comprises a plurality of sets of primer pair reagents directed to a portion of a V gene framework region and a portion of a J gene of rearranged target immune receptor genes selected from the group consisting of TCR beta, TCR alpha, TCR gamma, TCR delta, immunoglobulin heavy chain, immunoglobulin light chain lambda, and immunoglobulin light chain kappa.

Amplification by PCR is performed with at least two primers. For the methods provided herein, a set of primers is used that is sufficient to amplify all or a defined portion of the variable sequences at the locus of interest, which locus may include any or all of the aforementioned TCR and Immunoglobulin loci. In some embodiments, various parameters or criteria outlined herein may be used to select the set of target-specific primers for the multiplex amplification.

In some embodiments, primer sets used in the multiplex reactions are designed to amplify at least 50% of the known expressed rearrangements at the locus of interest. In certain embodiments, primer sets used in the multiplex reactions are designed to amplify at least 75%, at least 85%, at least 90%, at least 95%, at least 97%, at least 98% or more of the known expressed rearrangements at the locus of interest. For example, use of at least 49 forward primers of Table 2, each directed to a portion of the FR1 region from different TCR beta V genes, in combination with at least one of the reverse primers of Table 4 directed to a portion of the TCR beta C gene will amplify at least 50% of the known expressed TCR beta rearrangements. For another example, use of 64 forward primers of Table 2, each directed to a portion of the FR1 region from different TCR beta V genes, in combination with two reverse primers of Table 4, each directed to a portion of the TCR beta C genes, will amplify all of the currently known expressed TCR beta rearrangements. For another example, use of 59 forward primers of Table 3, each directed to a portion of the FR3 region from different TCR beta V genes, in combination with two reverse primers of Table 4, each directed to a portion of the TCR beta C genes, will amplify all of the currently known expressed TCR beta rearrangements. For another example, use of 59 forward primers of Table 3, each directed to a portion of the FR3 region from different TCR beta V genes, in combination with 16 reverse primers of Table 5, each directed to a portion of different TCR beta J genes, will amplify all of the currently known expressed TCR beta rearrangements. In some embodiments, use of 59 forward primers of Table 3, each directed to a portion of the FR3 region from different TCR beta V genes, in combination with 14 reverse primers of Table 5, each directed to a portion of different TCR beta J genes, will amplify all of the currently known expressed TCR beta rearrangements For another example, use of 64 forward primers of Table 2, each directed to a portion of the FR1 region from different TCR beta V genes, in combination with 16 reverse primers of Table 5, each directed to a portion of different TCR beta J genes, will amplify all of the currently known expressed TCR beta rearrangements. In other embodiments, use of 64 forward primers of Table 2, each directed to a portion of the FR1 region from different TCR beta V genes, in combination with 14 reverse primers of Table 5, each directed to a portion of different TCR beta J genes, will amplify all of the currently known expressed TCR beta rearrangements.

For example, such a multiplex amplification reaction includes at least 20, 25, 30, 40, 45, 49, preferably 50, 55, 60, 65, 70, 75, 80, 85, or 90 reverse primers in which each reverse primer is directed to a sequence corresponding to at least a portion of one or more TCR V gene FR1 regions. In such embodiments, the plurality of reverse primers directed to the TCR V gene FR1 regions is combined with at least 1 forward primer directed to a sequence corresponding to at least a portion of the constant gene of the same TCR gene. In some embodiments, the plurality of reverse primers directed to the TCR V gene FR1 regions is combined with at least 2, at least 3, at least 4, at least 5, or about 2 to about 6 forward primers each directed to a sequence corresponding to at least a portion to the constant gene of the same TCR gene. In some embodiments of the multiplex amplification reactions, the TCR V gene FR1 directed primers may be the forward primers and the TCR C gene-directed primer(s) may be the reverse primer(s). Accordingly, in some embodiments, a multiplex amplification reaction includes at least 20, 25, 30, 40, 45, 49, preferably 50, 55, 60, 65, 70, 75, 80, 85, or 90 forward primers in which each forward primer is directed to a sequence corresponding to at least a portion of one or more TCR V gene FR1 regions. In such embodiments, the plurality of forward primers directed to the TCR V gene FR1 regions is combined with at least 1 reverse primer directed to a sequence corresponding to at least a portion of the C gene of the same TCR gene. In some embodiments, the plurality of forward primers directed to the TCR V gene FR1 regions is combined with at least 2, at least 3, at least 4, at least 5, or about 2 to about 6 reverse primers each directed to a sequence corresponding to at least a portion to the C gene of the same TCR gene. In some embodiments, such FR1 and C gene amplification primer sets may be directed to TCR beta gene sequences. In some preferred embodiments, about 60 to about 70 forward primers directed to different TRB V gene FR1 regions are combined with 2 reverse primers directed to a portion of the TRB C gene. In some preferred embodiments, the forward primers directed to TRB V gene FR1 regions are selected from those listed in Table 2 and the reverse primers directed to the TRB C gene are selected from those listed in Table 4. In other embodiments, the FR1 and C gene amplification primer sets may be directed to TCR alpha, TCR gamma, TCR delta, immunoglobulin heavy chain, immunoglobulin light chain lambda, or immunoglobulin light chain kappa gene sequences.

In some embodiments, a multiplex amplification reaction includes at least 20, 25, 30, 40, 45, 50, 55, 60, 65, 70, 75, 80, 85, or 90 reverse primers in which each reverse primer is directed to a sequence corresponding to at least a portion of one or more TCR V gene FR2 regions. In such embodiments, the plurality of reverse primers directed to the TCR V gene FR2 regions is combined with at least 1 forward primer directed to a sequence corresponding to at least a portion of the C gene of the same TCR gene. In some embodiments, the plurality of reverse primers directed to the TCR V gene FR2 regions is combined with at least 2, at least 3, at least 4, at least 5, or about 2 to about 6 forward primers each directed to a sequence corresponding to at least a portion to the C gene of the same TCR gene. In some embodiments of the multiplex amplification reactions, the TCR V gene FR2 directed primers may be the forward primers and the TCR C gene-directed primer(s) may be the reverse primer(s). Accordingly, in some embodiments, a multiplex amplification reaction includes at least 20, 25, 30, 40, 45, 50, 55, 60, 65, 70, 75, 80, 85, or 90 reverse primers in which each forward primer is directed to a sequence corresponding to at least a portion of one or more TCR V gene FR2 regions. In such embodiments, the plurality of forward primers directed to the TCR V gene FR2 regions is combined with at least 1 reverse primer directed to a sequence corresponding to at least a portion of the C gene of the same TCR gene. In some embodiments, the plurality of forward primers directed to the TCR V gene FR2 regions is combined with at least 2, at least 3, at least 4, at least 5, or about 2 to about 6 reverse primers each directed to a sequence corresponding to at least a portion to the C gene of the same TCR gene. In some embodiments, such FR2 and C gene amplification primer sets may be directed to TCR beta gene sequences. In some embodiments, about 20 to about 30 forward primers directed to different TRB V gene FR2 regions are combined with 2 reverse primers directed to a portion of the TRB C gene. In some preferred embodiments, the forward primers directed to TRB V gene FR2 regions are selected from those listed in Table 6 and the reverse primers directed to the TRB C gene are selected from those listed in Table 4. In other embodiments, the FR2 and C gene amplification primer sets may be directed to TCR alpha, TCR gamma, TCR delta, immunoglobulin heavy chain, immunoglobulin light chain lambda, or immunoglobulin light chain kappa gene sequences.

In some embodiments, a multiplex amplification reaction includes at least 20, 25, 30, 40, 45, preferably 50, 55, 60, 65, 70, 75, 80, 85, or 90 reverse primers in which each reverse primer is directed to a sequence corresponding to at least a portion of one or more TCR V gene FR3 regions. In such embodiments, the plurality of reverse primers directed to the TCR V gene FR3 regions is combined with at least 1 forward primer directed to a sequence corresponding to at least a portion of the C gene of the same TCR gene. In some embodiments, the plurality of reverse primers directed to the TCR V gene FR3 regions is combined with at least 2, at least 3, at least 4, at least 5, or about 2 to about 6 forward primers each directed to a sequence corresponding to at least a portion to the C gene of the same TCR gene. In some embodiments of the multiplex amplification reactions, the TCR V gene FR3 directed primers may be the forward primers and the TCR C gene-directed primer(s) may be the reverse primer(s). Accordingly, in some embodiments, a multiplex amplification reaction includes at least 20, 25, 30, 40, 45, preferably 50, 55, 60, 65, 70, 75, 80, 85, or 90 reverse primers in which each forward primer is directed to a sequence corresponding to at least a portion of one or more TCR V gene FR3 regions. In such embodiments, the plurality of forward primers directed to the TCR V gene FR3 regions is combined with at least 1 reverse primer directed to a sequence corresponding to at least a portion of the C gene of the same TCR gene. In some embodiments, the plurality of forward primers directed to the TCR V gene FR3 regions is combined with at least 2, at least 3, at least 4, at least 5, or about 2 to about 6 reverse primers each directed to a sequence corresponding to at least a portion to the C gene of the same TCR gene. In some embodiments, such FR3 and C gene amplification primer sets may be directed to TCR beta gene sequences. In some preferred embodiments, about 55 to about 65 forward primers directed to different TRB V gene FR3 regions are combined with 2 reverse primers directed to a portion of the TRB C gene. In some preferred embodiments, the forward primers directed to TRB V gene FR3 regions are selected from those listed in Table 3 and the reverse primers directed to the TRB C gene are selected from those listed in Table 4. In other embodiments, the FR3 and C gene amplification primer sets may be directed to TCR alpha, TCR gamma, TCR delta, immunoglobulin heavy chain, immunoglobulin light chain lambda, and immunoglobulin light chain kappa gene sequences.

In some embodiments, such a multiplex amplification reaction includes at least 20, 25, 30, 40, 45, 49, preferably 50, 55, 60, 65, 70, 75, 80, 85, or 90 reverse primers in which each reverse primer is directed to a sequence corresponding to at least a portion of one or more TCR V gene FR1 regions. In such embodiments, the plurality of reverse primers directed to the TCR V gene FR1 regions is combined with at least 10, 12, 14, 16, 18, 20, or about 15 to about 20 forward primers directed to a sequence corresponding to at least a portion of a J gene of the same TCR gene. In some embodiments of the multiplex amplification reactions, the TCR V gene FR1-directed primers may be the forward primers and the TCR J gene-directed primers may be the reverse primers. Accordingly, in some embodiments, a multiplex amplification reaction includes at least 20, 25, 30, 40, 45, 49, preferably 50, 55, 60, 65, 70, 75, 80, 85, or 90 forward primers in which each forward primer is directed to a sequence corresponding to at least a portion of one or more TCR V gene FR1 regions. In such embodiments, the plurality of forward primers directed to the TCR V gene FR1 regions is combined with at least 10, 12, 14, 16, 18, 20, or about 15 to about 20 reverse primers directed to a sequence corresponding to at least a portion of a J gene of the same TCR gene. In some embodiments, such FR1 and J gene amplification primer sets may be directed to TCR beta gene sequences. In some preferred embodiments, about 60 to about 70 forward primers directed to different TRB V gene FR1 regions are combined with about 15 to about 20 reverse primers directed to different TRB J genes. In some preferred embodiments, about 60 to about 70 forward primers directed to different TRB V gene FR1 regions are combined with about 12 to about 18 reverse primers directed to different TRB J genes. In some preferred embodiments, the forward primers directed to TRB V gene FR1 regions are selected from those listed in Table 2 and the reverse primers directed to the TRB J gene are selected from those listed in Table 5. In other embodiments, the FR1 and J gene amplification primer sets may be directed to TCR alpha, TCR gamma, TCR delta, immunoglobulin heavy chain, immunoglobulin light chain lambda, or immunoglobulin light chain kappa gene sequences.

In some embodiments, a multiplex amplification reaction includes at least 20, 25, 30, 40, 45, 50, 55, 60, 65, 70, 75, 80, 85, or 90 reverse primers in which each reverse primer is directed to a sequence corresponding to at least a portion of one or more TCR V gene FR2 regions. In such embodiments, the plurality of reverse primers directed to the TCR V gene FR2 regions is combined with at least 10, 12, 14, 16, 18, 20, or about 15 to about 20 forward primers directed to a sequence corresponding to at least a portion of a J gene of the same TCR gene. In some embodiments of the multiplex amplification reactions, the TCR V gene FR2-directed primers may be the forward primers and the TCR J gene-directed primers may be the reverse primers. Accordingly, in some embodiments, a multiplex amplification reaction includes at least 20, 25, 30, 40, 45, 50, 55, 60, 65, 70, 75, 80, 85, or 90 forward primers in which each forward primer is directed to a sequence corresponding to at least a portion of one or more TCR V gene FR2 regions. In such embodiments, the plurality of forward primers directed to the TCR V gene FR2 regions is combined with at least 10, 12, 14, 16, 18, 20, or about 15 to about 20 reverse primers directed to a sequence corresponding to at least a portion of a J gene of the same TCR gene. In some embodiments, such FR2 and J gene amplification primer sets may be directed to TCR beta gene sequences. In some preferred embodiments, about 20 to about 30 forward primers directed to different TRB V gene FR2 regions are combined with about 15 to about 20 reverse primers directed to different TRB J genes. In some preferred embodiments, about 20 to about 30 forward primers directed to different TRB V gene FR2 regions are combined with about 12 to about 18 reverse primers directed to different TRB J genes. In some preferred embodiments, the forward primers directed to TRB V gene FR2 regions are selected from those listed in Table 6 and the reverse primers directed to the TRB J gene are selected from those listed in Table 5. In other embodiments, the FR2 and J gene amplification primer sets may be directed to TCR alpha, TCR gamma, TCR delta, immunoglobulin heavy chain, immunoglobulin light chain lambda, or immunoglobulin light chain kappa gene sequences.

In some embodiments, a multiplex amplification reaction includes at least 20, 25, 30, 40, 45, preferably 50, 55, 60, 65, 70, 75, 80, 85, or 90 reverse primers in which each reverse primer is directed to a sequence corresponding to at least a portion of one or more TCR V gene FR3 regions. In such embodiments, the plurality of reverse primers directed to the TCR V gene FR3 regions is combined with at least 10, 12, 14, 16, 18, 20, or about 15 to about 20 forward primers directed to a sequence corresponding to at least a portion of a J gene of the same TCR gene. In some embodiments of the multiplex amplification reactions, the TCR V gene FR3-directed primers may be the forward primers and the TCR J gene-directed primers may be the reverse primers. Accordingly, in some embodiments, a multiplex amplification reaction includes at least 20, 25, 30, 40, 45, preferably 50, 55, 60, 65, 70, 75, 80, 85, or 90 forward primers in which each forward primer is directed to a sequence corresponding to at least a portion of one or more TCR V gene FR3 regions. In such embodiments, the plurality of forward primers directed to the TCR V gene FR3 regions is combined with at least 10, 12, 14, 16, 18, 20, or about 15 to about 20 reverse primers directed to a sequence corresponding to at least a portion of a J gene of the same TCR gene. In some embodiments, such FR3 and J gene amplification primer sets may be directed to TCR beta gene sequences. In some preferred embodiments, about 55 to about 65 forward primers directed to different TRB V gene FR3 regions are combined with about 15 to about 20 reverse primers directed to different TRB J genes. In some preferred embodiments, about 55 to about 65 forward primers directed to different TRB V gene FR3 regions are combined with about 12 to about 18 reverse primers directed to different TRB J genes. In some preferred embodiments, the forward primers directed to TRB V gene FR3 regions are selected from those listed in Table 3 and the reverse primers directed to the TRB J gene are selected from those listed in Table 5. In other embodiments, the FR3 and J gene amplification primer sets may be directed to TCR alpha, TCR gamma, TCR delta, immunoglobulin heavy chain, immunoglobulin light chain lambda, and immunoglobulin light chain kappa gene sequences.

In some embodiments, the concentration of the forward primer is about equal to that of the reverse primer in a multiplex amplification reaction. In other embodiments, the concentration of the forward primer is about twice that of the reverse primer in a multiplex amplification reaction. In other embodiments, the concentration of the forward primer is about half that of the reverse primer in a multiplex amplification reaction. In some embodiments, the concentration of each of the primers targeting the V gene FR region is about 5 nM to about 2000 nM. In some embodiments, the concentration of each of the primers targeting the V gene FR region is about 50 nM to about 800 nM. In some embodiments, the concentration of each of the primers targeting the V gene FR region is about 50 nM to about 400 nM or about 100 nM to about 500 nM. In some embodiments, the concentration of each of the primers targeting the V gene FR region is about 200 nM, about 400 nM, about 600 nM, or about 800 nM. In some embodiments, the concentration of each of the primers targeting the V gene FR region is about 5 nM, about 10 nM, about 50 nM, about 100 nM, about 150 nM. In some embodiments, the concentration of each of the primers targeting the V gene FR region is about 1000 nM, about 1250 nM, about 1500 nM, about 1750 nM, or about 2000 nM. In some embodiments, the concentration of each of the primers targeting the V gene FR region is about 50 nM to about 800 nM. In some embodiments, the concentration of each of the primers targeting the J gene is about 5 nM to about 2000 nM. In some embodiments, the concentration of each of the primers targeting the J gene is about 50 nM to about 800 nM. In some embodiments, the concentration of each of the primers targeting the J gene is about 50 nM to about 400 nM or about 100 nM to about 500 nM. In some embodiments, the concentration of each of the primers targeting the J gene is about 200 nM, about 400 nM, about 600 nM, or about 800 nM. In some embodiments, the concentration of each of the primers targeting the J gene is about 5 nM, about 10 nM, about 50 nM, about 100 nM, about 150 nM. In some embodiments, the concentration of each of the primers targeting the J gene is about 1000 nM, about 1250 nM, about 1500 nM, about 1750 nM, or about 2000 nM. In some embodiments, the concentration of each of the primers targeting the J gene is about 50 nM to about 800 nM. In some embodiments, the concentration of each forward and reverse primer in a multiplex reaction is about 50 nM, about 100 nM, about 200 nM, or about 400 nM. In some embodiments, the concentration of each forward and reverse primer in a multiplex reaction is about 5 nM to about 2000 nM. In some embodiments, the concentration of each forward and reverse primer in a multiplex reaction is about 50 nM to about 800 nM. In some embodiments, the concentration of each forward and reverse primer in a multiplex reaction is about 50 nM to about 400 nM or about 100 nM to about 500 nM. In some embodiments, the concentration of each forward and reverse primer in a multiplex reaction is about 600 nM, about 800 nM, about 1000 nM, about 1250 nM, about 1500 nM, about 1750 nM, or about 2000 nM. In some embodiments, the concentration of each forward and reverse primer in a multiplex reaction is about 5 nM, about 10 nM, about 150 nM or 50 nM to about 800 nM.

In some embodiments, the V gene FR and C gene target-directed primers combine as amplification primer pairs to amplify target immune receptor cDNA sequences and generate target amplicons. Generally, the length of a target amplicon will depend upon which V gene primer set (eg, FR1, FR2, or FR3 directed primers) is paired with the C gene primer(s). Accordingly, in some embodiments, target amplicons can range from about 100 nucleotides (or bases or base pairs) in length to about 600 nucleotides (or bases or base pairs) in length. In some embodiments, target amplicons can range from about 80 nucleotides to about 600 nucleotides in length. In some embodiments, target amplicons are from about 200 to about 600 or about 300 to about 600 nucleotides in length. In some embodiments, target amplicons are about 80 to about 140, about 90 to about 130, or about 100 to about 120 nucleotides in length. In some embodiments, target amplicons are about 250 to about 275, about 250 to about 350, about 300 to about 350, about 310 to about 330, about 325 to about 375, about 300 to about 400, about 350 to about 400, about 350 to about 425, about 350 to about 450, about 380 to about 410, about 375 to about 425, about 400 to about 500, about 425 to about 500, about 450 to about 550, about 500 to about 600, about 400 to about 500, or about 400 to about 600 nucleotides in length. In some embodiments, target amplicons are about 80, about 100, about 120, about 140, about 200, about 250, about 275, about 300, about 320, about 350, about 375, about 400, about 425, about 450, about 500, about 550, or about 600 nucleotides in length. In some embodiments, TCR beta amplicons are about 100, about 80 to about 140, about 90 to about 130, or about 100 to about 120 nucleotides in length. In some embodiments, TCR beta amplicons are about 320, about 300 to about 350 or about 310 to about 330 nucleotides in length. In some embodiments, TCR beta amplicons are about 400, about 375 to about 425 or about 390 to about 410 nucleotides in length.

In some embodiments, the V gene FR and J gene target-directed primers combine as amplification primer pairs to amplify target immune receptor cDNA sequences and generate target amplicons. Generally, the length of a target amplicon will depend upon which V gene primer set (eg, FR1, FR2, or FR3 directed primers) is paired with the J gene primers. Accordingly, in some embodiments, target amplicons can range from about 50 nucleotides to about 350 nucleotides in length. In some embodiments, target amplicons are about 50 to about 200, about 70 to about 170, about 200 to about 350, about 250 to about 320, about 270 to about 300, about 225 to about 300, about 250 to about 275, about 200 to about 235, about 200 to about 250, or about 175 to about 275 nucleotides in length. In some embodiments, TCR beta amplicons are about 80, about 60 to about 100, or about 70 to about 90 nucleotides in length. In some embodiments, TCR beta amplicons, such as those generated using V gene FR3- and J gene-directed primer pairs, are about 50 to about 200 nucleotides in length, preferably about 60 to about 160, about 65 to about 120, about 70 to about 90 nucleotides, or about 80 nucleotides in length.

In some embodiments, amplification primers may include a barcode sequence, for example to distinguish or separate a plurality of amplified target sequences in a sample. In some embodiments, amplification primers may include two or more barcode sequences, for example to distinguish or separate a plurality of amplified target sequences in a sample. In some embodiments, amplification primers may include a tagging sequence that can assist in subsequent cataloguing, identification or sequencing of the generated amplicon. In some embodiments, the barcode sequence(s) or the tagging sequence(s) is incorporated into the amplified nucleotide sequence through inclusion in the amplification primer or by ligation of an adapter. Primers may further comprise nucleotides useful in subsequent sequencing, e.g. pyrosequencing. Such sequences are readily designed by commercially available software programs or companies.

In some embodiments, multiplex amplification is performed with target-directed amplification primers which do not include a tagging sequence. In other embodiments, multiplex amplification is performed with amplification primers each of which include a target-directed sequence and a tagging sequence such as, for example, the forward primer or primer set includes tagging sequence 1 and the reverse primer or primer set includes tagging sequence 2. In still other embodiments, multiplex amplification is performed with amplification primers where one primer or primer set includes target directed sequence and a tagging sequence and the other primer or primer set includes a target-directed sequence but does not include a tagging sequence, such as, for example, the forward primer or primer set includes a tagging sequence and the reverse primer or primer set does not include a tagging sequence.

Accordingly, in some embodiments, a plurality of target cDNA template molecules are amplified in a single multiplex amplification reaction mixture with TCR or BCR directed amplification primers in which the forward and/or reverse primers include a tagging sequence and the resultant amplicons include the target TCR or BCR sequence and a tagging sequence on one or both ends. In some embodiments, the forward and/or reverse amplification primer or primer sets may also include a barcode and the one or more barcode is then included in the resultant amplicon.

In some embodiments, a plurality of target cDNA template molecules are amplified in a single multiplex amplification reaction mixture with TCR or BCR directed amplification primers and the resultant amplicons contain only TCR or BCR sequences. In some embodiments, a tagging sequence is added to the ends of such amplicons through, for example, adapter ligation. In some embodiments, a barcode sequence is added to one or both ends of such amplicons through, for example, adapter ligation.

Nucleotide sequences suitable for use as barcodes and for barcoding libraries are known in the art. Adapters and amplification primers and primer sets including a barcode sequence are commercially available. Oligonucleotide adapters containing a barcode sequence are also commercially available including, for example, IonXpress™, IonCode™ and Ion Select barcode adapters (Thermo Fisher Scientific). Similarly, additional and other universal adapter/primer sequences described and known in the art (e.g., Illumina universal adapter/primer sequences, PacBio universal adapter/primer sequences, etc.) can be used in conjunction with the methods and compositions provided herein and the resultant amplicons sequenced using the associated analysis platform.

In some embodiments, two or more barcodes are added to amplicons when sequencing multiplexed samples. In some embodiments, at least two barcodes are added to amplicons prior to sequencing multiplexed samples to reduce the frequency of artefactual results (e.g., immune receptor gene rearrangements or clone identification) derived from barcode cross-contamination or barcode bleed-through between samples. In some embodiments, at least two bar codes are used to label samples when tracking low frequency clones of the immune repertoire. In some embodiments, at least two barcodes are added to amplicons when the assay is used to detect clones of frequency less than 1:1,000. In some embodiments, at least two barcodes are added to amplicons when the assay is used to detect clones of frequency less than 1:10,000. In other embodiments, at least two barcodes are added to amplicons when the assay is used to detect clones of frequency less than 1:20,000, less than 1:40,000, less than 1:100,000, less than 1:200,000, less than 1:400,000, less than 1:500,00, or less than 1:1,000,000. Methods for characterizing the immune repertoire which benefit from a high sequencing depth per clone and/or detection of clones at such low frequencies include, but are not limited to, monitoring a patient with a hyperproliferative disease undergoing treatment and testing for minimal residual disease following treatment.

In some embodiments, target-specific primers (e.g., the V gene FR1-, FR2- and FR3-directed primers, the J gene directed primers, and the C gene directed primers) used in the methods of the invention are selected or designed to satisfy any one or more of the following criteria: (1) includes two or more modified nucleotides within the primer sequence, at least one of which is included near or at the termini of the primer and at least one of which is included at, or about the center nucleotide position of the primer sequence; (2) length of about 15 to about 40 bases in length; (3) $T_m$ of from above 60° C. to about 70° C.; (4) has low cross-reactivity with non-target sequences present in the sample of interest; (5) at least the first four nucleotides (going from 3' to 5' direction) are non-complementary to any sequence within any other primer present in the same reaction; and (6) non-complementarity to any consecutive stretch of at least 5 nucleotides within any other produced target amplicon. In some embodiments, the target-specific primers used in the methods provided are selected or designed to satisfy any 2, 3, 4, 5, or 6 of the above criteria.

In some embodiments, the target-specific primers used in the methods of the invention include one or more modified nucleotides having a cleavable group. In some embodiments, the target-specific primers used in the methods of the invention include two or more modified nucleotides having cleavable groups. In some embodiments, the target-specific primers comprise at least one modified nucleotide having a cleavable group selected from methylguanine, 8-oxo-guanine, xanthine, hypoxanthine, 5,6-dihydrouracil, uracil, 5-methylcytosine, thymine-dimer, 7-methylguanosine, 8-oxo-deoxyguanosine, xanthosine, inosine, dihydrouridine, bromodeoxyuridine, uridine or 5-methylcytidine.

In some embodiments, target amplicons using the amplification methods (and associated compositions, systems, and kits) disclosed herein, are used in the preparation of an immune receptor repertoire library. In some embodiments, the immune receptor repertoire library includes introducing adapter sequences to the termini of the target amplicon sequences. In certain embodiments, a method for preparing an immune receptor repertoire library includes generating target immune receptor amplicon molecules according to any of the multiplex amplification methods described herein, treating the amplicon molecule by digesting a modified nucleotide within the amplicon molecules' primer sequences, and ligating at least one adapter to at least one of the treated amplicon molecules, thereby producing a library of adapter-ligated target immune receptor amplicon molecules comprising the target immune receptor repertoire. In some embodiments, the steps of preparing the library are carried out in a single reaction vessel involving only addition steps. In certain embodiments, the method further includes clonally amplifying a portion of the at least one adapter-ligated target amplicon molecule.

In some embodiments, target amplicons using the methods (and associated compositions, systems, and kits) disclosed herein, are coupled to a downstream process, such as but not limited to, library preparation and nucleic acid sequencing. For example, target amplicons can be amplified using bridge amplification, emulsion PCR or isothermal amplification to generate a plurality of clonal templates suitable for nucleic acid sequencing. In some embodiments, the amplicon library is sequenced using any suitable DNA sequencing platform such as any next generation sequencing platform, including semi-conductor sequencing technology such as the Ion Torrent sequencing platform. In some embodiments, an amplicon library is sequenced using an Ion Torrent S5 520™ System or an Ion Torrent S5 530™ System or an Ion Torrent PGM 318™ System. In some embodiments, an amplicon library is sequenced using an Ion Torrent S5 540™ System.

In some embodiments, sequencing of immune receptor amplicons generated using the methods (and associated compositions and kits) disclosed herein, produces contiguous sequence reads from about 200 to about 600 nucleotides in length. In some embodiments, contiguous read lengths are from about 300 to about 400 nucleotides. In some embodiments, contiguous read lengths are from about 350 to about 450 nucleotides. In some embodiments, read lengths average about 300 nucleotides, about 350 nucleotides, or about 400 nucleotides. In some embodiments, contiguous read lengths are from about 250 to about 350 nucleotides, about 275 to about 340, or about 295 to about 325 nucleotides in length. In some embodiments, read lengths average about 270, about 280, about 290, about 300, or about 325 nucleotides in length. In other embodiments, contiguous read lengths are from about 180 to about 300 nucleotides, about 200 to about 290 nucleotides, about 225 to about 280 nucleotides, or about 230 to about 250 nucleotides in length. In some embodiments, read lengths average about 200, about 220, about 230, about 240, or about 250 nucleotides in length. In other embodiments, contiguous read lengths are from about 70 to about 200 nucleotides, about 80 to about 150 nucleotides, about 90 to about 140 nucleotides, or about 100 to about 120 nucleotides in length. In some embodiments, contiguous read lengths are from about 50 to about 170 nucleotides, about 60 to about 160 nucleotides, about 60 to about 120 nucleotides, about 70 to about 100 nucleotides, about 70 to about 90 nucleotides, or about 80 nucleotides in length. In some embodiments, read lengths average about 70, about 80, about 90, about 100, about 110, or about 120 nucleotides. In some embodiments, the sequence read length include the amplicon sequence and a barcode sequence. In some embodiments, the sequence read length does not include a barcode sequence.

In some embodiments, the amplification primers and primer pairs are target-specific sequences that can amplify specific regions of a nucleic acid molecule. In some embodiments, the target-specific primers can amplify expressed RNA or cDNA. In some embodiments, the target-specific primers can amplify mammalian RNA, such as human RNA or cDNA prepared therefrom, or murine RNA or cDNA prepared therefrom.

In methods and compositions provided herein, for example those for determining, characterizing, and/or tracking the immune repertoire in a biological sample, the amount of input RNA required for amplification of target sequences will depend in part on the fraction of immune receptor bearing cells (e.g., T cells or B cells) in the sample. For example, a higher fraction of T cells in the sample, such as samples enriched for T cells, permits use of a lower amount of input RNA for amplification. In some embodiments, the amount of input RNA for amplification of one or more target sequences can be about 0.05 ng to about 10 micrograms. In some embodiments, the amount of input RNA used for multiplex amplification of one or more target sequences can be from about 5 ng to about 2 micrograms. In some embodiments, the amount of RNA used for multiplex amplification of one or more target sequences can be from about 5 ng to about 1 microgram or about 10 ng to about 1 microgram. In some embodiments, the amount of RNA used for multiplex amplification of one or more immune repertoire target sequences is about 1.5 micrograms, about 2 micrograms, about 2.5 micrograms, about 3 micrograms, about 3.5 micrograms, about 4.0 micrograms, about 5 micrograms, about 6 micrograms, about 7 micrograms, or about 10 micrograms. In some embodiments, the amount of RNA used for multiplex amplification of one or more immune repertoire target sequences is about 10 ng, about 25 ng, about 50 ng, about 100 ng, about 200 ng, about 250 ng, about 500 ng, about 750 ng, or about 1000 ng. In some embodiments, the amount of RNA used for multiplex amplification of one or more immune repertoire target sequences is from about 25 ng to about 500 ng RNA or from about 50 ng to about 200 ng RNA. In some embodiments, the amount of RNA used for multiplex amplification of one or more immune repertoire target sequences is from about 0.05 ng to about 10 ng RNA, from about 0.1 ng to about 5 ng RNA, from about 0.2 ng to about 2 ng RNA, or from about 0.5 ng to about 1 ng RNA. In some embodiments, the amount of RNA used for multiplex amplification of one or more immune repertoire target sequences is about 0.05 ng, about 0.1 ng, about 0.2 ng, about 0.5 ng, about 1.0 ng, about 2.0 ng, or about 5.0 ng.

As described herein, RNA from a biological sample is converted to cDNA, typically using reverse transcriptase in a reverse transcription reaction, prior to the multiplex amplification. In some embodiments, a reverse transcription reaction is performed with the input RNA and a portion of the cDNA from the reverse transcription reaction is used in the multiplex amplification reaction. In some embodiments, substantially all of the cDNA prepared from the input RNA is added to the multiplex amplification reaction. In other embodiments, a portion, such as about 80%, about 75%, about 66%, about 50%, about 33%, or about 25% of the cDNA prepared from the input RNA is added to the multiplex amplification reaction. In other embodiments, about 15%, about 10%, about 8%, about 6%, or about 5% of the cDNA prepared from the input RNA is added to the multiplex amplification reaction.

In some embodiments, the amount of cDNA from a sample added to the multiplex amplification reaction can be about 0.001 ng to about 5 micrograms. In some embodiments, the amount of cDNA used for multiplex amplification of one or more immune repertoire target sequences can be from about 0.01 ng to about 2 micrograms. In some embodiments, the amount of cDNA used for multiplex amplification of one or more target sequences can be from about 0.1 ng to about 1 microgram or about 1 ng to about 0.5 microgram. In some embodiments, the amount of cDNA used for multiplex amplification of one or more immune repertoire target sequences is about 0.5 ng, about 1 ng, about 5 ng, about 10 ng, about 25 ng, about 50 ng, about 100 ng, about 200 ng, about 250 ng, about 500 ng, about 750 ng, or about 1000 ng. In some embodiments, the amount of cDNA used for multiplex amplification of one or more immune repertoire target sequences is from about 0.01 ng to about 10 ng cDNA, from about 0.05 ng to about 5 ng cDNA, from about 0.1 ng to about 2 ng cDNA, or from about 0.01 ng to about 1 ng cDNA. In some embodiments, the amount of cDNA used for multiplex amplification of one or more immune repertoire target sequences is about 0.005 ng, about 0.01 ng, about 0.05 ng, about 0.1 ng, about 0.2 ng, about 0.5 ng, about 1.0 ng, about 2.0 ng, or about 5.0 ng.

In some embodiments, mRNA is obtained from a biological sample and converted to cDNA for amplification purposes using conventional methods. Methods and reagents for extracting or isolating nucleic acid from biological samples are well known and commercially available. In some embodiments, RNA extraction from biological samples is performed by any method described herein or otherwise known to those of skill in the art, e.g., methods involving proteinase K tissue digestion and alcohol-based nucleic acid precipitation, treatment with DNAse to digest contaminating DNA, and RNA purification using silica-gel-membrane technology, or any combination thereof. Exemplary methods for RNA extraction from biological samples using commercially available kits including RecoverAll™ Multi-Sample RNA/DNA Workflow (Invitrogen), RecoverAll™ Total Nucleic Acid Isolation Kit (Invitrogen), NucleoSpin® RNA blood (Macherey-Nagel), PAXgene® Blood RNA system, TRI Reagent™ (Invitrogen), PureLink™ RNA Micro Scale kit (Invitrogen), MagMAX™ FFPE DNA/RNA Ultra Kit (Applied Biosystems) ZR RNA MicroPrep™ kit (Zymo Research), RNeasy Micro kit (Qiagen), and ReliaPrep™ RNA Tissue miniPrep system (Promega).

A sample or biological sample, as used herein, refers to a composition from an individual that contains or may contain cells related to the immune system. Exemplary biological samples, include without limitation, tissue (for example, lymph node, organ tissue, bone marrow), whole blood, synovial fluid, cerebral spinal fluid, tumor biopsy, and other clinical specimens containing cells. The sample may include normal and/or diseased cells and be a fine needle aspirate, fine needle biopsy, core sample, or other sample. In some embodiments, the biological sample may comprise hematopoietic cells, peripheral blood mononuclear cells (PBMCs), T cells, B cells, tumor infiltrating lymphocytes ("TILs") or other lymphocytes. In some embodiments, the sample may be fresh (e.g., not preserved), frozen, or formalin-fixed paraffin-embedded tissue (FFPE). Some samples comprise cancer cells, such as carcinomas, melanomas, sarcomas, lymphomas, myelomas, leukemias, and the like, and the cancer cells may be circulating tumor cells.

The biological sample can be a mix of tissue or cell types, a preparation of cells enriched for at least one particular category or type of cell, or an isolated population of cells of a particular type or phenotype. Samples can be separated by centrifugation, elutriation, density gradient separation, apheresis, affinity selection, panning, FACS, centrifugation with Hypaque, etc. prior to analysis. Methods for sorting, enriching for, and isolating particular cell types are well-known and can be readily carried out by one of ordinary skill. In some embodiments, the sample may a preparation enriched for T cells, for example CD3+ T cells.

In one aspect, the provided methods and systems include processes for identification and/or removing PCR or sequencing-derived error(s) from the determined immune receptor sequence.

In some embodiments, the error correction strategy includes the following steps:
1) Align the sequenced rearrangement to a reference database of variable, diversity and joining/constant genes to produce a query sequence/reference sequence pair. Many alignment procedures may be used for this purpose including, for example, IgBLAST, a freely-available tool from the NCBI, and custom computer scripts.
2) Realign the reference and query sequences to each other, taking into account the flow order used for sequencing. The flow order provides information that allows one to identify and correct some types of erroneous alignments.
3) Identify the borders of the CDR3 region by their characteristic sequence motifs.
4) Over the aligned portion of the rearrangement corresponding to the variable gene and joining/constant genes, excluding the CDR3 region, identify indels in the query with respect to the reference and alter the mismatching query base position so that it is consistent with the reference.
5) For the CDR3 region, if the CDR3 length is not a multiple of three (indicative of an indel error):
   (a) Search the CDR3 for the homopolymer stretch having the highest probability of containing a sequence error, based on PHRED score (denoted e).
   (b) Obtain the probability of error over the entire CDR3 region based on PHRED score (denoted t)
   (c) If e/t is greater than a defined threshold, edit the homopolymer by either increasing or decreasing the length of the homopolymer by one base such that the CDR3 nucleotide length is a multiple of three.
   (d) As an alternative to steps a-c, search the CDR3 for the longest homopolymer, and if the length of the homopolymer is above a defined threshold, edit the homopolymer by either increasing or decreasing the length of the homopolymer by one base such that the CDR3 nucleotide length is a multiple of three.

Figure 2:
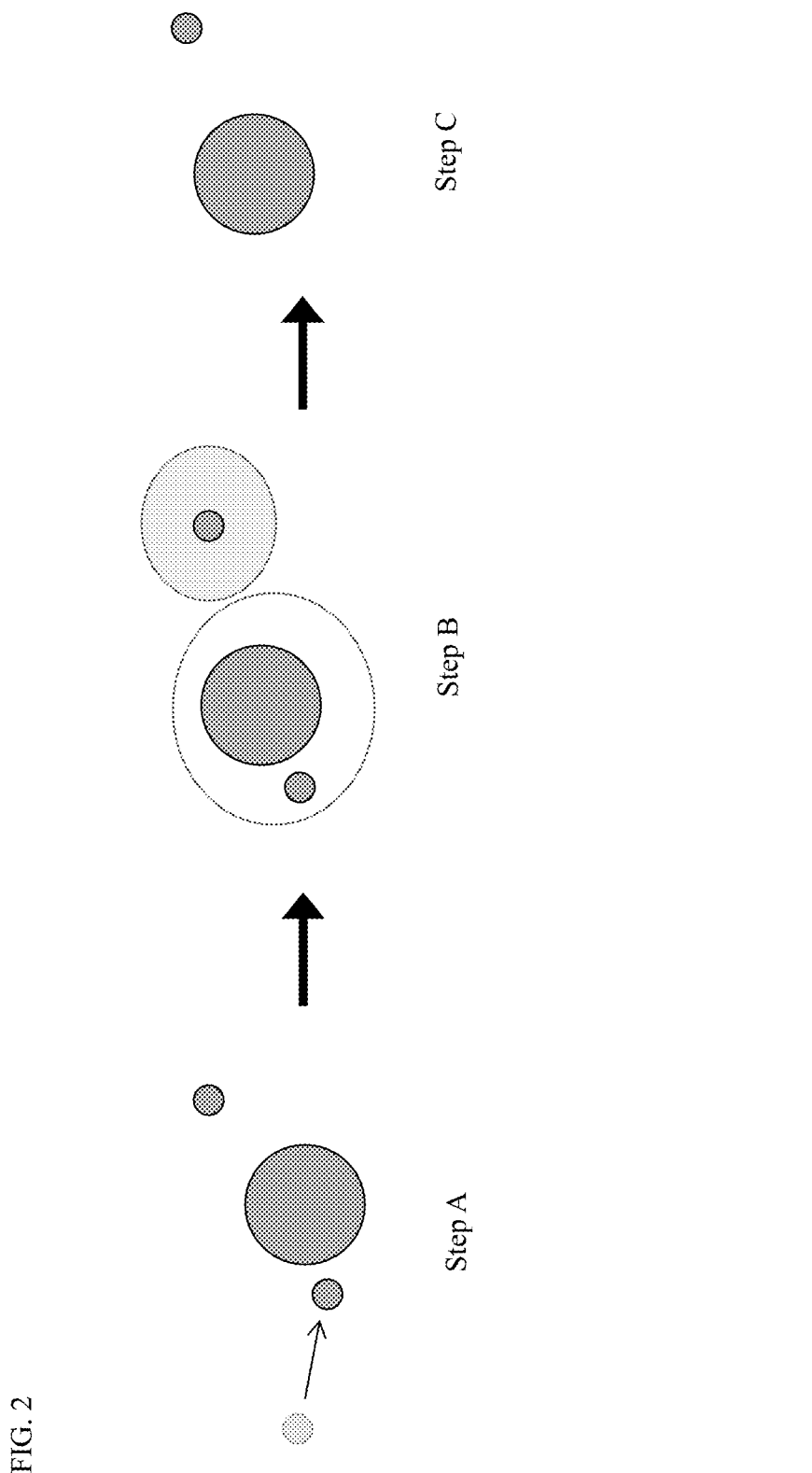
FIG. 2 is a diagram of an exemplary workflow for removal of residual insertion/deletion (indel) error by comparing homopolymer collapsed CDR3 sequences using Levenshtein distance with the steps: (A) collapse homopolymers and calculate Levenshtein distances between cluster representatives; (b) merge reads that now cluster together, these represent complex indel errors; (C) report lineages to user.

In some embodiments, methods are provided to identify T cell or B cell clones in repertoire data that are robust to PCR and sequencing error. Accordingly, the following describes steps that may be employed in such methods to identify T cell or B cell clones in a manner that is robust to PCR and sequencing error. Table 1 in FIG. 10 is a diagram of an exemplary workflow for use in identifying and removing PCR or sequencing-derived errors from immune receptor sequencing data. Exemplary portions and embodiments of this workflow are also represented in FIGS. 1-2.

For a set of TCR or BCR sequences derived from mRNA, where 1) each sequence has been annotated as a productive rearrangement, either natively or after error correction, such as previously described, and 2) each sequence has an identified V gene and CDR3 nucleotide region, in some embodiments, methods include the following:
1) Identify and exclude chimeric sequences. For each unique CDR3 nucleotide sequence present in the dataset, tally the number of reads having that CDR3 nucleotide sequence and any of the possible V genes. Any V gene-CDR3 combination making up less than 10% of total reads for that CDR3 nucleotide sequence is flagged as a chimera and eliminated from downstream analyses. As an example, for the sequences below having the same CDR3 nucleotide sequence, e.g., the sequences having TRBV3 and TRBV6 paired with CDR3nt sequence AATTGGT will be flagged as chimeric.

| V gene | CDR3nt | Read counts |
|--------|--------|-------------|
| TRBV2  | AATTGGT | 1000 |
| TRBV3  | AATTGGT | 10 |
| TRBV6  | AATTGGT | 3 |

2) Identify and exclude sequences containing simple indel errors. For each read in the dataset, obtain the homopolymer-collapsed representation of the CDR3 sequence of that read. For each set of reads having the same V gene and collapsed-CDR3 combination, tally the number of occurrences of each non-collapsed CDR3 nucleotide sequence. Any non-collapsed CDR3 sequence making up <10% of total reads for that read set is flagged as having a simple homopolymer error. As an example, three different V gene-CDR3 nucleotide sequences are presented that are identical after homopolymer collapsing of the CDR3 nucleotide sequence. The two less frequent V gene-CDR3 combinations make up <10% of total reads for the read set and will be flagged as containing a simple indel error. For example:

| V gene | CDR3nt | Homopolymer collapsed CDR3nt | Read counts |
|--------|--------|------------------------------|-------------|
| TRBV2 | AATTGGT | ATGT | 1000 |
| TRBV2 | AAATGGT | ATGT | 10 |
| TRBV2 | AAAATTTGGT (SEQ ID NO: 521) | ATGT | 3 |

3) Identify and exclude singleton reads. For each read in the dataset, tally the number of times that the exact read sequence is found in the dataset. Reads that appear only once in the dataset will be flagged as singleton reads.
4) Identify and exclude truncated reads. For each read in the dataset, determine whether the read possesses an annotated V gene FR1, CDR1, FR2, CDR2, and FR3 region, as indicated by the IgBLAST alignment of the read to the IgBLAST reference V gene set. Reads that do not possess the above regions are flagged as truncated if the region(s) is expected based on the particular V gene primer used for amplification.
5) Identify and exclude rearrangements lacking bidirectional support. For each read in the dataset, obtain the V gene and CDR3 sequence of the read as well as the strand orientation of the read (plus or minus strand). For each V gene-CDR3 combination in the dataset, tally the number of plus and minus strand reads having that V gene-CDR3nt combination. V gene-CDR3nt combinations that are only present in reads of one orientation will be deemed to be a spurious. All reads having a spurious V gene-CDR3nt combination will be flagged as lacking bidirectional support.
6) For genes that have not been flagged, perform stepwise clustering based on CDR3 nucleotide similarity. Separate the sequences into groups based on the V gene identity of the read, excluding allele information (v-gene groups). For each group:

a. Arrange reads in each group into clusters using cd-hit-est and the following parameters:
cd-hit-est -i vgene_groups.fa -o clustered_vgene_groups.cdhit -T 24 -d 0 -M 100000 -B 0 -r 0 -g 1 -S-U 2-uL 0.05 -n 10-1 7
Where vgene_groups.fa is a fasta format file of the CDR3 nucleotide regions of sequences having the same V gene and clustered_vgene_groups.cdhit is the output, containing the subdivided sequences.
b. Assign each sequence in a cluster the same clone ID, used to denote that members of the subgroup are believed to represent the same T cell clone or B cell clone.
c. Chose a representative sequence for each cluster, such that the representative sequence is the sequence that appears the greatest number of times, or, in cases of a tie, is randomly chosen.
d. Merge all other reads in the cluster into the representative sequence such that the number of reads for the representative sequence is increased according to the number of reads for the merged sequences.
e. Compare the representative sequences within a v-gene group to each other on the basis of hamming distance. If a representative sequence is within a hamming distance of 1 to a representative sequence that is >50 times more abundant, merge that sequence into the more common representative sequence. If a representative sequence is within a hamming distance of 2 to a representative sequence that is >10000 times more abundant, merge that sequence into the more common representative sequence.
f. Identify complex sequence errors. Homopolymer-collapse the representative sequences within each V gene group, then compare to each other using Levenshtein distances. If a representative sequence is within a Levenshtein distance of 1 to a representative sequence that is >50 times more abundant, merge that sequence into the more common representative sequence.
g. Identify CDR3 misannotation errors. Homopolymer-collapse the representative sequences within each V gene group, then perform a pairwise comparison of each homopolymer-collapsed sequence. For each pair of sequences, determine whether one sequence is a subset of the other sequence. If so, merge the less abundant sequence into the more abundant sequence if the more abundance sequence is >500 fold more abundant.

7) Report cluster representatives to user.

An example of the performance of this workflow on a test dataset is presented in the Examples and in FIG. 3 and Table 7. Using the same dataset, the performance of this workflow was compared to that of three academic software packages: IMSEQ, MiXCR, and RTCR. The academic packages report many artifactual lineages, and in the case of MiXCR, three of the 10 plasmid CDR3 sequences are incorrectly reported. As demonstrated herein, the presently provided workflow yields far fewer clonotypes than the other packages and far closer to the true number of clonotypes present in the library. The presently provided workflow also provides the highest read assignment accuracy.

In some embodiments, the provided workflow is not limited to the frequency ratios listed in the various steps, and other frequency ratios may be substituted for the representative ratios included above. For example, in some embodiments, comparing the representative sequences within a v-gene group to each other on the basis of hamming distance may use a frequency ratio other than those listed in step (e) above. For example and without limitation, frequency ratios of 1000, 5000, 20,000, etc may be used if a representative sequence is within a hamming distance of 2 to a representative sequence. For example and without limitation, frequency ratios of 20, 100, 200, etc may be used if a representative sequence is within a hamming distance of 1 to a representative sequence. The frequency ratios provided are representative of the general process of labeling the more abundant sequence of a similar pair as a correct sequence.

Similarly, when comparing the frequencies of two sequences at other steps in the workflow, eg, step (1), step (2), step (6f) and step (6g), frequency ratios other than those listed in the step above may be used.

As used herein, the term "homopolymer-collapsed sequence" is intended to represent a sequence where repeated bases are collapsed to a single base representative. As an example, for the non-collapsed sequence AAAAT-TTTTATCCCCCCCCGGG (SEQ ID NO: 522), the homopolymer-collapsed sequence is ATATCG.

As used herein, the terms "clone," "clonotype," "lineage," or "rearrangement" are intended to describe a unique V gene nucleotide combination for an immune receptor, such as a TCR or BCR. For example, a unique V gene-CDR3 nucleotide combination.

As used herein, the term "productive reads" refers to a TCR or BCR sequence reads that have no stop codon and have in-frame variable gene and joining gene segments. Productive reads are biologically plausible in coding for a polypeptide.

As used herein, "chimeras" or chimeric sequences" refer to artefactual sequences that arise from template switching during target amplification, such as PCR. Chimeras typically present as a CDR3 sequence grafted onto an unrelated V gene, resulting in a CDR3 sequence that is associated with multiple V genes within a dataset. The chimeric sequence is usually far less abundant than the true sequence in the dataset.

As used herein, the term "indel" refers to an insertion and/or deletion of one or more nucleotide bases in a nucleic acid sequence. In coding regions of a nucleic acid sequence, unless the length of an indel is a multiple of 3, it will produce a frameshift when the sequence is translated. As used herein, "simple indel errors" are errors that do not alter the homopolymer-collapsed representation of the sequence. As used herein, "complex indel errors" are indel sequencing errors that alter the homopolymer-collapsed representation of the sequence and include, without limitation, errors that eliminate a homopolymer, insert a homopolymer into the sequence, or create a dyslexic-type error.

As used herein, "singleton reads" refer to sequence reads whose indel-corrected sequence appears only once in a dataset. Typically, singleton reads are enriched for reads containing a PCR or sequencing error.

As used herein, "truncated reads" refer to immune receptor sequence reads that are missing annotated V gene regions. For example, truncated reads include, without limitation, sequence reads that are missing annotated TCR or BCR V gene FR1, CDR1, FR2, CDR2, or FR3 regions. Such reads typically are missing a portion of the V gene sequence due to quality trimming. Truncated reads can give rise to artifacts if the truncation leads one to misidentify the V gene.

In the context of identified V gene-CDR3 sequences (clonotypes), "bidirectional support" indicates that a particular V gene-CDR3 sequence is found in at least one read that maps to the plus strand (proceeding from the V gene to constant gene) and at least one reads that maps to the minus strand (proceeding form the constant gene to the V gene). Systematic sequencing errors often lead to identification of V gene-CDR3 sequences having unidirectional support.

For a set of sequences that have been grouped according to a predetermined sequence similarity threshold to account for variation due to PCR or sequencing error, the "cluster representative" is the sequence that is chosen as most likely to be error free. This is typically the most abundant sequence.

As used herein, "IgBLAST annotation error" refers to rare events where the border of the CDR3 is identified to be in an incorrect adjacent position. These events typically add three bases to the 5' or 3' end of a CDR3 nucleotide sequence.

For two sequences of equal length, the "Hamming distance" is the number of positions at which the corresponding bases are different. For any two sequences, the "Levenshtein distance" or the "edit distance" is the number of single base edits required to make one sequence into another sequence.

In some embodiments in which J gene-directed primers are used in amplification of the immune receptor sequences, for example multiplex amplification with primers directed to V gene FR3 regions and primers directed to J genes, raw sequence reads derived from the assay undergo a J gene sequence inference process before any downstream analysis. In this process, the beginning and end of raw read sequences are interrogated for the presence of characteristic sequences of 10-30 nucleotides corresponding to the portion of the J gene sequences expected to exist after amplification with the J primer and any subsequent manipulation or processing (for example, digestion) of the amplicon termini prior to sequencing. The characteristic nucleotide sequences permit one to infer the sequence of the J primer, as well as the remaining portion of the J gene that was targeted since the sequence of each J gene is known. To complete the J gene sequence inference process, the inferred J gene sequence is added to the raw read to create an extended read that then spans the entire J gene. The extended read then contains the entire J gene sequence, the entire sequence of the CDR3 region, and at least a portion of the V gene sequence, which will be reported after downstream analysis. The portion of V gene sequence in the extended read will depend on the V gene-directed primers used for the multiplex amplification, for example, FR3-, FR2-, or FR1-directed primers.

Use of V gene FR3 and J gene primers to amplify expressed immune receptor sequences yields a minimum length amplicon (for example, about 60-100 or about 80 nucleotides in length) while still producing data that allows for reporting of the entire CDR3 region. With the expectation of short amplicon length, reads of amplicons <100 nucleotides in length are not eliminated as low-quality and/or off target products during the sequence analysis workflow. However, the explicit search for the expected J gene sequences in the raw reads allows one to eliminate amplicons deriving from off-target amplifications by the J gene primers. In addition, this short amplicon length improves the performance of the assay on highly degraded template material, such as that derived from an FFPE sample.

In some embodiments, provided methods comprise sequencing an immune receptor library and subjecting the obtained sequence data to error identification and correction processes to generate rescued productive reads, and identifying productive and rescued productive sequence reads. In some embodiments, provided methods comprise sequencing an immune receptor library and subjecting the obtained sequence dataset to error identification and correction processes, identifying productive and rescued productive sequence reads, and grouping the sequence reads by clonotype to identify immune receptor clonotypes in the library.

In some embodiments, the provided error identification and correction workflow is used for identifying and resolving PCR or sequencing-derived errors that lead to a sequence read being identified as from an unproductive rearrangement. In some embodiments, the provided error identification and correction workflow is applied to immune receptor sequence data generated from a sequencing platform in which indel or other frameshift-causing errors occur while generating the sequence data.

In some embodiments, the provided error identification and correction workflow is applied to sequence data generated by an Ion Torrent sequencing platform. In some embodiments, the provided error identification and correction workflow is applied to sequence data generated by Roche 454 Life Sciences sequencing platforms, PacBio sequencing platforms, and Oxford Nanopore sequencing platforms.

In some embodiments, provided methods comprise preparation and formation of a plurality of immune receptor-specific amplicons. In some embodiments, the method comprises hybridizing a plurality of V gene-specific primers and at least one C gene-specific primer to a cDNA molecule, extending a first primer (e.g., a V gene-specific primer) of the primer pair, denaturing the extended first primer from the cDNA molecule, hybridizing to the extended first primer product, a second primer (e.g., a C gene-specific primer) of the primer pair and extending the second primer, digesting the target-specific primer pairs to generate a plurality of target amplicons. In other embodiments, the method comprises hybridizing a plurality of V gene gene-specific primers and a plurality of J gene-specific primers to a cDNA molecule, extending a first primer (e.g., a V gene-specific primer) of the primer pair, denaturing the extended first primer from the cDNA molecule, hybridizing to the extended first primer product, a second primer (e.g., a J gene-specific primer) of the primer pair and extending the second primer, digesting the target-specific primer pairs to generate a plurality of target amplicons. In some embodiments, adapters are ligated to the ends of the target amplicons prior to performing a nick translation reaction to generate a plurality of target amplicons suitable for nucleic acid sequencing. In some embodiments, at least one of the ligated adapters includes at least one barcode sequence. In some embodiments, each adapter ligated to the ends of the target amplicons includes a barcode sequence. In some embodiments, the one or more target amplicons can be amplified using bridge amplification, emulsion PCR or isothermal amplification to generate a plurality of clonal templates suitable for nucleic acid sequencing.

In some embodiments, the disclosure provides methods for sequencing target amplicons and processing the sequence data to identify productive immune receptor rearrangements expressed in the biological sample from which the cDNA was derived. In embodiments in which J gene-directed primers are used to amplify the expressed immune receptor sequences, processing the sequence data includes inferring the nucleotide sequence of the J gene primer used for amplification as well as the remaining portion of the J gene that was targeted, as described herein. In some embodiments, processing the sequence data includes performing provided error identification and correction steps to generate rescued productive sequences. In some embodiments, use of the provided error identification and correction workflow can result in a combination of productive reads and rescued productive reads being at least 50% of the sequencing reads for an immune receptor cDNA sample. In some embodiments, use of the provided error identification and correction workflow can result in a combination of productive reads and rescued productive reads being at least 60%, at least 70%, at least 80%, at least 90%, or at least 95% of the sequencing reads for an immune receptor cDNA sample. In some embodiments, use of the provided error identification and correction workflow can result in a combination of productive reads and rescued productive reads being about 50-60%, about 60-70%, about 70-80%, about 80-90%, about 50-80%, or about 60-90% of the sequencing reads for an immune receptor cDNA sample. In some embodiments, use of the provided error identification and correction workflow can result in a combination of productive reads and rescued productive reads averaging about 50%, about 55%, about 60%, about 65%, about 70%, about 75%, about 80%, about 85%, about 90% of the sequencing reads for an immune receptor cDNA sample.

With particular samples, the provided error identification and correction workflow can result in a combination of productive reads and rescued productive reads being less than 50% of the sequencing reads for an immune receptor cDNA sample when particular samples are used. Such samples include, for example, those in which the RNA is highly degraded such as FFPE samples, and those in which the number of target immune cells is very low such as, for example, samples with very low T cell count or samples from subjects experiencing severe leukopenia. Accordingly, in some embodiments, use of the provided error identification and correction workflow can result in a combination of productive reads and rescued productive reads being about 30-50%, about 40-50%, about 30-40%, about 40-60%, at least 30%, or at least 40% of the sequencing reads for an immune receptor cDNA sample.

In certain embodiments, methods of the invention comprise the use of target immune receptor primer sets wherein the primers are directed to sequences of the same target immune receptor gene. Immune receptors are selected from T cell receptors and antibody receptors. In some embodiments a T cell receptor is a T cell receptor selected from the group consisting of TCR alpha, TCR beta, TCR gamma, and TCR delta. In some embodiments the immune receptor is an antibody receptor selected from the group consisting of heavy chain alpha, heavy chain delta, heavy chain epsilon, heavy chain gamma, heavy chain mu, light chain kappa, and light chain lambda.

In certain embodiments, provided is a method for amplification of expression nucleic acid sequences of an immune receptor repertoire in a sample, comprising performing a multiplex amplification reaction to amplify immune receptor nucleic acid template molecules having a constant portion and a variable portion using at least one set of: i) a plurality of V gene primers directed to a majority of different V genes of an immune receptor coding sequence comprising at least a portion of a framework region within the V gene, and ii) one or more C gene primers directed to at least a portion of the respective target constant gene of the immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region.

In certain embodiments, provided is a method for amplification of expression nucleic acid sequences of an immune receptor repertoire in a sample, comprising performing a multiplex amplification reaction to amplify immune receptor nucleic acid template molecules having a constant portion and a variable portion using at least one set of: i) a plurality of V gene primers directed to a majority of different V genes of at least one immune receptor coding sequence comprising at least a portion of framework region 1 (FR1) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In some embodiments the one or more plurality of V gene primers of i) anneal to at least a portion of the framework region 1 of the template molecules. In certain embodiments the one or more C gene primers of ii) comprises at least two primers that anneal to at least a portion of the C gene portion of the template molecules. In particular embodiments at least one set of the generated amplicons includes complementarity determining regions CDR1, CDR2, and CDR3 of an immune receptor expression sequence. In some embodiments the amplicons are about 300 to about 600 nucleotides in length or at least about 350 to about 500 nucleotides in length. In some embodiments the nucleic acid template used in methods is cDNA produced by reverse transcribing nucleic acid molecules extracted from a biological sample.

In certain embodiments, methods are provided for providing sequence of the immune repertoire in a sample, comprising performing a multiplex amplification reaction to amplify immune receptor nucleic acid template molecules having a constant portion and a variable portion using at least one set of primers comprising i) a plurality of V gene primers directed to a majority of different V genes of at least one immune receptor coding sequence comprising at least a portion of framework region 1 (FR1) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence of the immune repertoire in the sample. In particular embodiments, determining the sequence of the immune receptor amplicon molecules includes obtaining initial sequence reads, aligning the initial sequence read to a reference sequence and identifying a productive reads, correcting one or more indel errors to generate rescued productive sequence reads; and determining the sequences of the resulting immune receptor molecules. In particular embodiments the combination of productive reads and rescued productive reads is at least 50%, at least 60% at least 70% or at least 75% of the sequencing reads for the immune receptors. In additional embodiments the method further comprises sequence read clustering and immune receptor clonotype reporting. In some embodiments, the sequences of the identified immune repertoire are compared to a contemporaneous or current version of the IMGT database and the sequence of at least one allelic variant absent from that IMGT database is identified. In some embodiments the average sequence read length is between 300 and 600 nucleotides, or is between 350 and 550 nucleotides, or is between 330 and 425 nucleotides, or is about 350 to about 425 nucleotides, depending in part on inclusion of any barcode sequence in the read length. In certain embodiments at least one set of the sequenced amplicons includes complementarity determining regions CDR1, CDR2, and CDR3 of an immune receptor expression sequence.

In particular embodiments, methods provided utilize target immune receptor primer sets comprising V gene primers wherein the one or more of a plurality of V gene primers are directed to sequences over an FR1 region about 70 nucleotides in length. In other particular embodiments the one or more of a plurality of V gene primers are directed to sequences over an FR1 region about 50 nucleotides in length. In certain embodiments a target immune receptor primer set comprises V gene primers comprising about 45 to about 90 different FR1-directed primers. In some embodiments a target immune receptor primer set comprises V gene primers comprising about 50 to about 80 different FR1-directed primers. In some embodiments a target immune receptor primer set comprises V gene primers comprising about 55 to about 75 different FR1-directed primers. In some embodiments a target immune receptor primer set comprises V gene primers comprising about 60 to about 70 different FR1-directed primers. In some embodiments the target immune receptor primer set comprises one or more C gene primers. In particular embodiments a target immune receptor primer set comprises at least two C gene primers wherein each is directed to at least a portion of the same 50 nucleotide region within the target C gene.

In particular embodiments, methods of the invention comprise use of at least one set of primers comprising V gene primers i) and C gene primers ii) selected from Tables 2 and 4, respectively. In other certain embodiments methods of the invention comprise use of at least one set of primers i) and ii) comprising primers selected from SEQ ID NOs: 1-89 and 181-184 or selected from SEQ ID NOs: 90-180 and 181-184. In some embodiments methods of the invention comprise use of at least one set of primers i) and ii) comprising primers selected from SEQ ID NOs: 90-155 and 181-182 or selected from SEQ ID NOs: 90-155 and 183-184. In some embodiments methods of the invention comprise use of at least one set of primers i) and ii) comprising primers selected from SEQ ID NOs: 1-89 and 181-182 or selected from SEQ ID NOs: 1-89 and 183-184. In some embodiments methods of the invention comprise use of at least one set of primers i) and ii) comprising primers selected from SEQ ID NOs: 90-180 and 181-182 or selected from SEQ ID NOs: 90-180 and 183-184. In other certain embodiments methods of the invention comprise use of at least one set of primers i) and ii) comprising primers SEQ ID NOs: 1-64 and 183-184. In other certain embodiments methods of the invention comprise use of at least one set of primers i) and ii) comprising primers SEQ ID NOs: 1-64 and 181-182. In still other certain embodiments methods of the invention comprise use of at least one set of primers of i) and ii) comprising primers SEQ ID NOs: 90-153 and 181-182. In certain embodiments methods of the invention comprise use of at least one set of primers i) and ii) comprising primers SEQ ID NOs: 90-92, 95-155, and 181-182 or at least one set of primers i) and ii) comprising primers SEQ ID NOs: 90-92, 95-155, and 183-184. In still other certain embodiments methods of the invention comprise use of at least one set of primers of i) and ii) comprising primers SEQ ID NOs: 90-153 and 183-184. In still other certain embodiments methods of the invention comprise use of at least one set of primers of i) and ii) comprising primers SEQ ID NOs: 90-92, 95-180, and 181-182. In still other certain embodiments methods of the invention comprise use of at least one set of primers of i) and ii) comprising primers SEQ ID NOs: 90-92, 95-180, and 183-184.

In some embodiments methods of the invention comprise the use of at least one set of primers i) and ii) comprising at least 50 primers selected from SEQ ID NOs: 1-89 and at least one primer selected from SEQ ID NOs: 181-182. In other embodiments methods of the invention comprise the use of at least one set of primers i) and ii) comprising at least 50 primers selected from SEQ ID NOs: 1-89 and at least one primer selected from SEQ ID NOs: 183-184. In some embodiments methods of the invention comprise the use of at least one set of primers i) and ii) comprising at least 60 primers selected from SEQ ID NOs: 1-89 and at least one primer selected from SEQ ID NOs: 181-182. In other embodiments methods of the invention comprise the use of at least one set of primers i) and ii) comprising at least 60 primers selected from SEQ ID NOs: 1-89 and at least one primer selected from SEQ ID NOs: 183-184.

In some embodiments methods of the invention comprise the use of at least one set of primers i) and ii) comprising at least 50 primers selected from SEQ ID NOs: 90-180 and at least one primer selected from SEQ ID NOs: 181-182. In other embodiments methods of the invention comprise the use of at least one set of primers i) and ii) comprising at least 50 primers selected from SEQ ID NOs: 90-180 and at least one primer selected from SEQ ID NOs: 183-184. In some embodiments methods of the invention comprise the use of at least one set of primers i) and ii) comprising at least 60 primers selected from SEQ ID NOs: 90-180 and at least one primer selected from SEQ ID NOs: 181-182. In other embodiments methods of the invention comprise the use of at least one set of primers i) and ii) comprising at least 60 primers selected from SEQ ID NOs: 90-180 and at least one primer selected from SEQ ID NOs: 183-184.

In certain embodiments, provided is a method for amplification of expression nucleic acid sequences of an immune receptor repertoire in a sample, comprising performing a multiplex amplification reaction to amplify immune receptor nucleic acid template molecules having a constant portion and a variable portion using at least one set of: i) a plurality of V gene primers directed to a majority of different V genes of at least one immune receptor coding sequence comprising at least a portion of framework region 3 (FR3) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In more particular embodiments the one or more plurality of V gene primers of i) are directed to sequences over about a 40 to about a 60 nucleotide portion of the framework region. In some embodiments the one or more plurality of V gene primers of i) anneal to at least a portion of the framework 3 region of the template molecules. In certain embodiments the one or more C gene primers of ii) comprises at least two primers that anneal to at least a portion of the C gene of the template molecules. In particular embodiments at least one set of the generated amplicons includes complementarity determining region CDR3 of an immune receptor expression sequence. In some embodiments the amplicons are about 80 to about 200 nucleotides in length, about 80 to about 140 nucleotides in length, about 90 to about 130 nucleotides in length or at least about 100 to about 120 nucleotides in length. In some embodiments the nucleic acid template used in methods is cDNA produced by reverse transcribing nucleic acid molecules extracted from a biological sample.

In certain embodiments, methods are provided for providing sequence of the immune repertoire in a sample, comprising performing a multiplex amplification reaction to amplify immune receptor nucleic acid template molecules having a constant portion and a variable portion using at least one set of primers comprising i) a plurality of V gene primers directed to a majority of different V genes of at least one immune receptor coding sequence comprising at least a portion of framework region 3 (FR3) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence of the immune repertoire in the sample. In particular embodiments, determining the sequence of the immune receptor amplicon molecules includes obtaining initial sequence reads, aligning the initial sequence read to a reference sequence and identifying a productive reads, correcting one or more indel errors to generate rescued productive sequence reads; and determining the sequences of the resulting immune receptor molecules. In particular embodiments the combination of productive reads and rescued productive reads is at least 50%, at least 60% at least 70% or at least 75% of the sequencing reads for the immune receptors. In additional embodiments the method further comprises sequence read clustering and immune receptor clonotype reporting. In some embodiments, the sequences of the identified immune repertoire are compared to a contemporaneous or current version of the IMGT database and the sequence of at least one allelic variant absent from that IMGT database is identified. In some embodiments the average sequence read length is between 80 and 185 nucleotides, is between 115 and 200 nucleotides, is between 90 and 130 nucleotides, or is between about 100 and about 120 nucleotides, depending in part on inclusion of any barcode sequence in the read length. In certain embodiments at least one set of the sequenced amplicons includes complementarity determining region CDR3 of an immune receptor expression sequence.

In certain embodiments, methods provided utilize target immune receptor primer sets comprising V gene primers wherein the one or more of a plurality of V gene primers are directed to sequences over an FR3 region about 70 nucleotides in length. In particular embodiments, methods provided utilize target immune receptor primer sets comprising V gene primers wherein the one or more of a plurality of V gene primers are directed to sequences over an FR3 region about 50 nucleotides in length. In other particular embodiments the one or more of a plurality of V gene primers are directed to sequences over an FR3 region about 40 to about 60 nucleotides in length. In certain embodiments a target immune receptor primer set comprises V gene primers comprising about 45 to about 80 different FR3-directed primers. In certain embodiments a target immune receptor primer set comprises V gene primers comprising about 50 to about 70 different FR3-directed primers. In some embodiments, a target immune receptor primer set comprises V gene primers comprising about 55 to about 65 different FR3-directed primers. In some embodiments, a target immune receptor primer set comprises V gene primers comprising about 58, 59, 60, 61, or 62 different FR3-directed primers. In some embodiments the target immune receptor primer set comprises one or more C gene primers. In particular embodiments a target immune receptor primer set comprises at least two C gene primers wherein each is directed to at least a portion of the same 50 nucleotide region within the target C gene.

In particular embodiments, methods of the invention comprise the use of at least one set of primers comprising V gene primers i) and C gene primers ii) selected from Tables 3 and 4, respectively. In other certain embodiments methods of the invention comprise the use of at least one set of primers i) and ii) comprising primers selected from SEQ ID NOs: 185-248 and 181-184 or selected from SEQ ID NOs: 249-312 and 181-184. In some embodiments methods of the invention comprise the use of at least one set of primers i) and ii) comprising primers selected from SEQ ID NOs: 185-248 and 183-184 or selected from SEQ ID NOs: 185-248 and 181-182. In other certain embodiments methods of the invention comprise the use of at least one set of primers i) and ii) comprising primers SEQ ID NOs: 185-243 and 183-184. In other certain embodiments methods of the invention comprise the use of at least one set of primers i) and ii) comprising primers SEQ ID NOs: 185-243 and 181-182. In other certain embodiments methods of the invention comprise the use of at least one set of primers of i) and ii) comprising primers selected from SEQ ID NOs: 249-312 and 181-182 or selected from SEQ ID NOs: 249-312 and 183-184. In still other certain embodiments methods of the invention comprise the use of at least one set of primers of i) and ii) comprising primers SEQ ID NOs: 249-307 and 181-182. In still other certain embodiments methods of the invention comprise use of at least one set of primers of i) and ii) comprising primers SEQ ID NOs: 249-307 and 183-184.

In some embodiments methods of the invention comprise the use of at least one set of primers i) and ii) comprising at least 50 primers selected from SEQ ID NOs: 249-312 and at least one primer selected from SEQ ID NOs: 181-182. In other embodiments methods of the invention comprise the use of at least one set of primers i) and ii) comprising at least 50 primers selected from SEQ ID NOs: 249-312 and at least one primer selected from SEQ ID NOs: 183-184. In some embodiments methods of the invention comprise the use of at least one set of primers i) and ii) comprising at least 50 primers selected from SEQ ID NOs: 185-248 and at least one primer selected from SEQ ID NOs: 181-182. In other embodiments methods of the invention comprise the use of at least one set of primers i) and ii) comprising at least 50 primers selected from SEQ ID NOs: 185-248 and at least one primer selected from SEQ ID NOs: 183-184.

In certain embodiments, provided is a method for amplification of expression nucleic acid sequences of an immune receptor repertoire in a sample, comprising performing a multiplex amplification reaction to amplify immune receptor nucleic acid template molecules having a constant portion and a V gene portion using at least one set of: i) a plurality of V gene primers directed to a majority of different V genes of at least one immune receptor coding sequence comprising at least a portion of framework region 2 (FR2) within the V gene, and ii) one or more C gene primers directed to at least a portion of the C gene of the respective immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In some embodiments the one or more plurality of V gene primers of i) anneal to at least a portion of the FR2 region of the template molecules. In certain embodiments the one or more C gene primers of ii) comprises at least two primers that anneal to at least a portion of the constant portion C gene of the template molecules. In particular embodiments at least one set of the generated amplicons includes complementarity determining regions CDR2 and CDR3 of an immune receptor expression sequence. In some embodiments the amplicons are about 180 to about 375 nucleotides in length, about 200 to about 350 nucleotides, about 225 to about 325 nucleotides, or about 250 to about 300 nucleotides in length. In some embodiments the nucleic acid template used in methods is cDNA produced by reverse transcribing nucleic acid molecules extracted from a biological sample.

In certain embodiments, methods are provided for providing sequence of the immune repertoire in a sample, comprising performing a multiplex amplification reaction to amplify immune receptor nucleic acid template molecules having a constant portion and a variable portion using at least one set of primers comprising i) a plurality of V gene primers directed to a majority of different V genes of at least one immune receptor coding sequence comprising at least a portion of FR2 within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence of the immune repertoire in the sample. In particular embodiments, determining the sequence of the immune receptor amplicon molecules includes obtaining initial sequence reads, aligning the initial sequence read to a reference sequence and identifying productive reads, correcting one or more indel errors to generate rescued productive sequence reads; and determining the sequences of the resulting immune receptor molecules. In particular embodiments the combination of productive reads and rescued productive reads is at least 40%, at least 50%, at least 60% at least 70% or at least 75% of the sequencing reads for the immune receptors. In additional embodiments the method further comprises sequence read clustering and immune receptor clonotype reporting. In some embodiments, the sequences of the identified immune repertoire are compared to a contemporaneous or current version of the IMGT database and the sequence of at least one allelic variant absent from that IMGT database is identified. In some embodiments the average sequence read length is between about 200 and about 375 nucleotides, between about 250 and about 350 nucleotides, or between about 275 and about 350 nucleotides, depending in part on inclusion of any barcode sequence in the read length. In certain embodiments at least one set of the sequenced amplicons includes complementarity determining regions CDR2 and CDR3 of an immune receptor expression sequence.

In particular embodiments, methods provided utilize target immune receptor primer sets comprising V gene primers wherein the one or more of a plurality of V gene primers are directed to sequences over an FR2 region about 70 nucleotides in length. In other particular embodiments the one or more of a plurality of V gene primers are directed to sequences over an FR2 region about 50 nucleotides in length. In certain embodiments a target immune receptor primer set comprises V gene primers comprising about 45 to about 90 different FR2-directed primers. In some embodiments a target immune receptor primer set comprises V gene primers comprising about 30 to about 60 different FR2-directed primers. In some embodiments a target immune receptor primer set comprises V gene primers comprising about 20 to about 50 different FR2-directed primers. In some embodiments a target immune receptor primer set comprises V gene primers comprising about 60 to about 70 different FR2-directed primers. In some embodiments a target immune receptor primer set comprises V gene primers comprising about 20 to about 30 different FR2-directed primers. In some embodiments the target immune receptor primer set comprises one or more C gene primers. In particular embodiments a target immune receptor primer set comprises at least two C gene primers wherein each is directed to at least a portion of the same 50 nucleotide region within the target C gene.

In particular embodiments, methods of the invention comprise use of at least one set of primers comprising V gene primers i) and C gene primers ii) selected from Tables 6 and 4, respectively. In certain other embodiments methods of the invention comprise use of at least one set of primers i) and ii) comprising primers selected from SEQ ID NOs: 483-505 and 181-182. In other embodiments methods of the invention comprise use of at least one set of primers i) and ii) comprising primers selected from SEQ ID NOs: 483-505 and 183-184. In other embodiments methods of the invention comprise use of at least one set of primers i) and ii) comprising primers SEQ ID NOs: 483-505 and 181-182. In other embodiments methods of the invention comprise use of at least one set of primers i) and ii) comprising primers SEQ ID NOs: 483-505 and 183-184.

In some embodiments methods of the invention comprise the use of at least one set of primers i) and ii) comprising at least 20 primers selected from SEQ ID NOs: 483-505 and at least one primer selected from SEQ ID NOs: 181-182. In other embodiments methods of the invention comprise the use of at least one set of primers i) and ii) comprising at least 20 primers selected from SEQ ID NOs: 483-505 and at least one primer selected from SEQ ID NOs: 183-184.

In certain embodiments, provided is a method for amplification of expression nucleic acid sequences of an immune receptor repertoire in a sample, comprising performing a multiplex amplification reaction to amplify immune receptor nucleic acid template molecules having a J gene portion and a V gene portion using at least one set of: i) a plurality of V gene primers directed to a majority of different V genes of an immune receptor coding sequence comprising at least a portion of a framework region within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In particular embodiments the one or more plurality of J gene primers of ii) are directed to sequences over about a 50 nucleotide portion of the J gene. In more particular embodiments the one or more plurality of J gene primers of ii) are directed to sequences over about a 30 nucleotide portion of the J gene. In certain embodiments, the one or more plurality of J gene primers of ii) are directed to sequences completely within the J gene.

In certain embodiments, provided is a method for amplification of expression nucleic acid sequences of an immune receptor repertoire in a sample, comprising performing a multiplex amplification reaction to amplify immune receptor nucleic acid template molecules having a J gene portion and a V gene portion using at least one set of: i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In more particular embodiments the one or more plurality of V gene primers of i) are directed to sequences over about a 40 to about a 60 nucleotide portion of the framework region. In some embodiments the one or more plurality of V gene primers of i) anneal to at least a portion of the framework 3 region of the template molecules. In certain embodiments the plurality of J gene primers of ii) comprises at least ten primers that anneal to at least a portion of the J gene portion of the template molecules. In some embodiments the plurality of J gene primers of ii) comprises about 14 primers that anneal to at least a portion of the J gene portion of the template molecules. In some embodiments the plurality of J gene primers of ii) comprises about 16 primers that anneal to at least a portion of the J gene portion of the template molecules. In some embodiments the plurality of J gene primers of ii) comprises about 10 to about 20 primers that anneal to at least a portion of the J gene portion of the template molecules. In some embodiments the plurality of J gene primers of ii) comprises about 12 to about 18 primers that anneal to at least a portion of the J gene portion of the template molecules. In particular embodiments at least one set of the generated amplicons includes complementarity determining region CDR3 of an immune receptor expression sequence. In some embodiments the amplicons are about 60 to about 160 nucleotides in length, about 70 to about 100 nucleotides in length, at least about 70 to about 90 nucleotides in length, about 80 to about 90 nucleotides in length, or about 80 nucleotides in length. In some embodiments the nucleic acid template used in methods is cDNA produced by reverse transcribing nucleic acid molecules extracted from a biological sample.

In certain embodiments, methods are provided for providing sequence of the immune repertoire in a sample, comprising performing a multiplex amplification reaction to amplify immune receptor nucleic acid template molecules having a J gene portion and a V gene portion using at least one set of primers comprising i) a plurality of V gene primers directed to a majority of different V gene of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence of the immune repertoire in the sample. In some embodiments, determining the sequence of the immune receptor amplicon molecules includes obtaining initial sequence reads, aligning the initial sequence read to a reference sequence, identifying productive reads, correcting one or more indel errors to generate rescued productive sequence reads, and determining the sequences of the resulting immune receptor molecules. In particular embodiments, determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads, and determining the sequences of the resulting immune receptor molecules. In particular embodiments the combination of productive reads and rescued productive reads is at least 50%, at least 60% at least 70% or at least 75% of the sequencing reads for the immune receptors. In additional embodiments the method further comprises sequence read clustering and immune receptor clonotype reporting. In some embodiments, the sequences of the identified immune repertoire are compared to a contemporaneous or current version of the IMGT database and the sequence of at least one allelic variant absent from that IMGT database is identified. In some embodiments the sequence read lengths are about 60 to about 185 nucleotides, depending in part on inclusion of any barcode sequence in the read length. In some embodiments the average sequence read length is between 70 and 90 nucleotides, or is between about 75 and about 85 nucleotides, or is about 80 nucleotides. In certain embodiments at least one set of the sequenced amplicons includes complementarity determining region CDR3 of an immune receptor expression sequence.

In particular embodiments, methods provided utilize target immune receptor primer sets comprising V gene primers wherein the one or more of a plurality of V gene primers are directed to sequences over an FR3 region about 50 nucleotides in length. In other embodiments the one or more of a plurality of V gene primers are directed to sequences over an FR3 region about 70 nucleotides in length. In other particular embodiments the one or more of a plurality of V gene primers are directed to sequences over an FR3 region about 40 to about 60 nucleotides in length. In some embodiments a target immune receptor primer set comprises V gene primers comprising about 45 to about 80 different FR3-directed primers. In certain embodiments a target immune receptor primer set comprises V gene primers comprising about 50 to about 70 different FR3-directed primers. In some embodiments, a target immune receptor primer set comprises V gene primers comprising about 55 to about 65 different FR3-directed primers. In some embodiments, a target immune receptor primer set comprises V gene primers comprising about 58, 59, 60, 61, or 62 different FR3-directed primers. In some embodiments the target immune receptor primer set comprises a plurality of J gene primers. In some embodiments a target immune receptor primer set comprises at least ten J gene primers wherein each is directed to at least a portion of a J gene within target polynucleotides. In some embodiments a target immune receptor primer set comprises at least 16 J gene primers wherein each is directed to at least a portion of a J gene within target polynucleotides. In some embodiments a target immune receptor primer set comprises about 10 to about 20 different J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, methods of the invention comprise the use of at least one set of primers comprising V gene primers i) and J gene primers ii) selected from Tables 3 and 5, respectively. In certain other embodiments methods of the invention comprise the use of at least one set of primers i) and ii) comprising primers selected from SEQ ID NOs: 185-248 and 313-397 or selected from SEQ ID NOs: 185-248 and 398-482. In certain other embodiments methods of the invention comprise the use of at least one set of primers i) and ii) comprising primers selected from SEQ ID NOs: 185-248 and 313-329 or selected from SEQ ID NOs: 185-248 and 329-342. In still other embodiments methods of the invention comprise the use of at least one set of primers i) and ii) comprising primers selected from SEQ ID NOs: 185-248 and 398-414 or selected from SEQ ID NOs: 185-248 and 414-427. In other embodiments methods of the invention comprise the use of at least one set of primers i) and ii) comprising primers SEQ ID NOs: 185-243 and 313-328. In still other embodiments methods of the invention comprise the use of at least one set of primers i) and ii) comprising primers SEQ ID NOs: 185-243 and 398-413. In certain other embodiments methods of the invention comprise the use of at least one set of primers i) and ii) comprising primers selected from SEQ ID NOs: 249-312 and 313-397 or selected from SEQ ID NOs: 249-312 and 398-482. In other embodiments methods of the invention comprise the use of at least one set of primers i) and ii) comprising primers selected from SEQ ID NOs: 249-312 and 313-329 or selected from SEQ ID NOs: 249-312 and 329-342. In other embodiments methods of the invention comprise the use of at least one set of primers i) and ii) comprising primers selected from SEQ ID NOs: 249-312 and 398-414 or selected from SEQ ID NOs: 249-312 and 414-427. In certain other embodiments methods of the invention comprise the use of at least one set of primers i) and ii) comprising primers SEQ ID NOs: 249-312 and 398-413. In still other embodiments methods of the invention comprise use of at least one set of primers of i) and ii) comprising primers SEQ ID NOs: 249-312 and 313-328.

In some embodiments methods of the invention comprise the use of at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 398-482. In some embodiments methods of the invention comprise the use of at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 313-397. In some embodiments methods of the invention comprise the use of at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 313-397. In some embodiments methods of the invention comprise the use of at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 398-482.

In some embodiments methods of the invention comprise the use of at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 398-427. In some embodiments methods of the invention comprise the use of at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 313-342. In some embodiments methods of the invention comprise the use of at least one set of primers i) and ii) comprising at least 50 primers selected from SEQ ID NOs:

185-248 and at least 10 primers, at least 12 primers, at least 14 primers, at least 16 primers, at least 18 primers, or at least 20 primers selected from SEQ ID NOs: 313-342. In some embodiments methods of the invention comprise the use of at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 398-427.

In certain embodiments, provided is a method for amplification of expression nucleic acid sequences of an immune receptor repertoire in a sample, comprising performing a multiplex amplification reaction to amplify immune receptor nucleic acid template molecules having a J gene portion and a V gene portion using at least one set of: i) a plurality of V gene primers directed to a majority of different V genes of at least one immune receptor coding sequence comprising at least a portion of framework region 1 (FR1) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In some embodiments the one or more plurality of V gene primers of i) anneal to at least a portion of the framework 1 region of the template molecules. In certain embodiments the plurality of J gene primers of ii) comprise at least ten primers that anneal to at least a portion of the J gene of the template molecules. In some embodiments the plurality of J gene primers of ii) comprises about 14 primers that anneal to at least a portion of the J gene portion of the template molecules. In some embodiments the plurality of J gene primers of ii) comprises about 16 primers that anneal to at least a portion of the J gene portion of the template molecules. In some embodiments the plurality of J gene primers of ii) comprises about 10 to about 20 primers that anneal to at least a portion of the J gene portion of the template molecules. In some embodiments the plurality of J gene primers of ii) comprises about 12 to about 18 primers that anneal to at least a portion of the J gene portion of the template molecules. In particular embodiments at least one set of the generated amplicons includes complementarity determining regions CDR1, CDR2, and CDR3 of an immune receptor expression sequence. In some embodiments the amplicons are about 220 to about 350 nucleotides in length, about 225 to about 300 nucleotides, about 250 to about 325 nucleotides, about 250 to about 275 nucleotides, or about 270 to about 300 nucleotides in length. In some embodiments the nucleic acid template used in methods is cDNA produced by reverse transcribing nucleic acid molecules extracted from a biological sample.

In certain embodiments, methods are provided for providing sequence of the immune repertoire in a sample, comprising performing a multiplex amplification reaction to amplify immune receptor nucleic acid template molecules having a J gene portion and a V gene portion using at least one set of primers comprising i) a plurality of V gene primers directed to a majority of different V genes of at least one immune receptor coding sequence comprising at least a portion of framework region 1 (FR1) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence of the immune repertoire in the sample. In some embodiments, determining the sequence of the immune receptor amplicon molecules includes obtaining initial sequence reads, aligning the initial sequence read to a reference sequence, identifying productive reads, correcting one or more indel errors to generate rescued productive sequence reads, and determining the sequences of the resulting immune receptor molecules. In particular embodiments, determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads, and determining the sequences of the resulting immune receptor molecules. In particular embodiments the combination of productive reads and rescued productive reads is at least 50%, at least 60% at least 70% or at least 75% of the sequencing reads for the immune receptors. In additional embodiments the method further comprises sequence read clustering and immune receptor clonotype reporting. In some embodiments, the sequences of the identified immune repertoire are compared to a contemporaneous or current version of the IMGT database and the sequence of at least one allelic variant absent from that IMGT database is identified. In some embodiments the average sequence read length is between 200 and 350 nucleotides, between 225 and 325 nucleotides, between 250 and 300 nucleotides, between 270 and 300 nucleotides, or is between 295 and 325 nucleotides, depending in part on inclusion of any barcode sequence in the read length. In certain embodiments at least one set of the sequenced amplicons includes complementarity determining regions CDR1, CDR2, and CDR3 of an immune receptor expression sequence.

In particular embodiments, methods provided utilize target immune receptor primer sets comprising V gene primers wherein the one or more of a plurality of V gene primers are directed to sequences over an FR1 region about 70 nucleotides in length. In other certain embodiments the one or more of a plurality of V gene primers are directed to sequences over an FR1 region about 80 nucleotides in length. In other particular embodiments the one or more of a plurality of V gene primers are directed to sequences over an FR1 region about 50 nucleotides in length. In certain embodiments a target immune receptor primer set comprises V gene primers comprising about 45 to about 90 different FR1-directed primers. In some embodiments a target immune receptor primer set comprises V gene primers comprising about 50 to about 80 different FR1-directed primers. In some embodiments a target immune receptor primer set comprises V gene primers comprising about 55 to about 75 different FR1-directed primers. In some embodiments a target immune receptor primer set comprises V gene primers comprising about 60 to about 70 different FR1-directed primers. In some embodiments the target immune receptor primer set comprises a plurality of J gene primers. In some embodiments a target immune receptor primer set comprises at least ten J gene primers wherein each is directed to at least a portion of a J gene within target polynucleotides. In particular embodiments a target immune receptor primer set comprises at least 16 J gene primers wherein each is directed to at least a portion of a J gene within target polynucleotides. In some embodiments a target immune receptor primer set comprises about 10 to about 20 different J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, methods of the invention comprise use of at least one set of primers comprising V gene primers i) and J gene primers ii) selected from Tables 2 and 5, respectively. In certain other embodiments methods of the invention comprise use of at least one set of primers i) and ii) comprising primers selected from SEQ ID NOs: 1-89 and 313-397 or selected from SEQ ID NOs: 90-180 and 398-482. In other embodiments methods of the invention comprise use of at least one set of primers i) and ii) comprising primers selected from SEQ ID NOs: 1-89 and 398-482 or selected from SEQ ID NOs: 90-180 and 313-397. In other embodiments methods of the invention comprise use of at least one set of primers i) and ii) comprising primers selected from SEQ ID NOs: 1-64 and 313-397 or selected from SEQ ID NOs: 1-64 and 398-482. In other embodiments methods of the invention comprise use of at least one set of primers i) and ii) comprising primers selected from SEQ ID NOs: 1-64 and 313-329 or selected from SEQ ID NOs: 1-64 and 329-342. In still other embodiments methods of the invention comprise use of at least one set of primers i) and ii) comprising primers selected from SEQ ID NOs: 1-64 and 398-414 or selected from SEQ ID NOs: 1-64 and 414-427. In other embodiments methods of the invention comprise use of at least one set of primers i) and ii) comprising primers SEQ ID NOs: 1-64 and 313-328. In certain other embodiments methods of the invention comprise use of at least one set of primers i) and ii) comprising primers SEQ ID NOs: 1-64 and 398-413. In certain other embodiments methods of the invention comprise use of at least one set of primers i) and ii) comprising primers selected from SEQ ID NOs: 90-180 and 313-342 or selected from SEQ ID NOs: 90-180 and 398-427. In other embodiments methods of the invention comprise use of at least one set of primers i) and ii) comprising primers selected from SEQ ID NOs: 90-155 and 313-342 or selected from SEQ ID NOs: 90-155 and 398-427. In other embodiments methods of the invention comprise use of at least one set of primers i) and ii) comprising primers selected from SEQ ID NOs: 90-155 and 398-414 or selected from SEQ ID NOs: 90-155 and 414-427. In other embodiments methods of the invention comprise use of at least one set of primers i) and ii) comprising primers selected from SEQ ID NOs: 90-155 and 313-329 or selected from SEQ ID NOs: 90-155 and 329-342. In still other embodiments methods of the invention comprise use of at least one set of primers of i) and ii) comprising primers SEQ ID NOs: 90-153 and 398-414. In still other embodiments methods of the invention comprise use of at least one set of primers of i) and ii) comprising primers SEQ ID NOs: 90-153 and 313-328. In still other embodiments methods of the invention comprise use of at least one set of primers i) and ii) comprising primers selected from SEQ ID NOs: 90-92, 95-180 and 329-342 or selected from SEQ ID NOs: 90-92, 95-180 and 313-329. In other embodiments methods of the invention comprise use of at least one set of primers i) and ii) comprising primers selected from SEQ ID NOs: 90-92, 95-180 and 398-414 or selected from SEQ ID NOs: 90-92, 95-180 and 414-427. In certain other embodiments methods of the invention comprise use of at least one set of primers of i) and ii) comprising primers SEQ ID NOs: 90-92, 95-180 and 398-413. In still other embodiments methods of the invention comprise use of at least one set of primers of i) and ii) comprising primers SEQ ID NOs: 90-92, 95-180, and 313-328.

In some embodiments methods of the invention comprise the use of at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 398-482. In some embodiments methods of the invention comprise the use of at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 398-482.

In some embodiments methods of the invention comprise the use of at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 398-427. In some embodiments methods of the invention comprise the use of at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 398-427.

In some embodiments methods of the invention comprise the use of at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 398-482. In some embodiments methods of the invention comprise the use of at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 398-482.

In some embodiments methods of the invention comprise the use of at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 398-427. In some embodiments methods of the invention comprise the use of at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 398-427.

In certain embodiments, provided is a method for amplification of expression nucleic acid sequences of an immune receptor repertoire in a sample, comprising performing a multiplex amplification reaction to amplify immune receptor nucleic acid template molecules having a J gene portion and a V gene portion using at least one set of: i) a plurality of V gene primers directed to a majority of different V genes of at least one immune receptor coding sequence comprising at least a portion of framework region 2 (FR2) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In some embodiments the one or more plurality of V gene primers of i) anneal to at least a portion of the FR2 region of the template molecules. In certain embodiments the plurality of J gene primers of ii) comprise at least ten primers that anneal to at least a portion of the J gene of the template molecules. In some embodiments the plurality of J gene primers of ii) comprises about 14 primers that anneal to at least a portion of the J gene portion of the template molecules. In some embodiments the plurality of J gene primers of ii) comprises about 16 primers that anneal to at least a portion of the J gene portion of the template molecules. In some embodiments the plurality of J gene primers of ii) comprises about 10 to about 20 primers that anneal to at least a portion of the J gene portion of the template molecules. In some embodiments the plurality of J gene primers of ii) comprises about 12 to about 18 primers that anneal to at least a portion of the J gene portion of the template molecules. In particular embodiments at least one set of the generated amplicons includes complementarity determining regions CDR2 and CDR3 of an immune receptor gene sequence. In some embodiments the amplicons are about 160 to about 270 nucleotides in length, about 180 to about 250 nucleotides, or about 195 to about 225 nucleotides in length. In some embodiments the nucleic acid template used in methods is cDNA produced by reverse transcribing nucleic acid molecules extracted from a biological sample.

In certain embodiments, methods are provided for providing sequence of the immune repertoire in a sample, comprising performing a multiplex amplification reaction to amplify immune receptor nucleic acid template molecules having a J gene portion and a V gene portion using at least one set of primers comprising i) a plurality of V gene primers directed to a majority of different V genes of at least one immune receptor coding sequence comprising at least a portion of FR2 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence of the immune repertoire in the sample. In some embodiments, determining the sequence of the immune receptor amplicon molecules includes obtaining initial sequence reads, aligning the initial sequence read to a reference sequence, identifying productive reads, correcting one or more indel errors to generate rescued productive sequence reads, and determining the sequences of the resulting immune receptor molecules. In particular embodiments, determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads, and determining the sequences of the resulting immune receptor molecules. In particular embodiments the combination of productive reads and rescued productive reads is at least 40%, at least 50%, at least 60% at least 70% or at least 75% of the sequencing reads for the immune receptors. In additional embodiments the method further comprises sequence read clustering and immune receptor clonotype reporting. In some embodiments, the sequences of the identified immune repertoire are compared to a contemporaneous or current version of the IMGT database and the sequence of at least one allelic variant absent from that IMGT database is identified. In some embodiments the average sequence read length is between 160 and 300 nucleotides, between 180 and 280 nucleotides, between 200 and 260 nucleotides, or between 225 and 270 nucleotides, depending in part on inclusion of any barcode sequence in the read length. In certain embodiments at least one set of the sequenced amplicons includes complementarity determining regions CDR2 and CDR3 of an immune receptor expression sequence.

In particular embodiments, methods provided utilize target immune receptor primer sets comprising V gene primers wherein the one or more of a plurality of V gene primers are directed to sequences over an FR2 region about 70 nucleotides in length. In other particular embodiments the one or more of a plurality of V gene primers are directed to sequences over an FR2 region about 50 nucleotides in length. In certain embodiments a target immune receptor primer set comprises V gene primers comprising about 45 to about 90 different FR2-directed primers. In some embodiments a target immune receptor primer set comprises V gene primers comprising about 30 to about 60 different FR2-directed primers. In some embodiments a target immune receptor primer set comprises V gene primers comprising about 20 to about 50 different FR2-directed primers. In some embodiments a target immune receptor primer set comprises V gene primers comprising about 60 to about 70 different FR2-directed primers. In some embodiments a target immune receptor primer set comprises V gene primers comprising about 20 to about 30 different FR2-directed primers. In some embodiments the target immune receptor primer set comprises a plurality of J gene primers. In some embodiments a target immune receptor primer set comprises at least ten J gene primers wherein each is directed to at least a portion of a J gene within target polynucleotides. In particular embodiments a target immune receptor primer set comprises at least 16 J gene primers wherein each is directed to at least a portion of a J gene within target polynucleotides. In some embodiments a target immune receptor primer set comprises about 10 to about 20 different J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, methods of the invention comprise use of at least one set of primers comprising V gene primers i) and J gene primers ii) selected from Tables 6 and 5, respectively. In certain other embodiments methods of the invention comprise use of at least one set of primers i) and ii) comprising primer selected from SEQ ID NOs: 483-505 and 313-397 or selected from SEQ ID NOs: 483-505 and 398-482. In some embodiments methods of the invention comprise use of at least one set of primers i) and ii) comprising primer selected from SEQ ID NOs: 483-505 and 313-342 or selected from SEQ ID NOs: 483-505 and 398-427. In other embodiments methods of the invention comprise use of at least one set of primers i) and ii) comprising primer selected from SEQ ID NOs: 483-505 and 313-329 or selected from SEQ ID NOs: 483-505 and 329-342. In other embodiments methods of the invention comprise use of at least one set of primers i) and ii) comprising primer selected from SEQ ID NOs: 483-505 and 398-414 or selected from SEQ ID NOs: 483-505 and 414-427. In other embodiments methods of the invention comprise use of at least one set of primers i) and ii) comprising primers SEQ ID NOs: 483-505 and 313-328. In certain other embodiments methods of the invention comprise use of at least one set of primers i) and ii) comprising primers SEQ ID NOs: 483-505 and 398-413.

In some embodiments methods of the invention comprise the use of at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 398-482. In some embodiments methods of the invention comprise the use of at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 398-427.

In certain embodiments, methods of the invention comprise use of a biological sample selected from the group consisting of hematopoietic cells, lymphocytes, and tumor cells. In some embodiments the biological sample is selected from the group consisting of peripheral blood mononuclear cells (PBMCs), T cells, B cells, circulating tumor cells, and tumor infiltrating lymphocytes (herein "TILs" or "TIL"). In some embodiments, the biological sample comprises T cells undergoing ex vivo activation and/or expansion.

In some embodiments, methods, compositions, and systems are provided for determining the immune repertoire of a biological sample by assessing both expressed immune receptor RNA and rearranged immune receptor genomic DNA (gDNA) from a biological sample. Expression nucleic acid sequences of a sample may be assessed using the methods, compositions, and systems provided herein. The sample gDNA may be assessed for rearranged immune receptor gene sequences using the methods, composition, and systems described in the co-owned U.S. Provisional Application No. 62/553,736, filed Sep. 1, 2017, entitled "Compositions and Methods for Immune Repertoire Sequencing", the entirety of which is incorporated herein by reference. In some embodiments, the sample RNA and gDNA may be assessed concurrently and following reverse transcription of the RNA to form cDNA, the cDNA and gDNA may be amplified in the same multiplex amplification reaction. In some embodiments, cDNA from the sample RNA and the sample gDNA may undergo multiplex amplification in separate reactions. In some embodiments, cDNA from the sample RNA and sample gDNA may under multiplex amplification with parallel primer pools. In some embodiments, the same immune receptor-directed primer pools are used to assess the immune repertoire of gDNA and RNA from the sample. In some embodiments, the different immune receptor-directed primer pools are used to assess the immune repertoire of gDNA and RNA from the sample. In some embodiments, multiplex amplification reactions are performed separately with cDNA from the sample RNA and with sample gDNA to amplify target immune receptor molecules from the sample and the resulting immune receptor amplicons are sequenced, thereby providing sequence of the expressed immune receptor RNA and rearranged immune receptor gDNA of a biological sample.

In some embodiments, the methods and compositions provided are used to identify and/or characterize an immune repertoire of a subject. In some embodiments, methods and compositions provided are used to identify and characterize novel or non-canonical TCR or BCR alleles of a subject's immune repertoire. In some embodiments, the sequences of the identified immune repertoire are compared to a contemporaneous or current version of the IMGT database and the sequence of at least one allelic variant absent from that IMGT database is identified. In some embodiments, identified allelic variants absent from the IMGT database are subjected to evidence-based filtering using, for example, criteria such as clone number support, sequence read support and/or number of individuals having the allelic variant. Allelic variants identified and reported as absent from IMGT may be compared to other databases containing immune repertoire sequence information, such as NCBI NR database and Lym1K database, to cross-validate the reported novel or non-canonical TCR or BCR alleles. Characterizing the existence of undocumented or non-canonical TRB polymorphism, for example, may help with understanding factors that influence autoimmune disease and response to immunotherapy. Thus, in some embodiments, methods and compositions are provided to identify novel or non-canonical TRBV gene allele polymorphisms and allelic variants that may predict or detect autoimmune disease or immune-mediated adverse events. In other embodiments, provided are methods for making recombinant nucleic acids encoding identified novel TRBV allelic variants. In some embodiments, provided are methods for making recombinant TRBV allelic variant molecules and for making recombinant cells which express the same.

In some embodiments, methods and compositions provided are used to identify and characterize novel or non-canonical TCR or BCR alleles of a subject's immune repertoire. In some embodiments, a patient's immune repertoire may be identified or characterized before and/or after a therapeutic treatment, for example treatment for a cancer or immune disorder. In some embodiments, identification or characterization of an immune repertoire may be used to assess the effect or efficacy of a treatment, to modify therapeutic regimens, and to optimize the selection of therapeutic agents. In some embodiments, identification or characterization of the immune repertoire may be used to assess a patient's response to an immunotherapy, e.g., CAR (chimeric antigen receptor)-T cell therapy, a cancer vaccine and/or other immune-based treatment or combination(s) thereof. In some embodiments, identification or characterization of the immune repertoire may indicate a patient's likelihood to respond to a therapeutic agent or may indicate a patient's likelihood to not be responsive to a therapeutic agent.

In some embodiments, a patient's immune repertoire may be identified or characterized to monitor progression and/or treatment of hyperproliferative diseases, including detection of residual disease following patient treatment, monitor progression and/or treatment of autoimmune disease, transplantation monitoring, and to monitor conditions of antigenic stimulation, including following vaccination, exposure to bacterial, fungal, parasitic, or viral antigens, or infection by bacteria, fungi, parasites or virus. In some embodiments, identification or characterization of the immune repertoire may be used to assess a patient's response to an anti-infective or anti-inflammatory therapy.

In certain embodiments, the methods and compositions provided are used to monitor changes in immune repertoire clonal populations, for example changes in clonal expansion, changes in clonal contraction, and changes in relative ratios of clones or clonal populations. In some embodiments, the provided methods and compositions are used to monitor changes in immune repertoire clonal populations (e.g., clonal expansion, clonal contraction, changes in relative ratios) in response to tumor growth. In some embodiments, the provided methods and compositions are used to monitor changes in immune repertoire clonal populations (e.g., clonal expansion, clonal contraction, changes in relative ratios) in response to tumor treatment. In some embodiments, the provided methods and compositions provided are used to monitor changes in immune repertoire clonal populations (e.g., clonal expansion, clonal contraction, changes in relative ratios) during a remission period. For many lymphoid malignancies, a clonal B cell receptor or T cell receptor sequence can be used a biomarker for the malignant cells of the particular cancer (e.g., leukemia) and to monitor residual disease, tumor expansion, contraction, and/or treatment response. In certain embodiments a clonal B cell receptor or T cell receptor may be identified and further characterized to confirm a new utility in therapeutic, biomarker and/or diagnostic use.

In some embodiments, methods and compositions are provided for identifying and/or characterizing immune repertoire clonal populations in a sample from a subject, comprising performing one or more multiplex amplification reactions with the sample or with cDNA prepared from the sample to amplify immune repertoire nucleic acid template molecules having a constant portion and a variable portion using at least one set of primers comprising i) a plurality of V gene primers directed to a majority of different V gene of at least one immune receptor coding sequence comprising at least a portion of framework region 1 (FR1) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying one or more immune repertoire clonal populations for the target immune receptor from the sample. In particular, embodiments determining the sequence of the immune receptor amplicon molecules includes obtaining initial sequence reads, aligning the initial sequence read to a reference sequence and identifying productive reads, correcting one or more indel errors to generate rescued productive sequence reads; and determining the sequences of the resulting immune receptor molecules. In other embodiments of such methods and compositions, the one or more multiplex amplification reaction is performed using at least one set of primers comprising i) a plurality of V gene primers directed to a majority of different V gene of at least one immune receptor coding sequence comprising at least a portion of framework region 3 (FR3) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor. In other embodiments of such methods and compositions, the one or more multiplex amplification reaction is performed using at least one set of primers comprising i) a plurality of V gene primers directed to a majority of different V gene of at least one immune receptor coding sequence comprising at least a portion of framework region 2 (FR2) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor.

In some embodiments, methods and compositions are provided for identifying and/or characterizing immune repertoire clonal populations in a sample from a subject, comprising performing one or more multiplex amplification reactions with the sample or with cDNA prepared from the sample to amplify immune repertoire nucleic acid template molecules having a J gene portion and a V gene portion using at least one set of primers comprising i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying one or more immune repertoire clonal populations for the target immune receptor from the sample. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads, and determining the sequences of the resulting immune receptor molecules. In other embodiments of such methods and compositions, the multiplex amplification reaction is performed using at least one set of primers comprising i) a plurality of V gene primers directed to a majority of different V genes of at least one immune receptor coding sequence comprising at least a portion of framework region 1 (FR1) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor. In other embodiments of such methods and compositions, the multiplex amplification reaction is performed using at least one set of primers comprising i) a plurality of V gene primers directed to a majority of different V genes of at least one immune receptor coding sequence comprising at least a portion of framework region 2 (FR2) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor.

In some embodiments, methods and compositions are provided for monitoring changes in immune repertoire clonal populations in a subject, comprising performing one or more multiplex amplification reaction with a subject's sample to amplify immune repertoire nucleic acid template molecules having a constant portion and a variable portion using at least one set of primers directed to a majority of different V gene of at least one immune receptor coding sequence comprising at least a portion of FR1, FR2 or FR3 within the V gene, and ii) one or more C gene primers directed to at least a portion of the respective target C gene of the immune receptor coding sequence, sequencing the resultant immune receptor amplicons, identifying immune repertoire clonal populations for the target immune receptor from the sample, and comparing the identified immune repertoire clonal populations to those identified in samples obtained from the subject at a different time. In some embodiments, methods and compositions are provided for monitoring changes in immune repertoire clonal populations in a subject, comprising performing one or more multiplex amplification reaction with a subject's sample to amplify immune repertoire nucleic acid template molecules having a J gene portion and a V gene portion using at least one set of primers directed to a majority of different V genes of at least one immune receptor coding sequence comprising at least a portion of FR1, FR2 or FR3 within the V gene, and ii) a plurality of J gene primers directed to a majority of different J genes of the respective target immune receptor coding sequence, sequencing the resultant immune receptor amplicons, identifying immune repertoire clonal populations for the target immune receptor from the sample, and comparing the identified immune repertoire clonal populations to those identified in samples obtained from the subject at a different time. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in monitoring changes in immune repertoire clonal populations include, without limitation, samples obtained prior to a diagnosis, samples obtained at any stage of diagnosis, samples obtained during a remission, samples obtained at any time prior to a treatment (pre-treatment sample), samples obtained at any time following completion of treatment (post-treatment sample), and samples obtained during the course of treatment.

In certain embodiments, methods and compositions are provided for identifying and/or characterizing the immune repertoire of a patient to monitor progression and/or treatment of the patient's hyperproliferative disease. In some embodiments, the methods and compositions provided are used for minimal residual disease (MRD) monitoring for a patient following treatment. In some embodiments, the methods and compositions are used to identify and/or track B cell lineage malignancies or T cell lineage malignancies. In some embodiments, the methods and compositions are used to detect and/or monitor MRD in patients diagnosed with leukemia or lymphoma, including without limitation, acute lymphoblastic leukemia, chronic myeloid leukemia, chronic lymphocytic leukemia, chronic myelogenous leukemia, cutaneous T cell lymphoma, B cell lymphoma, mantle cell lymphoma, and multiple myeloma. In some embodiments, the methods and compositions are used to detect and/or monitor MRD in patients diagnosed with solid tumors, including without limitation, breast cancer, lung cancer, colorectal, and neuroblastoma. In some embodiments, the methods and compositions are used to detect and/or monitor MRD in patients following cancer treatment including without limitation bone marrow transplant, lymphocyte infusion, adoptive T-cell therapy, other cell-based immunotherapy, and antibody-based immunotherapy.

In some embodiments, methods and compositions are provided for identifying and/or characterizing the immune repertoire of a patient to monitor progression and/or treatment of the patient's hyperproliferative disease, comprising performing one or more multiplex amplification reactions with a sample from the patient or with cDNA prepared from the sample to amplify immune repertoire nucleic acid template molecules having a constant portion and a variable portion using at least one set of primers comprising i) a plurality of V gene primers directed to a majority of different V genes of at least one immune receptor coding sequence comprising at least a portion of framework region 1 (FR1) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In particular, embodiments determining the sequence of the immune receptor amplicon molecules includes obtaining initial sequence reads, aligning the initial sequence read to a reference sequence and identifying productive reads, correcting one or more indel errors to generate rescued productive sequence reads; and determining the sequences of the resulting immune receptor molecules. In other embodiments of such methods and compositions, the multiplex amplification reaction is performed using at least one set of primers comprising i) a plurality of V gene primers directed to a majority of different V genes of at least one immune receptor coding sequence comprising at least a portion of FR3 within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor. In other embodiments of such methods and compositions, the multiplex amplification reaction is performed using at least one set of primers comprising i) a plurality of V gene primers directed to a majority of different V genes of at least one immune receptor coding sequence comprising at least a portion of FR2 within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor.

In some embodiments, methods and compositions are provided for identifying and/or characterizing the immune repertoire of a patient to monitor progression and/or treatment of the patient's hyperproliferative disease, comprising performing one or more multiplex amplification reaction with a sample from the patient or with cDNA prepared from the sample to amplify immune repertoire nucleic acid template molecules having a J gene portion and a V gene portion using at least one set of primers comprising i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads; and determining the sequences of the resulting immune receptor molecules. In other embodiments of such methods and compositions, the multiplex amplification reaction is performed using at least one set of primers comprising i) a plurality of V gene primers directed to a majority of different V genes of at least one immune receptor coding sequence comprising at least a portion of FR1 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor. In other embodiments of such methods and compositions, the multiplex amplification reaction is performed using at least one set of primers comprising i) a plurality of V gene primers directed to a majority of different V genes of at least one immune receptor coding sequence comprising at least a portion of FR2 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor.

In some embodiments, methods and compositions are provided for MRD monitoring for a patient having a hyperproliferative disease, comprising performing one or more multiplex amplification reaction with a patient's sample to amplify immune repertoire nucleic acid template molecules having a constant portion and a variable portion using at least one set of primers directed to a majority of different V genes of at least one immune receptor coding sequence comprising at least a portion of FR1, FR2 or FR3 within the V gene, and ii) one or more C gene primers directed to at least a portion of the respective target C gene of the immune receptor coding sequence, sequencing the resultant immune receptor amplicons, identifying immune repertoire sequences for the target immune receptor, and detecting the presence or absence of immune receptor sequence(s) in the sample associated with the hyperproliferative disease. In some embodiments, methods and compositions are provided for MRD monitoring for a patient having a hyperproliferative disease, comprising performing one or more multiplex amplification reaction with a patient's sample to amplify immune repertoire nucleic acid template molecules having a J gene portion and a V gene portion using at least one set of primers directed to a majority of different V genes of at least one immune receptor coding sequence comprising at least a portion of FR1, FR2 or FR3 within the V gene, and ii) a plurality of J gene primers directed to a majority of different J genes of the respective target immune receptor coding sequence, sequencing the resultant immune receptor amplicons, identifying immune repertoire sequences for the target immune receptor, and detecting the presence or absence of immune receptor sequence(s) in the sample associated with the hyperproliferative disease. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in MRD monitoring include, without limitation, samples obtained during a remission, samples obtained at any time following completion of treatment (post-treatment sample), and samples obtained during the course of treatment.

In certain embodiments, methods and compositions are provided for identifying and/or characterizing the immune repertoire of a subject in response to a treatment. In some embodiments, the methods and compositions are used to characterize and/or monitor populations or clones of tumor infiltrating lymphocytes (TILs) before, during, and/or following tumor treatment. In some embodiments, profiling immune receptor repertoires of TILs provides characterization and/or assessment of the tumor microenvironment and T cell expansion permissiveness within the tumor microenvironment. For example, a dearth of highly expanded TIL clones within the tumor, for example as indicated by higher evenness of T cell clone sizes through characterization of the TCR repertoire, may indicate a repressive tumor microenvironment. On the other hand, identification of multiple highly expanded T cell clones and less evenness of T cell clone sizes may indicate a tumor microenvironment permissive for T cell expansion. In some embodiments, the methods and compositions for determining immune repertoire are used to identify and/or track therapeutic T cell population(s) and B cell population(s). In some embodiments, the methods and compositions provided are used to identify and/or monitor the persistence of cell-based therapies following patient treatment, including but not limited to, presence (e.g., persistent presence) of engineered T cell populations including without limitation CAR-T cell populations, TCR engineered T cell populations, persistent CAR-T expression, presence (e.g., persistent presence) of administered TIL populations, TIL expression (e.g., persistent expression) following adoptive T-cell therapy, and/or immune reconstitution after allogeneic hematopoietic cell transplantation.

In some embodiments, the methods and compositions provided are used to characterize and/or monitor T cell clones or populations present in patient sample following administration of cell-based therapies to the patient, including but not limited to, e.g., cancer vaccine cells, CAR-T, TIL, and/or other engineered T cell-based therapy. In some embodiments, the provided methods and compositions are used to characterize and/or monitor immune repertoire in a patient sample following cell-based therapies in order to assess and/or monitor the patient's response to the administered cell-based therapy. Samples for use in such characterizing and/or monitoring following cell-based therapy include, without limitation, circulating blood cells, circulating tumor cells, TILs, tissue, and tumor sample(s) from a patient.

In some embodiments, methods and compositions are provided for monitoring T cell-based therapy for a patient receiving such therapy, comprising performing one or more multiplex amplification reactions with a patient's sample to amplify immune repertoire nucleic acid template molecules having a constant portion and a variable portion using at least one set of primers directed to a majority of different V genes of at least one immune receptor coding sequence comprising at least a portion of FR1, FR2 or FR3 within the V gene, and ii) one or more C gene primers directed to at least a portion of the respective target C gene of the immune receptor coding sequence, sequencing the resultant immune receptor amplicons, identifying immune repertoire sequences for the target immune receptor, and detecting the presence or absence of immune receptor sequence(s) in the sample associated with the T cell-based therapy. In some embodiments, methods and compositions are provided for monitoring T cell-based therapy for a patient receiving such therapy, comprising performing one or more multiplex amplification reactions with a patient's sample to amplify immune repertoire nucleic acid template molecules having a J gene portion and a V gene portion using at least one set of primers directed to a majority of different V genes of at least one immune receptor coding sequence comprising at least a portion of FR1, FR2 or FR3 within the V gene, and ii) a plurality of J gene primers directed to a majority of different J genes of the respective target immune receptor coding sequence, sequencing the resultant immune receptor amplicons, identifying immune repertoire sequences for the target immune receptor, and detecting the presence or absence of immune receptor sequence(s) in the sample associated with the T cell-based therapy.

In some embodiments, methods and compositions are provided for monitoring a patient's response following administration of a T cell-based therapy, comprising performing one or more multiplex amplification reactions with a patient's sample to amplify immune repertoire nucleic acid template molecules having a constant portion and a variable portion using at least one set of primers directed to a majority of different V genes of at least one immune receptor coding sequence comprising at least a portion of FR1, FR2 or FR3 within the V gene, and ii) one or more C gene primers directed to at least a portion of the respective target C gene of the immune receptor coding sequence, sequencing the resultant immune receptor amplicons, identifying immune repertoire sequences for the target immune receptor, and comparing the identified immune repertoire to the immune receptor sequence(s) identified in samples obtained from the patient at a different time. In some embodiments, methods and compositions are provided for monitoring a patient's response following administration of a T cell-based therapy, comprising performing one or more multiplex amplification reactions with a patient's sample to amplify immune repertoire nucleic acid template molecules having a J gene portion and a V gene portion using at least one set of primers directed to a majority of different V genes of at least one immune receptor coding sequence comprising at least a portion of FR1, FR2 or FR3 within the V gene, and ii) a plurality of J gene primers directed to a majority of different J genes of the respective target immune receptor coding sequence, sequencing the resultant immune receptor amplicons, identifying immune repertoire sequences for the target immune receptor, and comparing the identified immune repertoire to the immune receptor sequence(s) identified in samples obtained from the patient at a different time. T cell-based therapies suitable for such monitoring include, without limitation, CAR-T cells, TCR engineered T cells, TILs, and other enriched autologous T cells. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in such monitoring include, without limitation, samples obtained prior to a diagnosis, samples obtained at any stage of diagnosis, samples obtained during a remission, samples obtained at any time prior to a treatment (pre-treatment sample), samples obtained at any time following completion of treatment (post-treatment sample), and samples obtained during the course of treatment.

In some embodiments, the methods and compositions for determining T cell and/or B cell receptor repertoires are used to measure and/or assess immunocompetence before, during, and/or following a treatment, including without limitation, solid organ transplant or bone marrow transplant. For example, the diversity of the T cell receptor beta repertoire can be used to measure immunocompetence and immune cell reconstitution following a hematopoietic stem cell transplant treatment. Also, the rate of change in diversity of the TRB repertoire between time points following a transplant can be used to modify patient treatment.

In some embodiments, methods and compositions are provided for identifying and/or characterizing the immune repertoire of a subject in response to a treatment, comprising obtaining a sample from the subject following initiation of a treatment, performing one or more multiplex amplification reactions with the sample or with cDNA prepared from the sample to amplify immune repertoire nucleic acid template molecules having a constant portion and a variable portion using at least one set of primers comprising i) a plurality of V gene primers directed to a majority of different V gene of at least one immune receptor coding sequence comprising at least a portion of framework region 1 (FR1) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In some embodiments, the method further comprises comparing the identified immune repertoire from the sample obtained following treatment initiation to the immune repertoire from a sample of the patient obtained prior to treatment. In particular, embodiments determining the sequence of the immune receptor amplicon molecules includes obtaining initial sequence reads, aligning the initial sequence read to a reference sequence and identifying productive reads, correcting one or more indel errors to generate rescued productive sequence reads; and determining the sequences of the resulting immune receptor molecules. In other embodiments of such methods and compositions, the multiplex amplification reaction is performed using at least one set of primers comprising i) a plurality of V gene primers directed to a majority of different V genes of at least one immune receptor coding sequence comprising at least a portion of FR3 within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor. In other embodiments of such methods and compositions, the multiplex amplification reaction is performed using at least one set of primers comprising i) a plurality of V gene primers directed to a majority of different V genes of at least one immune receptor coding sequence comprising at least a portion of FR2 within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor.

In some embodiments, methods and compositions are provided for identifying and/or characterizing the immune repertoire of a subject in response to a treatment, comprising obtaining a sample from the subject following initiation of a treatment, performing one or more multiplex amplification reactions with the sample or with cDNA prepared from the sample to amplify immune repertoire nucleic acid template molecules having a J gene portion and a V gene portion using at least one set of primers comprising i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In some embodiments, the method further comprises comparing the identified immune repertoire from the sample obtained following treatment initiation to the immune repertoire from a sample of the patient obtained prior to treatment. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads; and determining the sequences of the resulting immune receptor molecules. In other embodiments of such methods and compositions, the multiplex amplification reaction is performed using at least one set of primers comprising i) a plurality of V gene primers directed to a majority of different V genes of at least one immune receptor coding sequence comprising at least a portion of FR1 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor. In other embodiments of such methods and compositions, the multiplex amplification reaction is performed using at least one set of primers comprising i) a plurality of V gene primers directed to a majority of different V genes of at least one immune receptor coding sequence comprising at least a portion of FR2 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor.

In some embodiments, methods and compositions are provided for monitoring changes in the immune repertoire of a subject in response to a treatment, comprising performing one or more multiplex amplification reactions with a subject's or patient's sample to amplify immune repertoire nucleic acid template molecules having a constant portion and a variable portion using at least one set of primers directed to a majority of different V genes of at least one immune receptor coding sequence comprising at least a portion of FR1, FR2 or FR3 within the V gene, and ii) one or more C gene primers directed to at least a portion of the respective target C gene of the immune receptor coding sequence, sequencing the resultant immune receptor amplicons, identifying immune repertoire sequences for the target immune receptor from the sample, and comparing the identified immune repertoire to those identified in samples obtained from the subject at a different time. In some embodiments, methods and compositions are provided for monitoring changes in the immune repertoire of a subject in response to a treatment, comprising performing one or more multiplex amplification reactions with a subject's or patient's sample to amplify immune repertoire nucleic acid template molecules having a J gene portion and a V gene portion using at least one set of primers directed to a majority of different V genes of at least one immune receptor coding sequence comprising at least a portion of FR1, FR2 or FR3 within the V gene, and ii) a plurality of J gene primers directed to a majority of different J genes of the respective target immune receptor coding sequence, sequencing the resultant immune receptor amplicons, identifying immune repertoire sequences for the target immune receptor from the sample, and comparing the identified immune repertoire to those identified in samples obtained from the subject at a different time. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in monitoring changes in immune repertoire include, without limitation, samples obtained prior to a diagnosis, samples obtained at any stage of diagnosis, samples obtained during a remission, samples obtained at any time prior to a treatment (pre-treatment sample), samples obtained at any time following completion of treatment (post-treatment sample), and samples obtained during the course of treatment.

In certain embodiments, the methods and compositions provided are used to characterize and/or monitor immune repertoires associated with immune system-mediated adverse event(s), including without limitation, those associated with inflammatory conditions, autoimmune reactions, and/or autoimmune diseases or disorders. In some embodiments, the methods and compositions provided are used to identify and/or monitor T cell and/or B cell immune repertoires associated with chronic autoimmune diseases or disorders including, without limitation, multiple sclerosis, Type I diabetes, narcolepsy, rheumatoid arthritis, ankylosing spondylitis, asthma, and SLE. In some embodiments, a systemic sample, such as a blood sample, is used to determine the immune repertoire(s) of an individual with an autoimmune condition. In some embodiments, a localized sample, such as a fluid sample from an affected joint or region of swelling, is used to determine the immune repertoire(s) of an individual with an autoimmune condition. In some embodiments, comparison of the immune repertoire found in a localized or affected area sample to the immune repertoire found in the systemic sample can identify clonal T or B cell populations to be targeted for removal.

In some embodiments, methods and compositions are provided for identifying and/or monitoring an immune repertoire associated with a patient's immune system-mediated adverse event(s), comprising performing one or more multiplex amplification reactions with a sample from the patient or with cDNA prepared from the sample to amplify immune repertoire nucleic acid template molecules having a constant portion and a variable portion using at least one set of primers comprising i) a plurality of V gene primers directed to a majority of different V genes of at least one immune receptor coding sequence comprising at least a portion of framework region 1 (FR1) within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In some embodiments, the method further comprises comparing the identified immune repertoire from the sample to an identified immune repertoire from a sample from the patient obtained at a different time. In particular, embodiments determining the sequence of the immune receptor amplicon molecules includes obtaining initial sequence reads, aligning the initial sequence read to a reference sequence and identifying a productive reads, correcting one or more indel errors to generate rescued productive sequence reads; and determining the sequences of the resulting immune receptor molecules. In other embodiments of such methods and compositions, the multiplex amplification reaction is performed using at least one set of primers comprising i) a plurality of V gene primers directed to a majority of different V genes of at least one immune receptor coding sequence comprising at least a portion of FR3 within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor. In other embodiments of such methods and compositions, the multiplex amplification reaction is performed using at least one set of primers comprising i) a plurality of V gene primers directed to a majority of different V genes of at least one immune receptor coding sequence comprising at least a portion of FR2 within the V gene, and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor.

In some embodiments, methods and compositions are provided for identifying and/or monitoring an immune repertoire associated with a patient's immune system-mediated adverse event(s), comprising performing one or more multiplex amplification reactions with a sample from the patient or with cDNA prepared from the sample to amplify immune repertoire nucleic acid template molecules having a J gene portion and a V gene portion using at least one set of primers comprising i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In some embodiments, the method further comprises comparing the identified immune repertoire from the sample to an identified immune repertoire from a sample from the patient obtained at a different time. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads; and determining the sequences of the resulting immune receptor molecules. In other embodiments of such methods and compositions, the multiplex amplification reaction is performed using at least one set of primers comprising i) a plurality of V gene primers directed to a majority of different V genes of at least one immune receptor coding sequence comprising at least a portion of FR1 within the V gene, and ii) a plurality of J gene primers directed to a majority of different J genes of the respective immune receptor coding sequence, wherein each set of i) and ii) primers directed to the same target immune receptor sequences is selected from the group consisting of a T cell receptor and an antibody receptor. In other embodiments of such methods and compositions, the multiplex amplification reaction is performed using at least one set of primers comprising i) a plurality of V gene primers directed to a majority of different V genes of at least one immune receptor coding sequence comprising at least a portion of FR2 within the V gene, and ii) a plurality of J gene primers directed to a majority of different J genes of the respective immune receptor coding sequence, wherein each set of i) and ii) primers directed to the same target immune receptor sequences is selected from the group consisting of a T cell receptor and an antibody receptor.

In some embodiments, methods and compositions are provided for identifying and/or monitoring an immune repertoire associated with progression and/or treatment of a patient's immune system-mediated adverse event(s), comprising performing one or more multiplex amplification reactions with a patient's sample to amplify immune repertoire nucleic acid template molecules having a constant portion and a variable portion using at least one set of primers directed to a majority of different V genes of at least one immune receptor coding sequence comprising at least a portion of FR1, FR2 or FR3 within the V gene, and ii) one or more C gene primers directed to at least a portion of the respective target C gene of the immune receptor coding sequence, sequencing the resultant immune receptor amplicons, identifying immune repertoire sequences for the target immune receptor from the sample, and comparing the identified immune repertoire to the immune repertoire(s) identified in samples obtained from the patient at a different time. In some embodiments, methods and compositions are provided for identifying and/or monitoring an immune repertoire associated with progression and/or treatment of a patient's immune system-mediated adverse event(s), comprising performing one or more multiplex amplification reactions with a patient's sample to amplify immune repertoire nucleic acid template molecules having a J gene portion and a V gene portion using at least one set of primers directed to a majority of different V genes of at least one immune receptor coding sequence comprising at least a portion of FR1 or FR3 within the V gene, and ii) a plurality of J gene primers directed to a majority of different J genes of the respective target immune receptor coding sequence, sequencing the resultant immune receptor amplicons, identifying immune repertoire sequences for the target immune receptor from the sample, and comparing the identified immune repertoire to the immune repertoire(s) identified in samples obtained from the patient at a different time. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in monitoring changes in immune repertoire associated with immune system-mediated adverse event(s) include, without limitation, samples obtained prior to a diagnosis, samples obtained at any stage of diagnosis, samples obtained during a remission, samples obtained at any time prior to a treatment (pre-treatment sample), samples obtained at any time following completion of treatment (post-treatment sample), and samples obtained during the course of treatment.

In some embodiments, the methods and compositions provided are used to characterize and/or monitor immune repertoires associated with passive immunity, including naturally acquired passive immunity and artificially acquired passive immunity therapies. For example, the methods and compositions provided may be used to identify and/or monitor protective antibodies that provide passive immunity to the recipient following transfer of antibody-mediated immunity to the recipient, including without limitation, antibody-mediated immunity conveyed from a mother to a fetus during pregnancy or to an infant through breast-feeding, or conveyed via administration of antibodies to a recipient. In another example, the methods and compositions provided may be used to identify and/or monitor B cell and/or T cell immune repertoires associated with passive transfer of cell-mediated immunity to a recipient, such as the administration of mature circulating lymphocytes to a recipient histocompatible with the donor. In some embodiments, the methods and compositions provided are used to monitor the duration of passive immunity in a recipient.

In some embodiments, the methods and compositions provided are used to characterize and/or monitor immune repertoires associated with active immunity or vaccination therapies. For example, following exposure to a vaccine or infectious agent, the methods and compositions provided may be used to identify and/or monitor protective antibodies or protective clonal B cell or T cell populations that may provide active immunity to the exposed individual. In some embodiments, the methods and compositions provided are used to monitor the duration of B or T cell clones which contribute to immunity in an exposed individual. In some embodiments, the methods and compositions provided are used to identify and/or monitor B cell and/or T cell immune repertoires associated with exposure to bacterial, fungal, parasitic, or viral antigens. In some embodiments, the methods and compositions provided are used to identify and/or monitor B cell and/or T cell immune repertoires associated with bacterial, fungal, parasitic, or viral infection.

In some embodiments, the methods and compositions provided are used to screen or characterize lymphocyte populations which are grown and/or activated in vitro for use as immunotherapeutic agents or in immunotherapeutic-based regimens. In some embodiments, the methods and compositions provided are used to screen or characterize TIL populations or other harvested T cell populations which are grown and/or activated in vitro, for example, TILs or other harvested T cells grown and/or activated for use in adoptive immunotherapy. In some embodiments, the methods and compositions provided are used to screen or characterize CAR-T populations or other engineered T cell populations which are grown and/or activated in vitro, for use, for example, in immunotherapy.

In some embodiments, the methods and compositions provided are used to assess cell populations by monitoring immune repertoires during ex vivo workflows for manufacturing engineered T cell preparations, for example, for quality control or regulatory testing purposes.

In some embodiments, the sequences of novel or non-canonical TCR or BCR alleles identified as described herein may be used to generate recombinant TCR or BCR nucleic acids or molecules. For example, as described herein, used of the provided methods and compositions led to the identification of fifteen TRB allelic variants not found in the IMGT database. Such novel or non-canonical allele sequence information and amplicons can be used to generate new recombinant TRB allelic variants and/or nucleic acids encoding the same.

In some embodiments, the methods and compositions provided are used in the screening and/or production of recombinant antibody libraries. Compositions provided which directed to identifying BCRs can be used to rapidly evaluate recombinant antibody library size and composition to identify antibodies of interest.

In some embodiments, profiling immune receptor repertoires as provided herein may be combined with profiling immune response gene expression to provide characterization of the tumor microenvironment. In some embodiments, combining or correlating a tumor sample's immune receptor repertoire profile with a targeted immune response gene expression profile provides a more thorough analysis of the tumor microenvironment and may suggest or provide guidance for immunotherapy treatments.

Suitable cells for analysis include, without limitation, various hematopoietic cells, lymphocytes, and tumor cells, such as peripheral blood mononuclear cells (PBMCs), T cells, B cells, circulating tumor cells, and tumor infiltrating lymphocytes (TILs). Lymphocytes expressing immunoglobulin include pre-B cells, B-cells, e.g. memory B cells, and plasma cells. Lymphocytes expressing T cell receptors include thymocytes, NK cells, pre-T cells and T cells, where many subsets of T cells are known in the art, e.g. Th1, Th2, Th17, CTL, T reg, etc. For example, in some embodiments, a sample comprising PBMCs may be used as a source for TCR and/or antibody immune repertoire analysis. The sample may contain, for example, lymphocytes, monocytes, and macrophages as well as antibodies and other biological constituents.

Analysis of the immune repertoire is of interest for conditions involving cellular proliferation and antigenic exposure, including without limitation, the presence of cancer, exposure to cancer antigens, exposure to antigens from an infectious agent, exposure to vaccines, exposure to allergens, exposure to food stuffs, presence of a graft or transplant, and the presence of autoimmune activity or disease. Conditions associated with immunodeficiency are also of interest for analysis, including congenital and acquired immunodeficiency syndromes.

B cell lineage malignancies of interest include, without limitation, multiple myeloma; acute lymphocytic leukemia (ALL); relapsed/refractory B cell ALL, chronic lymphocytic leukemia (CLL); diffuse large B cell lymphoma; mucosa-associated lymphatic tissue lymphoma (MALT); small cell lymphocytic lymphoma; mantle cell lymphoma (MCL); Burkitt lymphoma; mediastinal large B cell lymphoma; Waldenström macroglobulinemia; nodal marginal zone B cell lymphoma (NMZL); splenic marginal zone lymphoma (SMZL); intravascular large B-cell lymphoma; primary effusion lymphoma; lymphomatoid granulomatosis, etc. Non-malignant B cell hyperproliferative conditions include monoclonal B cell lymphocytosis (MBL).

T cell lineage malignancies of interest include, without limitation, precursor T-cell lymphoblastic lymphoma; T-cell prolymphocytic leukemia; T-cell granular lymphocytic leukemia; aggressive NK cell leukemia; adult T-cell lymphoma/leukemia (HTLV 1-positive); extranodal NK/T-cell lymphoma; enteropathy-type T-cell lymphoma; hepatosplenic γδ T-cell lymphoma; subcutaneous panniculitis-like T-cell lymphoma; mycosis fungoides/Sezary syndrome; anaplastic large cell lymphoma, T/null cell; peripheral T-cell lymphoma; angioimmunoblastic T-cell lymphoma; chronic lymphocytic leukemia (CLL); acute lymphocytic leukemia (ALL); prolymphocytic leukemia; and hairy cell leukemia.

Other malignancies of interest include, without limitation, acute myeloid leukemia, head and neck cancers, brain cancer, breast cancer, ovarian cancer, cervical cancer, colorectal cancer, endometrial cancer, gallbladder cancer, gastric cancer, bladder cancer, prostate cancer, testicular cancer, liver cancer, lung cancer, kidney (renal cell) cancer, esophageal cancer, pancreatic cancer, thyroid cancer, bile duct cancer, pituitary tumor, wilms tumor, kaposi sarcoma, osteosarcoma, thymus cancer, skin cancer, heart cancer, oral and larynx cancer, neuroblastoma and non-hodgkin lymphoma.

Neurological inflammatory conditions are of interest, e.g. Alzheimer's Disease, Parkinson's Disease, Lou Gehrig's Disease, etc. and demyelinating diseases, such as multiple sclerosis, chronic inflammatory demyelinating polyneuropathy, etc. as well as inflammatory conditions such as rheumatoid arthritis. Systemic lupus erythematosus (SLE) is an autoimmune disease characterized by polyclonal B cell activation, which results in a variety of anti-protein and non-protein autoantibodies (see Kotzin et al. (1996) Cell 85:303-306). These autoantibodies form immune complexes that deposit in multiple organ systems, causing tissue damage. An autoimmune component may be ascribed to atherosclerosis, where candidate autoantigens include Hsp60, oxidized LDL, and 2-Glycoprotein I (2GPI).

A sample for use in the methods described herein may be one that is collected from a subject with a malignancy or hyperproliferative condition, including lymphomas, leukemias, and plasmacytomas. A lymphoma is a solid neoplasm of lymphocyte origin, and is most often found in the lymphoid tissue. Thus, for example, a biopsy from a lymph node, e.g. a tonsil, containing such a lymphoma would constitute a suitable biopsy. Samples may be obtained from a subject or patient at one or a plurality of time points in the progression of disease and/or treatment of the disease.

In some embodiments, the disclosure provides methods for performing target-specific multiplex PCR on a cDNA sample having a plurality of expressed immune receptor target sequences using primers having a cleavable group.

In certain embodiments, library and/or template preparation to be sequenced are prepared automatically from a population of nucleic acid samples using the compositions provided herein using an automated systems, e.g., the Ion Chef™ system.

As used herein, the term "subject" includes a person, a patient, an individual, someone being evaluated, etc.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or.

As used herein, "antigen" refers to any substance that, when introduced into a body, e.g., of a subject, can stimulate an immune response, such as the production of an antibody or T cell receptor that recognizes the antigen. Antigens include molecules such as nucleic acids, lipids, ribonucleoprotein complexes, protein complexes, proteins, polypeptides, peptides and naturally occurring or synthetic modifications of such molecules against which an immune response involving T and/or B lymphocytes can be generated. With regard to autoimmune disease, the antigens herein are often referred to as autoantigens. With regard to allergic disease the antigens herein are often referred to as allergens. Autoantigens are any molecule produced by the organism that can be the target of an immunologic response, including peptides, polypeptides, and proteins encoded within the genome of the organism and post-translationally-generated modifications of these peptides, polypeptides, and proteins. Such molecules also include carbohydrates, lipids and other molecules produced by the organism. Antigens also include vaccine antigens, which include, without limitation, pathogen antigens, cancer associated antigens, allergens, and the like.

As used herein, "amplify", "amplifying" or "amplification reaction" and their derivatives, refer to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR).

As used herein, "amplification conditions" and its derivatives, refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences includes polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{2+}$ or $Mn^{2+}$ (e.g., $MgCl_2$, etc) and can also include various modifiers of ionic strength.

As used herein, "target sequence" or "target sequence of interest" and its derivatives, refers to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

As defined herein, "sample" and its derivatives, is used in its broadest sense and includes any specimen, culture and the like that is suspected of including a target. In some embodiments, the sample comprises cDNA, RNA, PNA, LNA, chimeric, hybrid, or multiplex-forms of nucleic acids. The sample can include any biological, clinical, surgical, agricultural, atmospheric or aquatic-based specimen containing one or more nucleic acids. The term also includes any isolated nucleic acid sample such as expressed RNA, fresh-frozen or formalin-fixed paraffin-embedded nucleic acid specimen.

As used herein, "contacting" and its derivatives, when used in reference to two or more components, refers to any process whereby the approach, proximity, mixture or commingling of the referenced components is promoted or achieved without necessarily requiring physical contact of such components, and includes mixing of solutions containing any one or more of the referenced components with each other. The referenced components may be contacted in any particular order or combination and the particular order of recitation of components is not limiting. For example, "contacting A with B and C" encompasses embodiments where A is first contacted with B then C, as well as embodiments where C is contacted with A then B, as well as embodiments where a mixture of A and C is contacted with B, and the like. Furthermore, such contacting does not necessarily require that the end result of the contacting process be a mixture including all of the referenced components, as long as at some point during the contacting process all of the referenced components are simultaneously present or simultaneously included in the same mixture or solution. Where one or more of the referenced components to be contacted includes a plurality (e.g., "contacting a target sequence with a plurality of target-specific primers and a polymerase"), then each member of the plurality can be viewed as an individual component of the contacting process, such that the contacting can include contacting of any one or more members of the plurality with any other member of the plurality and/or with any other referenced component (e.g., some but not all of the plurality of target specific primers can be contacted with a target sequence, then a polymerase, and then with other members of the plurality of target-specific primers) in any order or combination.

As used herein, the term "primer" and its derivatives refer to any polynucleotide that can hybridize to a target sequence of interest. In some embodiments, the primer can also serve to prime nucleic acid synthesis. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof, which may be optionally linked to form a linear polymer of any suitable length. In some embodiments, the primer is a single-stranded oligonucleotide or polynucleotide. (For purposes of this disclosure, the terms 'polynucleotide" and "oligonucleotide" are used interchangeably herein and do not necessarily indicate any difference in length between the two). In some embodiments, the primer is single-stranded but it can also be double-stranded. The primer optionally occurs naturally, as in a purified restriction digest, or can be produced synthetically. In some embodiments, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some embodiments, the primer is an oligodeoxyribonucleotide or an oligoribonucleotide. In some embodiments, the primer can include one or more nucleotide analogs. The exact length and/or composition, including sequence, of the target-specific primer can influence many properties, including melting temperature ($T_m$), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some embodiments, a primer can be paired with a compatible primer within an amplification or synthesis reaction to form a primer pair consisting or a forward primer and a reverse primer. In some embodiments, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some embodiments, one end of an amplification or synthesis product is defined by the forward primer and the other end of the amplification or synthesis product is defined by the reverse primer. In some embodiments, where the amplification or synthesis of lengthy primer extension products is required, such as amplifying an exon, coding region, or gene, several primer pairs can be created than span the desired length to enable sufficient amplification of the region. In some embodiments, a primer can include one or more cleavable groups. In some embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPs and a polymerase. In some embodiments, the primer includes one or more cleavable groups at one or more locations within the primer.

As used herein, "target-specific primer" and its derivatives, refers to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some embodiments, the target-specific primer is capable of hybridizing to at least a portion of its corresponding target sequence (or to a complement of the target sequence); such hybridization can optionally be performed under standard hybridization conditions or under stringent hybridization conditions. In some embodiments, the target-specific primer is not capable of hybridizing to the target sequence, or to its complement, but is capable of hybridizing to a portion of a nucleic acid strand including the target sequence, or to its complement. In some embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In some embodiments, the target-specific primer is substantially non-complementary to other target sequences present in the sample; optionally, the target-specific primer is substantially non-complementary to other nucleic acid molecules present in the sample. In some embodiments, nucleic acid molecules present in the sample that do not include or correspond to a target sequence (or to a complement of the target sequence) are referred to as "non-specific" sequences or "non-specific nucleic acids". In some embodiments, the target-specific primer is designed to include a nucleotide sequence that is substantially complementary to at least a portion of its corresponding target sequence. In some embodiments, a target-specific primer is at least 95% complementary, or at least 99% complementary, or identical, across its entire length to at least a portion of a nucleic acid molecule that includes its corresponding target sequence. In some embodiments, a target-specific primer is at least 90%, at least 95% complementary, at least 98% complementary or at least 99% complementary, or identical, across its entire length to at least a portion of its corresponding target sequence. In some embodiments, a forward target-specific primer and a reverse target-specific primer define a target-specific primer pair that are used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some embodiments, amplification is performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In some embodiments, the target-specific primer is substantially non-complementary at its 3' end or its 5' end to any other target-specific primer present in an amplification reaction. In some embodiments, the target-specific primer can include minimal cross hybridization to other target-specific primers in the amplification reaction. In some embodiments, target-specific primers include minimal cross-hybridization to non-specific sequences in the amplification reaction mixture. In some embodiments, the target-specific primers include minimal self-complementarity. In some embodiments, the target-specific primers can include one or more cleavable groups located at the 3' end. In some embodiments, the target-specific primers can include one or more cleavable groups located near or about a central nucleotide of the target-specific primer. In some embodiments, one of more targets-specific primers includes only non-cleavable nucleotides at the 5' end of the target-specific primer. In some embodiments, a target specific primer includes minimal nucleotide sequence overlap at the 3'end or the 5' end of the primer as compared to one or more different target-specific primers, optionally in the same amplification reaction. In some embodiments 1, 2, 3, 4, 5, 6, 7, 8, 9, 10 or more, target-specific primers in a single reaction mixture include one or more of the above embodiments. In some embodiments, substantially all of the plurality of target-specific primers in a single reaction mixture includes one or more of the above embodiments.

As used herein, "polymerase" and its derivatives, refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase is a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase is optionally reactivated, for example through the use of heat, chemicals or re-addition of new amounts of polymerase into a reaction mixture. In some embodiments, the polymerase can include a hot-start polymerase or an aptamer based polymerase that optionally is reactivated.

As used herein, the term "nucleotide" and its variants comprises any compound, including without limitation any naturally occurring nucleotide or analog thereof, which can bind selectively to, or is polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain is attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain is linked together with intervening O, NH, S, methylene, substituted methylene, ethylene, substituted ethylene, $CNH_2$, C(O), $C(CH_2)$, $CH_2CH_2$, or C(OH)$CH_2R$ (where R can be a 4-pyridine or 1-imidazole). In one embodiment, the phosphorus atoms in the chain has side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in U.S. Pat. No. 7,405,281. In some embodiments, the nucleotide comprises a label and referred to herein as a "labeled nucleotide"; the label of the labeled nucleotide is referred to herein as a "nucleotide label." In some embodiments, the label is in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. alpha-thio-nucleotide 5'-triphosphates. For a review of nucleic acid chemistry, see: Shabarova, Z. and Bogdanov, A. Advanced Organic Chemistry of Nucleic Acids, VCH, New York, 1994.

The term "extension" and its variants, as used herein, when used in reference to a given primer, comprises any in vivo or in vitro enzymatic activity characteristic of a given polymerase that relates to polymerization of one or more nucleotides onto an end of an existing nucleic acid molecule. Typically but not necessarily such primer extension occurs in a template-dependent fashion; during template-dependent extension, the order and selection of bases is driven by established base pairing rules, which can include Watson-Crick type base pairing rules or alternatively (and especially in the case of extension reactions involving nucleotide analogs) by some other type of base pairing paradigm. In one non-limiting example, extension occurs via polymerization of nucleotides on the 3'OH end of the nucleic acid molecule by the polymerase.

The term "portion" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences and/or primers) that can undergo cumulative base pairing at two or more individual corresponding positions in antiparallel orientation, as in a hybridized duplex. Such base pairing can proceed according to any set of established rules, for example according to Watson-Crick base pairing rules or according to some other base pairing paradigm. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some embodiments, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some embodiments, two non-complementary or substantially non-complementary sequences cannot hybridize to each other under standard or stringent hybridization conditions. A "mismatch" is present at any position in the sequences where two opposed nucleotides are not complementary. Complementary nucleotides include nucleotides that are efficiently incorporated by DNA polymerases opposite each other during DNA replication under physiological conditions. In a typical embodiment, complementary nucleotides can form base pairs with each other, such as the A-T/U and G-C base pairs formed through specific Watson-Crick type hydrogen bonding, or base pairs formed through some other type of base pairing paradigm, between the nucleobases of nucleotides and/or polynucleotides in positions antiparallel to each other. The complementarity of other artificial base pairs can be based on other types of hydrogen bonding and/or hydrophobicity of bases and/or shape complementarity between bases.

As used herein, "amplified target sequences" and its derivatives, refers to a nucleic acid sequence produced by the amplification of/amplifying the target sequences using target-specific primers and the methods provided herein. The amplified target sequences may be either of the same sense (the positive strand produced in the second round and subsequent even-numbered rounds of amplification) or anti-sense (i.e., the negative strand produced during the first and subsequent odd-numbered rounds of amplification) with respect to the target sequences. In some embodiments, the amplified target sequences is less than 50% complementary to any portion of another amplified target sequence in the reaction. In other embodiments, the amplified target sequences is greater than 50%, greater than 60%, greater than 70%, greater than 80%, or greater than 90% complementary to any portion of another amplified target sequence in the reaction.

As used herein, the terms "ligating", "ligation" and their derivatives refer to the act or process for covalently linking two or more molecules together, for example, covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, for example embodiments wherein the nucleic acid molecules to be ligated include conventional nucleotide residues, the ligation can include forming a covalent bond between a 5' phosphate group of one nucleic acid and a 3' hydroxyl group of a second nucleic acid thereby forming a ligated nucleic acid molecule. In some embodiments, any means for joining nicks or bonding a 5'phosphate to a 3' hydroxyl between adjacent nucleotides can be employed. In an exemplary embodiment, an enzyme such as a ligase is used. For the purposes of this disclosure, an amplified target sequence can be ligated to an adapter to generate an adapter-ligated amplified target sequence.

As used herein, "ligase" and its derivatives, refers to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. In some embodiments, the ligase is an isothermal ligase. In some embodiments, the ligase is a thermostable ligase. Suitable ligases may include, but not limited to, T4 DNA ligase, T4 RNA ligase, and *E. coli* DNA ligase.

As used herein, "ligation conditions" and its derivatives, refers to conditions suitable for ligating two molecules to each other. In some embodiments, the ligation conditions are suitable for sealing nicks or gaps between nucleic acids. As defined herein, a "nick" or "gap" refers to a nucleic acid molecule that lacks a directly bound 5' phosphate of a mononucleotide pentose ring to a 3' hydroxyl of a neighboring mononucleotide pentose ring within internal nucleotides of a nucleic acid sequence. As used herein, the term nick or gap is consistent with the use of the term in the art. Typically, a nick or gap is ligated in the presence of an enzyme, such as ligase at an appropriate temperature and pH. In some embodiments, T4 DNA ligase can join a nick between nucleic acids at a temperature of about 70-72° C.

As used herein, "blunt-end ligation" and its derivatives, refers to ligation of two blunt-end double-stranded nucleic acid molecules to each other. A "blunt end" refers to an end of a double-stranded nucleic acid molecule wherein substantially all of the nucleotides in the end of one strand of the nucleic acid molecule are base paired with opposing nucleotides in the other strand of the same nucleic acid molecule. A nucleic acid molecule is not blunt ended if it has an end that includes a single-stranded portion greater than two nucleotides in length, referred to herein as an "overhang". In some embodiments, the end of nucleic acid molecule does not include any single stranded portion, such that every nucleotide in one strand of the end is based paired with opposing nucleotides in the other strand of the same nucleic acid molecule. In some embodiments, the ends of the two blunt ended nucleic acid molecules that become ligated to each other do not include any overlapping, shared or complementary sequence. Typically, blunted-end ligation excludes the use of additional oligonucleotide adapters to assist in the ligation of the double-stranded amplified target sequence to the double-stranded adapter, such as patch oligonucleotides as described in US Pat. Publication No. 2010/0129874. In some embodiments, blunt-ended ligation includes a nick translation reaction to seal a nick created during the ligation process.

As used herein, the terms "adapter" or "adapter and its complements" and their derivatives, refers to any linear oligonucleotide which is ligated to a nucleic acid molecule of the disclosure. Optionally, the adapter includes a nucleic acid sequence that is not substantially complementary to the 3' end or the 5' end of at least one target sequences within the sample. In some embodiments, the adapter is substantially non-complementary to the 3' end or the 5' end of any target sequence present in the sample. In some embodiments, the adapter includes any single stranded or double-stranded linear oligonucleotide that is not substantially complementary to an amplified target sequence. In some embodiments, the adapter is substantially non-complementary to at least one, some or all of the nucleic acid molecules of the sample. In some embodiments, suitable adapter lengths are in the range of about 10-100 nucleotides, about 12-60 nucleotides and about 15-50 nucleotides in length. An adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. The structure and properties of universal amplification primers are well known to those skilled in the art and can be implemented for utilization in conjunction with provided methods and compositions to adapt to specific analysis platforms (e.g., as described herein universal P1 and A primers have been described in the art and utilized for sequencing on Ion Torrent sequencing platforms). Similarly, additional and other universal adaptor/primer sequences described and known in the art (e.g., Illumina universal adaptor/primer sequences, PacBio universal adaptor/primer sequences, etc.) can be used in conjunction with the methods and compositions provided herein. In some embodiments, the adapter can include a barcode or tag to assist with downstream cataloguing, identification or sequencing. In some embodiments, a single-stranded adapter can act as a substrate for amplification when ligated to an amplified target sequence, particularly in the presence of a polymerase and dNTPs under suitable temperature and pH.

In some embodiments, an adapter is ligated to a polynucleotide through a blunt-end ligation. In other embodiments, an adapter is ligated to a polynucleotide via nucleotide overhangs on the ends of the adapter and the polynucleotide. For overhang ligation, an adapter may have a nucleotide overhang added to the 3' and/or 5' ends of the respective strands if the polynucleotides to which the adapters are to be ligated (eg, amplicons) have a complementary overhang added to the 3' and/or 5' ends of the respective strands. For example, adenine nucleotides can be added to the 3' terminus of an end-repaired PCR product. Adapters having with an overhang formed by thymine nucleotides can then dock with the A-overhang of the amplicon and be ligated to the amplicon by a DNA ligase, such as T4 DNA ligase.

As used herein, "reamplifying" or "reamplification" and their derivatives refer to any process whereby at least a portion of an amplified nucleic acid molecule is further amplified via any suitable amplification process (referred to in some embodiments as a "secondary" amplification or "reamplification", thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the reamplification can involve the use of different amplification conditions and/or different primers, including different target-specific primers than the primary amplification.

As defined herein, a "cleavable group" refers to any moiety that once incorporated into a nucleic acid can be cleaved under appropriate conditions. For example, a cleavable group can be incorporated into a target-specific primer, an amplified sequence, an adapter or a nucleic acid molecule of the sample. In an exemplary embodiment, a target-specific primer can include a cleavable group that becomes incorporated into the amplified product and is subsequently cleaved after amplification, thereby removing a portion, or all, of the target-specific primer from the amplified product. The cleavable group can be cleaved or otherwise removed from a target-specific primer, an amplified sequence, an adapter or a nucleic acid molecule of the sample by any acceptable means. For example, a cleavable group can be removed from a target-specific primer, an amplified sequence, an adapter or a nucleic acid molecule of the sample by enzymatic, thermal, photo-oxidative or chemical treatment. In one aspect, a cleavable group can include a nucleobase that is not naturally occurring. For example, an oligodeoxyribonucleotide can include one or more RNA nucleobases, such as uracil that can be removed by a uracil glycosylase. In some embodiments, a cleavable group can include one or more modified nucleobases (such as 7-methylguanine, 8-oxo-guanine, xanthine, hypoxanthine, 5,6-dihydrouracil or 5-methylcytosine) or one or more modified nucleosides (i.e., 7-methylguanosine, 8-oxo-deoxyguanosine, xanthosine, inosine, dihydrouridine or 5-methylcytidine). The modified nucleobases or nucleotides can be removed from the nucleic acid by enzymatic, chemical or thermal means. In one embodiment, a cleavable group can include a moiety that can be removed from a primer after amplification (or synthesis) upon exposure to ultraviolet light (i.e., bromodeoxyuridine). In another embodiment, a cleavable group can include methylated cytosine. Typically, methylated cytosine can be cleaved from a primer for example, after induction of amplification (or synthesis), upon sodium bisulfite treatment. In some embodiments, a cleavable moiety can include a restriction site. For example, a primer or target sequence can include a nucleic acid sequence that is specific to one or more restriction enzymes, and following amplification (or synthesis), the primer or target sequence can be treated with the one or more restriction enzymes such that the cleavable group is removed. Typically, one or more cleavable groups can be included at one or more locations with a target-specific primer, an amplified sequence, an adapter or a nucleic acid molecule of the sample.

As used herein, "cleavage step" and its derivatives, refers to any process by which a cleavable group is cleaved or otherwise removed from a target-specific primer, an amplified sequence, an adapter or a nucleic acid molecule of the sample. In some embodiments, the cleavage step involves a chemical, thermal, photo-oxidative or digestive process.

As used herein, the term "hybridization" is consistent with its use in the art, and refers to the process whereby two nucleic acid molecules undergo base pairing interactions. Two nucleic acid molecule molecules are said to be hybridized when any portion of one nucleic acid molecule is base paired with any portion of the other nucleic acid molecule; it is not necessarily required that the two nucleic acid molecules be hybridized across their entire respective lengths and in some embodiments, at least one of the nucleic acid molecules can include portions that are not hybridized to the other nucleic acid molecule. The phrase "hybridizing under stringent conditions" and its variants refers to conditions under which hybridization of a target-specific primer to a target sequence occurs in the presence of high hybridization temperature and low ionic strength. In one exemplary embodiment, stringent hybridization conditions include an aqueous environment containing about 30 mM magnesium sulfate, about 300 mM Tris-sulfate at pH 8.9, and about 90 mM ammonium sulfate at about 60-68° C., or equivalents thereof. As used herein, the phrase "standard hybridization conditions" and its variants refers to conditions under which hybridization of a primer to an oligonucleotide (i.e., a target sequence), occurs in the presence of low hybridization temperature and high ionic strength. In one exemplary embodiment, standard hybridization conditions include an aqueous environment containing about 100 mM magnesium sulfate, about 500 mM Tris-sulfate at pH 8.9, and about 200 mM ammonium sulfate at about 50-55° C., or equivalents thereof.

As used herein, "GC content" and its derivatives, refers to the cytosine and guanine content of a nucleic acid molecule. The GC content of a target-specific primer (or adapter) of the disclosure is 85% or lower. More typically, the GC content of a target-specific primer or adapter of the disclosure is between 15-85%.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and is referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the 30 nucleotides located adjacent to the 3' hydroxyl, typically the terminal 20 and even more typically the terminal 15 nucleotides. One or more linked nucleotides can be represented as a percentage of the nucleotides present in the oligonucleotide or can be provided as a number of linked nucleotides adjacent to the unlinked 3' hydroxyl. For example, the 3' end can include less than 50% of the nucleotide length of the oligonucleotide. In some embodiments, the 3' end does not include any unlinked 3' hydroxyl group but can include any moiety capable of serving as a site for attachment of nucleotides via primer extension and/or nucleotide polymerization. In some embodiments, the term "3' end" for example when referring to a target-specific primer, can include the terminal 10 nucleotides, the terminal 5 nucleotides, the terminal 4, 3, 2 or fewer nucleotides at the 3'end. In some embodiments, the term "3' end" when referring to a target-specific primer can include nucleotides located at nucleotide positions 10 or fewer from the 3' terminus.

As used herein, "5' end", and its derivatives, refers to an end of a nucleic acid molecule, for example a target sequence or amplified target sequence, which includes a free 5' phosphate group or its equivalent. In some embodiments, the 5' end includes a 5' phosphate group that is not linked to a 3' hydroxyl of a neighboring mononucleotide pentose ring. Typically, the 5' end includes to one or more linked nucleotides located adjacent to the 5' phosphate, typically the 30 nucleotides located adjacent to the nucleotide including the 5' phosphate group, typically the terminal 20 and even more typically the terminal 15 nucleotides. One or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary embodiment, the 5' end can include about 15 nucleotides adjacent to the nucleotide including the terminal 5' phosphate. In some embodiments, the 5' end does not include any unlinked 5' phosphate group but can include any moiety capable of serving as a site of attachment to a 3' hydroxyl group, or to the 3'end of another nucleic acid molecule. In some embodiments, the term "5' end" for example when referring to a target-specific primer, can include the terminal 10 nucleotides, the terminal 5 nucleotides, the terminal 4, 3, 2 or fewer nucleotides at the 5'end. In some embodiments, the term "5' end" when referring to a target-specific primer can include nucleotides located at positions 10 or fewer from the 5' terminus. In some embodiments, the 5' end of a target-specific primer can include only non-cleavable nucleotides, for example nucleotides that do not contain one or more cleavable groups as disclosed herein, or a cleavable nucleotide as would be readily determined by one of ordinary skill in the art.

As used herein, "DNA barcode" and its derivatives, refers to a unique short (e.g., 6-14 nucleotide) nucleic acid sequence within an adapter that can act as a 'key' to distinguish or separate a plurality of amplified target sequences in a sample. For the purposes of this disclosure, a DNA barcode can be incorporated into the nucleotide sequence of an adapter.

As used herein, the phrases "two rounds of target-specific hybridization" or "two rounds of target-specific selection" and their derivatives refers to any process whereby the same target sequence is subjected to two consecutive rounds of hybridization-based target-specific selection, wherein a target sequence is hybridized to a target-specific sequence. Each round of hybridization based target-specific selection can include multiple target-specific hybridizations to at least some portion of a target-specific sequence. In one exemplary embodiment, a round of target-specific selection includes a first target-specific hybridization involving a first region of the target sequence and a second target-specific hybridization involving a second region of the target sequence. The first and second regions can be the same or different. In some embodiments, each round of hybridization-based target-specific selection can include use of two target specific oligonucleotides (e.g., a forward target-specific primer and a reverse target-specific primer), such that each round of selection includes two target-specific hybridizations.

As used herein, "comparable maximal minimum melting temperatures" and its derivatives, refers to the melting temperature ($T_m$) of each nucleic acid fragment for a single adapter or target-specific primer after cleavage of the cleavable groups. The hybridization temperature of each nucleic acid fragment generated by a single adapter or target-specific primer is compared to determine the maximal minimum temperature required preventing hybridization of any nucleic acid fragment from the target-specific primer or adapter to the target sequence. Once the maximal hybridization temperature is known, it is possible to manipulate the adapter or target-specific primer, for example by moving the location of the cleavable group along the length of the primer, to achieve a comparable maximal minimum melting temperature with respect to each nucleic acid fragment.

As used herein, "addition only" and its derivatives, refers to a series of steps in which reagents and components are added to a first or single reaction mixture. Typically, the series of steps excludes the removal of the reaction mixture from a first vessel to a second vessel in order to complete the series of steps. An addition only process excludes the manipulation of the reaction mixture outside the vessel containing the reaction mixture. Typically, an addition-only process is amenable to automation and high-throughput.

As used herein, "synthesizing" and its derivatives, refers to a reaction involving nucleotide polymerization by a polymerase, optionally in a template-dependent fashion. Polymerases synthesize an oligonucleotide via transfer of a nucleoside monophosphate from a nucleoside triphosphate (NTP), deoxynucleoside triphosphate (dNTP) or dideoxy-nucleoside triphosphate (ddNTP) to the 3' hydroxyl of an extending oligonucleotide chain. For the purposes of this disclosure, synthesizing includes to the serial extension of a hybridized adapter or a target-specific primer via transfer of a nucleoside monophosphate from a deoxynucleoside triphosphate.

As used herein, "polymerizing conditions" and its derivatives, refers to conditions suitable for nucleotide polymerization. In typical embodiments, such nucleotide polymerization is catalyzed by a polymerase. In some embodiments, polymerizing conditions include conditions for primer extension, optionally in a template-dependent manner, resulting in the generation of a synthesized nucleic acid sequence. In some embodiments, the polymerizing conditions include polymerase chain reaction (PCR). Typically, the polymerizing conditions include use of a reaction mixture that is sufficient to synthesize nucleic acids and includes a polymerase and nucleotides. The polymerizing conditions can include conditions for annealing of a target-specific primer to a target sequence and extension of the primer in a template dependent manner in the presence of a polymerase. In some embodiments, polymerizing conditions are practiced using thermocycling. Additionally, polymerizing conditions can include a plurality of cycles where the steps of annealing, extending, and separating the two nucleic strands are repeated. Typically, the polymerizing conditions include a cation such as $MgCl_2$. Polymerization of one or more nucleotides to form a nucleic acid strand includes that the nucleotides be linked to each other via phosphodiester bonds, however, alternative linkages may be possible in the context of particular nucleotide analogs.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH^{4+}$, trialkylammonium, $Mg^{2+}$, $Na^+$ and the like. An oligonucleotide can be composed entirely of deoxyribonucleotides, entirely of ribonucleotides, or chimeric mixtures thereof. Oligonucleotides can be comprised of nucleobase and sugar analogs. Polynucleotides typically range in size from a few monomeric units, e.g. 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U' denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As defined herein, the term "nick translation" and its variants comprise the translocation of one or more nicks or gaps within a nucleic acid strand to a new position along the nucleic acid strand. In some embodiments, a nick is formed when a double stranded adapter is ligated to a double stranded amplified target sequence. In one example, the primer can include at its 5' end, a phosphate group that can ligate to the double stranded amplified target sequence, leaving a nick between the adapter and the amplified target sequence in the complementary strand. In some embodiments, nick translation results in the movement of the nick to the 3' end of the nucleic acid strand. In some embodiments, moving the nick can include performing a nick translation reaction on the adapter-ligated amplified target sequence. In some embodiments, the nick translation reaction is a coupled 5' to 3' DNA polymerization/degradation reaction, or coupled to a 5' to 3' DNA polymerization/strand displacement reaction. In some embodiments, moving the nick can include performing a DNA strand extension reaction at the nick site. In some embodiments, moving the nick can include performing a single strand exonuclease reaction on the nick to form a single stranded portion of the adapter-ligated amplified target sequence and performing a DNA strand extension reaction on the single stranded portion of the adapter-ligated amplified target sequence to a new position. In some embodiments, a nick is formed in the nucleic acid strand opposite the site of ligation.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of expressed RNA or cDNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules are PCR amplified using a plurality of different primer pairs, in some cases, one or more primer pairs per target nucleic acid molecule of interest, thereby forming a multiplex PCR reaction. In some embodiments provided herein, multiplex PCR amplifications are performed using a plurality of different primer pairs, in typical cases, one primer pair per target nucleic acid molecule. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of $^{32}$P-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from RNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers to the number of different target-specific sequences that are amplified during that single multiplex amplification. In some embodiments, the plexy is about 12-plex, 24-plex, 48-plex, 74-plex, 96-plex, 120-plex, 144-plex, 168-plex, 192-plex, 216-plex, 240-plex, 264-plex, 288-plex, 312-plex, 336-plex, 360-plex, 384-plex, or 398-plex. In some embodiments, highly multiplexed amplification reactions include reactions with a plexy of greater than 12-plex.

In some embodiments, the amplified target sequences are formed via PCR. Extension of target-specific primers can be accomplished using one or more DNA polymerases. In one embodiment, the polymerase is any Family A DNA polymerase (also known as pol I family) or any Family B DNA polymerase. In some embodiments, the DNA polymerase is a recombinant form capable of extending target-specific primers with superior accuracy and yield as compared to a non-recombinant DNA polymerase. For example, the polymerase can include a high-fidelity polymerase or thermostable polymerase. In some embodiments, conditions for extension of target-specific primers can include 'Hot Start' conditions, for example Hot Start polymerases, such as Amplitaq Gold® DNA polymerase (Applied Biosciences), Platinum® Taq DNA Polymerase High Fidelity (Invitrogen) or KOD Hot Start DNA polymerase (EMD Biosciences). A 'Hot Start' polymerase includes a thermostable polymerase and one or more antibodies that inhibit DNA polymerase and 3'-5' exonuclease activities at ambient temperature. In some instances, 'Hot Start' conditions can include an aptamer.

In some embodiments, the polymerase is an enzyme such as Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*). In some embodiments, the DNA polymerase can include at least one polymerase such as Amplitaq Gold® DNA polymerase (Applied Biosciences), Stoffel fragment of Amplitaq® DNA Polymerase (Roche), KOD polymerase (EMD Biosciences), KOD Hot Start polymerase (EMD Biosciences), Deep Vent™ DNA polymerase (New England Biolabs), Phusion polymerase (New England Biolabs), Klentaq1 polymerase (DNA Polymerase Technology, Inc), Klentaq Long Accuracy polymerase (DNA Polymerase Technology, Inc), Omni KlenTaq™ DNA polymerase (DNA Polymerase Technology, Inc), Omni KlenTaq™ LA DNA polymerase (DNA Polymerase Technology, Inc), Platinum® Taq DNA Polymerase (Invitrogen), Hemo Klentag™ (New England Biolabs), Platinum® Taq DNA Polymerase High Fidelity (Invitrogen), Platinum® Pfx (Invitrogen), Accuprime™ Pfx (Invitrogen), or Accuprime™ Taq DNA Polymerase High Fidelity (Invitrogen).

In some embodiments, the DNA polymerase is a thermostable DNA polymerase. In some embodiments, the mixture of dNTPs is applied concurrently, or sequentially, in a random or defined order. In some embodiments, the amount of DNA polymerase present in the multiplex reaction is significantly higher than the amount of DNA polymerase used in a corresponding single plex PCR reaction. As defined herein, the term "significantly higher" refers to an at least 3-fold greater concentration of DNA polymerase present in the multiplex PCR reaction as compared to a corresponding single plex PCR reaction.

In some embodiments, the amplification reaction does not include a circularization of amplification product, for example as disclosed by rolling circle amplification.

The practice of the present subject matter may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, polymerization techniques, chemical and physical analysis of polymer particles, preparation of nucleic acid libraries, nucleic acid sequencing and analysis, and the like. Specific illustrations of suitable techniques can be used by reference to the examples provided herein. Other equivalent conventional procedures can also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press), Hermanson, Bioconjugate Techniques, Second Edition (Academic Press, 2008); Merkus, Particle Size Measurements (Springer, 2009); Rubinstein and Colby, Polymer Physics (Oxford University Press, 2003); and the like.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various additional exemplary embodiments may be derived by repeating, adding, or substituting any generically or specifically described features and/or components and/or substances and/or steps and/or operating conditions set forth in one or more of the above-described exemplary embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed exemplary embodiments may be considered to be a potential optional feature, component, aspect, step, or other characteristic of any other of the above-discussed exemplary embodiments so long as the objective of such any other of the above-discussed exemplary embodiments remains achievable, unless specifically stated otherwise.

In certain embodiments, compositions of the invention comprise target immune receptor primer sets wherein the primers are directed to sequences of the same target immune receptor gene. Immune receptors are selected from T cell receptors and antibody receptors. In some embodiments a T cell receptor is a T cell receptor selected from the group consisting of TCR alpha, TCR beta, TCR gamma, and TCR delta. In some embodiments the immune receptor is an antibody receptor selected from the group consisting of heavy chain alpha, heavy chain delta, heavy chain epsilon, heavy chain gamma, heavy chain mu, light chain kappa, and light chain lambda.

In some embodiments, compositions of the invention comprise target immune receptor primer sets selected to have various parameters or criteria outlined herein. In some embodiments, compositions of the invention comprise a plurality of target-specific primers (e.g., V gene FR1-, FR2- and FR3-directed primers, the J gene directed primers, and the C gene directed primers) of about 15 nucleotides to about 40 nucleotides in length and having at least two or more following criteria: a cleavable group located at a 3' end of substantially all of the plurality of primers, a cleavable group located near or about a central nucleotide of substantially all of the plurality of primers, substantially all of the plurality of primers at a 5' end including only non-cleavable nucleotides, minimal cross-hybridization to substantially all of the primers in the plurality of primers, minimal cross-hybridization to non-specific sequences present in a sample, minimal self-complementarity, and minimal nucleotide sequence overlap at a 3' end or a 5' end of substantially all of the primers in the plurality of primers. In some embodiments, the composition can include primers with any 3, 4, 5, 6 or 7 of the above criteria.

In some embodiments, composition comprise a plurality of target-specific primers of about 15 nucleotides to about 40 nucleotides in length having two or more of the following criteria: a cleavable group located near or about a central nucleotide of substantially all of the plurality of primers, substantially all of the plurality of primers at a 5' end including only non-cleavable nucleotides, substantially all of the plurality of primers having less than 20% of the nucleotides across the primer's entire length containing a cleavable group, at least one primer having a complementary nucleic acid sequence across its entire length to a target sequence present in a sample, minimal cross-hybridization to substantially all of the primers in the plurality of primers, minimal cross-hybridization to non-specific sequences present in a sample, and minimal nucleotide sequence overlap at a 3' end or a 5' end of substantially all of the primers in the plurality of primers. In some embodiments, the composition can include primers with any 3, 4, 5, 6 or 7 of the above criteria.

In some embodiments, target-specific primers (e.g., the V gene FR1-, FR2- and FR3-directed primers, the J gene directed primers, and the C gene directed primers) used in the compositions of the invention are selected or designed to satisfy any one or more of the following criteria: (1) includes two or more modified nucleotides within the primer sequence, at least one of which is included near or at the termini of the primer and at least one of which is included at, or about the center nucleotide position of the primer sequence; (2) length of about 15 to about 40 bases in length; (3) $T_m$ of from above 60° C. to about 70° C.; (4) low cross-reactivity with non-target sequences present in the sample; (5) at least the first four nucleotides (going from 3' to 5' direction) are non-complementary to any sequence within any other primer present in the composition; and (6) non-complementary to any consecutive stretch of at least 5 nucleotides within any other sequence targeted for amplification with the primers. In some embodiments, the target-specific primers used in the compositions are selected or designed to satisfy any 2, 3, 4, 5, or 6 of the above criteria. In some embodiments, the two or more modified nucleotides have cleavable groups. In some embodiments, each of the plurality of target-specific primers comprises two or more modified nucleotides selected from a cleavable group of methylguanine, 8-oxo-guanine, xanthine, hypoxanthine, 5,6-dihydrouracil, uracil, 5-methylcytosine, thymine-dimer, 7-methylguanosine, 8-oxo-deoxyguanosine, xanthosine, inosine, dihydrouridine, bromodeoxyuridine, uridine or 5-methylcytidine.

In some embodiments compositions are provided for analysis of an immune repertoire in a sample, comprising at least one set of i) a plurality of V gene primers directed to a majority of different V genes of at least one immune receptor coding sequence comprising at least a portion of framework region 1 (FR1) within the V gene; and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such set comprises primers directed to an immune receptor comprising a T cell receptor. In more particular embodiments such set comprises primers directed to TCR beta. In other embodiments such set comprises primers directed to TCR alpha. In still other embodiments at least two sets of primers are encompassed in a composition wherein the sets are directed to TCR alpha and TCR beta.

In particular embodiments, compositions provided include target immune receptor primer sets comprising one or more of a plurality of V gene primers directed to a sequence over an FR1 region about 70 nucleotides in length. In other particular embodiments, the one or more of a plurality of V gene primers are directed to sequences over an FR1 region about 50 nucleotides in length. In certain embodiments a target immune receptor primer set comprises V gene primers comprising about 45 to about 90 different FR1-directed primers. In some embodiments a target immune receptor primer set comprises V gene primers comprising about 50 to about 80 different FR1-directed primers. In some embodiments a target immune receptor primer set comprises V gene primers comprising about 55 to about 75 different FR1-directed primers. In some embodiments a target immune receptor primer set comprises V gene primers comprising about 60 to about 70 different FR1-directed primers. In some embodiments the target immune receptor primer set comprises one or more C gene primers. In particular embodiments a target immune receptor primer set comprises at least two C gene primers wherein each is directed to at least a portion of the same 50 nucleotide region within the target C gene.

In particular embodiments, compositions of the invention comprise at least one set of primers comprising V gene primers i) and C gene primers ii) selected from Tables 2 and 4, respectively. In other certain embodiments compositions of the invention comprise at least one set of primers i) and ii) comprising primers selected from SEQ ID NOs: 1-89 and 181-184 or selected from SEQ ID NOs: 90-180 and 181-184. In some embodiments compositions of the invention comprise at least one set of primers i) and ii) comprising primers selected from SEQ ID NOs: 90-155 and 181-182 or selected from SEQ ID NOs: 90-155 and 183-184. In some embodiments compositions of the invention comprise at least one set of primers i) and ii) comprising primers selected from SEQ ID NOs: 1-89 and 181-182 or selected from SEQ ID NOs: 1-89 and 183-184. In other certain embodiments compositions of the invention comprise at least one set of primers i) and ii) comprising primers SEQ ID NOs: 1-64 and 183-184. In other certain embodiments compositions of the invention comprise at least one set of primers i) and ii) comprising primers SEQ ID NOs: 1-64 and 181-182. In certain embodiments compositions of the invention comprise at least one set of primers i) and ii) comprising primers SEQ ID NOs: 90-92, 95-155, and 181-182 or at least one set of primers i) and ii) comprising primers SEQ ID NOs: 90-92, 95-155, and 183-184. In still other certain embodiments compositions of the invention comprise at least one set of primers of i) and ii) comprising primers SEQ ID NOs: 90-153 and 181-182. In still other certain embodiments compositions of the invention comprise at least one set of primers of i) and ii) comprising primers SEQ ID NOs: 90-153 and 183-184. In still other certain embodiments compositions of the invention comprise at least one set of primers of i) and ii) comprising primers SEQ ID NOs: 90-92 and 95-182. In still other certain embodiments compositions of the invention comprise at least one set of primers of i) and ii) comprising primers SEQ ID NOs: 90-92, 95-180, and 183-184.

In some embodiments compositions of the invention comprise at least one set of primers i) and ii) comprising at least 50 primers selected from SEQ ID NOs: 1-89 and at least one primer selected from SEQ ID NOs: 181-182. In other embodiments compositions of the invention comprise at least one set of primers i) and ii) comprising at least 50 primers selected from SEQ ID NOs: 1-89 and at least one primer selected from SEQ ID NOs: 183-184. In some embodiments compositions of the invention comprise at least one set of primers i) and ii) comprising at least 60 primers selected from SEQ ID NOs: 1-89 and at least one primer selected from SEQ ID NOs: 181-182. In other embodiments compositions of the invention comprise at least one set of primers i) and ii) comprising at least 60 primers selected from SEQ ID NOs: 1-89 and at least one primer selected from SEQ ID NOs: 183-184.

In some embodiments compositions of the invention comprise at least one set of primers i) and ii) comprising at least 50 primers selected from SEQ ID NOs: 90-180 and at least one primer selected from SEQ ID NOs: 181-182. In other embodiments compositions of the invention comprise at least one set of primers i) and ii) comprising at least 50 primers selected from SEQ ID NOs: 90-180 and at least one primer selected from SEQ ID NOs: 183-184. In some embodiments compositions of the invention comprise at least one set of primers i) and ii) comprising at least 60 primers selected from SEQ ID NOs: 90-180 and at least one primer selected from SEQ ID NOs: 181-182. In other embodiments compositions of the invention comprise at least one set of primers i) and ii) comprising at least 60 primers selected from SEQ ID NOs: 90-180 and at least one primer selected from SEQ ID NOs: 183-184.

In some embodiments compositions are provided for analysis of an immune repertoire in a sample, comprising at least one set of i) a plurality of V gene primers directed to a majority of different V genes of at least one immune receptor coding sequence comprising at least a portion of framework region 3 (FR3) within the V gene; and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such set comprises primers directed to an immune receptor comprising a T cell receptor. In more particular embodiments such set comprises primers directed to TCR beta. In other embodiments such set comprises primers directed to TCR alpha. In still other embodiments at least two sets of primers are encompassed in a composition wherein the sets are directed to TCR alpha and TCR beta.

In certain embodiments, compositions provided include target immune receptor primer sets comprising V gene primers wherein the one or more of a plurality of V gene primers are directed to sequences over an FR3 region about 70 nucleotides in length. In particular embodiments, compositions provided include target immune receptor primer sets comprising V gene primers wherein the one or more of a plurality of V gene primers are directed to sequences over an FR3 region about 50 nucleotides in length. In other particular embodiments the one or more of a plurality of V gene primers are directed to sequences over an FR3 region about 40 to about 60 nucleotides in length. In certain embodiments a target immune receptor primer set comprises V gene primers comprising about 45 to about 80 different FR3-directed primers. In certain embodiments a target immune receptor primer set comprises V gene primers comprising about 50 to about 70 different FR3-directed primers. In some embodiments a target immune receptor primer set comprises V gene primers comprising about 55 to about 65 different FR3-directed primers. In some embodiments, a target immune receptor primer set comprises V gene primers comprising about 58, 59, 60, 61, or 62 different FR3-directed primers. In some embodiments the target immune receptor primer set comprises one or more C gene primers. In particular embodiments a target immune receptor primer set comprises at least two C gene primers wherein each is directed to at least a portion of the same 50 nucleotide region within the target C gene.

In particular embodiments, compositions of the invention comprise at least one set of primers comprising V gene primers i) and C gene primers ii) selected from Tables 3 and 4, respectively. In certain other embodiments compositions of the invention comprise at least one set of primers i) and ii) comprising primers selected from SEQ ID NOs: 185-248 and 181-184 or selected from SEQ ID NOs: 249-312 and 181-184. In some embodiments compositions of the invention comprise at least one set of primers i) and ii) comprising primers selected from SEQ ID NOs: 185-248 and 183-184 or selected from SEQ ID NOs: 185-248 and 181-182. In other certain embodiments compositions of the invention comprise at least one set of primers i) and ii) comprising primers SEQ ID NOs: 185-243 and 181-182. In other certain embodiments compositions of the invention comprise at least one set of primers i) and ii) comprising primers SEQ ID NOs: 185-243 and 183-184. In other certain embodiments compositions of the invention comprise at least one set of primers of i) and ii) comprising primers selected from SEQ ID NOs: 249-312 and 181-182 or selected from SEQ ID NOs: 249-312 and 183-184. In other certain embodiments compositions of the invention comprise at least one set of primers i) and ii) comprising primers SEQ ID NOs: 181-182 and 185-243. In still other certain embodiments compositions of the invention comprise at least one set of primers of i) and ii) comprising primers SEQ ID NOs: 249-307 and 181-182. In still other certain embodiments compositions of the invention comprise at least one set of primers of i) and ii) comprising primers SEQ ID NOs: 249-307 and 183-184.

In some embodiments compositions of the invention comprise at least one set of primers i) and ii) comprising at least 50 primers selected from SEQ ID NOs: 249-312 and at least one primer selected from SEQ ID NOs: 181-182. In other embodiments compositions of the invention comprise at least one set of primers i) and ii) comprising at least 50 primers selected from SEQ ID NOs: 249-312 and at least one primer selected from SEQ ID NOs: 183-184. In some embodiments compositions of the invention comprise at least one set of primers i) and ii) comprising at least 50 primers selected from SEQ ID NOs: 185-248 and at least one primer selected from SEQ ID NOs: 181-182. In other embodiments compositions of the invention comprise at least one set of primers i) and ii) comprising at least 50 primers selected from SEQ ID NOs: 185-248 and at least one primer selected from SEQ ID NOs: 183-184.

In some embodiments compositions are provided for analysis of an immune repertoire in a sample, comprising at least one set of i) a plurality of V gene primers directed to a majority of different V genes of at least one immune receptor coding sequence comprising at least a portion of FR2 within the V gene; and ii) one or more C gene primers directed to at least a portion of the respective target C gene of the immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such set comprises primers directed to an immune receptor comprising a T cell receptor. In more particular embodiments such set comprises primers directed to TCR beta. In other embodiments such set comprises primers directed to TCR alpha. In still other embodiments at least two sets of primers are encompassed in a composition wherein the sets are directed to TCR alpha and TCR beta.

In particular embodiments, compositions provided include target immune receptor primer sets comprising V gene primers wherein the one or more of a plurality of V gene primers are directed to sequences over an FR2 region about 70 nucleotides in length. In other particular embodiments the one or more of a plurality of V gene primers are directed to sequences over an FR2 region about 50 nucleotides in length. In certain embodiments a target immune receptor primer set comprises V gene primers comprising about 45 to about 90 different FR2-directed primers. In some embodiments a target immune receptor primer set comprises V gene primers comprising about 30 to about 60 different FR2-directed primers. In some embodiments a target immune receptor primer set comprises V gene primers comprising about 20 to about 50 different FR2-directed primers. In some embodiments a target immune receptor primer set comprises V gene primers comprising about 60 to about 70 different FR2-directed primers. In some embodiments, a target immune receptor primer set comprises about 20 to about 30 different FR2-directed primers. In some embodiments the target immune receptor primer set comprises one or more C gene primers. In particular embodiments a target immune receptor primer set comprises at least two C gene primers wherein each is directed to at least a portion of the same 50 nucleotide region within the target C gene.

In particular embodiments, compositions of the invention comprise at least one set of primers comprising V gene primers i) and C gene primers ii) selected from Tables 6 and 4, respectively. In certain other embodiments compositions of the invention comprise at least one set of primers i) and ii) comprising primers selected from SEQ ID NOs: 483-505 and 181-182. In other embodiments compositions of the invention comprise at least one set of primers i) and ii) comprising primers selected from SEQ ID NOs: 483-505 and 183-184. In other embodiments compositions of the invention comprise at least one set of primers i) and ii) comprising primers SEQ ID NOs: 483-505 and 181-182. In other embodiments compositions of the invention comprise at least one set of primers i) and ii) comprising primers SEQ ID NOs: 483-505 and 183-184.

In some embodiments compositions of the invention comprise at least one set of primers i) and ii) comprising at least 20 primers selected from SEQ ID NOs: 483-505 and at least one primer selected from SEQ ID NOs: 181-182. In other embodiments compositions of the invention comprise at least one set of primers i) and ii) comprising at least 20 primers selected from SEQ ID NOs: 483-505 and at least one primer selected from SEQ ID NOs: 183-184.

In some embodiments compositions are provided for analysis of an immune repertoire in a sample, comprising at least one set of i) a plurality of V gene primers directed to a majority of different V gene of at least one immune receptor coding sequence comprising at least a portion of framework region 3 (FR3) within the V gene; and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such set comprises primers directed to an immune receptor comprising a T cell receptor. In more particular embodiments such set comprises primers directed to TCR beta. In other embodiments such set comprises primers directed to TCR alpha. In still other embodiments at least two sets of primers are encompassed in a composition wherein the sets are directed to TCR alpha and TCR beta.

In particular embodiments, compositions provided include target immune receptor primer sets comprising V gene primers wherein the one or more of a plurality of V gene primers are directed to sequences over an FR3 region about 50 nucleotides in length. In other embodiments the one or more of a plurality of V gene primers are directed to sequences over an FR3 region about 70 nucleotides in length. In other particular embodiments the one or more of a plurality of V gene primers are directed to sequences over an FR3 region about 40 to about 60 nucleotides in length. In some embodiments a target immune receptor primer set comprises V gene primers comprising about 45 to about 80 different FR3-directed primers. In certain embodiments a target immune receptor primer set comprises V gene primers comprising about 50 to about 70 different FR3-directed primers. In some embodiments a target immune receptor primer set comprises V gene primers comprising about 55 to about 65 different FR3-directed primers. In some embodiments, a target immune receptor primer set comprises V gene primers comprising about 58, 59, 60, 61, or 62 different FR3-directed primers. In some embodiments the target immune receptor primer set comprises a plurality of J gene primers. In some embodiments a target immune receptor primer set comprises at least 10 J gene primers wherein each is directed to at least a portion of a J gene within target polynucleotides. In certain embodiments a target immune receptor primer set comprises at least 10 J gene primers wherein each is directed to at least a portion of the same 50 nucleotide region within a target J gene region. In some embodiments a target immune receptor primer set comprises at least 16 J gene primers wherein each is directed to at least a portion of a J gene within target polynucleotides. In some embodiments a target immune receptor primer set comprises about 10 to about 20 J gene primers wherein each is directed to at least a portion of a J gene within target polynucleotides. In some embodiments a target immune receptor primer set comprises about 12 to about 18 J gene primers wherein each is directed to at least a portion of the J gene portion within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, compositions of the invention comprise at least one set of primers comprising V gene primers i) and J gene primers ii) selected from Tables 3 and 5, respectively. In certain embodiments compositions of the invention comprise at least one set of primers i) and ii) comprising primers selected from SEQ ID NOs: 185-248 and 313-397 or selected from SEQ ID NOs: 185-248 and 398-482. In other certain embodiments compositions of the invention comprise at least one set of primers i) and ii) comprising primers selected from SEQ ID NOs: 185-248 and 313-329 or selected from SEQ ID NOs: 185-248 and 313-342. In other embodiments compositions of the invention comprise at least one set of primers i) and ii) comprising primers selected from SEQ ID NOs: 185-248 and 398-414 or selected from SEQ ID NOs: 185-248 and 414-427. In certain other embodiments compositions of the invention comprise at least one set of primers i) and ii) comprising primers SEQ ID NOs: 185-243 and 313-328. In still other embodiments compositions of the invention comprise at least one set of primers of i) and ii) comprising primers SEQ ID NOs: 185-243 and 398-413. In other embodiments compositions of the invention comprise at least one set of primers i) and ii) comprising primers selected from SEQ ID NOs: 249-312 and 313-328 or selected from SEQ ID NOs: 249-312 and 398-413. In certain embodiments compositions of the invention comprise at least one set of primers i) and ii) comprising primers selected from SEQ ID NOs: 249-312 and 313-397 or selected from SEQ ID NOs: 249-312 and 398-482. In other embodiments compositions of the invention comprise at least one set of primers i) and ii) comprising primers selected from SEQ ID NOs: 249-312 and 313-329 or selected from SEQ ID NOs: 249-312 and 329-342. In other embodiments compositions of the invention comprise at least one set of primers i) and ii) comprising primers selected from SEQ ID NOs: 249-312 and 398-414 or selected from SEQ ID NOs: 249-312 and 414-427. In certain other embodiments compositions of the invention comprise at least one set of primers i) and ii) comprising primers SEQ ID NOs: 249-312 and 398-413. In still other embodiments compositions of the invention comprise at least one set of primers of i) and ii) comprising primers SEQ ID NOs: 249-312 and 313-328.

In some embodiments compositions of the invention comprise at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 398-482. In some embodiments compositions of the invention comprise at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 313-397. In some embodiments compositions of the invention comprise at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 313-397. In some embodiments compositions of the invention comprise at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 398-482.

In some embodiments compositions of the invention comprise at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 398-427. In some embodiments compositions of the invention comprise at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 313-342. In some embodiments compositions of the invention comprise at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 313-342. In some embodiments compositions of the invention comprise at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 398-427.

In some embodiments compositions are provided for analysis of an immune repertoire in a sample, comprising at least one set of i) a plurality of V gene primers directed to a majority of different V gene of at least one immune receptor coding sequence comprising at least a portion of framework region 1 (FR1) within the V gene; and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such set comprises primers directed to an immune receptor comprising a T cell receptor. In more particular embodiments such set comprises primers directed to TCR beta. In other embodiments such set comprises primers directed to TCR alpha. In still other embodiments at least two sets of primers are encompassed in a composition wherein the sets are directed to TCR alpha and TCR beta.

In particular embodiments, compositions provided include target immune receptor primer sets comprising one or more of a plurality of V gene primers directed to a sequence over an FR1 region about 70 nucleotides in length. In other embodiments the one or more of a plurality of V gene primers are directed to sequences over an FR1 region about 80 nucleotides in length. In other particular embodiments, the one or more of a plurality of V gene primers are directed to sequences over an FR1 region about 50 nucleotides in length. In certain embodiments a target immune receptor primer set comprises V gene primers comprising about 45 to about 90 different FR1-directed primers. In some embodiments a target immune receptor primer set comprises V gene primers comprising about 50 to about 80 different FR1-directed primers. In some embodiments a target immune receptor primer set comprises V gene primers comprising about 55 to about 75 different FR1-directed primers. In some embodiments a target immune receptor primer set comprises V gene primers comprising about 60 to about 70 different FR1-directed primers. In some embodiments the target immune receptor primer set comprises a plurality of J gene primers. In some embodiments a target immune receptor primer set comprises at least 10 J gene primers wherein each is directed to at least a portion of a J gene within target polynucleotides. In certain embodiments a target immune receptor primer set comprises at least 10 J gene primers wherein each is directed to at least a portion of the same 50 nucleotide region within a target J gene region. In some embodiments a target immune receptor primer set comprises at least 16 J gene primers wherein each is directed to at least a portion of a J gene within target polynucleotides. In some embodiments a target immune receptor primer set comprises about 10 to about 20 J gene primers wherein each is directed to at least a portion of a J gene within target polynucleotides. In some embodiments a target immune receptor primer set comprises about 12 to about 18 J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, compositions of the invention comprise at least one set of primers comprising V gene primers i) and J gene primers ii) selected from Tables 2 and 5, respectively. In certain other embodiments compositions of the invention comprise at least one set of primers i) and ii) comprising primers selected from SEQ ID NOs: 1-89 and 313-397 or selected from SEQ ID NOs: 90-180 and 313-397. In other embodiments compositions of the invention comprise at least one set of primers i) and ii) comprising primers selected from SEQ ID NOs: 1-89 and 398-482 or selected from SEQ ID NOs: 90-180 and 398-482. In other embodiments compositions of the invention comprise least one set of primers i) and ii) comprising primers selected from SEQ ID NOs: 1-64 and 398-482 or selected from SEQ ID NOs: 1-64 and 313-397. In still other embodiments compositions of the invention comprise least one set of primers i) and ii) comprising primers selected from SEQ ID NOs: 1-64 and 313-329 or selected from SEQ ID NOs: 1-64 and 329-342. In other embodiments compositions of the invention comprise at least one set of primers i) and ii) comprising primers selected from SEQ ID NOs: 1-64 and 398-414 or selected from SEQ ID NOs: 1-64 and 414-427. In other embodiments compositions of the invention comprise at least one set of primers i) and ii) comprising primers SEQ ID NOs: 1-64 and 313-328. In certain other embodiments compositions of the invention comprise at least one set of primers i) and ii) comprising primers SEQ ID NOs: 1-64 and 398-413. In certain embodiments compositions of the invention comprise at least one set of primers i) and ii) comprising primers selected from SEQ ID NOs: 90-180 and 313-342 or selected from SEQ ID NOs: 90-180 and 398-427. In certain embodiments compositions of the invention comprise at least one set of primers i) and ii) comprising primers selected from SEQ ID NOs: 90-155 and 313-342 or selected from SEQ ID NOs: 90-155 and 398-427. In other embodiments compositions of the invention comprise at least one set of primers i) and ii) comprising primers selected from SEQ ID NOs: 90-155 and 398-414 or selected from SEQ ID NOs: 90-155 and 414-427. In other embodiments compositions of the invention comprise at least one set of primers i) and ii) comprising primers selected from SEQ ID NOs: 90-155 and 313-329 or selected from SEQ ID NOs: 90-155 and 329-342. In still other embodiments compositions of the invention comprise at least one set of primers of i) and ii) comprising primers SEQ ID NOs: 90-153 and 398-414. In still other embodiments compositions of the invention comprise at least one set of primers of i) and ii) comprising primers SEQ ID NOs: 90-153 and 313-328. In still other embodiments compositions of the invention comprise at least one set of primers i) and ii) comprising primers selected from SEQ ID NOs: 90-92, 95-180 and 329-342 or selected from SEQ ID NOs: 90-92, 95-180 and 313-329. In other embodiments compositions of the invention comprise at least one set of primers i) and ii) comprising primers selected from SEQ ID NOs: 90-92, 95-180 and 398-414 or selected from SEQ ID NOs: 90-92, 95-180 and 414-427. In certain other embodiments compositions of the invention comprise at least one set of primers of i) and ii) comprising primers SEQ ID NOs: 90-92, 95-180 and 313-328. In still other embodiments compositions of the invention comprise at least one set of primers of i) and ii) comprising primers SEQ ID NOs: 90-92, 95-180, and 303-318.

In some embodiments compositions of the invention comprise at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 398-482. In some embodiments compositions of the invention comprise at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 398-482.

In some embodiments compositions of the invention comprise at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 398-427. In some embodiments compositions of the invention comprise at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 398-427.

In some embodiments compositions of the invention comprise at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 398-482. In some embodiments compositions of the invention comprise at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 398-482.

In some embodiments compositions of the invention comprise at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 398-427. In some embodiments compositions of the invention comprise at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 398-427. In some embodiments compositions are provided for analysis of an immune repertoire in a sample, comprising at least one set of i) a plurality of V gene primers directed to a majority of different V gene of at least one immune receptor coding sequence comprising at least a portion of FR2 within the V gene; and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such set comprises primers directed to an immune receptor comprising a T cell receptor. In more particular embodiments such set comprises primers directed to TCR beta. In other embodiments such set comprises primers directed to TCR alpha. In still other embodiments at least two sets of primers are encompassed in a composition wherein the sets are directed to TCR alpha and TCR beta.

In particular embodiments, compositions provided include target immune receptor primer sets comprising V gene primers wherein the one or more of a plurality of V gene primers are directed to sequences over an FR2 region about 70 nucleotides in length. In other particular embodiments the one or more of a plurality of V gene primers are directed to sequences over an FR2 region about 50 nucleotides in length. In certain embodiments a target immune receptor primer set comprises V gene primers comprising about 45 to about 90 different FR2-directed primers. In some embodiments a target immune receptor primer set comprises V gene primers comprising about 30 to about 60 different FR2-directed primers. In some embodiments a target immune receptor primer set comprises V gene primers comprising about 20 to about 50 different FR2-directed primers. In some embodiments a target immune receptor primer set comprises V gene primers comprising about 60 to about 70 different FR2-directed primers. In some embodiments, a target immune receptor primer set comprises about 20 to about 30 different FR2-directed primers. In some embodiments the target immune receptor primer set comprises a plurality of J gene primers. In some embodiments a target immune receptor primer set comprises at least 10 J gene primers wherein each is directed to at least a portion of a J gene within target polynucleotides. In some embodiments a target immune receptor primer set comprises at least 16 J gene primers wherein each is directed to at least a portion of a J gene within target polynucleotides. In some embodiments a target immune receptor primer set comprises about 10 to about 20 J gene primers wherein each is directed to at least a portion of a J gene within target polynucleotides. In some embodiments a target immune receptor primer set comprises about 12 to about 18 J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, compositions of the invention comprise at least one set of primers comprising V gene primers i) and J gene primers ii) selected from Tables 6 and 5, respectively. In some embodiments compositions of the invention comprise at least one set of primers i) and ii) comprising primers selected from SEQ ID NOs: 483-505 and 313-397 or selected from SEQ ID NOs: 483-505 and 398-482. In certain embodiments compositions of the invention comprise at least one set of primers i) and ii) comprising primers selected from SEQ ID NOs: 483-505 and 313-342 or selected from SEQ ID NOs: 483-505 and 398-427. In some embodiments compositions of the invention comprise at least one set of primers i) and ii) comprising primers selected from SEQ ID NOs: 483-505 and 313-329 or selected from SEQ ID NOs: 483-505 and 329-342. In certain embodiments compositions of the invention comprise at least one set of primers i) and ii) comprising primers selected from SEQ ID NOs: 483-505 and 398-414 or selected from SEQ ID NOs: 483-505 and 414-427. In other embodiments compositions of the invention comprise at least one set of primers i) and ii) comprising primers SEQ ID NOs: 483-505 and 313-328 or comprising primers SEQ ID NOs: 483-505 and 398-413.

In some embodiments compositions of the invention comprise at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 398-482. In some embodiments compositions of the invention comprise at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 398-427.

In some embodiments, multiple different primers including at least one modified nucleotide can be used in a single amplification reaction. For example, multiplexed primers including modified nucleotides can be added to the amplification reaction mixture, where each primer (or set of primers) selectively hybridizes to, and promotes amplification of different rearranged target nucleic acid molecules within the nucleic acid population. In some embodiments, the target specific primers can include at least one uracil nucleotide.

In some embodiments, multiplex amplification may be performed using PCR and cycles of denaturation, primer annealing, and polymerase extension steps at set temperatures for set times. In some embodiments, about 12 cycles to about 30 cycles are used to generate the amplicon library in the multiplex amplification reaction. In some embodiments, 13 cycles, 14 cycles, 15 cycles, 16 cycles, 17 cycles, 18 cycles, 19 cycles, preferably 20 cycles, 23 cycles, or 25 cycles are used to generate the amplicon library in the multiplex amplification reaction. In some embodiments, 17-25 cycles are used to generate the amplicon library in the multiplex amplification reaction.

In some embodiments, the amplification reactions are conducted in parallel within a single reaction phase (for example, within the same amplification reaction mixture within a single well or tube). In some instances, an amplification reaction can generate a mixture of products including both the intended amplicon product as well as unintended, unwanted, nonspecific amplification artifacts such as primer-dimers. Post amplification, the reactions are then treated with any suitable agent that will selectively cleave or otherwise selectively destroy the nucleotide linkages of the modified nucleotides within the excess unincorporated primers and the amplification artifacts without cleaving or destroying the specification amplification products. For example, the primers can include uracil-containing nucleobases that can be selectively cleaved using UNG/UDG (optionally with heat and/or alkali). In some embodiments, the primers can include uracil-containing nucleotides that can be selectively cleaved using UNG and Fpg. In some embodiments, the cleavage treatment includes exposure to oxidizing conditions for selective cleavage of dithiols, treatment with RNAse H for selective cleavage of modified nucleotides including RNA-specific moieties (e.g., ribose sugars, etc.), and the like. This cleavage treatment can effectively fragment the original amplification primers and non-specific amplification products into small nucleic acid fragments that include relatively few nucleotides each. Such fragments are typically incapable of promoting further amplification at elevated temperatures. Such fragments can also be removed relatively easily from the reaction pool through the various post-amplification cleanup procedures known in the art (e.g., spin columns, NaEtOH precipitation, etc).

In some embodiments, amplification products following cleavage or other selective destruction of the nucleotide linkages of the modified nucleotides are optionally treated to generate amplification products that possess a phosphate at the 5' termini. In some embodiments, the phosphorylation treatment includes enzymatic manipulation to produce 5' phosphorylated amplification products. In one embodiment, enzymes such as polymerases can be used to generate 5' phosphorylated amplification products. For example, T4 polymerase can be used to prepare 5' phosphorylated amplicon products. Klenow can be used in conjunction with one or more other enzymes to produce amplification products with a 5' phosphate. In some embodiments, other enzymes known in the art can be used to prepare amplification products with a 5' phosphate group. For example, incubation of uracil nucleotide containing amplification products with the enzyme UDG, Fpg and T4 polymerase can be used to generate amplification products with a phosphate at the 5' termini. It will be apparent to one of skill in the art that other techniques, other than those specifically described herein, can be applied to generate phosphorylated amplicons. It is understood that such variations and modifications that are applied to practice the methods, systems, kits, compositions and apparatuses disclosed herein, without resorting to undue experimentation are considered within the scope of the disclosure.

In some embodiments, primers that are incorporated in the intended (specific) amplification products, these primers are similarly cleaved or destroyed, resulting in the formation of "sticky ends" (e.g., 5' or 3' overhangs) within the specific amplification products. Such "sticky ends" can be addressed in several ways. For example, if the specific amplification products are to be cloned, the overhang regions can be designed to complement overhangs introduced into the cloning vector, thereby enabling sticky ended ligations that are more rapid and efficient than blunt ended ligations. Alternatively, the overhangs may need to be repaired (as with several next-generation sequencing methods). Such repair can be accomplished either through secondary amplification reactions using only forward and reverse amplification primers (e.g., correspond to A and P1 primers) comprised of only natural bases. In this manner, subsequent rounds of amplification rebuild the double-stranded templates, with nascent copies of the amplicon possessing the complete sequence of the original strands prior to primer destruction. Alternatively, the sticky ends can be removed using some forms of fill-in and ligation processing, wherein the forward and reverse primers are annealed to the templates. A polymerase can then be employed to extend the primers, and then a ligase, optionally a thermostable ligase, can be utilized to connect the resulting nucleic acid strands. This could obviously be also accomplished through various other reaction pathways, such as cyclical extend-ligation, etc. In some embodiments, the ligation step can be performed using one or more DNA ligases.

In some embodiments, the amplicon library prepared using target-specific primer pairs can be used in downstream enrichment applications such as emulsion PCR, bridge PCR or isothermal amplification. In some embodiments, the amplicon library can be used in an enrichment application and a sequencing application. For example, an amplicon library can be sequenced using any suitable DNA sequencing platform, including any suitable next generation DNA sequencing platform. In some embodiments, an amplicon library can be sequenced using an Ion Torrent PGM Sequencer or an Ion Torrent S5 Sequencer (Thermo Fisher Scientific). In some embodiments, a PGM sequencer or S5 sequencer can be coupled to server that applies parameters or software to determine the sequence of the amplified target nucleic acid molecules. In some embodiments, the amplicon library can be prepared, enriched and sequenced in less than 24 hours. In some embodiments, the amplicon library can be prepared, enriched and sequenced in approximately 9 hours.

In some embodiments, methods for generating an amplicon library can include: amplifying cDNA of immune receptor genes using V gene-specific and C gene-specific primers to generate amplicons; purifying the amplicons from the input DNA and primers; phosphorylating the amplicons; ligating adapters to the phosphorylated amplicons; purifying the ligated amplicons; nick-translating the amplified amplicons; and purifying the nick-translated amplicons to generate the amplicon library. In some embodiments, methods for generating an amplicon library can include: amplifying cDNA of immune receptor genes using V gene-specific and J gene-specific primers to generate amplicons; purifying the amplicons from the input DNA and primers; phosphorylating the amplicons; ligating adapters to the phosphorylated amplicons; purifying the ligated amplicons; nick-translating the amplified amplicons; and purifying the nick-translated amplicons to generate the amplicon library. In some embodiments, additional amplicon library manipulations can be conducted following the step of amplification of rearranged immune receptor gene targets to generate the amplicons. In some embodiments, any combination of additional reactions can be conducted in any order, and can include: purifying; phosphorylating; ligating adapters; nick-translating; amplification and/or sequencing. In some embodiments, any of these reactions can be omitted or can be repeated. It will be readily apparent to one of skill in the art that the method can repeat or omit any one or more of the above steps. It will also be apparent to one of skill in the art that the order and combination of steps may be modified to generate the required amplicon library, and is not therefore limited to the exemplary methods provided.

A phosphorylated amplicon can be joined to an adapter to conduct a nick translation reaction, subsequent downstream amplification (e.g., template preparation), or for attachment to particles (e.g., beads), or both. For example, an adapter that is joined to a phosphorylated amplicon can anneal to an oligonucleotide capture primer which is attached to a particle, and a primer extension reaction can be conducted to generate a complimentary copy of the amplicon attached to the particle or surface, thereby attaching an amplicon to a surface or particle. Adapters can have one or more amplification primer hybridization sites, sequencing primer hybridization sites, barcode sequences, and combinations thereof. In some embodiments, amplicons prepared by the methods disclosed herein can be joined to one or more Ion Torrent™ compatible adapters to construct an amplicon library. Amplicons generated by such methods can be joined to one or more adapters for library construction to be compatible with a next generation sequencing platform. For example, the amplicons produced by the teachings of the present disclosure can be attached to adapters provided in the Ion AmpliSeq™ Library Kit 2.0 or Ion AmpliSeq™ Library Kit Plus (Thermo Fisher Scientific).

In some embodiments, amplification of rearranged immune receptor cDNA can be conducted using a 5× Ion AmpliSeq™ HiFi Master Mix. In some embodiments, the 5× Ion AmpliSeq™ HiFi Master Mix can include glycerol, dNTPs, and a DNA polymerase such as Platinum™ Taq DNA polymerase High Fidelity. In some embodiments, the 5× Ion AmpliSeq™ HiFi Master Mix can further include at least one of the following: a preservative, magnesium chloride, magnesium sulfate, tris-sulfate and/or ammonium sulfate.

In some embodiments, phosphorylation of the amplicons can be conducted using a FuPa reagent. In some embodiments, the FuPa reagent can include a DNA polymerase, a DNA ligase, at least one uracil cleaving or modifying enzyme, and/or a storage buffer. In some embodiments, the FuPa reagent can further include at least one of the following: a preservative and/or a detergent.

In some embodiments, phosphorylation of the amplicons can be conducted using a FuPa reagent. In some embodiments, the FuPa reagent can include a DNA polymerase, at least one uracil cleaving or modifying enzyme, an antibody and/or a storage buffer. In some embodiments, the FuPa reagent can further include at least one of the following: a preservative and/or a detergent. In some embodiments, the antibody is provided to inhibit the DNA polymerase and 3'-5' exonuclease activities at ambient temperature.

In some embodiments, the amplicon library produced by the teachings of the present disclosure are sufficient in yield to be used in a variety of downstream applications including the Ion Chef™ instrument and the Ion S5™ Sequencing Systems (Thermo Fisher Scientific).

It will be apparent to one of ordinary skill in the art that numerous other techniques, platforms or methods for clonal amplification such as wildfire PCR and bridge amplification can be used in conjunction with the amplified target sequences of the present disclosure. It is also envisaged that one of ordinary skill in art upon further refinement or optimization of the conditions provided herein can proceed directly to nucleic acid sequencing (for example using the Ion PGM™ or Ion S5™ or Ion Proton™ sequencers, Thermo Fisher Scientific) without performing a clonal amplification step.

In some embodiments, at least one of the amplified targets sequences to be clonally amplified can be attached to a support or particle. The support can be comprised of any suitable material and have any suitable shape, including, for example, planar, spheroid or particulate. In some embodiments, the support is a scaffolded polymer particle as described in U.S. Published App. No. 20100304982, hereby incorporated by reference in its entirety.

In some embodiments, a kit is provided for amplifying multiple immune receptor expression sequences from a population of nucleic acid molecules in a single reaction. In some embodiments, the kit includes a plurality of target-specific primer pairs containing one or more cleavable groups, one or more DNA polymerases, a mixture of dNTPs and at least one cleaving reagent. In one embodiment, the cleavable group is 8-oxo-deoxyguanosine, deoxyuridine or bromodeoxyuridine. In some embodiments, the at least one cleaving reagent includes RNaseH, uracil DNA glycosylase, Fpg or alkali. In one embodiment, the cleaving reagent is uracil DNA glycosylase. In some embodiments, the kit is provided to perform multiplex PCR in a single reaction chamber or vessel. In some embodiments, the kit includes at least one DNA polymerase, which is a thermostable DNA polymerase. In some embodiments, the concentration of the one or more DNA polymerases is present in a 3-fold excess as compared to a single PCR reaction. In some embodiments, the final concentration of each target-specific primer pair is present at about 5 nM to about 2000 nM. In some embodiments, the final concentration of each target-specific primer pair is present at about 25 nM to about 50 nM or about 100 nM to about 800 nM. In some embodiments, the final concentration of each target-specific primer pair is present at about 50 nM to about 400 nM or about 50 nM to about 200 nM. In some embodiments, the final concentration of each target-specific primer pair is present at about 200 nM or about 400 nM. In some embodiments, the kit provides amplification of immune repertoire expression sequences from TCR beta, TCR alpha, TCR gamma, TCR delta, immunoglobulin heavy chain gamma, immunoglobulin heavy chain mu, immunoglobulin heavy chain alpha, immunoglobulin heavy chain delta, immunoglobulin heavy chain epsilon, immunoglobulin light chain lambda, or immunoglobulin light chain kappa from a population of nucleic acid molecules in a single reaction chamber. In particular embodiments, a provided kit is a test kit. In some embodiments, the kit further comprises one or more adapters, barcodes, and/or antibodies.

TABLE 2

| Name | Sequence | SEQ ID NO. |
|---|---|---|
| TRBV_F1 | AAAATACCTGGTCACACAGACGGGA | 1 |
| TRBV_F2 | AAGATACCGGGTTACCCAGTTTGGA | 2 |
| TRBV_F3 | ACTCAAACTCCAAGACATCTGATCAAACG | 3 |
| TRBV_F4 | AGAATCCCAGACACAAGATCACAAA | 4 |
| TRBV_F5 | AGAGTCCAAGACACAAGATCACAGA | 5 |
| TRBV_F6 | AGTCCCCAAGACATCTGATCAGAGA | 6 |
| TRBV_F7 | ATCAATGGCCAGCGACCCTGG | 7 |
| TRBV_F8 | CCAAAGTCCCACACACCTGATCAAA | 8 |
| TRBV_F9 | CCCAGACACCAAAATACCTGG | 9 |
| TRBV_F10 | CTCAACATCCGAGTAGGGTTATCTGTA | 10 |
| TRBV_F11 | CTCAGTCCCCAAAGTACCTGT | 11 |
| TRBV_F12 | CTGGAATCACCCAGAGCCC | 12 |
| TRBV_F13 | CTGGAGTCTCCCACAACCC | 13 |
| TRBV_F14 | CTGGAGTCTCCCAGAACCC | 14 |
| TRBV_F15 | CTGGAGTCTCCCAGGACCC | 15 |
| TRBV_F16 | CTGGAGTCACTCAAACTCCAAGATATCT | 16 |
| TRBV_F17 | GAAAGCCAGTGACCCTGAGTTG | 17 |
| TRBV_F18 | CCCAGAGCTCGAGATATCTAGTCAA | 18 |
| TRBV_F19 | AAAAGCCAAGCAGGGATATCTGTC | 19 |
| TRBV_F20 | AAAATACCTGGTCACACAGATGGGA | 20 |
| TRBV_F21 | AAAATTCCACGTCCTGAAGACAGG | 21 |
| TRBV_F22 | AAAATTCCAGGTCCTGAAGACAGG | 22 |
| TRBV_F23 | AAAATTCCACATCCTGAAGACAGGAC | 23 |
| TRBV_F24 | AAAGCACCTGATCACAGCAACTG | 24 |
| TRBV_F25 | AACATCCGAGCAGGGTTATCTGTA | 25 |
| TRBV_F26 | AACATCCGAGCTGGGTTATCTGTA | 26 |
| TRBV_F27 | AACCCAAGATACCTCATCACAGTGAC | 27 |
| TRBV_F28 | AAGACACAGAATCATTGGGACAGG | 28 |
| TRBV_F29 | AAGCATGAGGTGACAGAAATGGGA | 29 |
| TRBV_F30 | AAGGCACAAGGTGACAGAGATG | 30 |
| TRBV_F31 | AATACCTGGTCACACAGATGGGAA | 31 |
| TRBV_F32 | AATTCTCAAGACACAGAATCATTGGGACA | 32 |
| TRBV_F33 | ACAAAGTCCCACACACCTGATCAAA | 33 |
| TRBV_F34 | ACACAAGGTCACCAACATGGG | 34 |
| TRBV_F35 | ACACCAAGACACCTGGTCATG | 35 |
| TRBV_F36 | ACCAACATCTCAGATCCTGGCA | 36 |
| TRBV_F37 | ACCAGACCCCAAGATACCTTGTTATA | 37 |
| TRBV_F38 | ACCCCAAGGAATAGGATCACAAAGA | 38 |
| TRBV_F39 | ACCCCCAGTAACAAGGTCACA | 39 |
| TRBV_F40 | ACCTAGACTTCTGGTCAAAGCAAGTG | 40 |
| TRBV_F41 | ACCTAGATTTCTGGTCAAAGCAAATGA | 41 |
| TRBV_F42 | ACTCCAGGATATTTGGTCAAAGGAAAAGGAA | 42 |

TABLE 2-continued

| Name | Sequence | SEQ ID NO. |
|---|---|---|
| TRBV_F43 | AGACACCAAAACACCTGGTCATG | 43 |
| TRBV_F44 | AGACTATTCATCAATGGCCAGCGA | 44 |
| TRBV_F45 | AGAGCCCAAGATACAAGATCACAGA | 45 |
| TRBV_F46 | AGCCACAGCGTAATAGAAGGG | 46 |
| TRBV_F47 | AGGACATTTGGTCAAAGGAAAAGGAC | 47 |
| TRBV_F48 | AGTCCCCAAGACATCTGATCAAAGA | 48 |
| TRBV_F49 | AGTCCCTGAGACACAAGGTAGCA | 49 |
| TRBV_F50 | AGTCTCCCAGATATAAGATTATAGAGAAAAGGC | 50 |
| TRBV_F51 | AGTCTCCCAGGTACAAAGTCACA | 51 |
| TRBV_F52 | AGTGGTTCAGTCTCCCAGATATAAGATTATAG | 52 |
| TRBV_F53 | AGTAACAAGGTCACAGAGAAGGGA | 53 |
| TRBV_F54 | CAAAATTCCGGGTCCTGAAGACA | 54 |
| TRBV_F55 | CAAGACACCTGGTCAGGAGGAG | 55 |
| TRBV_F56 | CAGACTCCAAAACATCTTGTCAGAGG | 56 |
| TRBV_F57 | CAGCCATCAGGTCACACAGATG | 57 |
| TRBV_F58 | CCAAGGTACAAAGTCGCAAAGAGG | 58 |
| TRBV_F59 | CCCAAAATTCCGCATCCTGAAGATA | 59 |
| TRBV_F60 | CCCAGTCCCCCAGATATAAGATTACA | 60 |
| TRBV_F61 | CCCTAGGTACAAAGTCGCAAAGAGA | 61 |
| TRBV_F62 | CGCCATGAGGTGACAGAGATGG | 62 |
| TRBV_F63 | CGGCACGAGGTGACAGAGATG | 63 |
| TRBV_F64 | GTCACCCAGGCACAAAGTGACA | 64 |
| TRBV_F65 | CAAGATATCTGATCAAAACGAGAGGACAG | 65 |
| TRBV_F66 | CCAAGATATCTGATCAAAACGAGAGGAC | 66 |
| TRBV_F67 | CTCCAAGATATCTGATCAAAACGAGAGG | 67 |
| TRBV_F68 | GAGAGGACAGCAAGTGACACTG | 68 |
| TRBV_F69 | GAGTCACTCAAACTCCAAGATATCTGATCA | 69 |
| TRBV_F70 | GCTGGAGTCACTCAAACTCCAAG | 70 |
| TRBV_F71 | GGAGTCACTCAAACTCCAAGATATCTGAT | 71 |
| TRBV_F 72 | GGCTGGAGTCACTCAAACTCC | 72 |
| TRBV_F 73 | CATGGTCATCCAGAACCCAAGATAC | 73 |
| TRBV_F74 | CCATGGTCATCCAGAACCCAAG | 74 |
| TRBV_F75 | GATGCCATGGTCATCCAGAACC | 75 |
| TRBV_F76 | GGAAAGCCAGTGACCCTGAG | 76 |
| TRBV_F77 | GGTTACCCAGTTTGGAAAGCCA | 77 |
| TRBV_F78 | GTTTGGAAAGCCAGTGACCCT | 78 |
| TRBV_F79 | GTTACCCAGTTTGGAAAGCCAGT | 79 |
| TRBV_F80 | TGCCATGGTCATCCAGAACC | 80 |
| TRBV_F81 | TTACCCAGTTTGGAAAGCCAGTG | 81 |
| TRBV_F82 | TTTGGAAAGCCAGTGACCCTG | 82 |
| TRBV_F83 | AGAGCTCGAGATATCTAGTCAAAAGGAC | 83 |
| TRBV_F84 | AGCTCGAGATATCTAGTCAAAAGGACG | 84 |
| TRBV_F85 | CGAGATATCTAGTCAAAAGGACGGGA | 85 |
| TRBV_F86 | GAAAGTAACCCAGAGCTCGAGATATCTAG | 86 |
| TRBV_F87 | GATGTGAAAGTAACCCAGAGCTCG | 87 |
| TRBV_F88 | GTAACCCAGAGCTCGAGATATCTAGTC | 88 |
| TRBV_F89 | GTGAAAGTAACCCAGAGCTCGAG | 89 |
| TRBV_F90 | AAAAUACCTGGUCACACAGACGGGA | 90 |
| TRBV_F91 | AAGATACCGGGUTACCCAGTTGGA | 91 |
| TRBV_F92 | ACTCAAACUCCAAGACATCTGAUCAAAACG | 92 |
| TRBV_F93 | AGAAUCCCAGACACAAGATCACAAA | 93 |
| TRBV_F94 | AGAGUCCAAGACACAAGATCACAGA | 94 |
| TRBV_F95 | AGTCCCCAAGACAUCTGAUCAGAGA | 95 |
| TRBV_F96 | ATCAAUGGCCAGCGACCCUGG | 96 |
| TRBV_F97 | CCAAAGUCCCACACACCTGAUCAAA | 97 |
| TRBV_F98 | CCCAGACACCAAAAUACCUGG | 98 |
| TRBV_F99 | CTCAACATCCGAGUAGGGUTATCTGUA | 99 |
| TRBV_F100 | CTCAGUCCCCAAAGTACCUGT | 100 |
| TRBV_F101 | CUGGAAUCACCCAGAGCCC | 101 |
| TRBV_F102 | CUGGAGTCUCCCACAACCC | 102 |
| TRBV_F103 | CUGGAGTCUCCCAGAACCC | 103 |
| TRBV_F104 | CUGGAGTCUCCCAGGACCC | 104 |
| TRBV_F105 | CTGGAGTCACUCAAACTCCAAGAUAUCT | 105 |
| TRBV_F106 | GAAAGCCAGUGACCCTGAGTUG | 106 |
| TRBV_F107 | CCCAGAGCUCGAGATATCTAGUCAA | 107 |
| TRBV_F108 | AAAAGCCAAGCAGGGAUATCTGUC | 108 |
| TRBV_F109 | AAAATACCTGGUCACACAGAUGGGA | 109 |
| TRBV_F110 | AAAATCCACGTCCUGAAGACAGG | 110 |
| TRBV_F111 | AAAAUCCAGGTCCUGAAGACAGG | 111 |
| TRBV_F112 | AAAAUTCCACATCCUGAAGACAGGAC | 112 |
| TRBV_F113 | AAAGCACCTGAUCACAGCAACUG | 113 |
| TRBV_F114 | AACATCCGAGCAGGGUTATCTGUA | 114 |
| TRBV_F115 | AACATCCGAGCUGGGTTATCTGUA | 115 |
| TRBV_F116 | AACCCAAGAUACCTCATCACAGUGAC | 116 |
| TRBV_F117 | AAGACACAGAAUCATGGGACAGG | 117 |
| TRBV_F118 | AAGCATGAGGUGACAGAAAUGGGA | 118 |
| TRBV_F119 | AAGGCACAAGGUGACAGAGAUG | 119 |

TABLE 2-continued

| Name | Sequence | SEQ ID NO. |
|---|---|---|
| TRBV_F120 | AATACCTGGUCACACAGAUGGGAA | 120 |
| TRBV_F121 | AATTCUCAAGACACAGAATCATUGGGACA | 121 |
| TRBV_F122 | ACAAAGUCCCACACACCTGAUCAAA | 122 |
| TRBV_F123 | ACACAAGGUCACCAACAUGGG | 123 |
| TRBV_F124 | ACACCAAGACACCUGGUCAUG | 124 |
| TRBV_F125 | ACCAACATCUCAGAUCCUGGCA | 125 |
| TRBV_F126 | ACCAGACCCCAAGAUACCUUGUUAUA | 126 |
| TRBV_F127 | ACCCCAAGGAAUAGGAUCACAAAGA | 127 |
| TRBV_F128 | ACCCCCAGUAACAAGGUCACA | 128 |
| TRBV_F129 | ACCTAGACTTCUGGTCAAAGCAAGUG | 129 |
| TRBV_F130 | ACCTAGATTTCUGGTCAAAGCAAUGA | 130 |
| TRBV_F131 | ACUCCAGGATATTTGGUCAAAGGAAAAGGAA | 131 |
| TRBV_F132 | AGACACCAAAACACCUGGUCAUG | 132 |
| TRBV_F133 | AGACUAUUCAUCAAUGGCCAGCGA | 133 |
| TRBV_F134 | AGAGCCCAAGAUACAAGAUCACAGA | 134 |
| TRBV_F135 | AGCCACAGCGUAAUAGAGAAGGG | 135 |
| TRBV_F136 | AGGACAUUUGGUCAAAGGAAAAGGAC | 136 |
| TRBV_F137 | AGTCCCCAAGACAUCUGAUCAAAGA | 137 |
| TRBV_F138 | AGTCCCUGAGACACAAGGUAGCA | 138 |
| TRBV_F139 | AGTCUCCCAGAUAUAAGAUUAUAGAGAAAAGGC | 139 |
| TRBV_F140 | AGTCUCCCAGGUACAAAGUCACA | 140 |
| TRBV_F141 | AGTGGUUCAGTCUCCCAGAUAUAAGAUUAUAG | 141 |
| TRBV_F142 | AGUAACAAGGUCACAGAGAAGGGA | 142 |
| TRBV_F143 | CAAAAUCCGGGUCCUGAAGACA | 143 |
| TRBV_F144 | CAAGACACCUGGUCAGGAGGAG | 144 |
| TRBV_F145 | CAGACUCCAAAACATCUUGUCAGAGG | 145 |
| TRBV_F146 | CAGCCAUCAGGUCACACAGAUG | 146 |
| TRBV_F147 | CCAAGGUACAAAGUCGCAAAGAGG | 147 |
| TRBV_F148 | CCCAAAAUUCCGCAUCCUGAAGAUA | 148 |
| TRBV_F149 | CCCAGUCCCCAGAUAUAAGAUUACA | 149 |
| TRBV_F150 | CCCUAGGUACAAAGUCGCAAAGAGA | 150 |
| TRBV_F151 | CGCCATGAGGUGACAGAGAUGG | 151 |
| TRBV_F152 | CGGCACGAGGUGACAGAGAUG | 152 |
| TRBV_F153 | GUCACCCAGGCACAAAGUGACA | 153 |
| TRBV_F154 | AGAGUCCAAGACACAAGAUCACAGA | 154 |
| TRBV_F155 | AGAAUCCCAGACACAAGAUCACAAA | 155 |
| TRBV_F156 | CUCCAAGAUAUCUGAUCAAAACGAGAGG | 156 |
| TRBV_F157 | GAGAGGACAGCAAGUGACACUG | 157 |
| TRBV_F158 | GAGUCACUCAAACUCCAAGAUAUCUGAUCA | 158 |
| TRBV_F159 | GCTGGAGUCACTCAAACUCCAAG | 159 |
| TRBV_F160 | GGAGTCACTCAAACUCCAAGAUAUCUGAT | 160 |
| TRBV_F161 | GGCTGGAGUCACTCAAACUCC | 161 |
| TRBV_F162 | CATGGUCAUCCAGAACCCAAGAUAC | 162 |
| TRBV_F163 | CCAUGGUCAUCCAGAACCCAAG | 163 |
| TRBV_F164 | GATGCCAUGGUCAUCCAGAACC | 164 |
| TRBV_F165 | GGAAAGCCAGUGACCCUGAG | 165 |
| TRBV_F166 | GGUUACCCAGUUGGAAAGCCA | 166 |
| TRBV_F167 | GTTUGGAAAGCCAGUGACCCT | 167 |
| TRBV_F168 | GUUACCCAGUUGGAAAGCCAGT | 168 |
| TRBV_F169 | TGCCAUGGUCAUCCAGAACC | 169 |
| TRBV_F170 | TTACCCAGUUGGAAAGCCAGUG | 170 |
| TRBV_F171 | TTTGGAAAGCCAGUGACCCUG | 171 |
| TRBV_F172 | AGAGCUCGAGATATCTAGUCAAAAGGAC | 172 |
| TRBV_F173 | AGCTCGAGAUAUCTAGUCAAAAGGACG | 173 |
| TRBV_F174 | CGAGAUAUCTAGUCAAAAGGACGGGA | 174 |
| TRBV_F175 | GAAAGUAACCCAGAGCUCGAGAUAUCUAG | 175 |
| TRBV_F176 | GATGUGAAAGUAACCCAGAGCUCG | 176 |
| TRBV_F177 | GTAACCCAGAGCUCGAGAUAUCUAGUC | 177 |
| TRBV_F178 | GTGAAAGUAACCCAGAGCUCGAG | 178 |
| TRBV_F179 | CAAGAUAUCTGAUCAAAACGAGAGGACAG | 179 |
| TRBV_F180 | CCAAGAUAUCTGAUCAAAACGAGAGGAC | 180 |

TABLE 3

| Name | Sequence | SEQ ID NO. |
|---|---|---|
| TRBV_F185 | AATCTTCACATCAATTCCCTGGAG | 185 |
| TRBV_F186 | ACATCCGCTCACCAGGC | 186 |
| TRBV_F187 | ACCTACACACCCTGCAGC | 187 |
| TRBV_F188 | AGGCTGGAGTCAGCTGC | 188 |
| TRBV_F189 | AGGTGCAGCCTGCAGAA | 189 |
| TRBV_F190 | ATGAATGTGAGCACCTTGGAG | 190 |
| TRBV_F191 | ATGAATGTGAGTGCCTTGGAG | 191 |
| TRBV_F192 | CAAGCTGGAGTCAGCTGC | 192 |
| TRBV_F193 | CATGAGCTCCTTGGAGCTG | 193 |
| TRBV_F194 | CATTCTGAGTTCTAAGAAGCTCCTC | 194 |
| TRBV_F195 | CCTGACCCTGAAGTCTGCT | 195 |
| TRBV_F196 | CCTGAGCTCTCTGGAGCTG | 196 |
| TRBV_F197 | CTAGACATCCGCTCACCAGGC | 197 |

TABLE 3-continued

| Name | Sequence | SEQ ID NO. |
|---|---|---|
| TRBV_F198 | CTCAAGATCCAGCCTGCAAAG | 198 |
| TRBV_F199 | CTCAAGATCCAGCCTGCAGAG | 199 |
| TRBV_F200 | CTCACGTTGGCGTCTGCTGTA | 200 |
| TRBV_F201 | CTCACTCTGGAGTCAGCTACC | 201 |
| TRBV_F202 | CTCACTCTGGAGTCCGCTACC | 202 |
| TRBV_F203 | CTCACTCTGGAGTCTGCTGCC | 203 |
| TRBV_F204 | CTCACTGTGACATCGGCCCAA | 204 |
| TRBV_F205 | CTGAAGATCCAGCCCTCAGAA | 205 |
| TRBV_F206 | CTGAAGATCCAGCCTGCAGAG | 206 |
| TRBV_F207 | CTGAAGATCCGGTCCACAAAG | 207 |
| TRBV_F208 | CTGAATGTGAACGCCTTGTTG | 208 |
| TRBV_F209 | CTGAATGTGAACGCCTTGGAG | 209 |
| TRBV_F210 | CTGACAGTGACCAGTGCCCAT | 210 |
| TRBV_F211 | CTGACAGTGACCTGTGCCCAT | 211 |
| TRBV_F212 | CTGACCCTGAAGTCTGCCAGC | 212 |
| TRBV_F213 | CTGACTGTGAGCAACATGAGC | 213 |
| TRBV_F214 | CTGAGGATCCAGCAGGTAGTG | 214 |
| TRBV_F215 | CTGAGGATCCAGCCCATGGAA | 215 |
| TRBV_F216 | CTGAGGATCCAGCCCTCAGAA | 216 |
| TRBV_F217 | CTGGCAATCCTGTCCTCAGAA | 217 |
| TRBV_F218 | CTGGCAATCCTGTCCTCGGAA | 218 |
| TRBV_F219 | CTGTCCCTAGAGTCTGCCATC | 219 |
| TRBV_F220 | CTCAAGATCCAGCCAGCAGAG | 220 |
| TRBV_F221 | CTGAAGATCCATCCCGCAGAG | 221 |
| TRBV_F222 | CTGAAGATCCAGCGCACACAG | 222 |
| TRBV_F223 | CTGAAGATCCAGCGCACAGAG | 223 |
| TRBV_F224 | CTGAAGTTCCAGCGCACACAG | 224 |
| TRBV_F225 | CTGACGATTCAGCGCACAGAG | 225 |
| TRBV_F226 | CTGACGATCCAGCGCACA | 226 |
| TRBV_F227 | CTGACTGTGAGCAACAGGAGA | 227 |
| TRBV_F228 | CTGATTCTGGAGTCCGCCAGC | 228 |
| TRBV_F229 | GCCTTGAGATCCAGGCTACG | 229 |
| TRBV_F230 | GGCTGGAGTTGGCTGCT | 230 |
| TRBV_F231 | GGTTGGAGTCGGCTGCT | 231 |
| TRBV_F232 | TCACCTACACGCCCTGC | 232 |
| TRBV_F233 | TCAGGCTGCTGTCGGCT | 233 |
| TRBV_F234 | TCAGGCTGGAGTCGGCT | 234 |
| TRBV_F235 | TCAGGCTGGTGTCGGCT | 235 |
| TRBV_F236 | TCATCCTGAGTTCTAAGAAGCTCC | 236 |
| TRBV_F237 | TCCTGAGTTCTAAGAAGCTCCTC | 237 |
| TRBV_F238 | TCTCAAGATCCAACCTGCAAAG | 238 |
| TRBV_F239 | TGACCCTGGAGTCTGCC | 239 |
| TRBV_F240 | TGATCCTGGAGTCGCCC | 240 |
| TRBV_F241 | TGTGGTCGCACTGCAGC | 241 |
| TRBV_F242 | TTGGAGATCCAGTCCACGGAG | 242 |
| TRBV_F243 | TTGGAGATCCAGCGCACAGAG | 243 |
| TRBV_F244 | CATGAGCTCCTTGGAGCTGG | 244 |
| TRBV_F245 | AACATGAGCTCCTTGGAGCTG | 245 |
| TRBV_F246 | GAACATGAGCTCCTTGGAGCTG | 246 |
| TRBV_F247 | TGAACTGAACATGAGCTCCTTGG | 247 |
| TRBV_F248 | CTGAACTGAACATGAGCTCCTTGG | 248 |
| TRBV_F249 | AATCTTCACAUCAATTCCCUGGAG | 249 |
| TRBV_F250 | ACAUCCGCUCACCAGGC | 250 |
| TRBV_F251 | ACCUACACACCCUGCAGC | 251 |
| TRBV_F252 | AGGCUGGAGTCAGCUGC | 252 |
| TRBV_F253 | AGGUGCAGCCUGCAGAA | 253 |
| TRBV_F254 | ATGAATGUGAGCACCTUGGAG | 254 |
| TRBV_F255 | ATGAATGUGAGTGCCTUGGAG | 255 |
| TRBV_F256 | CAAGCUGGAGTCAGCUGC | 256 |
| TRBV_F257 | CATGAGCUCCTTGGAGCTG | 257 |
| TRBV_F258 | CATTCTGAGTTCUAAGAAGCTCCUC | 258 |
| TRBV_F259 | CCTGACCCUGAAGTCUGCT | 259 |
| TRBV_F260 | CCTGAGCUCTCTGGAGCUG | 260 |
| TRBV_F261 | CTAGACAUCCGCUCACCAGGC | 261 |
| TRBV_F262 | CTCAAGAUCCAGCCUGCAAAG | 262 |
| TRBV_F263 | CTCAAGAUCCAGCCUGCAGAG | 263 |
| TRBV_F264 | CTCACGTUGGCGTCTGCTGUA | 264 |
| TRBV_F265 | CTCACTCUGGAGTCAGCUACC | 265 |
| TRBV_F266 | CTCACTCUGGAGTCCGCUACC | 266 |
| TRBV_F267 | CTCACTCUGGAGTCTGCUGCC | 267 |
| TRBV_F268 | CTCACUGTGACAUCGGCCCAA | 268 |
| TRBV_F269 | CTGAAGAUCCAGCCCUCAGAA | 269 |
| TRBV_F270 | CTGAAGAUCCAGCCUGCAGAG | 270 |
| TRBV_F271 | CTGAAGAUCCGGUCCACAAAG | 271 |
| TRBV_F272 | CTGAATGUGAACGCCTUGTUG | 272 |
| TRBV_F273 | CTGAATGUGAACGCCTUGGAG | 273 |
| TRBV_F274 | CTGACAGUGACCAGTGCCCAT | 274 |
| TRBV_F275 | CTGACAGUGACCTGTGCCCAT | 275 |

TABLE 3-continued

| Name | Sequence | SEQ ID NO. |
|---|---|---|
| TRBV_F276 | CTGACCCUGAAGTCUGCCAGC | 276 |
| TRBV_F277 | CTGACTGUGAGCAACAUGAGC | 277 |
| TRBV_F278 | CTGAGGAUCCAGCAGGTAGUG | 278 |
| TRBV_F279 | CTGAGGAUCCAGCCCAUGGAA | 279 |
| TRBV_F280 | CTGAGGAUCCAGCCCUCAGAA | 280 |
| TRBV_F281 | CTGGCAAUCCTGTCCUCAGAA | 281 |
| TRBV_F282 | CTGGCAAUCCTGTCCUCGGAA | 282 |
| TRBV_F283 | CTGTCCCUAGAGTCTGCCAUC | 283 |
| TRBV_F284 | CUCAAGAUCCAGCCAGCAGAG | 284 |
| TRBV_F285 | CUGAAGATCCAUCCCGCAGAG | 285 |
| TRBV_F286 | CUGAAGAUCCAGCGCACACAG | 286 |
| TRBV_F287 | CUGAAGAUCCAGCGCACAGAG | 287 |
| TRBV_F288 | CUGAAGUCCAGCGCACACAG | 288 |
| TRBV_F289 | CUGACGAUCAGCGCACAGAG | 289 |
| TRBV_F290 | CUGACGAUCCAGCGCACA | 290 |
| TRBV_F291 | CUGACTGUGAGCAACAGGAGA | 291 |
| TRBV_F292 | CUGATTCTGGAGUCCGCCAGC | 292 |
| TRBV_F293 | GCCTTGAGAUCCAGGCUACG | 293 |
| TRBV_F294 | GGCTGGAGUTGGCUGCT | 294 |
| TRBV_F295 | GGTTGGAGUCGGCUGCT | 295 |
| TRBV_F296 | TCACCUACACGCCCUGC | 296 |
| TRBV_F297 | TCAGGCUGCTGUCGGCT | 297 |
| TRBV_F298 | TCAGGCUGGAGUCGGCT | 298 |
| TRBV_F299 | TCAGGCUGGTGUCGGCT | 299 |
| TRBV_F300 | TCATCCTGAGUTCTAAGAAGCUCC | 300 |
| TRBV_F301 | TCCTGAGTTCUAAGAAGCTCCUC | 301 |
| TRBV_F302 | TCTCAAGAUCCAACCUGCAAAG | 302 |
| TRBV_F303 | TGACCCUGGAGTCUGCC | 303 |
| TRBV_F304 | TGATCCUGGAGTCGCCC | 304 |
| TRBV_F305 | TGTGGUCGCACUGCAGC | 305 |
| TRBV_F306 | TTGGAGAUCCAGUCCACGGAG | 306 |
| TRBV_F307 | TUGGAGAUCCAGCGCACAGAG | 307 |
| TRBV_F308 | CATGAGCUCCUUGGAGCUGG | 308 |
| TRBV_F309 | AACATGAGCUCCUUGGAGCUG | 309 |
| TRBV_F310 | GAACATGAGCUCCUUGGAGCUG | 310 |
| TRBV_F311 | TGAACTGAACAUGAGCUCCUGG | 311 |
| TRBV_F312 | CTGAACTGAACAUGAGCUCCUGG | 312 |

TABLE 4

| Name | Sequence | SEQ ID NO. |
|---|---|---|
| TRBC_R1 | CGACCUCGGGUGGGAACAC | 181 |
| TRBC_R2 | CGACCUTGGGUGGGAACAC | 182 |
| TRBC_R3 | CGACCTCGGGTGGGAACAC | 183 |
| TRBC_R4 | CGACCTTGGGTGGGAACAC | 184 |

TABLE 5

| Name | Sequence | SEQ ID NO. |
|---|---|---|
| TRBJ_R1 | AACCAGGAGTCCTCCGC | 313 |
| TRBJ_R2 | ACGGTCAGCCTAGAGCCTT | 314 |
| TRBJ_R3 | AGTCTGGTGCCTTGTCCAA | 315 |
| TRBJ_R4 | CACGGTCAGCCTGCTGC | 316 |
| TRBJ_R5 | CCCATCACCAAAATGCTGGG | 317 |
| TRBJ_R6 | CCTGGGCCAAAATACTGCG | 318 |
| TRBJ_R7 | CGGCCCGAAGTACTGCT | 319 |
| TRBJ_R8 | CGGCGCCGAAGTACTGA | 320 |
| TRBJ_R9 | CTGGCCCGAAGAACTGC | 321 |
| TRBJ_R10 | GAGCCAACTTCCCTCTCCAA | 322 |
| TRBJ_R11 | GCCTGGTCCCATTCCCAAA | 323 |
| TRBJ_R12 | GCTGGGTTCCACTGCCAAA | 324 |
| TRBJ_R13 | TCCCGTTCCCAAAGTGGAG | 325 |
| TRBJ_R14 | TGACCGTGAGCCTGGTG | 326 |
| TRBJ_R15 | TGGCCCGAAGTACTGGG | 327 |
| TRBJ_R16 | TTAACCTGGTCCCCGAACC | 328 |
| TRBJ_R17 | GACCGTGAGCCTGGTGC | 329 |
| TRBJ_R18 | CAGGAGCCGCGTGCCTG | 330 |
| TRBJ_R19 | AGCACTGTCAGCCGGGT | 331 |
| TRBJ_R20 | CCAGCACGGTCAGCCTG | 332 |
| TRBJ_R21 | CTAGCACGGTGAGCCGT | 333 |
| TRBJ_R22 | AGCACTGAGAGCCGGGTC | 334 |
| TRBJ_R23 | CAGTACGGTCAGCCTAGAGC | 335 |
| TRBJ_R24 | CCAGAACCAGGAGTCCTCCG | 336 |
| TRBJ_R25 | CTGTCACAGTGAGCCTGGTC | 337 |
| TRBJ_R26 | CCAAGACAGAGAGCTGGGTTC | 338 |
| TRBJ_R27 | CTACAACTGTGAGTCTGGTGCC | 339 |
| TRBJ_R28 | CTAGGATGGAGAGTCGAGTCCC | 340 |
| TRBJ_R29 | CTACAACGGTTAACCTGGTCCC | 341 |
| TRBJ_R30 | CTACAACAGTGAGCCAACTTCCC | 342 |
| TRBJ_R31 | GTGACCGTGAGCCTGGT | 343 |
| TRBJ_R32 | TGTGACCGTGAGCCTGG | 344 |

TABLE 5-continued

| Name | Sequence | SEQ ID NO. |
|---|---|---|
| TRBJ_R33 | GTGACCGTGAGCCTGGTG | 345 |
| TRBJ_R34 | TGTGACCGTGAGCCTGGT | 346 |
| TRBJ_R35 | CTGTGACCGTGAGCCTGG | 347 |
| TRBJ_R36 | CAGGAGTCCTCCGCCCA | 348 |
| TRBJ_R37 | ACCAGGAGTCCTCCGCC | 349 |
| TRBJ_R38 | ACTGAGAGCCGGGTCCC | 350 |
| TRBJ_R39 | CACTGAGAGCCGGGTCC | 351 |
| TRBJ_R40 | GCACTGAGAGCCGGGTC | 352 |
| TRBJ_R41 | GCACGGTCAGCCTGCTG | 353 |
| TRBJ_R42 | CAGCACGGTCAGCCTGC | 354 |
| TRBJ_R43 | TAGCACGGTGAGCCGTG | 355 |
| TRBJ_R44 | CCAGGAGCCGCGTGCCTG | 356 |
| TRBJ_R45 | AACCAGGAGTCCTCCGCC | 357 |
| TRBJ_R46 | GAACCAGGAGTCCTCCGC | 358 |
| TRBJ_R47 | TAGCACGGTGAGCCGTGT | 359 |
| TRBJ_R48 | ACCAGGAGCCGCGTGCCTG | 360 |
| TRBJ_R49 | AACGGTTAACCTGGTCCCC | 361 |
| TRBJ_R50 | AGAACCAGGAGTCCTCCGC | 362 |
| TRBJ_R51 | CAGAACCAGGAGTCCTCCG | 363 |
| TRBJ_R52 | TACGGTCAGCCTAGAGCCTT | 364 |
| TRBJ_R53 | GTACGGTCAGCCTAGAGCCT | 365 |
| TRBJ_R54 | GGATGGAGAGTCGAGTCCCA | 366 |
| TRBJ_R55 | CAACGGTTAACCTGGTCCCC | 367 |
| TRBJ_R56 | AGTACGGTCAGCCTAGAGCC | 368 |
| TRBJ_R57 | AGGATGGAGAGTCGAGTCCC | 369 |
| TRBJ_R58 | ACAACGGTTAACCTGGTCCC | 370 |
| TRBJ_R59 | TGTCACAGTGAGCCTGGTCC | 371 |
| TRBJ_R60 | CAACTGTGAGTCTGGTGCCTT | 372 |
| TRBJ_R61 | GTACGGTCAGCCTAGAGCCTT | 373 |
| TRBJ_R62 | GGATGGAGAGTCGAGTCCCAT | 374 |
| TRBJ_R63 | ACAACTGTGAGTCTGGTGCCT | 375 |
| TRBJ_R64 | AGTACGGTCAGCCTAGAGCCT | 376 |
| TRBJ_R65 | AGGATGGAGAGTCGAGTCCCA | 377 |
| TRBJ_R66 | TACAACTGTGAGTCTGGTGCC | 378 |
| TRBJ_R67 | CAAGACAGAGAGCTGGGTTCC | 379 |
| TRBJ_R68 | TAGGATGGAGAGTCGAGTCCC | 380 |
| TRBJ_R69 | TACAACGGTTAACCTGGTCCC | 381 |
| TRBJ_R70 | ACAACTGTGAGTCTGGTGCCTT | 382 |
| TRBJ_R71 | AAGACAGAGAGCTGGGTTCCAC | 383 |
| TRBJ_R72 | AGGATGGAGAGTCGAGTCCCAT | 384 |
| TRBJ_R73 | ACAACAGTGAGCCAACTTCCCT | 385 |
| TRBJ_R74 | TACAACTGTGAGTCTGGTGCCT | 386 |
| TRBJ_R75 | CAAGACAGAGAGCTGGGTTCCA | 387 |
| TRBJ_R76 | TAGGATGGAGAGTCGAGTCCCA | 388 |
| TRBJ_R77 | TACAACGGTTAACCTGGTCCCC | 389 |
| TRBJ_R78 | TACAACTGTGAGTCTGGTGCCTT | 390 |
| TRBJ_R79 | TAGGATGGAGAGTCGAGTCCCAT | 391 |
| TRBJ_R80 | TACAACAGTGAGCCAACTTCCCT | 392 |
| TRBJ_R81 | CTACAACTGTGAGTCTGGTGCCT | 393 |
| TRBJ_R82 | CTAGGATGGAGAGTCGAGTCCCA | 394 |
| TRBJ_R83 | CTACAACTGTGAGTCTGGTGCCTT | 395 |
| TRBJ_R84 | CTAGGATGGAGAGTCGAGTCCCAT | 396 |
| TRBJ_R85 | CTACAACAGTGAGCCAACTTCCCT | 397 |
| TRBJ_R86 | AACCAGGAGUCCUCCGC | 398 |
| TRBJ_R87 | ACGGTCAGCCUAGAGCCUT | 399 |
| TRBJ_R88 | AGTCTGGUGCCUUGUCCAA | 400 |
| TRBJ_R89 | CACGGUCAGCCUGCUGC | 401 |
| TRBJ_R90 | CCCAUCACCAAAATGCUGGG | 402 |
| TRBJ_R91 | CCUGGGCCAAAATACUGCG | 403 |
| TRBJ_R92 | CGGCCCGAAGUACUGCT | 404 |
| TRBJ_R93 | CGGCGCCGAAGUACUGA | 405 |
| TRBJ_R94 | CUGGCCCGAAGAACUGC | 406 |
| TRBJ_R95 | GAGCCAACUUCCCUCUCCAA | 407 |
| TRBJ_R96 | GCCTGGUCCCAUUCCCAAA | 408 |
| TRBJ_R97 | GCTGGGUUCCACUGCCAAA | 409 |
| TRBJ_R98 | TCCCGUUCCCAAAGUGGAG | 410 |
| TRBJ_R99 | TGACCGUGAGCCUGGUG | 411 |
| TRBJ_R100 | TGGCCCGAAGUACUGGG | 412 |
| TRBJ_R101 | TUAACCUGGUCCCCGAACC | 413 |
| TRBJ_R102 | GACCGUGAGCCUGGUGC | 414 |
| TRBJ_R103 | CAGGAGCCGCGUGCCUG | 415 |
| TRBJ_R104 | AGCACUGUCAGCCGGGT | 416 |
| TRBJ_R105 | CCAGCACGGUCAGCCUG | 417 |
| TRBJ_R106 | CUAGCACGGUGAGCCGT | 418 |
| TRBJ_R107 | AGCACUGAGAGCCGGGUC | 419 |
| TRBJ_R108 | CAGTACGGUCAGCCUAGAGC | 420 |
| TRBJ_R109 | CCAGAACCAGGAGUCCUCCG | 421 |
| TRBJ_R110 | CTGTCACAGUGAGCCUGGUC | 422 |

TABLE 5-continued

| Name | Sequence | SEQ ID NO. |
|---|---|---|
| TRBJ_R111 | CCAAGACAGAGAGCUGGGUUC | 423 |
| TRBJ_R112 | CTACAACTGUGAGTCTGGUGCC | 424 |
| TRBJ_R113 | CTAGGAUGGAGAGTCGAGUCCC | 425 |
| TRBJ_R114 | CTACAACGGUTAACCTGGUCCC | 426 |
| TRBJ_R115 | CTACAACAGUGAGCCAACTUCCC | 427 |
| TRBJ_R116 | GTGACCGUGAGCCUGGT | 428 |
| TRBJ_R117 | TGTGACCGUGAGCCUGG | 429 |
| TRBJ_R118 | GTGACCGUGAGCCUGGUG | 430 |
| TRBJ_R119 | TGTGACCGUGAGCCUGGT | 431 |
| TRBJ_R120 | CTGTGACCGUGAGCCUGG | 432 |
| TRBJ_R121 | CAGGAGUCCUCCGCCCA | 433 |
| TRBJ_R122 | ACCAGGAGUCCUCCGCC | 434 |
| TRBJ_R123 | ACUGAGAGCCGGGUCCC | 435 |
| TRBJ_R124 | CACUGAGAGCCGGGUCC | 436 |
| TRBJ_R125 | GCACUGAGAGCCGGGUC | 437 |
| TRBJ_R126 | GCACGGUCAGCCUGCUG | 438 |
| TRBJ_R127 | CAGCACGGUCAGCCUGC | 439 |
| TRBJ_R128 | TAGCACGGUGAGCCGUG | 440 |
| TRBJ_R129 | CCAGGAGCCGCGUGCCUG | 441 |
| TRBJ_R130 | AACCAGGAGUCCUCCGCC | 442 |
| TRBJ_R131 | GAACCAGGAGUCCUCCGC | 443 |
| TRBJ_R132 | TAGCACGGUGAGCCGUGT | 444 |
| TRBJ_R133 | ACCAGGAGCCGCGUGCCUG | 445 |
| TRBJ_R134 | AACGGUAACCTGGUCCCC | 446 |
| TRBJ_R135 | AGAACCAGGAGUCCUCCGC | 447 |
| TRBJ_R136 | CAGAACCAGGAGUCCUCCG | 448 |
| TRBJ_R137 | TACGGTCAGCCUAGAGCCUT | 449 |
| TRBJ_R138 | GTACGGUCAGCCUAGAGCCT | 450 |
| TRBJ_R139 | GGATGGAGAGUCGAGUCCCA | 451 |
| TRBJ_R140 | CAACGGUAACCTGGUCCCC | 452 |
| TRBJ_R141 | AGTACGGUCAGCCUAGAGCC | 453 |
| TRBJ_R142 | AGGATGGAGAGUCGAGUCCC | 454 |
| TRBJ_R143 | ACAACGGUTAACCTGGUCCC | 455 |
| TRBJ_R144 | TGTCACAGUGAGCCUGGUCC | 456 |
| TRBJ_R145 | CAACTGTGAGUCTGGTGCCUT | 457 |
| TRBJ_R146 | GTACGGUCAGCCUAGAGCCUT | 458 |
| TRBJ_R147 | GGATGGAGAGUCGAGUCCCAT | 459 |
| TRBJ_R148 | ACAACTGTGAGTCTGGUGCCT | 460 |
| TRBJ_R149 | AGTACGGUCAGCCUAGAGCCT | 461 |
| TRBJ_R150 | AGGATGGAGAGUCGAGUCCCA | 462 |
| TRBJ_R151 | TACAACTGUGAGTCTGGUGCC | 463 |
| TRBJ_R152 | CAAGACAGAGAGCUGGGUUCC | 464 |
| TRBJ_R153 | TAGGAUGGAGAGTCGAGUCCC | 465 |
| TRBJ_R154 | TACAACGGUTAACCTGGUCCC | 466 |
| TRBJ_R155 | ACAACTGTGAGUCTGGTGCCUT | 467 |
| TRBJ_R156 | AAGACAGAGAGCUGGGUUCCAC | 468 |
| TRBJ_R157 | AGGATGGAGAGUCGAGUCCCAT | 469 |
| TRBJ_R158 | ACAACAGUGAGCCAACTUCCCT | 470 |
| TRBJ_R159 | TACAACTGUGAGTCTGGUGCCT | 471 |
| TRBJ_R160 | CAAGACAGAGAGCUGGGUUCCA | 472 |
| TRBJ_R161 | TAGGAUGGAGAGTCGAGUCCCA | 473 |
| TRBJ_R162 | TACAACGGUTAACCTGGUCCCC | 474 |
| TRBJ_R163 | TACAACTGTGAGUCTGGTGCCUT | 475 |
| TRBJ_R164 | TAGGAUGGAGAGTCGAGUCCCAT | 476 |
| TRBJ_R165 | TACAACAGUGAGCCAACTUCCCT | 477 |
| TRBJ_R166 | CTACAACTGUGAGTCTGGUGCCT | 478 |
| TRBJ_R167 | CTAGGAUGGAGAGTCGAGUCCCA | 479 |
| TRBJ_R168 | CTACAACTGTGAGUCTGGTGCCUT | 480 |
| TRBJ_R169 | CTAGGAUGGAGAGTCGAGUCCCAT | 481 |
| TRBJ_R170 | CTACAACAGUGAGCCAACTUCCCT | 482 |

TABLE 6

| Name | Sequence | SEQ ID NO. |
|---|---|---|
| TRBV_F313 | AACTATGTTTTGGTATCGTCA | 483 |
| TRBV_F314 | CACGATGTTCTGGTACCGTCAGCA | 484 |
| TRBV_F315 | CAGTGTGTCCTGGTACCAACAG | 485 |
| TRBV_F316 | AACCCTTTATTGGTACCGACA | 486 |
| TRBV_F317 | ATCCTTTTTTGGTACCAACAG | 487 |
| TRBV_F318 | AACCCTTTATTGGTATCAACAG | 488 |
| TRBV_F319 | CGCTATGTATTGGTACAAGCA | 489 |
| TRBV_F320 | CTCCCGTTTTCTGGTACAGACAGAC | 490 |
| TRBV_F321 | CGCTATGTATTGGTATAAACAG | 491 |
| TRBV_F322 | TTATGTTTACTGGTATCGTAAGAAGC | 492 |
| TRBV_F323 | CAAAATGTACTGGTATCAACAA | 493 |
| TRBV_F324 | ATACATGTACTGGTATCGACAAGAC | 494 |
| TRBV_F325 | GGCCATGTACTGGTATAGACAAG | 495 |
| TRBV_F326 | GTATATGTCCTGGTATCGACAAGA | 496 |

TABLE 6-continued

| Name | Sequence | SEQ ID NO. |
|---|---|---|
| TRBV_F327 | TAACCTTTATTGGTATCGACGTGT | 497 |
| TRBV_F328 | GGCCATGTACTGGTACCGACA | 498 |
| TRBV_F329 | TCATGTTTACTGGTATCGGCAG | 499 |
| TRBV_F330 | TTATGTTTATTGGTATCAACAGAATCA | 500 |
| TRBV_F331 | CAACCTATACTGGTACCGACA | 501 |
| TRBV_F332 | TACCCTTTACTGGTACCGGCAG | 502 |
| TRBV_F333 | ATACTTCTATTGGTACAGACAAATCT | 503 |
| TRBV_F334 | CACGGTCTACTGGTACCAGCA | 504 |
| TRBV_F335 | CGTCATGTACTGGTACCAGCA | 505 |

The following description of various exemplary embodiments is exemplary and explanatory only and is not to be construed as limiting or restrictive in any way. Other embodiments, features, objects, and advantages of the present teachings will be apparent from the description and accompanying drawings, and from the claims.

Although the present description described in detail certain exemplary embodiments, other embodiments are also possible and within the scope of the present invention. Variations and modifications will be apparent to those skilled in the art from consideration of the specification and figures and practice of the teachings described in the specification and figures, and the claims.

EXAMPLES

Provided immune repertoire compositions include, without limitation, reagents designed for library preparation and sequencing of expressed TCR beta sequences. Generally, RNAs extracted from samples (e.g., blood samples, tumor samples, (e.g., fresh, frozen, FFPE, of various types)) were reverse transcribed; libraries were generated, templates prepared, e.g., using Ion Chef™ or Ion OneTouch™ 2 System, then prepared templates were sequenced using next generation sequencing technology, e.g., an Ion S5™, an Ion PGM™ System and sequence analysis was performed using Ion Torrent Suite™ software.

Example 1

Total RNA was extracted from samples with the RecoverAll™ Total Nucleic Acid Isolation Kit (Ambion, Inc.), according to manufacturer instructions, then quantified, e.g., using the Qubit™ RNA HS Assay Kit (Thermo Fisher) for quantifying RNA. A total of 100 ng of total RNA was first reverse transcribed to cDNA with SuperScript® VILO™ cDNA Synthesis Kit (Thermo Fisher) according to manufacturer instructions. Prepared cDNA was used in a multiplex polymerase chain reaction to amplify TCR beta V region sequences. Sets of forward and reverse primers selected from Table 2 were used as primer pairs in amplifying TCR beta sequences comprising sequence from the FR1 region to the C region.

In an exemplary reaction, the multiplex primer set included 49 different TCR Beta V gene (TRBV) forward primers SEQ ID NOs: 105, 108-153, 163, and 177, and 2 different TCR Beta C gene (TRBC) reverse primers SEQ ID NOs:181 and 182. In other reactions, the multiplex primer set of 49 different TRBV forward primers included SEQ ID NOs: 107, 108-153, 156, and 164, and the TRBC reverse primers SEQ ID NOs: 181 and 182. In still other reactions, the multiplex primer set included 64 different TRBV forward primers SEQ ID NOs: 90-153 and 2 different TRBC reverse primers SEQ ID NOs: 181 and 182. In still other reactions, the multiplex primer set included 64 different TRBV forward primers SEQ ID NOs: 90-92, 95-155 and 2 different TRBC reverse primers SEQ ID NOs: 181 and 182. The set of 64 TRBV forward primers was designed to amplify all known TCR beta V regions in an RNA expression sample.

To a single well of a 96-well PCR plate was added 10 microliters prepared cDNA, 1 microliter of 1 μM TRBV forward primer pool (containing 64 primers), 1 microliter of 1 μM TRBC forward primer pool (containing 2 primers), and 4 microliters of an amplification reaction mixture (5× AmpliSeq HiFi Master Mix) that can include glycerol, dNTPs, and Platinum® Taq High Fidelity DNA Polymerase (Invitrogen, Catalog No. 11304) to a final volume of 20 microliters with DNase/RNase Free water. More typically, the multiplex amplification reaction was performed with each primer present at 200 nM in the reaction.

The PCR plate was sealed and loaded into a thermal cycler (Veriti™ 96-well thermal cycler (Applied Biosystems)) and run on the following temperate profile to generate the amplicon library. An initial holding stage was performed at 99° C. for 2 minutes, followed by about 20 to 30 cycles of denaturing at 99° C. for 15 seconds and an annealing and extending stage at 60° C. for 4 minutes. After cycling, the amplicon library was held at 10° C. until proceeding. Typically, about 20 cycles are used to generate the amplicon library. For some applications, up to 30 cycles can be used.

The amplicon sample was briefly centrifuged to collect contents before proceeding. To the preamplified amplicon library (~20 microliters), 2 microliters of FuPa reagent was added. The reaction mixture was sealed, mixed thoroughly to ensure uniformity and incubated at 50° C. for 10 minutes, 55° C. for 10 minutes, 60° C. for 20 minutes, then held at 10° C. for up to 1 hour. The sample was briefly centrifuged to collect contents before proceeding.

After incubation, the reaction mixture proceeded directly to a ligation step. Here, the reaction mixture now containing the phosphorylated amplicon library was combined with 2 microliters of Ion Xpress™ Barcode Adapters, 5 μM each (Thermo Fisher), 4 microliters of Switch Solution (sold as a component of the Ion Xpress™ Plus Fragment Library Kit, Thermo Fisher) and 2 microliters of DNA ligase, added last (sold as a component of the Ion Xpress™ Plus Fragment Library Kit, Thermo Fisher), then incubated at the following: 22° C. for 30 minutes, 68° C. for 10 minutes, 72° C. for 10 minutes, then held at 10° C. for up to 1 hour. The sample was briefly centrifuged to collect contents before proceeding.

After the incubation step, 30 microliters (1x sample volume) of room temperature AMPure® XP beads (Beckman Coulter, CA) was added to ligated DNA and the mixture was pipetted thoroughly to mix the bead suspension with the DNA. The mixture was pulse-spin and incubated at room temperature for 5 minutes. Samples underwent another pulse-spin and were placed on a magnetic rack such as a DynaMag™-96 side magnet (Invitrogen, Part No. 12331D) for two minutes. After the solution had cleared, the supernatant was discarded. Without removing the tube from the magnetic rack, 150 microliters of freshly prepared 70% ethanol was introduced into the sample, and incubated while gently rotating the tube on the magnetic rack. After the solution cleared, the supernatant was discarded without disturbing the pellet. A second ethanol wash was performed, the supernatant discarded, and any remaining ethanol was removed by pulse-spinning the tube and carefully removing residual ethanol while not disturbing the pellet. The pellet was air-dried for about 5 minutes at room temperature. The ligated DNA was eluted from the beads in 50 microliters of low TE buffer.

The eluted libraries were quantitated by qPCR using the Ion Library TaqMan® Quantitation Kit (Ion Torrent, Cat. No. 4468802) with a 400 base pair control ladder, according to manufacturer instructions. After quantification, the libraries were diluted to a concentration of 50 picomolar.

The ligated preamplified library (~20 microliters) was combined with 50 microliters of Platinum® PCR SuperMix High Fidelity (Thermo Fisher, sold as a component of the Ion Fragment Library Kit) and 2 microliters of Library Amplification Primer Mix (sold as a component of the Ion Fragment Library Kit). The solution was applied to a single well of a 96-well PCR plate and sealed. The plate was loaded into a thermal cycler (GeneAmp® PCR system 9700 Dual 96-well thermal cycler (Life Technologies, CA, Part No. N8050200 and 4314445)) and run on the following temperate profile to generate the final amplicon library: hold at 98° C. for 2 minutes, followed by 5 cycles of denaturing at 98° C. for 15 seconds and an annealing and extending stage at 64° C. for 1 minute. After cycling, the final amplicon library was held at 4° C. until proceeding to the final purification step outlined below.

A two-round purification of the final library was carried out. 25 µL (0.5× sample volume) of Agencourt™ AMPure™ XP Reagent was added to each plate well containing ~50 µL of sample. The bead suspension was pipetted up and down to thoroughly mix the bead suspension with the final amplicon library. The sample was then pulse-spun and incubated for 5 minutes at room temperature. The plate containing the final amplicon library was placed on a magnetic rack such as a DynaMag™-side magnet (Thermo Fisher) for 5 minutes to capture the beads. Once the solution cleared, the supernatant was carefully transferred without disturbing the bead pellet. A second round of purification was carried out, adding 60 microliters (1.2× sample volume) of Agencourt™ AMPure™ XP Reagent was added to each plate well containing sample. The bead suspension was pipetted up and down to thoroughly mix the bead suspension and incubated for 5 minutes at room temperature. The plate containing the final amplicon library was placed on a magnetic rack for 3 minutes to capture the beads. Without removing the plate from the magnetic rack, 150 microliters of freshly prepared 70% ethanol was introduced into the beads containing sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

Once the tube was dry, the tube was removed from the magnetic rack and 50 microliters of Low TE was added (Thermo Fisher), pipetted and vortexed to ensure the sample was mixed thoroughly. The sample was pulse-spin and placed on the magnetic rack for two minutes. After the solution cleared, the supernatant containing the final amplicon library was analyzed using Qubit™ Fluorometer and Qubit™ dsDNA HS Assay Kit according to manufacturer instructions to quantify the library and calculate the dilution factor for template preparation and sequencing. Library was diluted to ~50 µM for use in template preparation or stored in 1.5-mL Eppendorf LoBind™ tube for long-term storage.

An aliquot of the final library was used in template preparation with either the Ion OneTouch™ 2 System or Ion Chef™ instrument according to the manufacturer's instructions.

Sequencing was performed on either the Ion S5™ System or the Ion PGM™ System according to manufacturer instructions, and TCR beta gene sequence analysis was performed with the Ion Torrent Suite™ software. In addition, the generated sequence data was further subjected to the error identification and removal programs provided herein.

Typically, a TCR beta assay using leukocyte RNA and the multiplex amplification primer set of 49 different TRBV forward primers and 2 different TRBC reverse primers performed as described above and with the error identification and removal program provided herein yielded 6-10 M reads, of which 45-55% were productive.

The set of 64 different TRBV forward primers described above was designed to amplify all of the known TCR beta V regions in an RNA expression sample. Typically, a TCR beta assay using leukocyte RNA and the multiplex amplification primer set of 64 different TRBV forward primers and 2 different TRBC reverse primers performed as described above and with the error identification and removal program provided herein yielded 15-20M reads, of which 60-80% are productive. Use of the larger number of V region primers in the multiplex amplification reaction resulted in an increase in TCR beta productive reads, thereby providing an effective reflection of the TCR beta repertoire for the sample.

Use of single-primer 5'-RACE methodology for preparing RNA from a biological sample for sequencing is presumably best known truth for immune repertoire characterization due to minimal primer bias. Single-primer 5'-RACE also provides complete characterization of CDR 1, 2, 3.

Figures 4A, 4B:
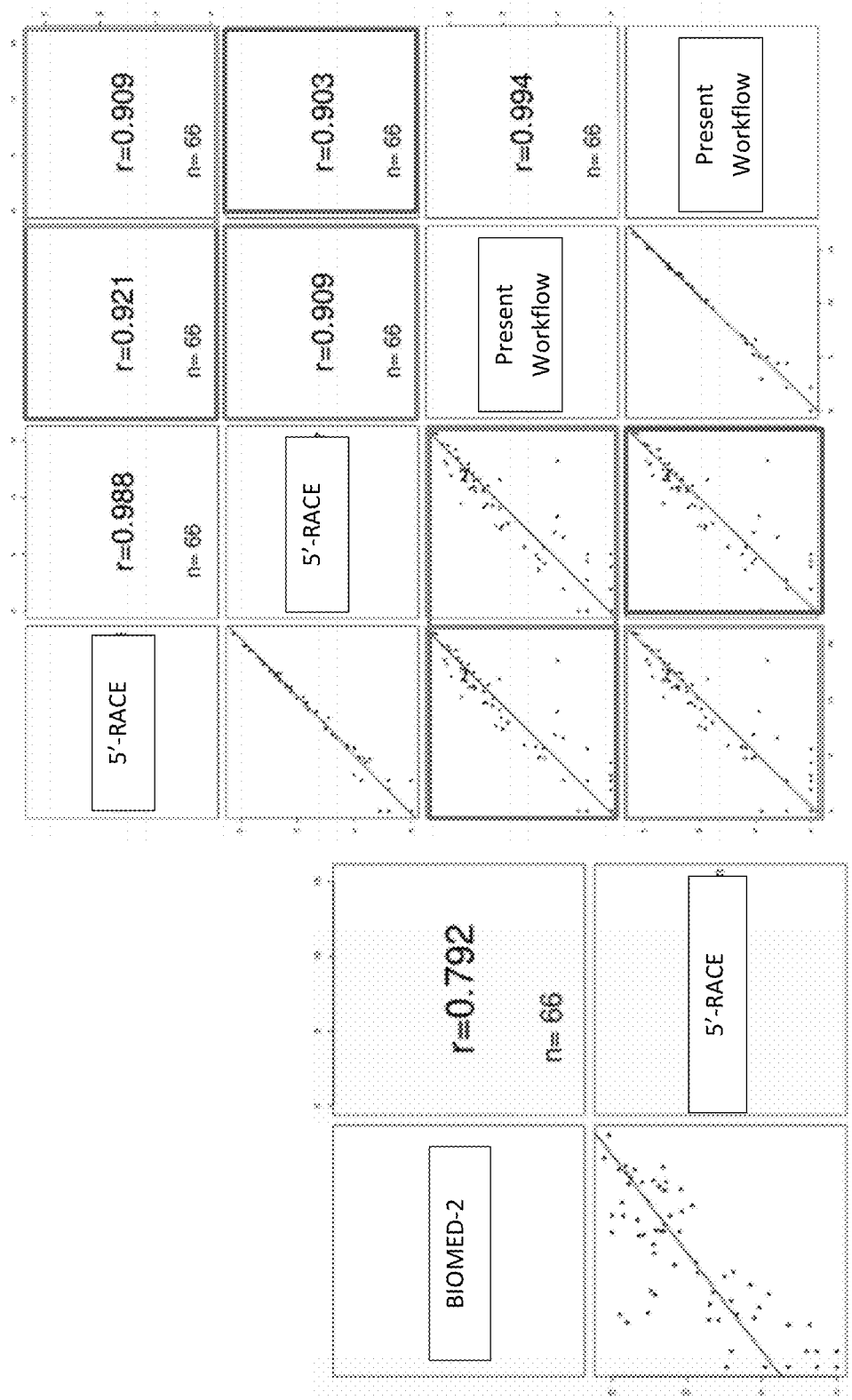
FIGS. 4A-4B depict correlation plots comparing TCR V gene usage characterization from the same peripheral blood mononuclear cell RNA sample prepared for sequencing using three different methodologies: single primer 5'-RACE, the presently provided primers and workflows, and the BIOMED-2 primer set.

RNA from a peripheral blood mononuclear cell (PBMC) sample was prepared for sequencing using single primer 5'-RACE, the present workflow using the 64 TRBV forward primer and 2 TRBC reverse primer sets, and the BIOMED-2 primer set. The amplified cDNA prepared by each of these methodologies was sequenced and the TCR beta V gene usage was determined. Comparison of the TCR beta V gene coverage obtained using the BIOMED-2 primer set to that obtained using 5'-RACE yielded correlation results in the range of r≈0.75-0.80. In contrast, the TCR beta V gene coverage obtained using the current workflow showed very high correlation in replicate (r≈0.90-0.92) when compared to 5'-RACE. See FIGS. 4A and 4B. The current workflow achieves sequence read lengths of about 400 nucleotides and provides complete characterization of CDR 1, 2, and 3 regions of the V-gene.

Figure 5:
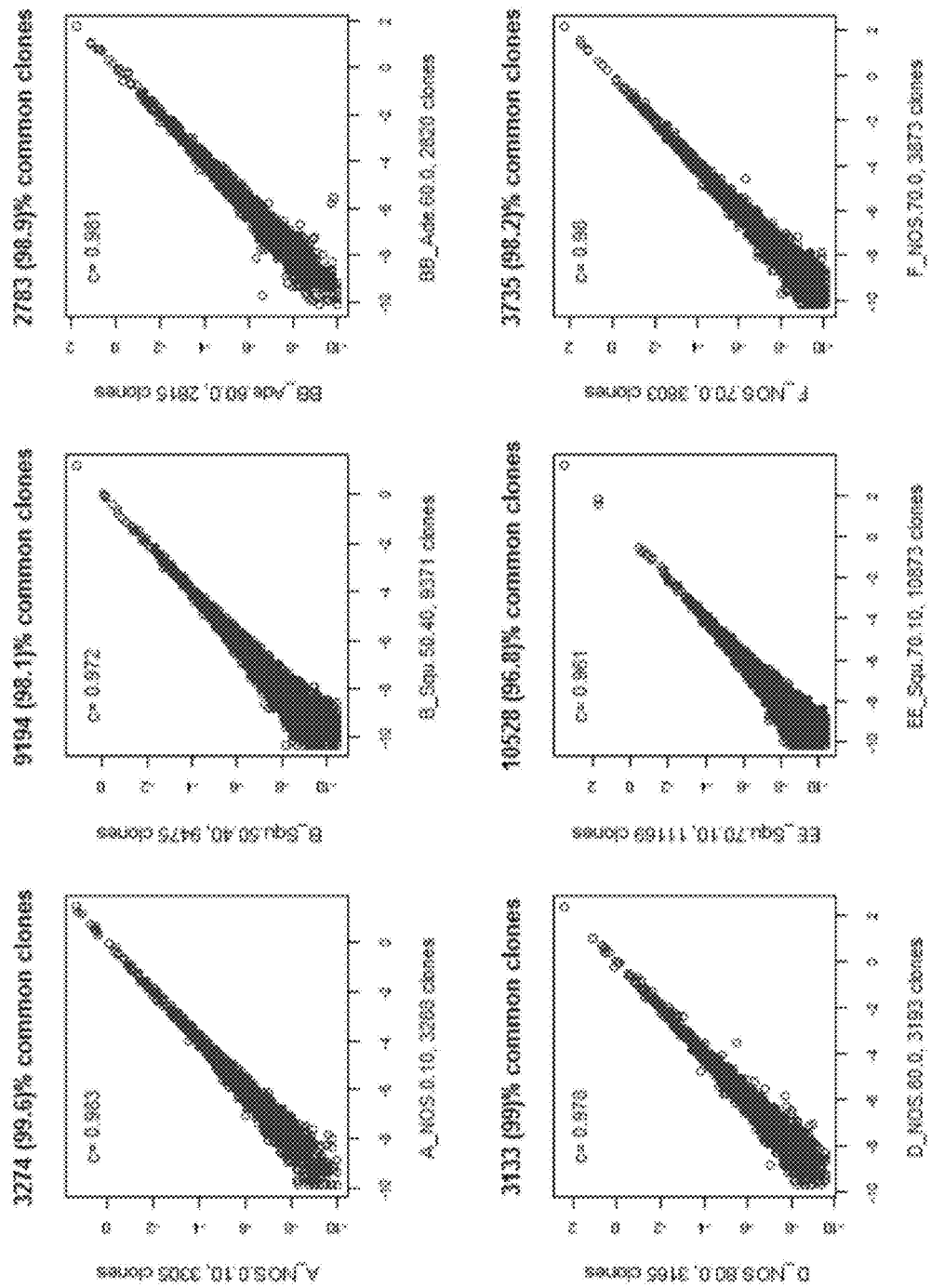
FIG. 5 depicts graphs comparing sequencing replicates from six tumor infiltrating lymphocyte (TIL) samples. The six samples were from a total of ten TIL samples sequenced on a single Ion Torrent S5 530™ chip.

Following the current workflow described above, ten fresh-frozen tumor infiltrating lymphocyte (TIL) samples taken from non-small cell lung carcinoma biopsy samples were sequenced on a single Ion Torrent S5 530™ chip. Sequencing runs of the samples run in replicates resulted in high concordance between identified clones (95.8%-99.6%), indicating sequencing to adequate depth to reflect sufficient characterization of the repertoire in the samples. Correlation plots depicting results from six of the ten samples are shown in FIG. 5. Depending on the sample type, up to 16 samples can be sequenced on a single Ion Torrent S5 530™ chip. The current workflow can be used as a high throughput immune repertoire profiling method, producing greater than 50,000

Example 2

T cell repertoires found in circulating leukocytes and in TILs in an individual with squamous cell carcinoma were characterized and compared. Total RNA was extracted from peripheral blood leukocytes (PBL) and from a tumor biopsy obtained from an individual with stage 1B squamous cell carcinoma of the lung. For each sample, cDNA was prepared from 100 ng of total RNA, the cDNA was amplified in a multiplex reaction using the primer set having 64 different TRBV forward primers and 2 different TRBC reverse primers (SEQ ID NOs: 90-153 and 181-182) with each primer at 200 nM, and sequencing was performed as described in Example 1. The generated sequence data was subjected to the error identification and removal programs provided herein.

Tumor biopsy sequencing revealed 589 unique T cell receptors and an oligoclonal repertoire with a small number of dominating clones (Shannon diversity index: 6.78). PBL sequencing revealed 45,305 unique T cell receptors and a diverse, polyclonal repertoire with few highly expanded T cells (Shannon diversity index: 13.95). About 91.78% of the peripheral blood T cell repertoire was unique to the peripheral blood and about 8.22% was shared with the tumor repertoire. Accordingly, about 8% of T cells in the peripheral blood repertoire were found in TILs in this individual.

Figure 6:
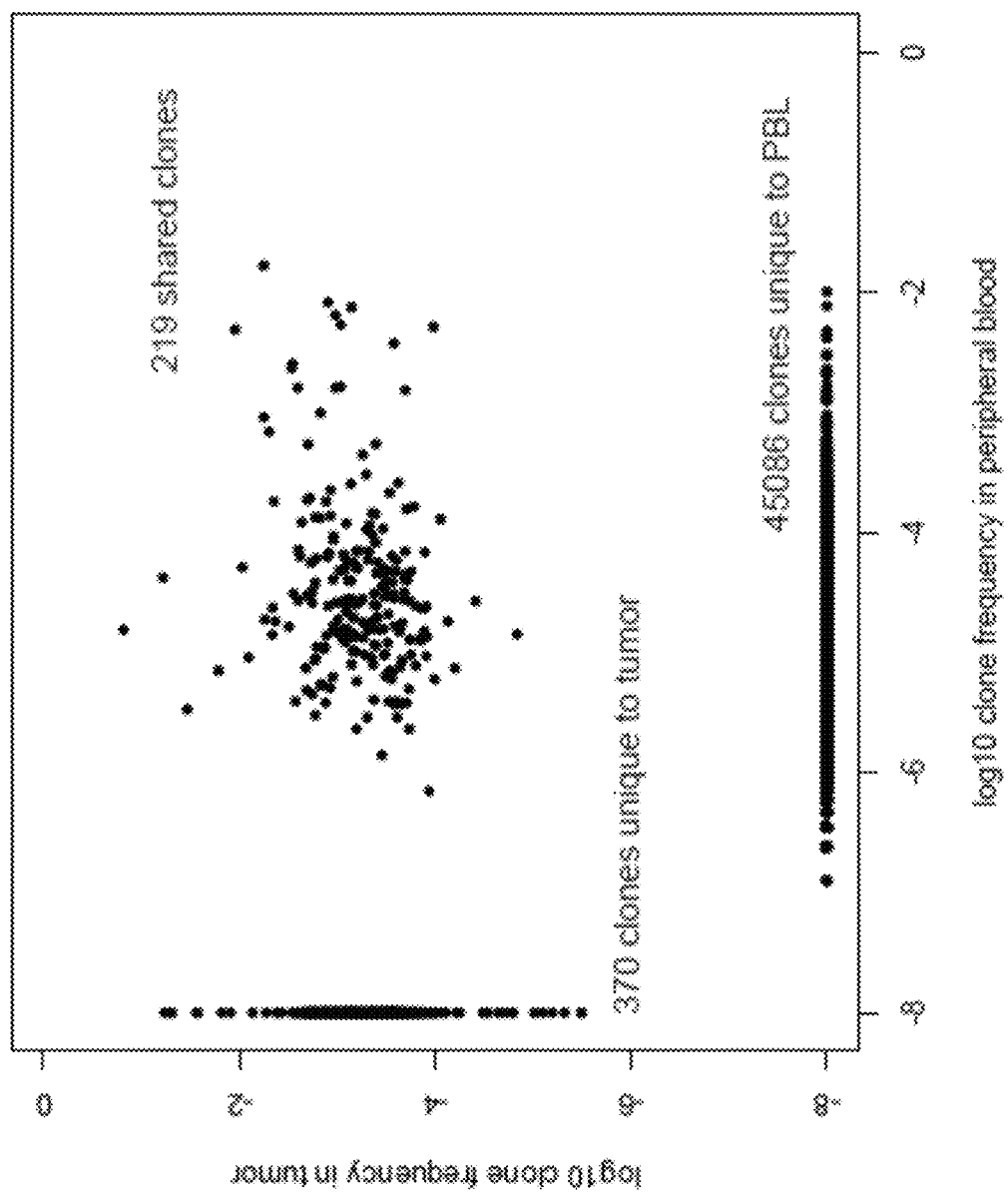
FIG. 6 is a graph comparing the TCR clone frequency in peripheral blood (x-axis) and the TCR clone frequency in tumor (y-axis) from an individual with squamous cell carcinoma of the lung. Sequencing of the TCR beta immune repertoire identified 219 TCR clones shared between peripheral blood and tumor and 370 TCR clones unique to the tumor.

The T cell repertoire sequencing results revealed that some T cell clones were enriched in tumor with respect to PBLs. As shown in FIG. 6, 370 clones were unique to the tumor and not found in PBL, while 219 clones were shared between tumor and PBL. The vast majority (45,086) of the clones were unique to PBL and not found in the tumor.

Example 3

The following demonstrates an alternative approach for amplification of an immune receptor repertoire which combines the use of a fusion primer for the constant region with a set of primers for the variable region.

A primer set containing 49 different TRBV forward primers SEQ ID NOs: 108-153, 162, 172, and 179 (see Table 2) was used with 2 different TRBC reverse fusion primers to amplify TCR beta V regions in an RNA sample. One of the TRBC reverse fusion primers contained the TRBC_R3 (SEQ ID NO: 183) primer sequence and the other contained the TRBC_R4 (SEQ ID NO: 184) primer sequence from Table 2. Each fusion primer also contained a barcode sequence and an A-key tagging sequence on the 5' end. RNA was extracted and cDNA prepared as described in Example 1. To a single well of a 96-well PCR plate was added 10 microliters prepared cDNA, 1 microliter of 1 µM TRBV forward primer pool (containing the 49 primers), 1 microliter of 1 µM TRBC reverse primer pool (containing the 2 fusion primers), and 4 microliters of an amplification reaction mixture (5× AmpliSeq HiFi Master Mix) that can include glycerol, dNTPs, and Platinum® Taq High Fidelity DNA Polymerase (Invitrogen, Catalog No. 11304) to a final volume of 20 microliters with DNase/RNase Free water.

The PCR plate was sealed and loaded into a thermal cycler and cycled as described in Example 1. The amplicon sample was briefly centrifuged to collect contents before proceeding. To the amplified amplicon library (~20 microliters), 2 microliters of FuPa reagent was added. The reaction mixture was sealed, mixed thoroughly to ensure uniformity and incubated at 50° C. for 10 minutes, 55° C. for 10 minutes, 60° C. for 20 minutes, then held at 10° C. for up to 1 hour. The sample was briefly centrifuged to collect contents before proceeding.

After incubation, 22 microliters of the digested amplicon library was combined with 2 microliters of P1 Adapter, 5 µM (Thermo Fisher), 4 microliters of Switch Solution (sold as a component of the Ion Xpress™ Plus Fragment Library Kit, Thermo Fisher) and 2 microliters of DNA ligase, added last (sold as a component of the Ion Xpress™ Plus Fragment Library Kit, Thermo Fisher), then incubated at the following: 22° C. for 30 minutes, 68° C. for 10 minutes, 72° C. for 10 minutes, then held at 10° C. for up to 1 hour. The sample was briefly centrifuged to collect contents before proceeding.

Purification, quantification, template preparation and sequencing were performed as described in Example 1. For this example, one primer set uses fusion primers which do not undergo adapter ligation following amplification and the other primer set uses primers to which an adapter is ligated following amplification. TCR beta assays were performed with such primer sets on total RNA from Jurkat cells and from PBMC. Sequence read lengths of about 350-375 nucleotides were obtained. Using the error identification and removal program provided herein yielded >90% productive reads for the Jurkat sample and >60% productive reads for the PBMC sample. Generally, performance of this fusion primer workflow assay was equivalent to the performance of the workflow using the 49 TRBV primer set in Example 1.

A primer set containing 64 different TRBV forward primers: either SEQ ID NOs: 90-153 or SEQ ID NOs: 90-92 and 95-155 (see Table 2) is used with 2 different TRBC reverse fusion primers to amplify TCR beta V regions in an RNA sample. One of the TRBC reverse fusion primers contains the TRBC_R3 (SEQ ID NO: 183) primer sequence and the other contains the TRBC_R4 (SEQ ID NO:184) primer sequence from Table 2. Each fusion primer also contains a barcode sequence and an A-key tagging sequence on the 5' end. RNA is extracted and cDNA is prepared as described in Example 1. To a single well of a 96-well PCR plate is added: 10 microliters prepared cDNA, 1 microliter of 1 µM TRBV forward primer pool (containing the 64 primers), 1 microliter of 1 µM TRBC reverse primer pool (containing the 2 fusion primers), and 4 microliters of an amplification reaction mixture (5× AmpliSeq HiFi Master Mix) that can include glycerol, dNTPs, and Platinum® Taq High Fidelity DNA Polymerase (Invitrogen, Catalog No. 11304) to a final volume of 20 microliters with DNase/RNase Free water.

The PCR plate is sealed and loaded into a thermal cycler and cycled as described in Example 1. The amplicon sample is briefly centrifuged to collect contents before proceeding. To the amplified amplicon library (~20 microliters), 2 microliters of FuPa reagent is added. The reaction mixture is sealed, mixed thoroughly to ensure uniformity and incubated at 50° C. for 10 minutes, 55° C. for 10 minutes, 60° C. for 20 minutes, then is held at 10° C. for up to 1 hour. The sample is briefly centrifuged to collect contents before proceeding.

After incubation, 22 microliters of the digested amplicon library is combined with 2 microliters of P1 Adapter, 5 µM (Thermo Fisher), 4 microliters of Switch Solution (sold as a component of the Ion Xpress™ Plus Fragment Library Kit, Thermo Fisher) and 2 microliters of DNA ligase, added last (sold as a component of the Ion Xpress™ Plus Fragment Library Kit, Thermo Fisher), then is incubated at the following: 22° C. for 30 minutes, 68° C. for 10 minutes, 72° C.

for 10 minutes, then is held at 10° C. for up to 1 hour. The sample is briefly centrifuged to collect contents before proceeding.

Purification, quantification, template preparation and sequencing are performed as described in Example 1. The sequence data set is subjected to the error identification and removal program provided herein. For this example, one primer set uses fusion primers which do not undergo adapter ligation following amplification and the other primer set uses primers to which an adapter is ligated following amplification. TCR beta assays are performed with such primer sets on total RNA from cells, such as T cell lines and/or PBMC.

Example 4

A library of control plasmids was generated to represent a set of TCR beta V genes and used to assess performance of the assays and workflows provided herein. Each control plasmid contained a TCR beta cDNA from a single T cell clone from a lymphoma cell line. TCR beta cDNA from the following cell lines are included in the library of control plasmids: JB6, CML-T1b, ARR, HPB-ALL, H-SB2, KE-37/SKW-3, K-T1a, SU-DHL-1, SUP-T3, TALL-104, TALL-1, MOLT 16/17, MT-1, Karpas 299, MOLT 3/4, HUT 78/H9, RPMI 8402, Peer/Be13, CCRF-CEM, SUP-T1, HUT-102, MOLT 13, P12-Ichikawa, Jurkat, DND-41, K-T1b, PF-382, CML-T1a, DU.528, and Karpas 45. See, for example, Sandberg et al. (2007) Leukemia 21:230, for sequences of exemplary TCR beta cDNA. Each plasmid was amplified individually and sequenced to confirm the detection of a single clonal population.

To assess the limit of detection for the assay and workflow, control libraries were prepared using 10 pooled plasmids or 30 pooled plasmids at single known input concentrations in a background of 100 ng leukocyte cDNA. Plasmid input concentrations ranged from 10 pg to 0.00001 pg (equivalent to 5M copies to about 5 copies).

The control plasmids were linearized (individually or in bulk) or left intact prior to use in the assays. The pooled libraries were amplified in multiplex reactions using the primer set having 64 different TRBV forward primers and 2 different TRBC reverse primers (SEQ ID NOs: 90-153 and 181-182) with each primer at 200 nM, and sequencing was performed as described in Example 1. The generated sequence data was subjected to the error identification and removal programs provided herein.

Figure 7:
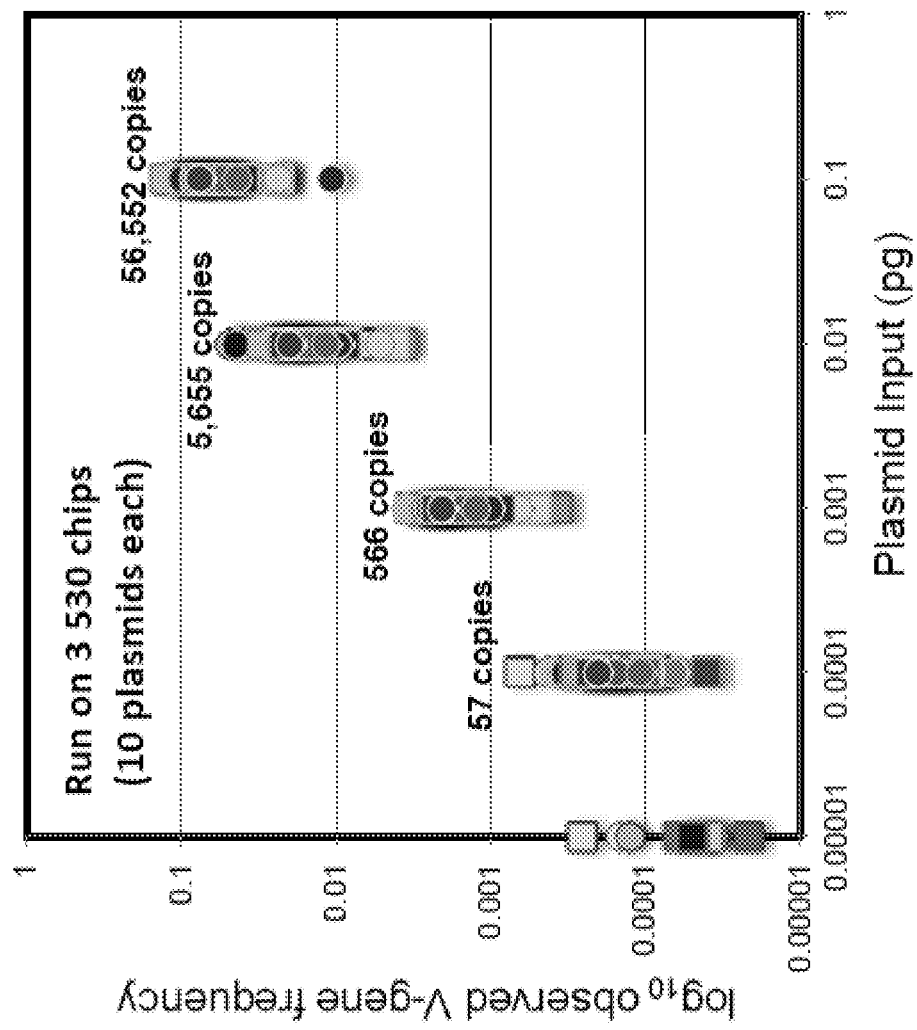
FIG. 7 is a graph comparing the amount of input plasmid (x-axis) to the observed V-gene frequency (y-axis) for pools of ten control plasmids. Each symbol at a given amount of plasmid represents a different plasmid in the pool. This graph shows the limit of detection and linearity of the assays.

Exemplary results for a pool of 10 plasmids at varying concentrations are shown in FIG. 7. Typically, the limit of detection for the control assays ranged from 10 to 50 copies of a control plasmid and the assays demonstrated linearity over 5-6 orders of magnitude of input. Similarly, limit of detection assays with a pool of 30 plasmids at varying concentrations resulted in as little as 5 copies of plasmid detected and assay linearity was observed over five orders of magnitude. Strong linearity in detection of clonal frequencies was also observed in populations of counted T cells.

Figure 8:
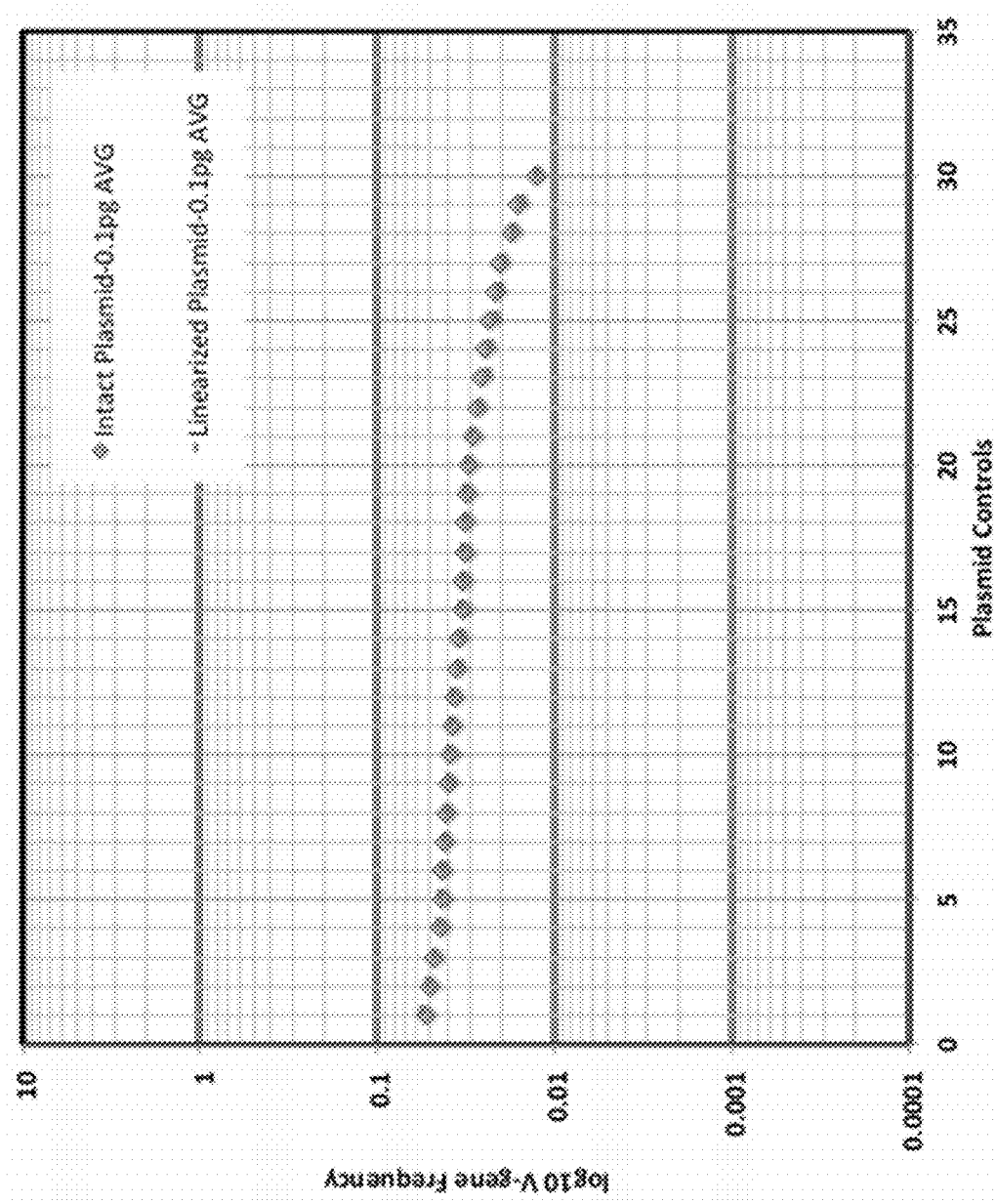
FIG. 8 depicts a graph showing the linearity of plasmid detection in pools of 30 control plasmids at equimolar concentrations magnitude. The diamond symbol represents the result using intact plasmid and the dash mark represents the result using linearized plasmid.

As shown in FIG. 8, performance of the assay on pools of 30 plasmids at equimolar concentrations resulted in detected plasmid frequencies within one order of magnitude. Also, when the 10 plasmids were mixed at the same concentration, only a 5 fold variation in the observed V-gene (or plasmid) frequency was observed at any single concentration across all plasmids.

Example 5

The following is an examination of validation of provided methods using a control system. For this examination, a TCR beta library was prepared from 10 plasmids (as described in Example 4) pooled at equimolar concentrations. The library was amplified in a multiplex reaction with primers SEQ ID NOs: 90-153 and 181-182 and at 200 nM each according to methods and compositions described in Example 1 and provided herein, sequenced using Ion Torrent sequencing system to a depth of 17.3 M reads using methods and compositions provided herein.

Comparison of error correction methodology. The sequencing data set was analyzed using the following workflow as well as three academic software packages: IMSEQ (Kuchenbecker et al. (2015) "IMSEQ—A Fast And Error Aware Approach To Immunogenetic Sequence Analysis," Bioinformatics 31:2963-2971), MiXCR (Bolotin et al. (2015) "MiXCR: Software For Comprehensive Adaptive Immunity Profiling," Nature Methods 12:380-381), and RTCR (Gerritsen et al. (2016) "RTCR: A Pipeline For Complete And Accurate Recovery Of T Cell Repertoires From High Throughput Sequencing Data," Bioinformatics 32:3098-3106). The academic packages were run with default setting unless noted otherwise.

Correction Workflow

1) Identify and exclude chimeric sequences: For each unique CDR3 nucleotide sequence present in the dataset, the number of reads having that CDR3 nucleotide sequence and any of the possible variable genes was tallied. Any V gene-CDR3 combination making up less than 10% of total reads for that CDR3 nucleotide sequence was flagged as a chimera and eliminated from downstream analyses.

2) Identify and exclude sequences containing simple indel errors: For each read in the dataset, the homopolymer-collapsed representation of the CDR3 sequence of that read was obtained. For each set of reads having the same V gene and collapsed-CDR3 combination, the number of occurrences of each non-collapsed CDR3 nucleotide sequence was tallied. Any non-collapsed CDR3 sequence making up <10% of total reads for that read set was flagged as having a simple homopolymer error.

3) Identify and exclude singleton reads: For each read in the dataset, the number of times that the exact read sequence is found in the dataset was tallied. Reads that appear only once in the dataset were flagged as singleton reads.

4) Identify and exclude truncated reads: For each read in the dataset, it was determined whether the read possessed an annotated V gene FR1, CDR1, FR2, CDR2, and FR3 region, as indicated by the IgBLAST alignment of the read to the IgBLAST reference V gene set. Reads that did not possess the above regions were flagged as truncated.

5) Identify and exclude rearrangements lacking bidirectional support: For each read in the dataset, the V gene and CDR3 sequence of the read as well as the strand orientation of the read (plus or minus strand) were obtained. For each V gene-CDR3 combination in the dataset, the number of plus and minus strand reads having that V gene-CDR3nt combination was tallied. V gene-CDR3nt combinations that are only present in reads of one orientation were deemed to be a spurious. All reads that had a spurious V gene-CDR3nt combination were flagged as lacking bidirectional support.

6) For genes that were not flagged, stepwise clustering was performed based on CDR3 nucleotide similarity. The sequences were separated into groups based on the V gene identity of the read, excluding allele information (v-gene groups). For each group:
  a. Reads in each group were arranged into clusters using cd-hit-est and the following parameters:
    cd-hit-est-i      vgene_groups.fa-o      clustered_vgene_groups.cdhit-T 24-d 0-M 100000-B 0-r 0-g 1-S 0-U 2-uL 0.05-n 10-1 7
    Where vgene_groups.fa is a fasta format file of the CDR3 nucleotide regions of sequences having the same V gene and clustered_vgene_groups.cdhit is the output, containing the subdivided sequences.
  b. Each sequence in a cluster was assigned to the same clone ID, used to denote that members of the subgroup are believed to represent the same T cell clone.
  c. A representative sequence was chosen for each cluster, such that the representative sequence is the sequence that appears the greatest number of times, or, in cases of a tie, is randomly chosen.
  d. All other reads in the cluster were merged into the representative sequence such that the number of reads for the representative sequence increased according to the number of reads for the merged sequences.
  e. The representative sequences within a v-gene group were compared to each other on the basis of hamming distance. If a representative sequence was within a hamming distance of 1 to a representative sequence that is >50 times more abundant, that sequence was merged into the more common representative sequence. If a representative sequence was within a hamming distance of 2 to a representative sequence that is >10000 times more abundant, that sequence was merged into the more common representative sequence.
  f. Identify complex sequence errors: The representative sequences within each V gene group was subjected to homopolymer-collapse and then compared to each other using Levenshtein distances. If a representative sequence was within a Levenshtein distance of 1 to a representative sequence that is >50 times more abundant, that sequence was merged into the more common representative sequence.
  g. Identify CDR3 misannotation errors: The representative sequences within each V gene group was subjected to homopolymer-collapse, then a pairwise comparison of each homopolymer-collapsed sequence was performed. For each pair of sequences, it was determined whether one sequence was a subset of the other sequence. If so, the less abundant sequence was merged into the more abundant sequence if the more abundance sequence was >500 fold more abundant.
7) Cluster representatives were reported to user.

Figures 3A, 3B, 3C:
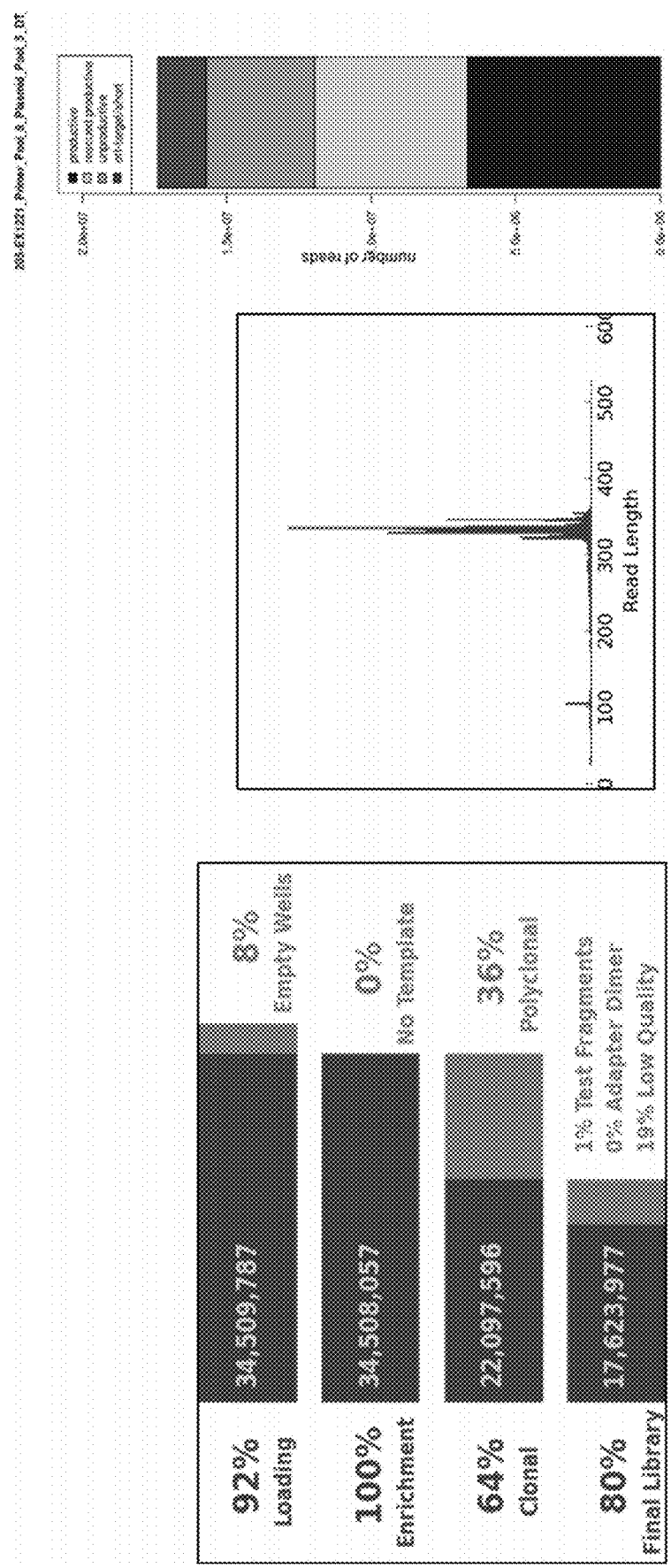
FIGS. 3A-3C depict an analysis summary of sequencing the TCR beta (TRB) repertoire from a 10 plasmid pool TRB library using methods and compositions provided herein. Results depict sequencing to ~17 million raw reads depth.

A summary of the sequencing analysis of the 10 plasmid pool is presented in FIGS. 3A-3C, including read lengths and classification of the reads as productive, rescued productive, unproductive, and off-target/short using the error identification and correction workflow described above. A comparison of the performance of this workflow (Correction Workflow) to that of MiXCR, IMSEQ, and RTCR packages on the test dataset is presented in Table 7. The Correction Workflow run time can vary from the example shown in Table 7, depending on the dataset being analyzed. In the absence of sequencing and PCR error, 10 clonotypes corresponding to the 10 plasmid sequences should have been identified. The academic packages MiXCR, IMSEQ, and RTCR report many artifactual lineages. In the case of MiXCR, three of the 10 plasmid CDR3 sequences are incorrectly reported (homopolymer errors) although these mistakes are not counted against it in the accuracy metrics in Table 7. IMSEQ was run with parameters—on to report translated clonotypes only. RTCR incorrectly identified the V gene in two cases due to use of an incomplete V gene reference file. Performance of the Correction Workflow described above yielded 12 clonotypes, far fewer than the other packages (by at least an order of magnitude) and far closer to the true number of clonotypes present in the library. Thus, it provided a far lower false positive rate. The presently provided workflow also provided the highest read assignment accuracy.

TABLE 7

CORRECTION WORKFLOW PERFORMANCE METRICS

| Dataset | Metric | MiXCR | IMSEQ | RTCR | Correction Workflow |
|---|---|---|---|---|---|
| 10 plasmids raw bam 63830 | Number of plasmids correctly identified | 7 | 10 | 10 | 10 |
| | Total number of clonotypes detected | 153 | 2336 | 227 | 12 |
| | Total reads reported | 10,751,394 | 1,753,226 | 11,233,604 | 9,984,353 |
| | Percentage of raw reads reported | 61.82% | 10.08% | 64.59% | 57.41% |
| | Percentage reads correctly assigned | 95% | 95% | 97% | 99.9999% |
| | Run time (hours) | 1.1 | 1.1 | 2.5 | 5.3 |

Example 6

The combination of targeted gene expression and immune repertoire profiling provides benefits and insights for tumor microenvironment studies and assessment. T cell repertoires were profiled for tumor infiltrating lymphocyte (TIL) samples from a cohort of 19 individuals with non-small cell lung cancer as described in Example 1. Gene expression profiling was also performed with RNA from the TIL samples using the Oncomine™ Immune Response Research Assay (Cat. No. A32881, Thermo Fisher Scientific) and the Ion Torrent™ NGS platform according to manufacture instructions. The TIL T cell repertoire features were then correlated with the immune response gene expression profile. Profiling of T cell repertoires in the lung cancer samples revealed a positive correlation between the number of clones detected in a particular sample and T cell-specific gene expression (e.g., CD4, CD8, CXCL9, CCL7, and MMP-6 genes). T cell clone evenness (i.e., normalized Shannon Entropy) correlated most strongly with expression of myeloid-specific genes and markers for T cell exhaustion and was anti-correlated with IFNG expression.

Example 7

T cell repertoire profiling is useful in monitoring manufacture of therapeutic T cells. T cells were isolated from PBMCs, activated and expanded using Gibco™ CTS™ Dynabeads™ CD3/CD28 magnetic beads and associated reagents and media (Thermo Fisher Scientific) according to manufacture instructions. T cell repertoires were sequenced for the T cells at different time points in the ex vivo process: before isolation (PBMCs), T cells after isolation, T cells after day 3 of incubation (before and after bead removal), and T cells after day 10 of incubation. Exemplary results are shown in Table 8. Sequencing of the T cells during the manufacture process revealed changes to repertoire diversity that coincide with in vitro expansion and allowed for quantification of clonal expansion.

TABLE 8

| Sample | Library | BC | Reads | Lineages Detected | Normalized Shannon Diversity Index |
|---|---|---|---|---|---|
| 1 | PBMC pre-isolation | 1 | 3,189,770 | 12,147 | 0.88222 |
| | CD3 post-isolation | 2 | 3,003,959 | 30,503 | 0.911586 |
| | CD3 day 3 pre-bead removal | 3 | 3,177,398 | 3,752 | 0.92871 |
| | CD3 day 3 post-bead removal | 4 | 2,897,928 | 2,576 | 0.93898 |
| | CD3 cells day 10 | 5 | 2,775,353 | 7,272 | 0.963997 |
| 2 | PBMC pre-isolation | 6 | 2,630,313 | 8,538 | 0.763292 |
| | CD3 post-isolation | 7 | 2,786,937 | 11,156 | 0.7671 |
| | CD3 day 3 pre-bead removal | 8 | 2,529,946 | 3,063 | 0.832452 |
| | CD3 day 3 post-bead removal | 9 | 2,691,294 | 2,678 | 0.828859 |
| | CD3 cells day 10 | 10 | 2,955,139 | 13,172 | 0.920759 |

Example 8

The methods and compositions provided herein provide long amplicon multiplex sequencing of rearranged CDR and Framework regions of T cell receptor beta sequences and thus, can be used to identify and characterize novel T cell receptor alleles. Using the method and compositions described in Example 1, cDNA prepared from 85 Caucasian subjects undergoing treatment for melanoma was subjected to multiplex amplification using the 64 TRBV (FR1) forward primers and the 2 TRBC reverse primers and produced amplicons about 330 nucleotides in length. The samples were sequenced in multiplex using Ion Torrent S5 530 chip to produce about 1.5M raw reads per sample. The sequencing data was subjected to the error identification and removal programs provided herein and uploaded to Ion Reporter for clonotyping and identification or rearrangements containing V gene sequences absent from the IMGT database. Putatively novel sequences were compared with those reported in the Lym1k database of alleles recovered from 1000 genomes sequence data and with those reported in the NCBI NR database.

This study resulted in identification of fifteen non-synonymous variants of TRB V gene alleles, absent from the IMGT database, which result in amino acid changes to the CDR or Framework regions of the T cell receptor beta gene. As these alleles were absent from IMGT, they are referred to as non-canonical alleles. The results and variant sequences are presented in Tables 9 and 10, respectively. Typically, a single individual was found to be heterozygous for a variant absent from the IMGT database, though there were two instances of such alleles that were found in multiple individuals within this cohort. Also found were nine novel V gene alleles absent from IMGT that were absent from the Lym1k database, possibly due to challenges in inferring receptor alleles from short-read population sequencing studies, and absent from the NCBI NR database. Evidence for six of the fifteen variant alleles absent from IMGT was found in either the Lym1k database or the NCBI NR database. TRB sequencing using multiplex reactions with FR1 and C region targeting primers is well suited for studying the role of T cell receptor diversity in autoimmune disease and the emergence of immune-related adverse events during immunotherapy.

TABLE 9

| Allele name | Location of amino acid variant | No. of individuals having allele | In Lym1k database? | In NCBI NR database? |
|---|---|---|---|---|
| TRVB11-2_x1 | FR3 | 1 | No | No |
| TRBV11-3_x1 | FR2 | 18 | No | Yes |
| TRBV12-4_x1 | FR2 | 1 | No | No |
| TRBV12-5_x1 | FR2 | 1 | No | No |
| TRBV19_x1 | FR2 | 1 | No | No |
| TRBV23-1_x1 | FR3 | 1 | No | No |
| TRBV24-1_x1 | FR2 | 43 | No | Yes |
| TRBV5-3_x1 | FR2 | 1 | No | No |
| TRBV5-8_x1 | FR1 | 17 | No | No |
| TRBV6-2_x1 | FR1, CDR1, FR2, CDR2, FR3 | 1 | No | No |
| TRBV6-5_x1 | CDR2 | 1 | No | No |
| TRVB11-1_x1 | CDR1, FR2/CDR2 | 1 | Yes | No |
| TRBV30_x1 | FR3 | 1 | Yes | No |
| TRBV5-5_x1 | FR3 | 2 | Yes | No |
| TRBV5-6_x1 | FR3 | 4 | Yes | No |

TABLE 10

| Allele Name | Allele Sequence | SEQ ID NO. |
|---|---|---|
| TRBV11-2_x1 | AGAGAAAAGGCAGAGTGTGGCTTTTTGGTGCAAT CCTATATCTGGCCATGCTACCCTTTACTGGTACC AGCAGATCCTGGGACAGGGCCCAAAGCTTCTGAT TCAGTTTCAGAATAACGGTGTAGTGGATGATTCA CAGTTGCCTAAGGTTCGATTTTCTGCAGAGAGGC TCAAAGGAGTAGACTCCACTCTCAAGATCCAGCC TGCAAAGCTTGAGGACTCGGCCGTGTATCTCTGT | 506 |
| TRBV11-3_x1 | CCCAGATATAAGATTATAGAGAAAAAACAGCCTG TGGCTTTTTGGTGCAATCCTATTTCTGGCCACAA TACCCTTTACTGGTACCGGCAGAACTTGGGACAG GGCCCGGAGCTTCTGATTCGATATGAGAATGAGG AAGCAGTAGACGATTCACAGTTGCCTAAGGATCG ATTTTCTGCAGAGAGGCTCAAAGGAGTAGACTCC ACTCTCAAGATCCAGCCTGCAGAGCTTGGGGACT CGGCCGTGTATCTCTGT | 507 |
| TRBV12-4_x1 | GACAGAGATGGGACAAGAAGTGACTCTGAGATGT AAACCAATTTCAGGACACGACTACCTTTTCTGGT ACAGACAGACCATGATGCAGGGACTGGAGTTGCT CATTTACTTTAACAACAACGTTCCGATAGATGAT TCAGGGATGCCCGAGGATCGATTCTCAGCTAAGA TGCCTAATGCATCATTCTCCACTCTGAAGATCCA GCCCTCAGAACCCAGGGACTCAGCTGTGTACTTC TGT | 508 |
| TRBV12-5_x1 | GACAGAGATGGGACAAGAAGTAACAATGAGATGT CAGCCAATTTTAGGCCACAATACTGTTTTCTGGT ACAGACAGACCATGAAGCAAGGACTGGAGTTGCT GGCTTACTTCCGCAACCGGGCTCCTCTAGATGAT TCGGGGATGCCGAAGGATCGATTCTCAGCAGAGA TGCCTGATGCAACTTTAGCCACTCTGAAGATCCA GCCCTCAGAACCCAGGGACTCAGCTGTGTATTTT TGT | 509 |
| TRBV19-x1 | GTTCAGAAAGGAAGGACAGAATGTGACCCTGAGT TGTAACAGAATTTGAACCACGATGCCATGTACT GGTACCAACAGGACCCAGGGCAAGGGCTGAGATT | 510 |

TABLE 10-continued

| Allele Name | Allele Sequence | SEQ ID NO. |
| --- | --- | --- |
|  | GATCTACTACTCACAGATAGTAAATGACTTTCAG AAAGGAGATATAGCTGAAGGGTACAGCGTCTCTC GGGAGAAGAAGGAATCCTTTCCTCTCACTGTGAC ATCGGCCCAAAAGAACCCGACAGCTTTCTATCTC TGT |  |
| TRBV23-1_x1 | CAAAGGAAAAGGACAGAAAACAAAGATGGATTGT ACCCCCGAAAAAGGACATACTTTTGTTTATTGGT ATCAACAGAATCAGAATAAAGAGTTTATGCTTTT GATTTCCTTTCAGAATGAACAAGTTCTTCAAGAA ACGGAGATGCACAAGAAGCGATTCTCATCTCAAT GCCCCAAGAACGCACCCTGCAGCCTGGCAATCCT GTCCTCAGAACCGGGAGACACGGCACTGCATCTC TGC | 511 |
| TRBV24-1_x1 | CACAAAGACAGGAAAGAGGATTATGCTGGAATGT TCTCAGACTAAGGGTCATGATAGAATGTACTGGT ATCGACAAGACCCAGGACTGGGCCTACAGTTGAT CTATTACTCCTTTGATGTCAAAGATATAAACAAA GGAGAGATCTCTGATGGATACAGTGTCTCTCGAC AGGCACAGGCTAAATTCTCCCTGTCCCTAGAGTC TGCCATCCCCAACCAGACAGCTCTTTACTTCGT | 512 |
| TRBV5-3_x1 | CAAAACGAGAGGACAGCAAGTGACTCTGAGATGC TCTCCTATCTCTGGGCACAGCAGTGTGTCCTGGT ACCAACAGGCCCCGGGTCAGGTGCCCCAGTTTAT CTTTGAATATGCTAATGAGTTAAGGAGATCAGAA GGAAACTTCCCTAATCGATTCTCAGGGCGCCAGT TCCATGACTGTTGCTCTGAGATGAATGTGAGTGC CTTGGAGCTGGGGGACTCGGCCCTGTATCTCTGT | 513 |
| TRBV5-8_x2 | CCCACACACCTGATCAAAACGAGAGGACAGCAAG TGACTCTGAGATGCTCTCCTATCTCTGGGCACAC CAGTGTGTACTGGTACCAACAGGCCCTGGGTCTG GGCCTCCAGTTCCTCCTTTGGTATGACGAGGGTG AAGAGAGAAACAGAGGAAACTTCCCTCCTAGATT TTCAGGTCGCCAGTTCCCTAATTATAGCTCTGAG CTGAATGTGAATGCCTTGGAGCTGGAGGACTCGG CCCTGTATCTCTGT | 514 |
| TRBV6-2_x1 | GAAGACAGGACAGAGCATGACACTGCAGTGTGCC CAGGATATGAACCATAACTCCATGTACTGGTATC GACAAGACCCAGGCATGGGACTGAGGCTGATTCA TTACTCAGCTTCTGAGGGTACCACTGACAAAGGA GAGGTCCCTGATGGCTACAATGTCTCCAGATTAA AAAAACAGAATTTCCTGCTGGGGTTGGAGTCGGC TGCTCCCTCCCAAACATCTGTGTACTTCTGT | 515 |
| TRBV6-5_x1 | GAAGACAGGACAGAGCATGACACTGCAGTGTGCC CAGGATATGAACCATGAATACATGTCCTGGTATC GACAAGACCCAGGCATGGGGCTGAGGCTGATTCA TTACTCAGTTAGTGCTGGTATCACTGACCAAGGA GAAGTCCCCAATGGCTACAATGTCTCCAGATCAA CCACAGAGGATTTCCCGCTCAGGCTGCTGTCGGC TGCTCCCTCCCAGACATCTGTGTACTTCTGT | 516 |
| TRBV11-1_x1 | ACAGAGAAAGCCAGGCTGTGGCTTTTTGGTGTG ATCCTATTTCTGGCCGTGCTACCCTTTATTGGTA CCGGCAGATCCTGGGACAGGGCCCGGAGCTTCTG GTTCGATTTCAGGATGAGAGTGTAGTAGATGATT CACAGTTGCCTAAGGATCGATTTTCTGCAGAGAG GCTCAAAGGAGTAGACTCCACTCTCAAGATCCAG CCTGCAGAGCTTGGGGACTCGGCCATGTATCTCT GT | 517 |
| TRBV30_x1 | GGCCAGCGACCCTGGTGCAGCCTGTGGGCAGCCC GCTCTCTCTGGAGTGCACTGTGGAGGGAACATCA AACCCCAACCTATACTGGTACCGACAGGCTGCAG GCAGGGGCCTCCAGCTGCTCTTCTACTCCGTTGG TATTGGCCAGATCAGCTCTGAGGTGCCCCAGAAT CTCTCAGCCTCCAGACCCCAGGACCGGCAGTTCA TCCTGAGTTCTAAGAAGCTCCTTCCAGTGACTCT AGCTTCTATCTCTGT | 518 |
| TRBV5-5_x1 | CAAAACGAGAGGACAGCAAGTGACTCTGAGATGC TCTCCTATCTCTGGGCACAAGAGTGTGTCCTGGT ACCAACAGGTCCTGGGTCAGGGGCCCCAGTTTAT | 519 |
|  | CTTTCAGTATTATGAGAAAGAAGAGAGAGGAAGA GGAAACTTCCCTGATCGATTCTCAGCTCGCCAGT TGCCTAACTATAGCTCTGAGCTGAATGTGAACGC CTTGTTGCTGGGGGACTCGGCCCTGTATCTCTGT |  |
| TRBV5-6_x1 | CAAAACGAGAGGACAGCAAGTGACTCTGAGATGC TCTCCTAAGTCTGGGCATGACACTGTGTCCTGGT ACCAACAGGCCCTGGGTCAGGGGCCCCAGTTTAT CTTTCAGTATTATGAGGAGGAAGAGAGACAGAGA GGCAACTTCCCTGATCGATTCTCAGGTCACCAGT TCCCTAACTATAGCTCTGAGCTGAATGTGAACGC CTTGTGGCTGGGGGACTCGGCCCTCTATCTCTGT | 520 |

Example 9

A total of 50 ng of total RNA from peripheral blood leukocytes was reverse transcribed to cDNA with SuperScript™ IV VILO™ Master Mix (Thermo Fisher Scientific) according to manufacturer instructions. Half the volume of prepared cDNA (25 ng cDNA) was used in multiplex polymerase chain reactions to amplify TCR beta CDR3 domain sequences. In one multiplex PCR, sets of forward and reverse primers selected from Tables 3 and 4 were used as primer pairs in amplifying sequences from the V gene FR3 region to the C gene of TCR beta cDNA. In other multiplex PCR, sets of forward and reverse primers selected from Tables 3 and 5 were used as primer pairs in amplifying sequences from the V gene FR3 region to the J gene of TCR beta cDNA.

In an exemplary V gene FR3-C amplification reaction, the multiplex primer set included 59 different TCR Beta V gene (TRBV) forward primers SEQ ID NOs: 249-307 and 2 different TCR Beta C gene (TRBC) reverse primers SEQ ID NOs: 181 and 182. In an exemplary V gene FR3-J amplification reaction, the multiplex primer set included 59 different TRBV forward primers SEQ ID NOs: 249-307 and 16 different TCR Beta J gene (TRBJ) reverse primers SEQ ID NOs: 398-413.

To a single well of a 96-well PCR plate was added 5 microliters prepared cDNA (25 ng), 2 microliters of 2 µM TRBV (FR3) forward primer pool (containing 59 primers), 2 microliters of 2 µM TRBC reverse primer pool (containing 2 primers), 4 microliters of 5× Ion AmpliSeq™ HiFi Mix (an amplification reaction mixture that can include glycerol, dNTPs, and Platinum® Taq High Fidelity DNA Polymerase (Invitrogen, Catalog No. 11304)), and 7 microliters DNase/RNase free water to bring the final reaction volume to 20 microliters. For the other amplification reaction, 5 microliters of prepared cDNA (25 ng), 2 microliters of 2 µM TRBV (FR3) forward primer pool (containing 59 primers), 2 microliters of 2 µM TRBJ reverse primer pool (containing 16 primers), 4 microliters of 5× Ion AmpliSeq™ HiFi Mix, and 7 microliters DNase/RNase free water to bring the final reaction volume to 20 microliters. These multiplex amplification reactions were performed with each primer present at 200 nM in the reaction.

The PCR plate was sealed, reaction mixtures mixed, and loaded into a thermal cycler (e.g., Veriti™ 96-well thermal cycler (Applied Biosystems)) and run on the following temperature profile to generate the amplicon library. An initial holding stage was performed at 95° C. for 7 minutes, followed by about 20 cycles of a denaturing stage at 95° C. for 30 seconds, an annealing stage at 60° C. for 45 seconds, and an extending stage for 72° C. for 45 seconds. After cycling, a final extension 72° C. for 10 minutes was performed and the amplicon library was held at 10° C. until proceeding. Typically, about 20 cycles are used to generate the amplicon library. For some applications, up to 30 cycles can be used.

The amplicon sample was briefly centrifuged to collect contents before proceeding. To the pre-amplified amplicon library (~20 microliters), 2 microliters of FuPa reagent was added. The reaction mixture was sealed, mixed thoroughly to ensure uniformity and incubated at 50° C. for 10 minutes, 55° C. for 10 minutes, 60° C. for 20 minutes, then held at 10° C. for up to 1 hour. The sample was briefly centrifuged to collect contents before proceeding.

After incubation, the reaction mixture proceeded directly to a ligation step. Here, the reaction mixture now containing the phosphorylated amplicon library was combined with 2 microliters of Ion Xpress™ Barcode Adapters, 5 µM each (Thermo Fisher), 4 microliters of Switch Solution (sold as a component of the Ion AmpliSeq™ Library Kit Plus, Thermo Fisher) and 2 microliters of DNA ligase, added last (sold as a component of the Ion AmpliSeq™ Library Kit Plus, Thermo Fisher), then incubated at the following: 22° C. for 30 minutes, 68° C. for 5 minutes, 72° C. for 5 minutes, then held at 10° C. for up to 24 hours. The sample was briefly centrifuged to collect contents before proceeding.

After the incubation step, 45 microliters (1.5× sample volume) of room temperature AMPure® XP beads (Beckman Coulter, CA) was added to ligated DNA and the mixture was pipetted thoroughly to mix the bead suspension with the DNA. The mixture was incubated at room temperature for 5 minutes, placed on a magnetic rack such as a DynaMag™-96 side magnet (Invitrogen, Part No. 12331D) for two minutes. After the solution had cleared, the supernatant was discarded. Without removing the plate from the magnetic rack, 150 microliters of freshly prepared 70% ethanol was introduced into the sample, and incubated while gently rotating the tube on the magnetic rack. After the solution cleared, the supernatant was discarded without disturbing the pellet. A second ethanol wash was performed, the supernatant discarded, and any remaining ethanol was removed by pulse-spinning the tube and carefully removing residual ethanol while not disturbing the pellet. The pellet was air-dried for about 5 minutes at room temperature. The ligated DNA was eluted from the beads in 50 microliters of low TE buffer.

The eluted libraries were quantitated by qPCR using the Ion Library TaqMan® Quantitation Kit (Ion Torrent, Cat. No. 4468802), according to manufacturer instructions. After quantification, the libraries were diluted to a concentration of about 25 picomolar.

An aliquot of the final library was used in template preparation and chip loading using the Ion Chef™ instrument according to the manufacturer's instructions. Sequencing was performed using Ion 530™ chips on the Ion S5™ System according to manufacturer instructions, and TCR beta gene sequence analysis was performed with the Ion Torrent Suite™ software. Sequences generated from use of J gene primers were subjected to a J gene sequence inference process involving adding the inferred J gene sequence to the sequence read to create an extended sequence read, aligning the extended sequence read to a reference sequence, and identifying productive reads, as described herein. In addition, all of the generated sequence data was further subjected to the error identification and removal programs provided herein.

Exemplary results from the TRB FR3-C and FR3-J assays using PBMC RNA as described above are shown in Table 11. Clone Normalized Shannon Entropy describes how "even" clone representation is in the sample; the closer to 1.0, the more evenly sized the clonal populations are. Both the FR3-C and FR3-J panels are similar in this regard.

TABLE 11

| Library | Reads | Mean Read Length (nt) | Mean CDR3 Length (nt) | % Productive | % Off-Target | Clones Identified | Clone Normalized Shannon Entropy | % Unproductive |
|---|---|---|---|---|---|---|---|---|
| FR3-C | 1,227,860 | 127 | 37 | 79.77% | 6.86% | 43,131 | 0.946324 | 13.37% |
| FR3-C | 1,070,307 | 127 | 37 | 78.85% | 7.79% | 33,086 | 0.944175 | 13.36% |
| FR3-J | 805,492 | 78 | 37 | 75.34% | 9.62% | 27,247 | 0.949755 | 15.04% |
| FR3-J | 784,543 | 78 | 37 | 71.90% | 13.17% | 21,458 | 0.943137 | 14.93% |

Example 10

Leukocyte cDNA was combined with a pool of 30 T cell receptor beta control plasmids (described in Example 4) and a TCR beta library was prepared using multiplex PCR to amplify TCR beta CDR3 domain sequences in the cDNA/plasmid mix. In the multiplex PCR, sets of forward and reverse primers selected from Tables 3 and 5 were used as primer pairs in amplifying sequences from the V gene FR3 region to the J gene of TCR beta cDNA and plasmid pool. In this exemplary V gene FR3-J amplification reaction, the multiplex primer set included 59 different TRBV forward primers SEQ ID NOs: 249-307 and 14 different TCR Beta J gene (TRBJ) reverse primers SEQ ID NOs: 414-427.

The cDNA was prepared from 50 ng of total RNA from peripheral blood leukocytes by reverse transcription with SuperScript™ IV VILO™ Master Mix (Thermo Fisher Scientific) according to manufacturer instructions. Half the volume of prepared leukocyte cDNA (25 ng cDNA) was combined with the 30 TRB control plasmids pooled at equimolar concentrations (0.01 pg/plasmid). To a single well of a 96-well PCR plate was added 5 microliters prepared cDNA (25 ng), 2 microliters of plasmid pool (0.01 pg/plasmid), 4 microliters of 1 µM Primer Mix (TRBV-FR3 forward primers and TRBJ reverse primers, 1 µM each), 4 microliters of 5× Ion AmpliSeq™ HiFi Mix (Invitrogen, Catalog No. 11304), and 5 microliters DNase/RNase free water to bring the final reaction volume to 20 microliters. The multiplex amplification reaction was performed with each primer present at 200 nM in the reaction.

The PCR plate was sealed, reaction mixtures mixed, and loaded into a thermal cycler (e.g., Veriti™ 96-well thermal cycler (Applied Biosystems)) and run on the following temperature profile to generate the amplicon library. An initial holding stage was performed at 99° C. for 2 minutes, followed by about 20 cycles of a denaturing stage at 98° C.

for 15 seconds and an annealing and extending stage at 60° C. for 4 minutes. The amplicon library was held at 10° C. until proceeding.

The amplicon sample was briefly centrifuged to collect contents before proceeding. Amplicon digestion, barcode ligation and further preparation, chip loading, and sequencing was performed as described in Example 9. Sequences generated were subjected to a J gene sequence inference process involving adding the inferred J gene sequence to the sequence read to create an extended sequence read, aligning the extended sequence read to a reference sequence, and identifying productive reads, as described herein. In addition, all of the generated sequence data was further subjected to the error identification and removal programs provided herein.

Figure 9:
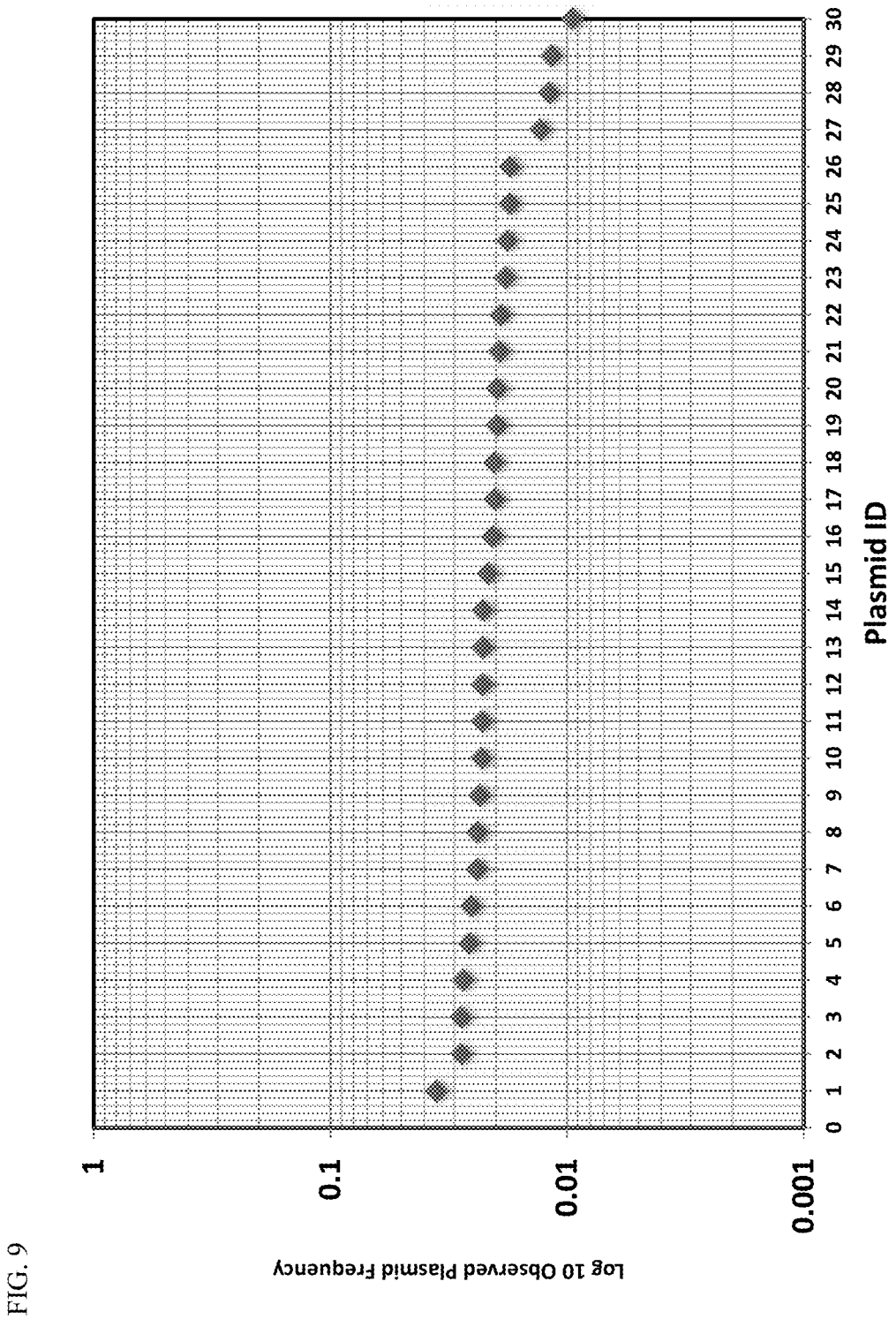
FIG. 9 depicts a graph showing the linearity of plasmid detection in TCR beta library generated from a pool of 30 control plasmids at equimolar concentrations mixed with leukocyte cDNA. The plasmid associated with the plasmid ID number is shown in Table 12.

The leukocyte cDNA+plasmid pool assay yielded >1.45M sequence reads, of which about 81% were productive, about 8% were off-target, and about 11% were unproductive. The mean sequence read length was 92 nucleotides and the mean CDR3 length was 38 nucleotides in length. The number of TCR beta clones identified was 23,075, including the 30 contributed by the control plasmids. The Clone Normalized Shannon Entropy was 0.544705. Performance of the assay on the pool of plasmids resulted in detected plasmid frequencies with only about a 3 fold variation across all 30 plasmids, as shown in FIG. 9 and Table 12.

TABLE 12

| Plasmid ID | Plasmid | Frequency |
| --- | --- | --- |
| 1 | RPMI 8402 | 0.0354595 |
| 2 | Jurkat | 0.0279832 |
| 3 | SUP-T3 | 0.0279173 |
| 4 | DND-41 | 0.0274278 |
| 5 | HUT 102 | 0.0257855 |
| 6 | Peer/Be13 | 0.0253639 |
| 7 | PF-382 | 0.0238889 |
| 8 | MOLT 13 | 0.0238659 |
| 9 | H-SB2 | 0.0233356 |
| 10 | MT-1 | 0.0229548 |
| 11 | HUT 78/H9 | 0.0227749 |
| 12 | KE-37/SKW-3 | 0.0227278 |
| 13 | SUP-Tl | 0.0226797 |
| 14 | Karpas 45 | 0.022663 |
| 15 | TALL-1 | 0.0215112 |
| 16 | JB6 | 0.0206033 |
| 17 | DU.528 | 0.0201221 |
| 18 | HPB-ALL | 0.0203062 |
| 19 | P12-Ichikawa | 0.0197465 |
| 20 | CML-T1b | 0.0196911 |
| 21 | CCRF-CEM | 0.0192538 |
| 22 | SU-DHL-1 | 0.0190269 |
| 23 | K-T1a | 0.0181262 |
| 24 | CML-Tia | 0.0178322 |
| 25 | MOLT 16/17 | 0.0174389 |
| 26 | K-T1b | 0.0174117 |
| 27 | TALL-104 | 0.0129346 |
| 28 | MOLT 3/4 | 0.0118446 |
| 29 | Karpas 299 | 0.0116186 |
| 30 | ARR | 0.0094847 |

What is claimed is:

1. A method for preparing an immune receptor repertoire library, comprising:
   A. generating target immune receptor amplicon molecules comprising performing a single multiplex amplification reaction to amplify expressed target immune receptor nucleic acid template molecules using at least one set of:
   i) (a) a plurality of V gene primers directed to a majority of different V genes of at least one immune receptor coding sequence comprising at least a portion of framework region 1 (FR1) within the V gene,
   (b) a plurality of V gene primers directed to a majority of different V genes of at least one immune receptor coding sequence comprising at least a portion of framework region 2 (FR2) within the V gene, or
   (c) a plurality of V gene primers directed to a majority of different V genes of at least one immune receptor coding sequence comprising at least a portion of framework region 3 (FR3) within the V gene; and
   ii) (a) one or more C gene primers directed to at least a portion of a C gene of the at least one immune receptor coding sequence, or
   (b) a plurality of J gene primers directed to at least a portion of a majority of different J genes of the at least one immune receptor coding sequence;
   wherein each set of i) and ii) primers is directed to coding sequences of the same target immune receptor gene selected from a T cell receptor gene or an antibody receptor gene and wherein performing the amplification using the at least one set of i) and ii) primers results in amplicon molecules representing a target immune receptor repertoire in a sample, thereby generating immune receptor amplicon molecules;

B. treating the amplicon molecules to form blunt-ended amplicon molecules; and

C. ligating at least one adapter to at least one of the treated amplicon molecules, thereby producing a library of adapter-ligated target immune receptor amplicon molecules comprising the target immune receptor repertoire;

wherein each of the plurality of V gene primers, the plurality of J gene primers and/or the one of more C gene primers includes two or more modified cleavable nucleotides within the primer sequence, at least one of which is included near or at the termini of the primer and at least one of which is included at, or about the center nucleotide position of the primer sequence.

2. The method of claim 1, wherein each of the plurality of V gene primers, the plurality of J gene primers and/or the one of more C gene primers has any one or more of the following criteria:
  (1) length is about 15 to about 40 bases in length;
  (2) Tm of from above 60° C. to about 70° C.;
  (3) has low cross-reactivity with non-target sequences present in the sample;
  (4) at least the first four nucleotides (going from 3' to 5' direction) are non-complementary to any sequence within any other primer present in the same reaction; and
  (5) are non-complementary to any consecutive stretch of at least 5 nucleotides within any other produced target amplicon.

3. The method of claim 1, wherein the at least one set of i) and ii) is i)(a) and ii)(a), wherein the plurality of V gene primers anneal to at least a portion of the FR1 region of the template molecules, and wherein the one or more C gene primers comprises at least two primers that anneal to at least a portion of the C gene portion of the template molecules.

4. The method of claim 3, wherein the generated immune receptor amplicons are about 300 to about 600 nucleotides in length.

5. The method of claim 3, wherein the at least one set of i) and ii) is selected from the primers of SEQ ID NO: 1-180 and SEQ ID NO: 181-184.

6. The method of claim 3, wherein the plurality of V gene primers is about 45 to about 90 different V gene primers.

7. The method of claim 1, wherein the at least one set of i) and ii) is i)(a) and ii)(b), wherein the plurality of V gene primers anneal to at least a portion of the FR1 region of the template molecules, and wherein the plurality of J gene primers comprises at least ten primers that anneal to at least a portion of the J gene portion of the template molecules.

8. The method of claim 7, wherein the at least one set of i) and ii) is selected from the primers of Table 2 and Table 5.

9. The method of claim 1, wherein the at least one set of i) and ii) is i)(c) and ii)(a), wherein the plurality of V gene primers anneal to at least a portion of the FR3 region of the template molecules, and wherein the one or more C gene primers comprises at least two primers that anneal to at least a portion of the C gene portion of the template molecules.

10. The method of claim 9, wherein the at least one set of i) and ii) is selected from the primers of Table 3 and Table 4.

11. The method of claim 1, wherein the at least one set of i) and ii) is i)(c) and ii)(b), wherein the plurality of V gene primers anneal to at least a portion of the FR3 region of the template molecules, and wherein the plurality of J gene primers comprises at least ten primers that anneal to at least a portion of the J gene portion of the template molecules.

12. The method of claim 11, wherein the at least one set of i) and ii) is selected from the primers of Table 3 and Table 5.

* * * * *

UNITED STATES PATENT AND TRADEMARK OFFICE
CERTIFICATE OF CORRECTION

PATENT NO. : 11,970,787 B2
APPLICATION NO. : 17/248722
DATED : April 30, 2024
INVENTOR(S) : Looney et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 282 days.

Signed and Sealed this
Eighth Day of October, 2024

Katherine Kelly Vidal
*Director of the United States Patent and Trademark Office*